United States Patent
Mori et al.

(10) Patent No.: US 9,488,914 B2
(45) Date of Patent: *Nov. 8, 2016

(54) FLUORINE-CONTAINING SULFONIC ACID SALT, FLUORINE-CONTAINING SULFONIC ACID SALT RESIN, RESIST COMPOSITION, AND PATTERN FORMING METHOD USING SAME

(71) Applicant: Central Glass Company, Limited, Ube-shi, Yamaguchi (JP)

(72) Inventors: Kazunori Mori, Kawagoe (JP); Satoru Narizuka, Kawagoe (JP); Yuji Hagiwara, Kawagoe (JP); Fumihiro Amemiya, Kawagoe (JP); Masaki Fujiwara, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/374,010

(22) PCT Filed: Jan. 17, 2013

(86) PCT No.: PCT/JP2013/050843
§ 371 (c)(1),
(2) Date: Feb. 5, 2015

(87) PCT Pub. No.: WO2013/111667
PCT Pub. Date: Aug. 1, 2013

(65) Prior Publication Data
US 2015/0198879 A1  Jul. 16, 2015

(30) Foreign Application Priority Data

Jan. 23, 2012 (JP) ................................ 2012-011132

(51) Int. Cl.
| | | |
|---|---|---|
| G03F 7/039 | (2006.01) | |
| G03F 7/038 | (2006.01) | |
| G03F 7/004 | (2006.01) | |
| G03F 7/20 | (2006.01) | |
| G03F 7/30 | (2006.01) | |
| C08F 220/38 | (2006.01) | |
| C07C 381/12 | (2006.01) | |
| C07C 309/10 | (2006.01) | |
| C07C 303/22 | (2006.01) | |
| C07D 307/93 | (2006.01) | |
| C07D 327/04 | (2006.01) | |
| C07D 307/20 | (2006.01) | |
| G03F 7/38 | (2006.01) | |
| C08F 222/18 | (2006.01) | |
| C08F 222/14 | (2006.01) | |

(52) U.S. Cl.
CPC .......... G03F 7/0397 (2013.01); C07C 303/22 (2013.01); C07C 309/10 (2013.01); C07C 381/12 (2013.01); C07D 307/20 (2013.01); C07D 307/93 (2013.01); C07D 327/04 (2013.01); C08F 220/38 (2013.01); C08F 222/14 (2013.01); C08F 222/18 (2013.01); G03F 7/0045 (2013.01); G03F 7/0046 (2013.01); G03F 7/038 (2013.01); G03F 7/0382 (2013.01); G03F 7/0392 (2013.01); G03F 7/0395 (2013.01); G03F 7/2002 (2013.01); G03F 7/2037 (2013.01); G03F 7/2041 (2013.01); G03F 7/30 (2013.01); G03F 7/38 (2013.01); C07C 2101/14 (2013.01); C07C 2102/42 (2013.01)

(58) Field of Classification Search
None
See application file for complete search history.

(56) References Cited

U.S. PATENT DOCUMENTS

| | | |
|---|---|---|
| 5,945,250 A | 8/1999 | Aoai et al. |
| 7,812,105 B2 | 10/2010 | Nagai et al. |
| 8,435,717 B2 | 5/2013 | Hagiwara et al. |

(Continued)

FOREIGN PATENT DOCUMENTS

| | | |
|---|---|---|
| JP | 5-45611 A | 2/1993 |
| JP | 9-325497 A | 12/1997 |

(Continued)

OTHER PUBLICATIONS

International Search Report dated Mar. 26, 2013 with English translation (five (5) pages).

(Continued)

Primary Examiner — Sin Lee
(74) Attorney, Agent, or Firm — Crowell & Moring LLP

(57) ABSTRACT

Disclosed is a fluorine-containing sulfonic acid salt resin having a repeating unit represented by the following general formula (3). In the formula, each A independently represents a hydrogen atom, a fluorine atom or a trifluoromethyl group, and n represents an integer of 1-10. W represents a bivalent linking group, $R^{01}$ represents a hydrogen atom or a monovalent organic group, and $M^+$ represents a monovalent cation. A resist composition containing this resin is further superior in sensitivity, resolution and reproducibility of mask pattern and is capable of forming a pattern with a low LER.

(3)

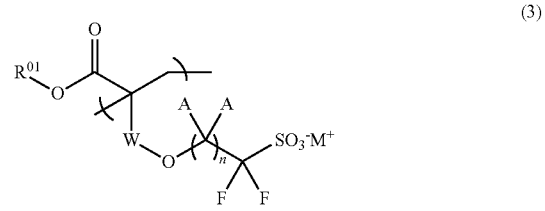

35 Claims, No Drawings

(56) References Cited

U.S. PATENT DOCUMENTS

| | | | |
|---|---|---|---|
| 8,663,897 B2 | 3/2014 | Masubuchi et al. | |
| 8,791,293 B2* | 7/2014 | Mori | C07C 309/10 430/921 |
| 2012/0270155 A1* | 10/2012 | Komuro | C07C 309/12 430/285.1 |
| 2013/0065182 A1* | 3/2013 | Mori | C07C 309/10 430/285.1 |
| 2013/0209937 A1 | 8/2013 | Takihana et al. | |
| 2014/0287359 A1* | 9/2014 | Mori | C07C 309/10 430/270.1 |

FOREIGN PATENT DOCUMENTS

| | | |
|---|---|---|
| JP | 2008-133448 A | 6/2006 |
| JP | 2006-178317 A | 7/2006 |
| JP | 2007-197718 A | 8/2007 |
| JP | 2009-7327 A | 1/2009 |
| JP | 2010-95643 A | 4/2010 |
| JP | 2011-164345 A | 8/2011 |
| JP | 2012-63728 A | 3/2012 |
| JP | 2012-102323 A | 5/2012 |
| JP | 2012-220927 A | 11/2012 |
| WO | WO 2006/121096 A1 | 11/2006 |

OTHER PUBLICATIONS

Japanese-language Written Opinion (PCT/ISA/237) dated Mar. 26, 2013 (three (3) pages).

* cited by examiner

FLUORINE-CONTAINING SULFONIC ACID SALT, FLUORINE-CONTAINING SULFONIC ACID SALT RESIN, RESIST COMPOSITION, AND PATTERN FORMING METHOD USING SAME

TECHNICAL FIELD

The present invention relates to a novel polymerizable fluorine-containing sulfonic acid salt having an anion structure, a fluorine-containing sulfonic acid salt resin, a resist composition, and a pattern forming method using the same. In particular, it relates to a resist composition that is preferable as a chemically amplified resist useful for fine processings using high energy rays, a novel fluorine-containing sulfonic acid salt resin used for the composition, and a novel fluorine-containing sulfonic acid salt used for synthesizing this fluorine-containing sulfonic acid salt resin.

BACKGROUND OF THE INVENTION

A resist composition used in pattern forming of lithography, which constitutes a semiconductor production step, has been required to have stricter resist characteristics, in which focal depth latitude (in the following, referred to as "DOF") is wider, line edge roughness (in the following, referred to as "LER") of patterns is lower, and resolution is superior, as a high energy ray to be applied has become shorter in wavelength in accordance with the pattern refinement, than at the time when required in a long wavelength irradiation.

As such resist suitable for short-wavelength exposure, a chemically amplified resist composition is used. This is a pattern forming material which contains a photoacid generator that forms an acid by a high energy ray irradiation (in the following, referred to as exposure) (in the following, referred to as photoacid generator) and which forms a pattern by changing solubility in a developing solution between an exposed portion and an unexposed portion by a reaction using an acid generated by the exposure as a catalyst.

In such pattern forming material, homogeneity of resist has increasingly been regarded as a problem as practical use of extreme ultraviolet rays has approached by the progress of refinement. Until now, resists in general have been composed of a resist resin, in which solubility in a developing solution changes by action of an acid, a solvent, and a photoacid generator (as an additive) to generate the acid. However, when seeking a further refinement, such formation has been insufficient in dispersion uniformity of the resist resin and the photoacid generator. Thus, recently, there have been reports (Patent Publications 1-7) of producing a resist resin by a copolymerization of a monomer having a photoacid generation function with a monomer of a conventional resist resin raw material to incorporate the photoacid generation function into the resist resin. For example, Patent Publications 6 and 7 disclose a resist composition containing a resin prepared by polymerization or copolymerization using a methacrylic acid ester having at a side chain a triphenylsulfonium salt structure of a sulfonic acid having fluorine atoms at α-position.

PRIOR ART PUBLICATION

Patent Publications

Patent Publication 1: Japanese Patent Application Publication Heisei 9-325497
Patent Publication 2: International Publication WO 2006/121096 Pamphlet
Patent Publication 3: Japanese Patent Application Publication 2006-178317
Patent Publication 4: Japanese Patent Application Publication 2007-197718
Patent Publication 5: Japanese Patent Application Publication 2008-133448
Patent Publication 6: Japanese Patent Application Publication 2009-7327
Patent Publication 7: Japanese Patent Application Publication 2010-95643

SUMMARY OF THE INVENTION

Task to be Solved by the Invention

As the refinement progresses in a pattern forming method using a short-wavelength ultraviolet ray having a wavelength of 300 nm or shorter, in which a high energy ray such as ArF excimer laser, KrF excimer laser, etc. is used as a light source, or using an electron beam, due to an insufficient uniformity of the resist composition, roughness may be generated after the pattern formation. This may result in generating a defect that the pattern itself cannot be well drawn.

Regarding this, a high uniformity of resist composition has been achieved by synthesizing a resist resin using a monomer having the above-mentioned photoacid generation function to incorporate the photoacid generation function into the resist resin.

However, in many cases, a moiety exhibiting the photoacid generation function generally takes an ionic structure, such as sulfonium salt. Therefore, its solubility is low in a polymerization solvent when synthesizing resist resins and in a resist solvent when dissolving the resist resins. Thus, in some cases, there tend to occur problems that synthesis (polymerization) of resist resins becomes difficult and that synthesized resist resins are not dissolved in resist solvents. Thus, in many cases, it becomes necessary to have means such as limiting usage of a monomer having the photoacid generation function, selecting a monomer that is highly soluble in the solvent as a copolymerization partner, etc.

If the content of a moiety exhibiting the photoacid generation function is low, there is a small number of places where the reaction using an acid as the catalyst occurs, thereby making the change of solubility insufficient and causing a fear that a pattern conforming to the photomask is not formed and a defect is generated.

Thus, it is a task of the present invention to improve solubility of a monomer or resist resin having the acid generation function incorporated, in the polymerization solvent or resist solvent.

Means for Solving the Task

The present inventors have repeated an eager study to solve the above-mentioned task. As a result, we have obtained a concept that, if both moieties of a moiety having the photoacid generation function and a moiety for improving solubility in the solvent are made to exist in a single molecule of a monomer used for synthesizing a resist resin, this monomer itself tends to become soluble in the solvent, thereby making the production (polymerization) of the resist resin easy and furthermore making the produced resist resin tend to become soluble in the resist solvent. Furthermore, we have obtained a concept that, after forming a resist, such group for improving solubility is expected to function as an adhesive group for improving adhesion with a material, which is brought into contact with the resist, such as a silicon wafer, an anti-reflection film and a top coat, or in some cases as a cross-linking group in a negative-type resist.

Based on such concept, as a result of searching specific resins and variously synthesizing monomers having particular structures suitable for obtaining such polymers and then measuring and observing resist characteristics about the obtained resins, it has been found that a single repeating unit can be provided with a soluble group and a fluorine-containing sulfonic acid salt and that its solubilities in various solvents can be improved. Furthermore, depending on the mode of the invention, it has been found to have not only a function as a sulfonic acid onium salt acid generating agent, but also a function of being capable of improving adhesion of the resist to the substrate or as a cross-linking group-containing resin. As a result, it has been found that a resist composition containing this resin is further superior in sensitivity, resolution and reproducibility of mask pattern and is capable of forming a pattern with a low LER.

That is, the invention of the present application is as follows.

[Invention 1] A fluorine-containing sulfonic acid salt resin having a repeating unit represented by the following general formula (3).

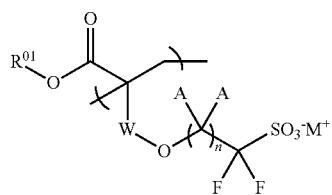

(3)

(In the formula, each A independently represents a hydrogen atom, a fluorine atom or a trifluoromethyl group, and n represents an integer of 1-10. W represents a bivalent linking group, $R^{01}$ represents a hydrogen atom or a monovalent organic group, and $M^+$ represents a monovalent cation.)

[Invention 2] The fluorine-containing sulfonic acid salt resin of Invention 1, wherein the monovalent organic group $R^{01}$ is a $C_{1-50}$ organic group and a group containing any group of the following (a) to (g).

(a) an alicyclic group having a carbon ring containing an ether bond (—O—) or carbonyl group (—C(=O)—) (any hydrogen atom bonded to a carbon of the ring may be replaced with a hydroxy group or an acetoxy group), (b) a group having an aromatic ring in which at least one hydrogen atom has been replaced with a hydroxy group, (c) a fluoroalcohol group, (d) a group having a ring prepared by a condensation of a ring containing an ether bond (—O—), a thioether bond (—S—), an imino group (—NH—), a carbonyl group (—C(=O)—) or a thiocarbonyl group (—C(=S)—), with an aromatic ring, (e) a $C_{1-3}$ alkyl group, (f) an alicyclic group in which a hydroxy group and a fluorine atom or trifluoromethyl group have been bonded to the same carbon of the ring, and (g) an alicyclic group in which any hydrogen atom has been replaced with a cyano group-containing group, a hydroxy group, or an acetoxy group.

[Invention 3] The fluorine-containing sulfonic acid salt resin of Invention 1 or 2, wherein the monovalent organic group $R^{01}$ comprises a group selected from a lactone ring group, a cyclic ether group, 2-hydroxy-hexafluoroisopropyl group (HFIP group), 2-acetoxy-hexafluoroisopropyl group, and a group represented by the following formula.

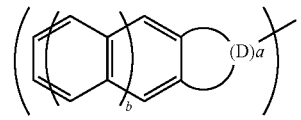

(23)

(In the formula, each D independently represents a methylene group (—CH$_2$—), a methine group (=C—), an oxygen atom, a sulfur atom, a carbonyl group, a thiocarbonyl group or an imino group, a ring portion containing D has at least one hetero atom, a represents an integer of 2-5, and b represents an integer of 0-2.)

[Invention 4] The fluorine-containing sulfonic acid salt resin of any of Inventions 1-3, wherein the repeating unit represented by the general formula (3) is a repeating unit represented by the following general formula (4).

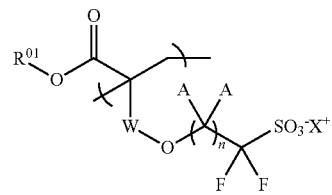

(4)

(In the formula, A, n, W and $R^{01}$ are respectively defined as those in the above-mentioned general formula (3). $X^+$ represents a sulfonium cation represented by the following general formula (CA-a) or an iodonium cation represented by the following general formula (CA-b).

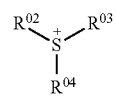

(CA-a)

(In the formula, $R^{02}$, $R^{03}$ and $R^{04}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or any two or more of $R^{02}$, $R^{03}$ and $R^{04}$ may be connected with each other to form a ring together with the sulfur atom in the formula.

The alkenyl groups take a carbon number of 2 or more.)

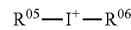

(CA-b)

(In the formula, $R^{05}$ and $R^{06}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or $R^{05}$ and $R^{06}$ may be connected with each other to form a ring together with the iodine atom in the formula. The alkenyl groups take a carbon number of 2 or more.)

[Invention 5] The fluorine-containing sulfonic acid salt resin of any of Inventions 1-3, comprising a repeating unit represented by the following general formula (5).

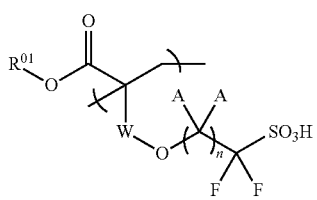

(5)

(In the formula, A, n, W and $R^{01}$ are respectively defined as those in the above-mentioned general formula (3).)

[Invention 6] The fluorine-containing sulfonic acid salt resin of any of Inventions 1-5, further comprising at least one repeating unit selected from the group consisting of repeating units formed by a cleavage of a polymerizable double bond contained in an olefin, a fluorine-containing olefin, an acrylic acid ester, a methacrylic acid ester, a fluorine-containing acrylic acid ester, a fluorine-containing methacrylic acid ester, a norbornene compound, a fluorine-containing norbornene compound, a styrene compound, a fluorine-containing styrene compound, a vinyl ether, or a fluorine-containing vinyl ether.

[Invention 7] The fluorine-containing sulfonic acid salt resin of Invention 6, wherein the olefin, the fluorine-containing olefin, the acrylic acid ester, the methacrylic acid ester, the fluorine-containing acrylic acid ester, the fluorine-containing methacrylic acid ester, the norbornene compound, the fluorine-containing norbornene compound, the styrene compound, the fluorine-containing styrene compound, the vinyl ether, or the fluorine-containing vinyl ether is a polymerizable compound containing in the molecule a moiety that generates an acid by a high-energy ray irradiation.

[Invention 8] The fluorine-containing sulfonic acid salt resin of Invention 6, wherein the olefin, the fluorine-containing olefin, the acrylic acid ester, the methacrylic acid ester, the fluorine-containing acrylic acid ester, the fluorine-containing methacrylic acid ester, the norbornene compound, the fluorine-containing norbornene compound, the styrene compound, the fluorine-containing styrene compound, the vinyl ether, or the fluorine-containing vinyl ether is a polymerizable compound containing in the molecule a moiety that is decomposed by an acid catalyst to become an acid.

[Invention 9] The fluorine-containing sulfonic acid salt resin of Invention 6, wherein the olefin, the fluorine-containing olefin, the acrylic acid ester, the methacrylic acid ester, the fluorine-containing acrylic acid ester, the fluorine-containing methacrylic acid ester, the norbornene compound, the fluorine-containing norbornene compound, the styrene compound, the fluorine-containing styrene compound, the vinyl ether, or the fluorine-containing vinyl ether is a polymerizable compound containing in the molecule a moiety that is lowered in solubility in alkali developing solutions through a reaction with a cross-linking agent by an acid catalyst.

[Invention 10] The fluorine-containing sulfonic acid salt resin of any of Inventions 1-9, further comprising a repeating unit represented by the following general formula (6).

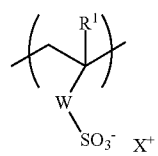

(6)

(In the formula, $R^1$ represents a hydrogen atom, a halogen atom, or a $C_{1-3}$ alkyl group or fluorine-containing alkyl group. W represents a bivalent linking group and is defined as in the general formula (3). $X^+$ is defined as in the general formula (4).)

[Invention 11] The fluorine-containing sulfonic acid salt resin of any of Inventions 1-10, further comprising a repeating unit represented by the following general formula (7).

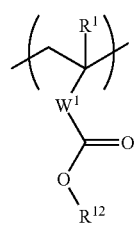

(7)

(In the formula, $R^1$ represents a hydrogen atom, a halogen atom, or a $C_{1-3}$ alkyl group or fluorine-containing alkyl group. $W^1$ represents a bivalent linking group. $R^{12}$ represents an acid-labile group.)

[Invention 12] The fluorine-containing sulfonic acid salt resin of any of Inventions 1-11, further comprising a repeating unit represented by the following general formula (13-1).

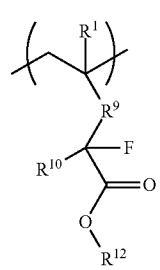

(13-1)

(In the formula, $R^1$ represents a hydrogen atom, a halogen atom, or a $C_{1-3}$ alkyl group or fluorine-containing alkyl group. $R^{10}$ represents a hydrogen atom, a fluorine atom, or a fluorine-containing alkyl group. $R^9$ represents a bivalent linking group. $R^{12}$ represents an acid-labile group.)

[Invention 13] The fluorine-containing sulfonic acid salt resin of any of Inventions 1-12, further comprising a repeating unit represented by the following general formula (13).

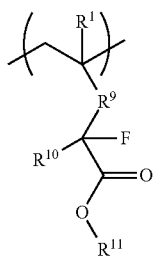

(13)

(In the formula, $R^1$ represents a hydrogen atom, a halogen atom, or a $C_{1-3}$ alkyl group or fluorine-containing alkyl group. $R^9$ represents a bivalent linking group. $R^{10}$ represents a hydrogen atom, a fluorine atom, or a fluorine-containing alkyl group. $R^{11}$ is a hydrogen atom, a substituted or unsubstituted, $C_{1-25}$ aliphatic hydrocarbon group or a substituted or unsubstituted, $C_{1-25}$ aromatic hydrocarbon group, and a part of $R^{11}$ may contain a fluorine atom, an ether bond, or a carbonyl group.)

[Invention 14] The fluorine-containing sulfonic acid salt resin of any of Inventions 1-13, further comprising a repeating unit represented by the following general formula (8).

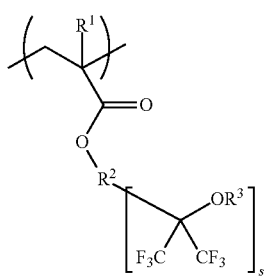

(8)

(In the formula, $R^1$ represents a hydrogen atom, a halogen atom, or a $C_{1-3}$ alkyl group or fluorine-containing alkyl group. $R^2$ is a substituted or unsubstituted aliphatic hydrocarbon group, a substituted or unsubstituted aromatic hydrocarbon group, or an organic group prepared by linking a plurality of those, and may have a fluorine atom substituted for an arbitrary number of hydrogen atom. $R^3$ is a hydrogen atom, a substituted or unsubstituted, $C_{1-25}$ aliphatic hydrocarbon group or a substituted or unsubstituted $C_{1-25}$ aromatic hydrocarbon group, may have a fluorine atom substituted for an arbitrary number of hydrogen atom, and may contain an ether bond or a carbonyl group. Furthermore, s represents an integer of 1-2.)

[Invention 15] The fluorine-containing sulfonic acid salt resin of any of Inventions 1-14, further comprising a repeating unit represented by the following general formula (8-1).

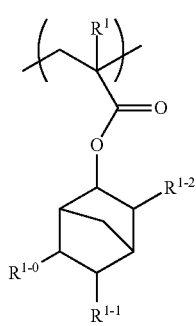

(8-1)

(In the formula, $R^1$ represents a hydrogen atom, a halogen atom, or a $C_{1-3}$ alkyl group or fluorine-containing alkyl group. Any one of $R^{1-0}$, $R^{1-1}$ and $R^{1-2}$ is a $CF_3C(CF_3)(OH)CH_2-$ group, and remaining two are hydrogen atoms.)

[Invention 16] The fluorine-containing sulfonic acid salt resin of any of Inventions 1-15, further comprising a repeating unit represented by the following general formula (9).

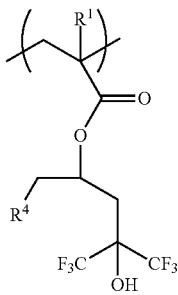

(9)

(In the formula, $R^1$ represents a hydrogen atom, a halogen atom, or a $C_{1-3}$ alkyl group or fluorine-containing alkyl group. $R^4$ represents a hydrogen atom, or a $C_{1-4}$ alkyl group or fluorine-containing alkyl group.)

[Invention 17] The fluorine-containing sulfonic acid salt resin of any of Inventions 1-16, further comprising a repeating unit represented by the following general formula (10).

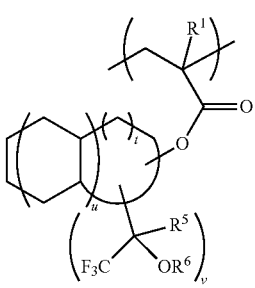

(10)

(In the formula, $R^1$ represents a hydrogen atom, a halogen atom, or a $C_{1-3}$ alkyl group or fluorine-containing alkyl group. $R^5$ represents a methyl group or a trifluoromethyl group. $R^6$ represents a hydrogen atom or a group containing a substituted or unsubstituted $C_{1-25}$ aliphatic hydrocarbon group or a substituted or unsubstituted $C_{1-25}$ aromatic hydrocarbon group. $R^6$ may contain a fluorine atom, an ether bond, or a carbonyl group. u represents an integer of 0-2. t and v are integers of 1-8, and $v \leq t+2$ is satisfied. In case that v is 2-8, $R^5$ and $R^6$ may respectively be the same or different.

[Invention 18] The fluorine-containing sulfonic acid salt resin of any of Inventions 1-17, further comprising a repeating unit represented by the following general formula (11).

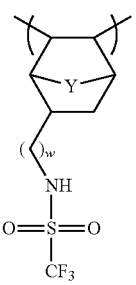

(11)

(In the formula, Y represents any of —$CH_2$—, —O—, and —S—. w presents an integer of 2-6.)

[Invention 19] The fluorine-containing sulfonic acid salt resin of any of Inventions 1-18, further comprising a repeating unit represented by the following general formula (12).

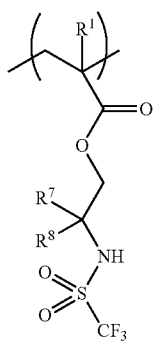

(12)

(In the formula, $R^1$ represents a hydrogen atom, a halogen atom, or a $C_{1-3}$ alkyl group or fluorine-containing alkyl group. Each of $R^7$ and $R^8$ independently represents a hydrogen atom, a substituted or unsubstituted $C_{1-25}$ aliphatic hydrocarbon group or a substituted or unsubstituted $C_{1-25}$ aromatic hydrocarbon group. A part of $R^7$ and $R^8$ may contain a fluorine atom, an ether bond, or a carbonyl group.)

[Invention 20] A resist composition comprising at least the fluorine-containing sulfonic acid salt resin of any of Inventions 1-19 and a solvent.

[Invention 21] The resist composition of Invention 20, further comprising an acid-labile group-containing resin.

[Invention 22] The resist composition of Invention 20, further comprising a cross-linking agent.

[Invention 23] The resist composition of Invention 22, further comprising a cross-linking group-containing resin.

[Invention 24] The resist composition of Inventions 20-23, further comprising a compound that generates an acid by radiation exposure.

[Invention 25] A pattern forming method, characterized by comprising the step of applying the resist composition of any of Inventions 20-24 onto a substrate, the step of conducting an exposure with a high-energy ray having a wavelength of 300 nm or less through a photomask after a heating treatment; and the step of conducting a development using a developing solution, after conducting a heating treatment if necessary.

[Invention 26] The pattern forming method of Invention 25, characterized by that the step of conducting the exposure is an immersion lithography method in which an ArF excimer laser having a wavelength of 193 nm is used, and in which water or a liquid having a refractive index higher than that of air and being other than water is inserted between a substrate, on which the resist composition has been applied, and a projection lens.

[Invention 27] The pattern forming method of Invention 25, characterized by that in the step of conducting the exposure a soft X-ray (EUV light) having a wavelength of 10-14 nm is used.

[Invention 28] A polymerizable fluorine-containing sulfonic acid or a polymerizable fluorine-containing sulfonic acid salt, having an anion represented by the following general formula (1).

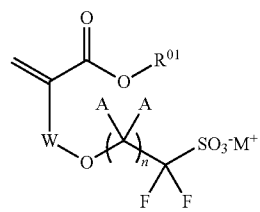

(1)

(In the formula, each A independently represents a hydrogen atom, a fluorine atom or a trifluoromethyl group, and n represents an integer of 1-10. W represents a bivalent linking group. $R^{01}$ represents a hydrogen atom or a monovalent organic group. $M^+$ represents a monovalent cation.)

[Invention 29] The polymerizable fluorine-containing sulfonic acid salt of Invention 28, which is a polymerizable fluorine-containing sulfonic acid onium salt represented by the following general formula (2).

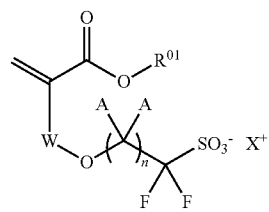

(2)

(In the formula, A, n, W and $R^{01}$ are respectively defined as those in the above-mentioned general formula (1). $X^+$ represents a sulfonium cation represented by the following general formula (CA-a) or an iodonium cation represented by the following general formula (CA-b).

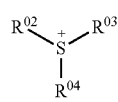

(CA-a)

(In the formula, $R^{02}$, $R^{03}$ and $R^{04}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or any two or more of $R^{02}$, $R^{03}$ and $R^{04}$ may be connected with each other to form a ring together with the sulfur atom in the formula. The alkenyl groups take a carbon number of 2 or more.)

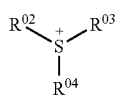
(CA-a)

(In the formula, $R^{02}$, $R^{03}$ and $R^{04}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or any two or more of $R^{02}$, $R^{03}$ and $R^{04}$ may be connected with each other to form a ring together with the sulfur atom in the formula. The alkenyl groups take a carbon number of 2 or more.)

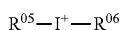
(CA-b)

(In the formula, $R^{05}$ and $R^{06}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or $R^{05}$ and $R^{06}$ may be connected with each other to form a ring together with the iodine atom in the formula. The alkenyl groups take a carbon number of 2 or more.)

[Invention 30]

A method for producing a polymerizable fluorine-containing sulfonic acid onium salt represented by the general formula (2)

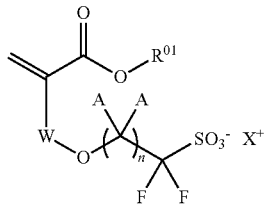
(2)

(In the formula, A, n, W, $R^{01}$ and $X^+$ are respectively defined as those in the general formulas (15) and (16)), characterized by that in the presence of a base catalyst a condensation reaction is conducted between an acrylic acid derivative represented by the following general formula (15)

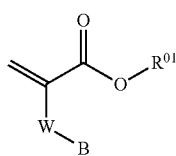
(15)

(In the formula, W represents a bivalent linking group, and $R^{01}$ represents a hydrogen atom or a monovalent organic group. B represents a halogen atom or a leaving group.)

and a hydroxyalkanesulfonic acid onium salt represented by the following general formula (16)

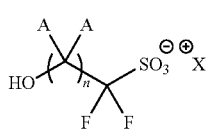
(16)

(In the formula, each A independently represents a hydrogen atom, a fluorine atom or a trifluoromethyl group, and n represents an integer of 1-10. $X^+$ represents a sulfonium cation represented by the following general formula (CA-a) or an iodonium cation represented by the following general formula (CA-b).

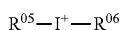
(CA-b)

(In the formula, $R^{05}$ and $R^{06}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or $R^{05}$ and $R^{06}$ may be connected with each other to form a ring together with the iodine atom in the formula. The alkenyl groups take a carbon number of 2 or more.)

[Invention 31]

The production method of Invention 30, wherein W of the acrylic acid derivative represented by the general formula (15) is methylene.

[Invention 32]

The production method of Invention 30 or 31, wherein the acrylic acid derivative represented by the general formula (15) is the following general formula (17) or general formula (18).

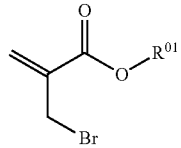
(17)

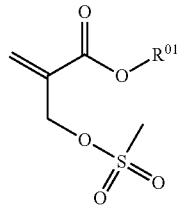
(18)

(In the formula, $R^{01}$ is defined as that in the above-mentioned general formula (2).)

[Invention 33]

The production method of any of Inventions 30-32, wherein, in the hydroxyalkanesulfonic acid onium salt represented by the general formula (16), n is 1, and A is a hydrogen.

[Invention 34]

The production method of any of Inventions 30-33, wherein $X^+$ of the hydroxyalkanesulfonic acid onium salt represented by the general formula (16) is a triphenylsulfonium.

[Invention 35]

A method for producing a polymerizable fluorine-containing sulfonic acid onium salt represented by the general formula (2)

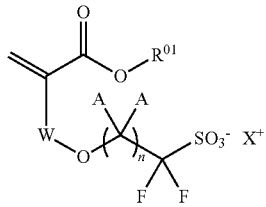
(2)

(In the formula, A, n, W, $R^{01}$ and $X^+$ are respectively defined as those in the general formulas (19) and (20)), characterized by that an acid chloride derivative represented by the following general formula (19)

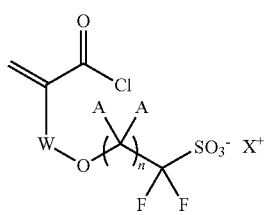
(19)

(In the formula, W is a bivalent linking group, and each A independently represents a hydrogen atom, a fluorine atom or a trifluoromethyl group. n represents an integer of 1-10. $X^+$ represents a sulfonium cation represented by the following general formula (CA-a) or an iodonium cation represented by the following general formula (CA-b).

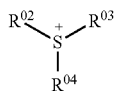
(CA-a)

(In the formula, $R^{02}$, $R^{03}$ and $R^{04}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or any two or more of $R^{02}$, $R^{03}$ and $R^{04}$ may be connected with each other to form a ring together with the sulfur atom in the formula. The alkenyl groups take a carbon number of 2 or more.)

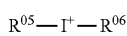
(CA-b)

(In the formula, $R^{05}$ and $R^{06}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or $R^{05}$ and $R^{06}$ may be connected with each other to form a ring together with the iodine atom in the formula. The alkenyl groups take a carbon number of 2 or more.)
is reacted with an alcohol body represented by the following general formula (20)

(20)

(In the formula, $R^{01}$ represents a monovalent organic group.)

[Invention 36]

The production method of Invention 35, wherein W of the acid chloride derivative represented by the general formula (19) is methylene.

[Invention 37]

The production method of Invention 35 or 36, wherein, in the acid chloride derivative represented by the general formula (19), n is 1, and A is a hydrogen.

[Invention 38]

The production method of any of Inventions 35-37, wherein $X^+$ of the acid chloride derivative represented by the general formula (19) is a triphenylsulfonium.

[Invention 39]

A method for producing a polymerizable fluorine-containing sulfonic acid onium salt represented by the general formula (2)

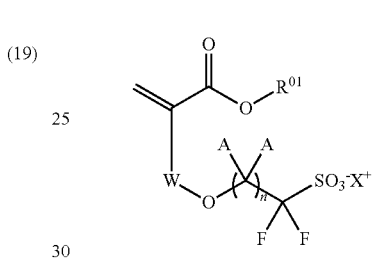
(2)

(In the formula, A, n, W, $R^{01}$ and $X^+$ are respectively defined as those in the general formulas (21) and (20)), characterized by that a carboxylic acid derivative represented by the following general formula (21)

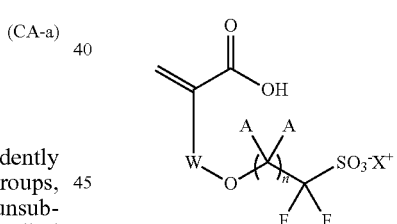
(21)

(In the formula, W is a bivalent linking group, and each A independently represents a hydrogen atom, a fluorine atom or a trifluoromethyl group. n represents an integer of 1-10. $X^+$ represents a sulfonium cation represented by the following general formula (CA-a) or an iodonium cation represented by the following general formula (CA-b).

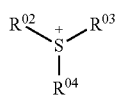
(CA-a)

(In the formula, $R^{02}$, $R^{03}$ and $R^{04}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or any two or more of $R^{02}$, $R^{03}$ and $R^{04}$ may be connected with each other to form a ring together with the sulfur atom in the formula. The alkenyl groups take a carbon number of 2 or more.)

$$R^{05}-I^{+}-R^{06} \qquad (CA\text{-}b)$$

(In the formula, $R^{05}$ and $R^{06}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or $R^{05}$ and $R^{06}$ may be connected with each other to form a ring together with the iodine atom in the formula. The alkenyl groups take a carbon number of 2 or more.)
is reacted with an alcohol body represented by the following general formula (20)

$$HO-R^{01} \qquad (20)$$

(In the formula, $R^{01}$ represents a monovalent organic group.)

[Invention 40]

The production method of Invention 39, wherein W of the carboxylic acid derivative represented by the general formula (21) is methylene.

[Invention 41]

The production method of Invention 39 or 40, wherein, in the carboxylic acid derivative represented by the general formula (21), n is 1, and A is a hydrogen.

[Invention 42]

The production method of any of Inventions 39-41, wherein $X^+$ of the carboxylic acid derivative represented by the general formula (21) is a triphenylsulfonium.

Advantageous Effect of the Invention

While the fluorine-containing sulfonic acid salt resin of the present invention is a so-called polymer-type sulfonic acid onium salt acid generating agent capable of providing a resist composition high in homogeneousness, it shows an advantageous effect of being high in solubility in solvents. With this, it is possible to suppress deficiency of moieties having the photoacid generation function, which has been hitherto a cause of defect due to that a sufficient amount of the acid generator cannot be contained in a resist composition. As a result, there has been brought a remarkable advantageous effect that a good pattern can be formed in terms of high sensitivity, high resolution, high reproducibility of mask pattern, and small LER.

On the other hand, in the case of having a group that improves solubility in solvents, it shows an advantageous effect of improving adhesion to substrates such as silicon wafer. Furthermore, in the case of having a cross-linking group, it may be used as a negative-type, base resin.

Furthermore, the monomer for synthesizing the fluorine-containing sulfonic acid salt resin of the present invention is high in solubility in polymerization solvents. Therefore, it is possible to make the range of polymerization composition wider, and it has become possible to precisely adjust the repeating unit composition of a copolymer to be obtained.

As a result, it is possible to freely adjust various characteristics, such as acidity strength of the sulfonic acid to be generated, solubility, and acid decomposition temperature, by variously combining the group that improves solubility in solvents or the moiety having the photoacid generation function, which is to be introduced.

MODE FOR IMPLEMENTING THE INVENTION

In the following, the best mode for implementing the present invention is explained. The present invention is, however, not limited to the following embodiments. It should be understood that, in a scope not deviating from the gist of the present invention, those made by suitably adding modification, improvement, etc., based on ordinary knowledge of a person skilled in the art, to the following embodiments are also in the scope of the present invention.

In the column of MODE FOR IMPLEMENTING THE INVENTION of the present specification, the item indicated by "[" and "]" or "<" and ">" is just a sign and has no meaning by itself.

In the present specification, a resin of which solubility in developing solutions changes by exposure is referred to as a base resin. A resist, in which solubility of the exposed portion in developing solutions becomes higher, is referred to as a positive-type resist. A resist, in which solubility becomes lower, is referred to as a negative-type resist. A positive-type resist and a positive-type resist composition of a chemically amplified type are referred to as a chemically amplified, positive-type resist and a chemically amplified, positive-type resist composition. A negative-type resist and a negative-type resist composition of a chemically amplified type are referred to as a chemically amplified, negative-type resist and a chemically amplified, negative-type resist composition.

In the present specification, alkyl group or alkylene group refers to a straight-chain, branched or cyclic alkyl group or alkylene group, unless otherwise explained.

In the present specification, the lower alkyl group refers to a $C_{1-4}$ alkyl group in the case of a chain compound and a $C_{3-7}$ alkyl group in the case of a cyclic compound.

In the present specification, the aliphatic ring is a monocyclic or polycyclic aliphatic hydrocarbon or a group in which a carbon atom of this aliphatic hydrocarbon has been replaced with an oxygen atom, a sulfur atom, a carbonyl group or an imino group, and contains at least the following structure (the carbon atom may be replaced with an oxygen atom, a sulfur atom, a carbonyl group or an imino group), and may contain a nonaromatic double bond.

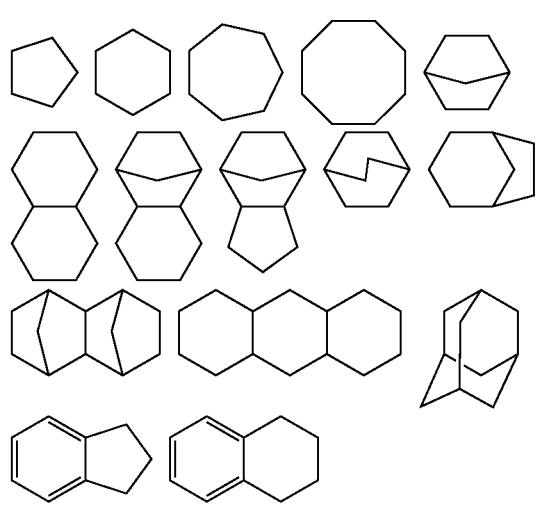

(i-1)

In the present specification, the high energy ray refers to an electromagnetic wave or a particle beam that acts on the resist composition to generate an acid. In general, it is an electromagnetic wave that is classified into near ultraviolet ray (wavelength: 380-200 nm), vacuum ultraviolet ray (far ultraviolet ray, VUV, wavelength: 200-10 nm), extreme ultraviolet ray (EUV, wavelength: 10 nm or less), soft X-ray, X-ray or γ-ray, etc., or a particle beam such as electron beam. The names of these electromagnetic waves are ones as a matter of convenience. For example, a wavelength of 10-14 nm may be called EUV light or soft X-ray, etc.

In the present specification, when referring to salt, it includes the case that the cation is $H^+$, unless otherwise noted.

The relationship between the substances related to the present invention is shown in Scheme (1).

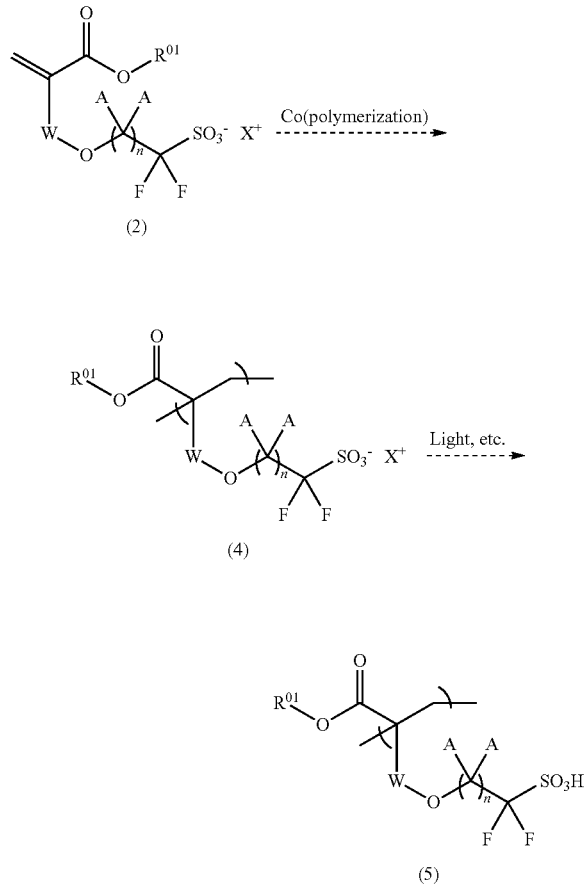

By homopolymerization or copolymerization of the polymerizable fluorine-containing sulfonic acid onium salt represented by the general formula (2), it is possible to obtain a sulfonic acid salt resin having a repeating unit represented by the general formula (4). This sulfonic acid salt resin is converted to a resin having a repeating unit represented by the general formula (5) by an action of high-energy ray, heat, etc. The generated fluorine-containing sulfonic acid functions as an acid catalyst. The general formulas (2), (4) and (5) are explained hereinafter.

[Polymerizable fluorine-containing sulfonic acid and polymerizable fluorine-containing sulfonic acid salt] A polymerizable fluorine-containing sulfonic acid or polymerizable fluorine-containing sulfonic acid salt having an anion represented by the general formula (1) of the present invention is described.

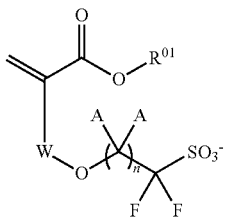

The polymerizable fluorine-containing sulfonic acid or polymerizable fluorine-containing sulfonic acid salt having an anion represented by the general formula (1) can be a polymerizable fluorine-containing sulfonic acid or polymerizable fluorine-containing sulfonic acid salt represented by the general formula (1-1).

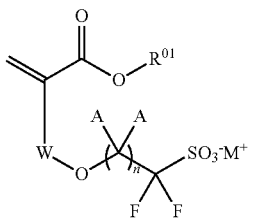

$M^+$ represents a monovalent cation. In the general formula (1-1), $M^+$ represents a proton, and a metal cation, such as lithium ion, sodium ion or potassium ion, or ammonium ions, and onium ions, such as sulfonium ions, iodonium ions and phosphonium ions.

In the general formula (1) and the general formula (1-1), each A independently represents a hydrogen atom, a fluorine atom or a trifluoromethyl group. n represents an integer of 1-10, preferably an integer of 1-6. W is a bivalent linking group. $R^{01}$ represents a hydrogen atom or a monovalent organic group.

In the general formula (1) and the general formula (1-1), the structure represented by $—(CA_2)_n—$ is a $C_{1-10}$ straight-chain alkylene group, which may be an alkylene group having a fluorine atom(s) substituted for any hydrogen atom(s). Of that, a structure represented by $—(CH_2)_p—(CF_2)_q—$ is preferable. Herein, p is an integer of 0-10, and q is an integer of 0-8. It is preferable that p is an integer of 1-6 and q is an integer of 0-5. It is more preferable that p is an integer of 1-4 and q is 0 or 1.

In the resin having a sulfonic acid onium salt fixed at a side chain of the polymer, a moiety to function as a chemically amplified photoacid generator is fixed at a side chain, thereby substantially limiting the acid diffusion distance. Therefore, it shows characteristics that DOF is wide and LER is small. It is, however, possible to adjust easiness of the diffusion and the diffusion distance by so specifying the chemical structure of the linking group, which sets the acid moiety and the main chain apart, and the length of the side chain.

Furthermore, in case that $R^{01}$ has a cross-linking moiety, both of a moiety to function as a chemically amplified photoacid generator and a cross-linking moiety exist in the same repeating unit, and both of them are fixed at the side chain. Therefore, it is possible to still more precisely control the diffusion distance.

<Linking group W> A group constituting a main skeleton of the linking group W is a linking group, such as an unsubstituted or substituted methylene group, an unsubstituted or substituted bivalent alicyclic hydrocarbon group, a bivalent aromatic group or an unsubstituted or substituted bivalent heterocyclic group, or a bivalent linking group prepared by a bonding with each other of at least one selected from the group consisting of these linking groups, an ether bond (—O—), a thioether bond (—S—), a carbonyl group, an ester bond, an oxycarbonyl group, an amide bond, a sulfonamide bond, a urethane bond and a urea bond. Any number of hydrogen atoms bonded to carbon atoms in this bivalent linking group may be replaced with fluorine atoms. Each carbon atom in the linking group may form a ring by including carbon atoms in the substituted group.

The substituted methylene group for constituting a main skeleton of the linking group W is represented by the following general formula (14).

$$—CR^{21}R^{22}— \quad (14)$$

Herein, a monovalent group represented by $R^{21}$ or $R^{22}$ of the substituted methylene group is not particularly limited, but is a hydrogen atom, a halogen atom or a hydroxy group, or a $C_{1-30}$ ($C_{3-30}$ in the case of including a ring) monovalent group selected from a substituted or unsubstituted alkyl group, a substituted or unsubstituted alicyclic hydrocarbon group, a substituted or unsubstituted alkoxy group, a substituted or unsubstituted aryl group, and a substituted or unsubstituted condensed polycyclic aromatic group. These monovalent groups can have fluorine atom, oxygen atom, sulfur atom, nitrogen atom, or carbon-carbon double bond. $R^{21}$ and $R^{22}$ may be the same or different. Furthermore, $R^{21}$ and $R^{22}$ may form a ring by a combination with an atom(s) in the molecule, and this ring is preferably an aliphatic ring. As a monovalent organic group represented by $R^{21}$ or $R^{22}$, it is possible to specifically cite the following ones.

As an acyclic, unsubstituted alkyl group in $R^{21}$ and $R^{22}$, the number of carbon atoms is 1-30, preferably 1-12. It is possible to cite, for example, methyl group, ethyl group, n-propyl group, i-propyl group, n-butyl group, 1-methylpropyl group, 2-methylpropyl group, tert-butyl group, n-pentyl group, i-pentyl group, 1,1-dimethylpropyl group, 1-methylbutyl group, 1,1-dimethylbutyl group, n-hexyl group, n-heptyl group, i-hexyl group, n-octyl group, i-octyl group, 2-ethylhexyl group, n-nonyl group, n-decyl group, n-undecyl group, n-dodecyl group, etc. Lower alkyl groups are preferable. It is possible to cite methyl group, ethyl group, n-propyl group, i-propyl group, etc. as particularly preferable ones.

As an acyclic, substituted alkyl group in $R^{21}$ and $R^{22}$, it is possible to cite those in which at least one hydrogen atom possessed by alkyl groups has been replaced with a $C_{1-4}$ alkoxy group(s), a halogen atom(s), an acyl group(s), an acyloxy group(s), a cyano group(s), a hydroxy group(s), a carboxy group(s), an alkoxycarbonyl group(s), a nitro group(s), etc. A fluoroalkyl group having a fluorine atom(s) substituted is preferable. Specifically, it is possible to cite lower fluoroalkyl groups, such as trifluoromethyl group, pentafluoroethyl group, 2,2,2-trifluoroethyl group, n-heptafluoropropyl group, 2,2,3,3,3-pentafluoropropyl group, 3,3,3-trifluoropropyl group, hexafluoroisopropyl group, etc.

In $R^{21}$ and $R^{22}$, first alicyclic hydrocarbon groups or second alicyclic hydrocarbon groups formed by including a carbon atom(s) to which the first alicyclic hydrocarbon groups are bonded may be monocyclic or polycyclic. Specifically, it is possible to cite a group having an at least three-membered, monocyclo, bicyclo, tricyclo, tetracyclo structure, etc. The number of carbon atoms is preferably 3-30, particularly preferably 3-25. These alicyclic hydrocarbon groups may have a substituent(s).

As the monocyclic group, 3 to 12-numbered ones are preferable. 3 to 7-numbered ones are more preferable. For example, it is possible to cite as preferable ones cyclopropyl group, cyclobutyl group, cyclopentyl group, cyclohexyl group, cycloheptyl group, cyclooctyl group, cyclodecanyl group, cyclododecanyl group, 4-tert-butylcyclohexyl group, etc. Furthermore, as the polycyclic group, it is possible to cite 7 to 15-membered, adamantyl group, noradamantyl group, decalin residue, tricyclodecanyl group, tetracyclodecanyl group, norbornyl group, cedrol group, etc. It is possible to cite monocyclic groups in which one or at least two of hydrogen atoms of ring carbons of these organic groups or the linking group have independently been replaced with the above-mentioned $C_{1-30}$ alkyl group(s) or substituted alkyl group(s), a hydroxy group(s), an alkoxy group(s), a carboxyl group(s), an alkoxycarbonyl group(s), or in which one or at least two hydrogen atoms contained therein have been replaced with a fluorine atom(s) or a trifluoromethyl group(s).

Herein, the $C_{1-30}$ alkyl group is preferably a lower alkyl group, more preferably an alkyl group selected from the group consisting of methyl group, ethyl group, propyl group, and isopropyl group. Furthermore, as the substituent of the substituted alkyl group, it is possible to cite hydroxy group, halogen atom, and alkoxy group. As the alkoxy group, it is possible to cite $C_{1-4}$ ones, such as methoxy group, ethoxy group, propoxy group, and butoxy group. As the alkoxycarbonyl group, it is possible to cite methoxycarbonyl group, ethoxycarbonyl group, and isopropoxycarbonyl group.

As the alkoxy group in $R^{21}$ and $R^{22}$, it is possible to cite $C_{1-4}$ ones, such as methoxy group, ethoxy group, propoxy group, and butoxy group.

The substituted or unsubstituted aryl group in $R^{21}$ and $R^{22}$ is $C_{6-30}$ one. As a monocyclic group, a 3 to 12-membered one is preferable, and a 3 to 6-membered one is more preferable. It is possible to cite, for example, phenyl group, biphenyl group, terphenyl group, o-tolyl group, m-tolyl group, p-tolyl group, p-hydroxyphenyl group, p-methoxyphenyl group, mesityl group, o-cumenyl group, 2,3-xylyl group, 2,4-xylyl group, 2,5-xylyl group, 2,6-xylyl group, 3,4-xylyl group, 3,5-xylyl group, o-fluorophenyl group, m-fluorophenyl group, p-fluorophenyl group, o-trifluoromethylphenyl group, m-trifluoromethylphenyl group, p-trifluoromethylphenyl group, 2,3-bistrifluoromethylphenyl group, 2,4-bistrifluoromethylphenyl group, 2,5-bistrifluoromethylphenyl group, 2,6-bistrifluoromethylphenyl group, 3,4-bistrifluoromethylphenyl group, 3,5-bistrifluoromethylphenyl group, p-chlorophenyl group, p-bromophenyl group, p-iodophenyl group, etc.

As the substituted or unsubstituted $C_{3-30}$ condensed polycyclic aromatic group, it is possible to cite monovalent organic groups obtained by removing one hydrogen atom from pentalene, indene, naphthalene, azlene, heptalene, biphenylene, indacene, acenaphthylene, fluorene, phenarene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene, etc. As preferable ones, it is possible to cite ones in which one or at least two hydrogen atoms of these have been replaced with fluorine atoms or $C_{1-4}$ alkyl groups or fluorine-containing alkyl groups.

As the 3 to 25-membered, monocyclic or polycyclic, heterocyclic group, it is possible to cite, for example, pyridyl group, furyl group, thienyl group, pyranyl group, pyrrolyl group, thiantrenyl group, pyrazolyl group, isothiazolyl group, isoxazolyl group, pyrazinyl group, pyrimidinyl group, pyridadinyl group, tetrahydropyranyl group, tetrahydrofuranyl group, tetrahydrothiopyranyl group, tetrahydrothiofuranyl group, 3-tetrahydrothiophen-1,1-dioxide group, etc., and heterocyclic groups in which one or at least two hydrogen atoms constituting these rings have been replaced with alkyl groups, alicyclic hydrocarbon groups, aryl groups or heterocyclic groups. Furthermore, ones having a monocyclic or polycyclic ether ring or lactone ring are preferable, and are exemplified by the following general formula (i-2).

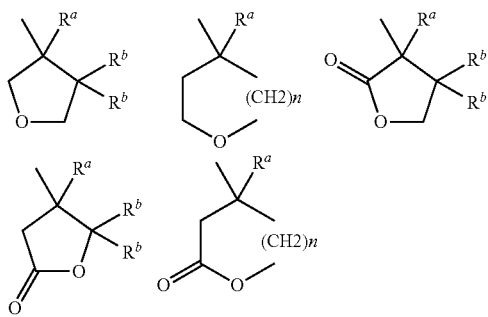

(i-2)

In the general formula (i-2), each of $R^a$ and $R^b$ independently represents a hydrogen atom or $C_{1-4}$ alkyl group, and n represents an integer of 2-4.

The bivalent alicyclic hydrocarbon group constituting a main skeleton of the linking group W may be monocyclic or polycyclic. Specifically, it is possible to cite a group having a monocyclo, bicyclo, tricyclo, tetracyclo structure, etc. having a carbon number of at least 3. The carbon number is preferably 3-30, and particularly a carbon number of 3-25 is preferable. These alicyclic hydrocarbon groups may have substituents.

The monocyclic group is preferably one having a ring carbon number of 3-12, and one having a ring carbon number of 3-7 is more preferable. For example, as preferable ones, it is possible to cite cyclopropylene group, cyclobutylene group, cyclopentylene group, cyclohexylene group, cycloheptylene group, cyclooctylene group, cyclodecanylene group, cyclododecanylene group, and 4-tert-butylcyclohexylene group. Furthermore, as the polycyclic group, it is possible to cite 7 to 15-membered, adamantylene group, noradamantylene group, a divalent residue of decalin, tricyclodecanylene group, tetracyclododecanylene group, norbornylene group, and a divalent residue of cedrol. The alicyclic hydrocarbon group may be a spiro ring, and on that occasion a spiro ring having a carbon number of 3-6 is preferable. Furthermore, it is possible to cite ones in which one or at least two of hydrogen atoms of the ring carbons or linking groups are independently be replaced with a $C_{1-30}$ alkyl group or substituted alkyl group, hydroxy group, alkoxy group, carboxyl group, or alkoxycarbonyl group.

Herein, specifically, as the substituent, it is possible to cite the following ones. The $C_{1-30}$ alkyl group is preferably a lower alkyl group, more preferably an alkyl group selected from the group consisting of methyl group, ethyl group, propyl group, and isopropyl group. Furthermore, as a substituent of the substituted alkyl group, it is possible to cite hydroxy group, halogen atom and alkoxy group. As the alkoxy group, it is possible to cite one having a carbon number of 1-4, such as methoxy group, ethoxy group, propoxy group, butoxy group, etc. As the alkoxycarbonyl group, it is possible to cite methoxycarbonyl group, ethoxycarbonyl group, and isopropoxycarbonyl group.

As the bivalent aromatic hydrocarbon group constituting a main skeleton of the linking group W, there is provided a $C_{3-30}$ monocyclic group or condensed polycyclic aromatic group. As the monocyclic group, a 3 to 12-membered one is preferable. A 3 to 6-membered one is more preferable. It is possible to cite bivalent groups obtained by removing two hydrogen atoms from, for example, benzene, biphenyl, terphenyl, toluene, phenol, anisole, mesitylene, cumene, 2,3-xylylene, 2,4-xylene, 2,5-xylene, 2,6-xylene, 3,4-xylene, 3,5-xylene, fluorobenzene, trifluoromethylbenzene, o-bistrifluoromethylbenzene, m-bistrifluoromethylbenzene, p-bistrifluoromethylbenzene, chlorobenzene, bromobenzene, iodobenzene, etc.

The condensed polycyclic aromatic group can be substituted or unsubstituted, and the number of its carbons is preferably 3-30. It is possible to cite bivalent organic groups obtained by removing two hydrogen atoms from pentalene, indene, naphthalene, azlene, heptalene, biphenylene, indacene, acenaphthylene, fluorene, phenarene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene, etc. It is possible to use ones in which one or at least two hydrogen atoms of these have been replaced with fluorine atoms or $C_{1-4}$ alkyl groups or fluorine-containing alkyl groups.

The 3 to 25-membered, monocyclic or polycyclic, heterocyclic group constituting a main skeleton of the linking group W may be an aromatic ring or nonaromatic ring. It is possible to cite bivalent organic groups obtained by removing two hydrogen atoms from, for example, pyridine, furan, thienine, pyranine, pyrroline, thianthrene, pyrazon, isothiazone, isooxazone, pyrazine, pyrimidine, pyridazine, tetrahydropyranine, tetrahydrofuranine, tetrahydrothiopyranine, tetrahydrothiofuran, etc., and heterocyclic groups in which one or at least two hydrogen atoms constituting these rings have been replaced with alkyl groups (lower alkyl groups are preferable), alicyclic hydrocarbon groups, aryl groups or heterocyclic groups. Of these, monocyclic or polycyclic ether rings are preferable. They are exemplified in the following formula (i-3). In the formula, an open-ended line segment indicates an unbonded arm.

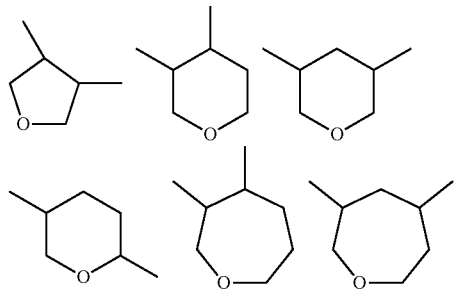

(i-3)

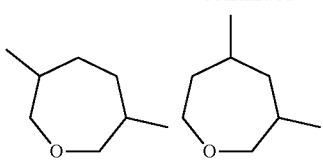

As mentioned above, the linking group W may be a bivalent group prepared by combining bivalent groups explained by the general formulas or specifically exemplified above.

The linking group W is preferably an alkylene group or a carbonyl group —C(=O)—. The alkylene group or an alkylene group contained in these bivalent groups may be chain-like (branched is contained) or cyclic or a mixture of these. The number of carbons of a main chain except the cyclic portion is preferably 1-5. It is more preferable that the number of carbon atoms of these alkylene groups is 1. It is still more preferably a methylene group. It is more preferable that the cyclic structure contained is 3 to 10-membered. It is more preferable that these alkylene groups are cyclopentylene, cyclohexylene, norbornylene, or adamantylene. Next, W is exemplified.

(i-4)

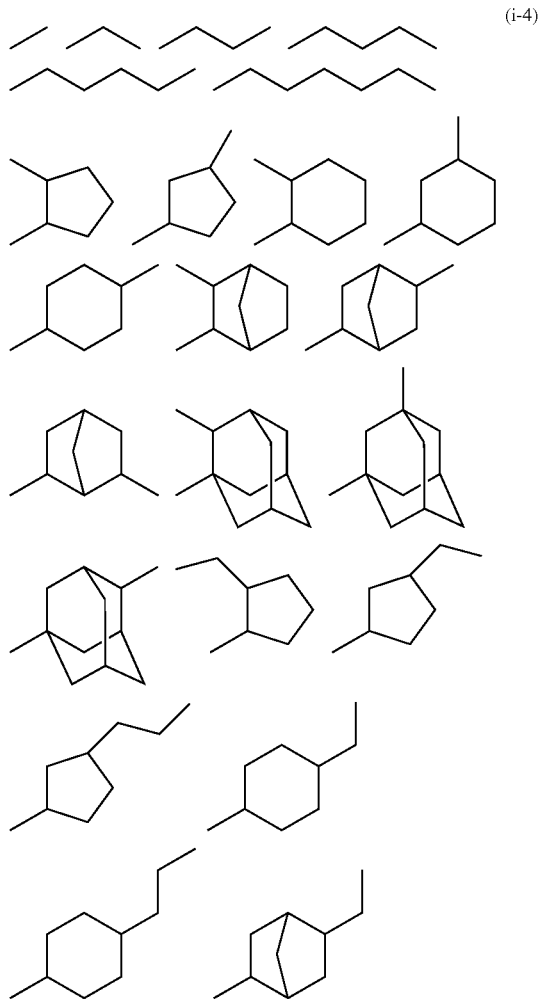

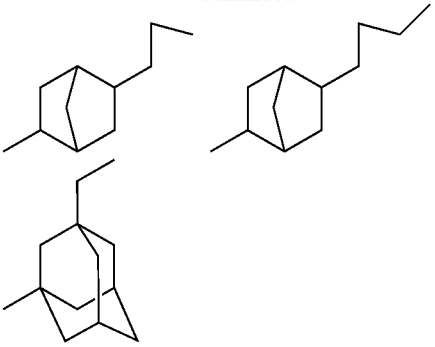

<Organic group $R^{01}$> By having an ester moiety, the anion represented by the general formula (1) is capable of improving solubility of the polymerizable fluorine-containing sulfonic acid salt. By selecting specific $R^{01}$, it is possible to further improve solubility, or, in the case of using as a resist, improve adhesion to the substrate or make it function as a cross-linking moiety of a negative-type resist.

$R^{01}$ is a hydrogen atom or a monovalent organic group. Monovalent organic groups $R^{01}$ are aliphatic hydrocarbon groups, aromatic hydrocarbon groups, and organic groups prepared by combining these. The carbon atom(s) may be replaced with ether bond(s), carbonyl group(s), thioether bond(s), thiocarbonyl group(s), and imino group(s). Herein, the aliphatic hydrocarbon group of the monovalent organic group may be a chain-like hydrocarbon group or a cyclic hydrocarbon group. The hydrogen atom(s) contained in the monovalent organic group may be replaced freely. As the substituent, it is possible to cite fluorine atom, trifluoromethyl group, hydroxy group, acetoxy group, cyano group, etc. It is preferable that the monovalent organic group $R^{01}$ is a $C_{1-50}$ organic group. It is preferable that the monovalent organic group is any group of the following (a) to (g) or a group containing the same.

(a) an alicyclic group having a carbon ring containing an ether bond (—O—) or a carbonyl group (—C(=O)—) (any hydrogen atom(s) bonded to the ring carbon(s) may be replaced with a hydroxy group(s) or an acetoxy group(s)); (b) a group having an aromatic ring in which at least one hydrogen atom has been replaced with a hydroxy group(s); (c) a fluoroalcohol group; (d) a group having a ring prepared by a condensation between a ring containing ether bond (—O—), thioether bond (—S—), imino group (—NH—), carbonyl group (—C(=O)—) or thiocarbonyl group (—C(=S)—), and an aromatic ring; (e) a $C_{1-3}$ alkyl group; (f) an alicyclic group in which a hydroxy group and a fluorine atom or trifluoromethyl group have been bonded to the same ring carbon; and (g) an alicyclic group in which any hydrogen atom(s) has been replaced with a cyano group-containing group(s), a hydroxy group(s) or an acetoxy group(s). The group containing any group of these (a) to (g) can contain at least one of the groups (a) to (g). These groups represented by (a) to (g) may be directly bonded to the oxygen atom at the end of the ester bond bonded to the polymer's main chain or may be bonded thereto via a linking group. That is, as the linking group, it is possible to cite a single bond, a straight-chain, branched or cyclic alkylene group, a cyclic ether group, a lactone ring group, an ester bond, an ether bond, an amide bond, or a group prepared by a combination of these. The cyclic alkylene group, the cyclic ether group, or the lactone ring group may be monocyclic or polycyclic and is a 5 to 20-membered monocyclic or polycyclic cyclic group.

The group represented by (a) is preferably a lactone ring group, a lactam group, a cyclic ketone group, or a cyclic ether group, more preferably a lactone group.

Although each of ether group (—O—) and carbonyl group even singly contributes to the improvement of solubility, they are useful as an ester bond (—C(=O)O—). Lactone ring group or lactam ring group as a cyclic ester is preferable as an adhesive group for improving adhesion to the substrate of resist. Lactone ring group is particularly preferable.

As the lactone group, it is possible to cite lactone groups represented by the following formula (i-5) and formula (i-6).

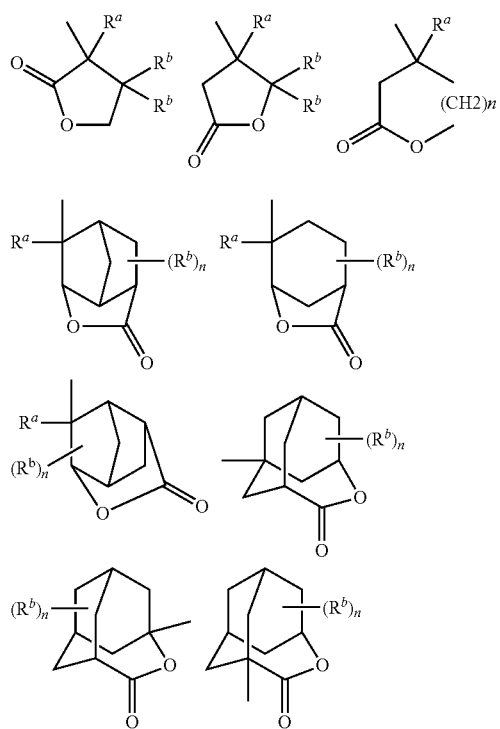

In the above formulas, $R^a$ represents a $C_1$-$C_4$ alkyl group or perfluoroalkyl group. Each of $R^b$'s independently represents a hydrogen atom, $C_1$-$C_4$ alkyl group or perfluoroalkyl group, hydroxy group, carboxylic acid group, alkyloxycarbonyl group, alkoxy group, etc., and n represents an integer of 1-4.

As these 5 to 20-membered, monocyclic or polycyclic lactone groups, it is possible to cite groups prepared by elimination of one hydrogen atom from γ-butyrolactone, γ-valerolactone, angelicalactone, γ-hexalactone, γ-heptalactone, γ-octalactone, γ-nonalactone, 3-methyl-4-octanolide (whiskey lactone), γ-decalactone, γ-undecalactone, γ-dodecalactone, γ-jasmolactone (7-decenolactone), δ-hexalactone, 4,6,6(4,4,6)-trimethyltetrahydropyran-2-one, δ-octalactone, δ-nonalactone, δ-decalactone, δ-2-decenolactone, δ-undecalactone, δ-dodecalactone, δ-tridecalactone, δ-tetradecalactone, lactoscatone, ε-decalactone, ε-dodecalactone, cyclohexyllactone, jasminelactone, cis-jasmonelactone, methyl γ-decalactone, etc., or the following. The dotted line shows the bonding position.

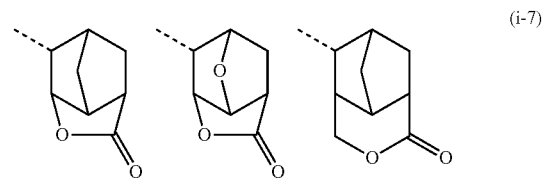

The cyclic ether group may be a monocyclic or polycyclic ether ring. It is possible to cite groups prepared by elimination of one hydrogen atom from the following compounds. The bonding arm may belong to any carbon atom.

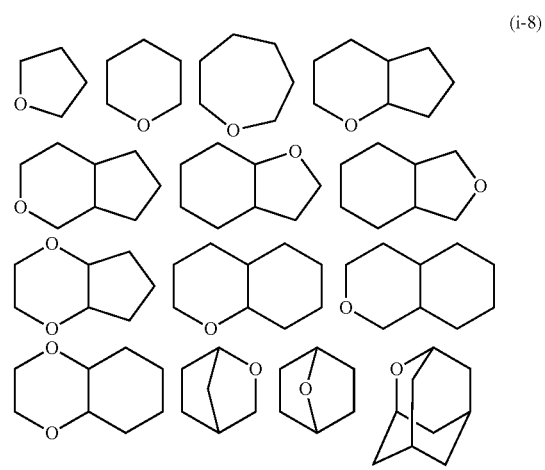

The group (b) having an aromatic ring in which at least one hydrogen atom has been replaced with a hydroxy group(s) can be accompanied with a ring prepared by condensation of a 5 to 20-membered aliphatic ring. The aromatic ring can be exemplified by benzene condensed rings, such as benzene, naphthalene, anthracene, and phenanthrene. The aliphatic ring is 4 to 7-membered, preferably 5 or 6-membered. Carbon atom(s) of the aliphatic ring can be replaced with oxygen atom(s), sulfur atom(s), carbonyl group(s), NH group(s), etc. It can contain at least one or at least one type of these atoms or groups. As this condensed aliphatic ring, it is possible to cite hydrocarbon rings, lactone rings, ether rings, cyclic ketones, etc. The number of hydroxy groups to be substituted is not limited, but preferably one. The unbonded arm may belong to any carbon atom of the aromatic ring or the aliphatic ring.

In a pattern forming method (EUV exposure) using an electron beam or a soft X-ray having a wavelength of 10-14 nm (EUV light), a phenolic hydroxy group has a sensitizing effect by electron beam and EUV exposure and can be used as a cross-linking group of a negative-type resist composition since it acts as a cross-linking group.

The fluoroalcohol group (c) is a group having at least a hydroxy group(s) and a fluorine atom(s). The fluoroalcohol group is 1-30 in carbon number and is a group in which at least one hydrogen atom has been replaced with a hydroxy group(s) and at least one hydrogen atom has been replaced with a fluorine atom(s) or a trifluoromethyl group(s) in a chain-like or cyclic alkyl group or an alkyl group prepared by a combination thereof. In the fluoroalcohol group, it is preferable that the hydroxy group is in the vicinity of the fluorine atom or trifluoromethyl group. Existing as 2-hydroxy-hexafluoroisopropyl group (HFIP group) is particularly preferable. Furthermore, an alicyclic group (f), in which a fluorine atom or trifluoromethyl group is geminally bonded with a hydroxy group, is also preferable. This alicyclic group is 5 to 20-membered and preferably 5 to 7-membered. It may be a hydrocarbon group, a cyclic ether or a lactone ring. A hydrogen atom(s) of the alicyclic group may be replaced with a fluorine atom(s). A hydroxy group of the fluoroalcohol group may be replaced with an acetoxy group, resulting in 2-acetoxy-hexafluoroisopropyl group.

The hydroxy group functions as a cross-linking group and has an effect of improving solubility. Therefore, it is capable of making solubility by the ester bond higher. The effect of making solubility high is striking in case that the hydroxy group is bonded to the same carbon atom to which a fluorine atom or a fluorine-containing group, such as a trifluoromethyl group, is bonded.

The group (d) having a ring prepared by a condensation of a ring containing an ether bond (—O—), a thioether bond (—S—), an imino group (—NH—), a carbonyl group (—C(=O)—) or a thiocarbonyl group (—C(=S)—), with an aromatic ring is preferably one represented by the following general formula (23). This group contributes to the improvement of solubility.

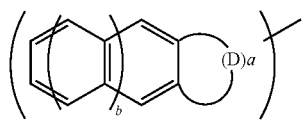
(23)

In the formula, each D independently represents a carbon atom, an oxygen atom, a sulfur atom, a carbonyl group, a thiocarbonyl group or an imino group. Herein, the carbon atom refers to a methylene group (—CH$_2$—) or a methine group (=CH—). The D-containing ring section contains at least one hetero atom (referring to oxygen, sulfur, or nitrogen). "a" is an integer of 2-5, preferably 3 or 4. "b" is an integer of 0-2, preferably 1. The aromatic ring can be exemplified by benzene condensed rings, such as benzene, naphthalene, anthracene, and phenanthrene.

As the C$_{1-3}$ alkyl group (e), it is possible to cite C$_{1-3}$ alkyl groups (containing isomers) such as methyl group and ethyl group.

The alicyclic group (g) in which any hydrogen atom(s) has been replaced with a cyano group(s), a cyano group-containing group(s), a hydroxy group(s) or an acetoxy group(s) contributes to the improvement of solubility. Herein, the alicyclic group may be monocyclic or polycyclic. Specifically, it is possible to cite groups having at least three-membered, monocyclo, bicyclo, tricyclo, tetracyclo structures, etc. The monocyclic group is preferably a 3 to 12-membered one, more preferably a 3 to 7-membered one. For example, as preferable ones, it is possible to cite cyclopropyl group, cyclobutyl group, cyclopentyl group, cyclohexyl group, cycloheptyl group, cyclooctyl group, cyclodecanyl group, cyclododecanyl group, and 4-tert-butylcyclohexyl group. Furthermore, as the polycyclic group, it is possible to cite 7 to 15-membered, adamantyl group, noradamantyl group, decalin residue, tricyclodecanyl group, tetracyclododecanyl group, norbornyl group, cedrol group, etc. The cyano group-containing group can be exemplified by cyanoalkyl groups as being preferable. Those in which a hydrogen atom(s) of a C$_{1-3}$ alkyl group has been replaced with a cyano group(s) are more preferable. Specifically, it is possible to cite cyanomethyl group, cyanoethyl group, etc.

The substituent-free, alicyclic groups, which are cited herein, can be monovalent organic groups R$^{01}$.

In the following, specifically, preferable structures as R$^{01}$ are exemplified.

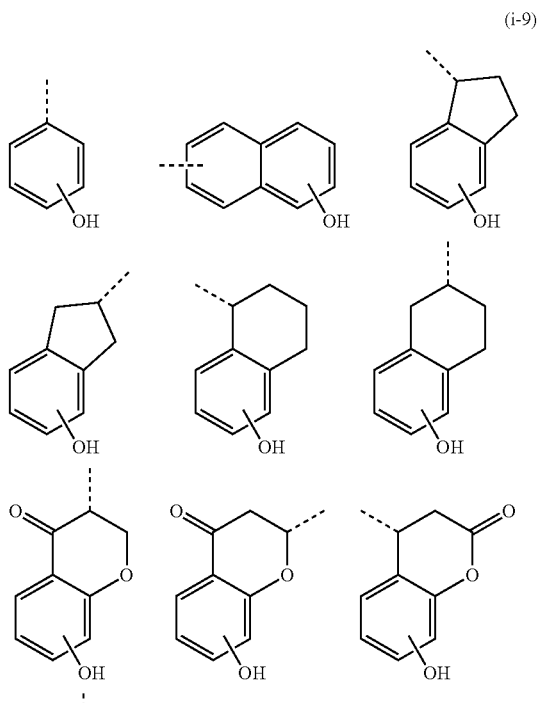
(i-9)

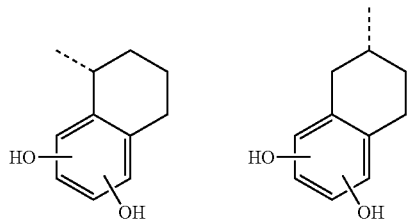
(i-10)

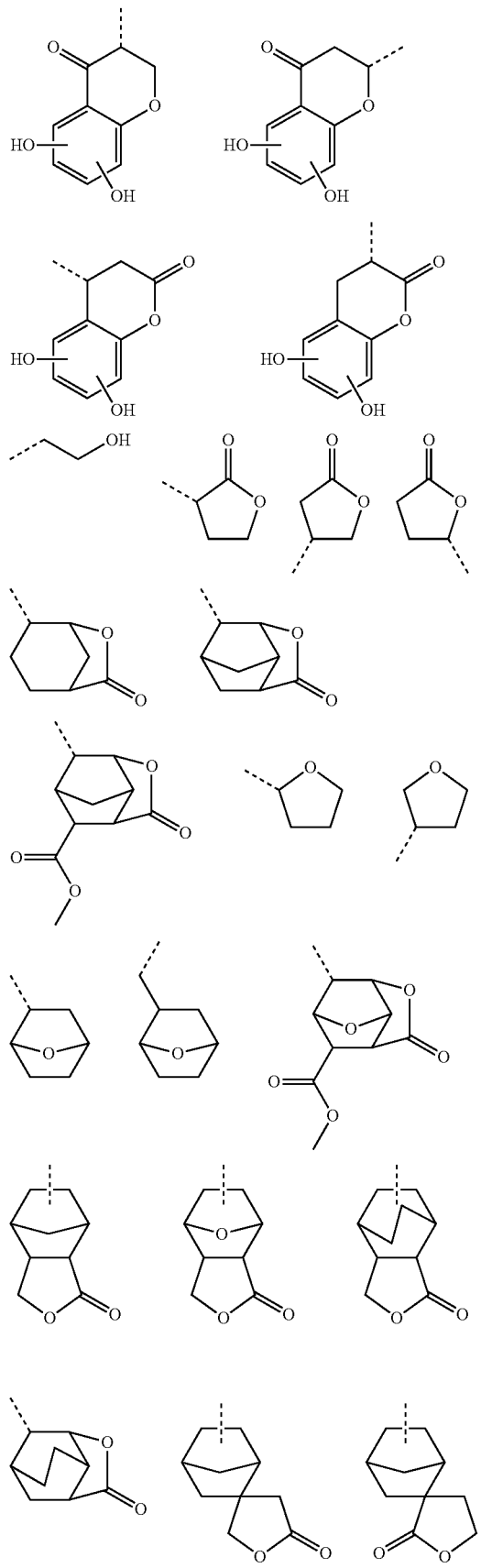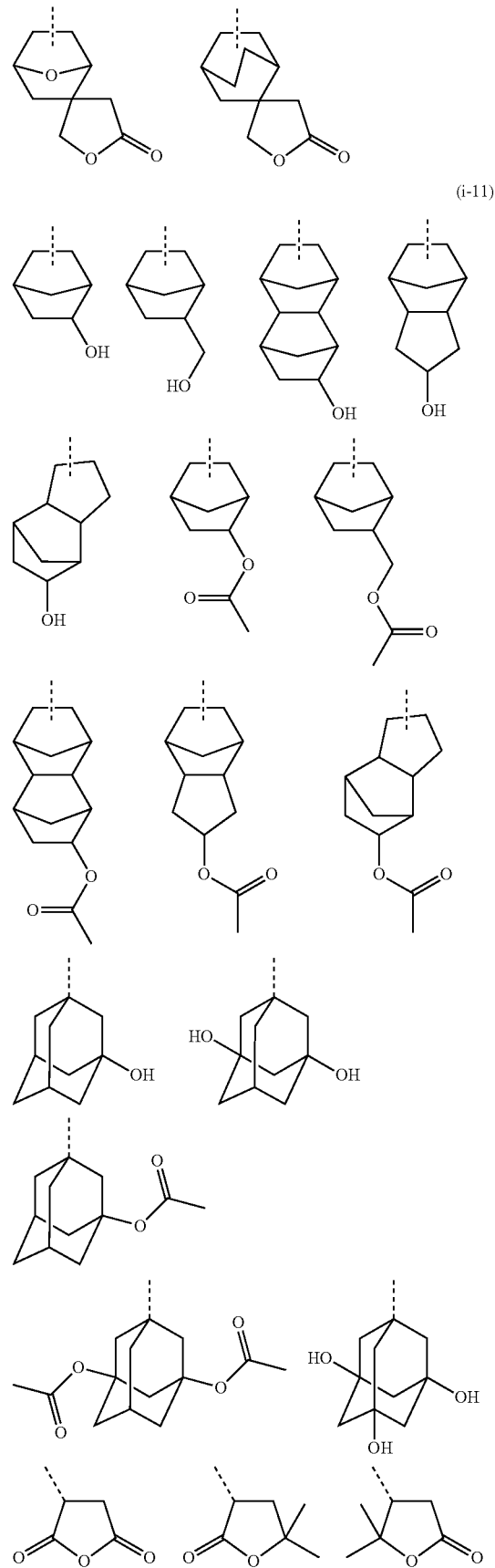
(i-11)

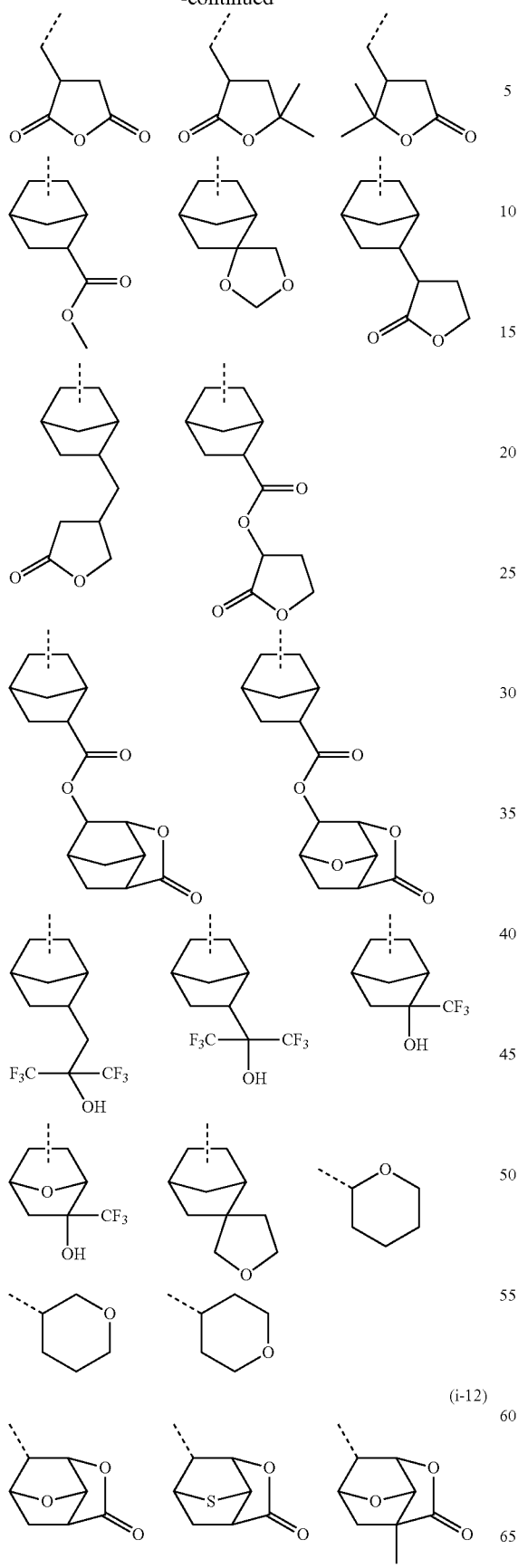
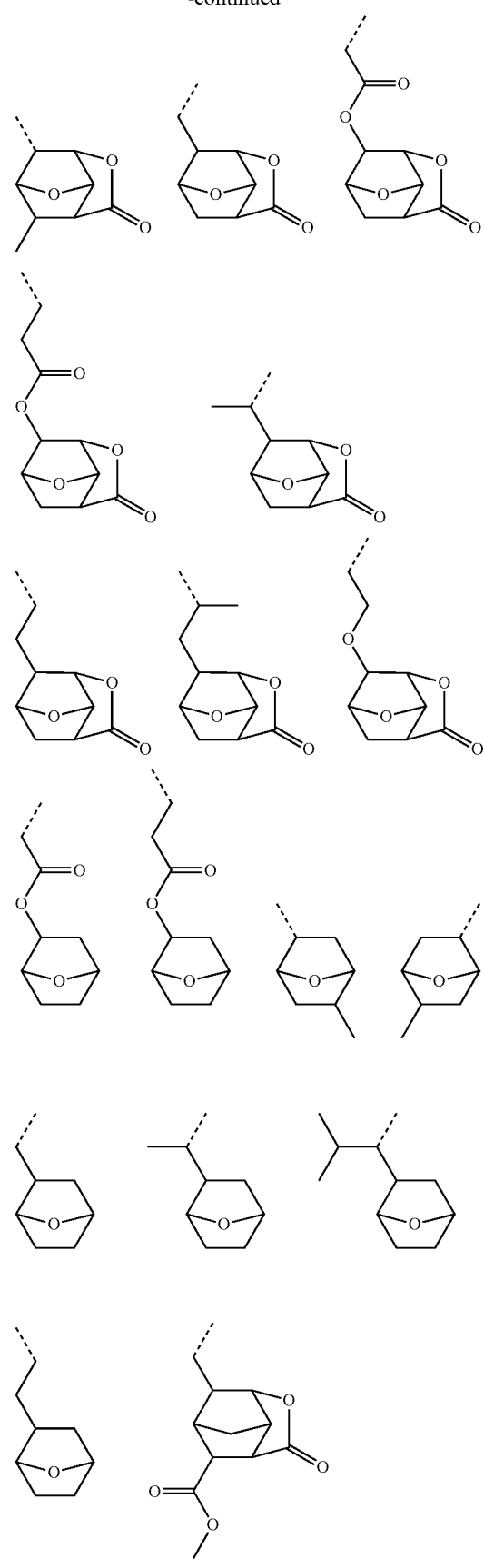

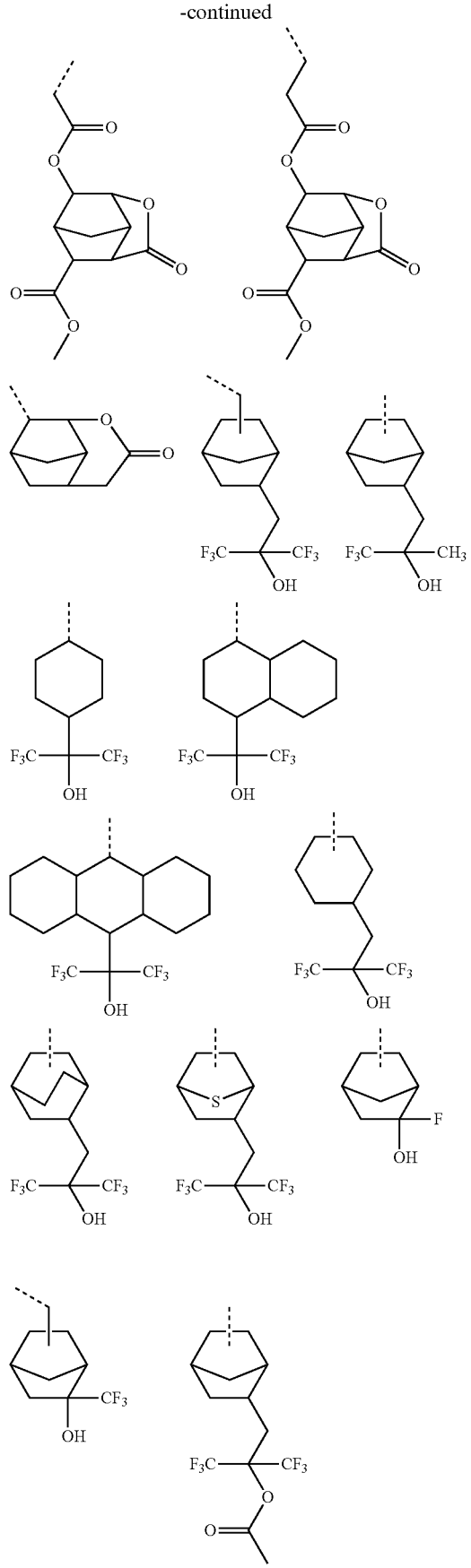
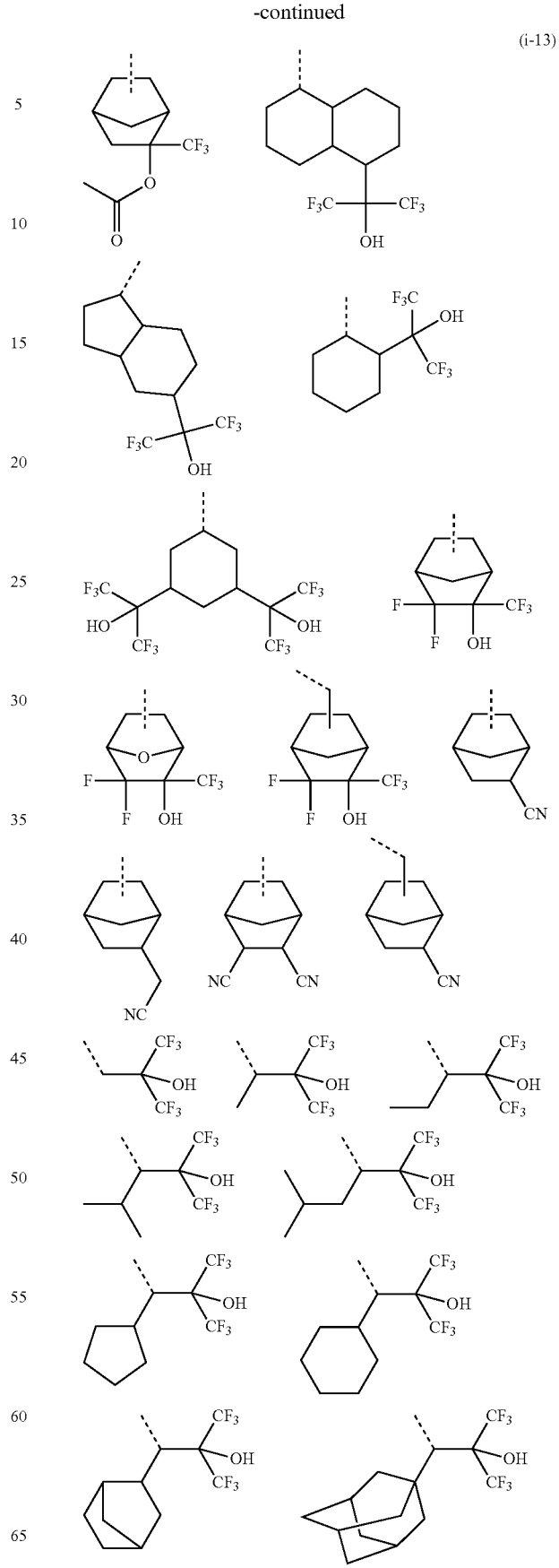
(i-13)

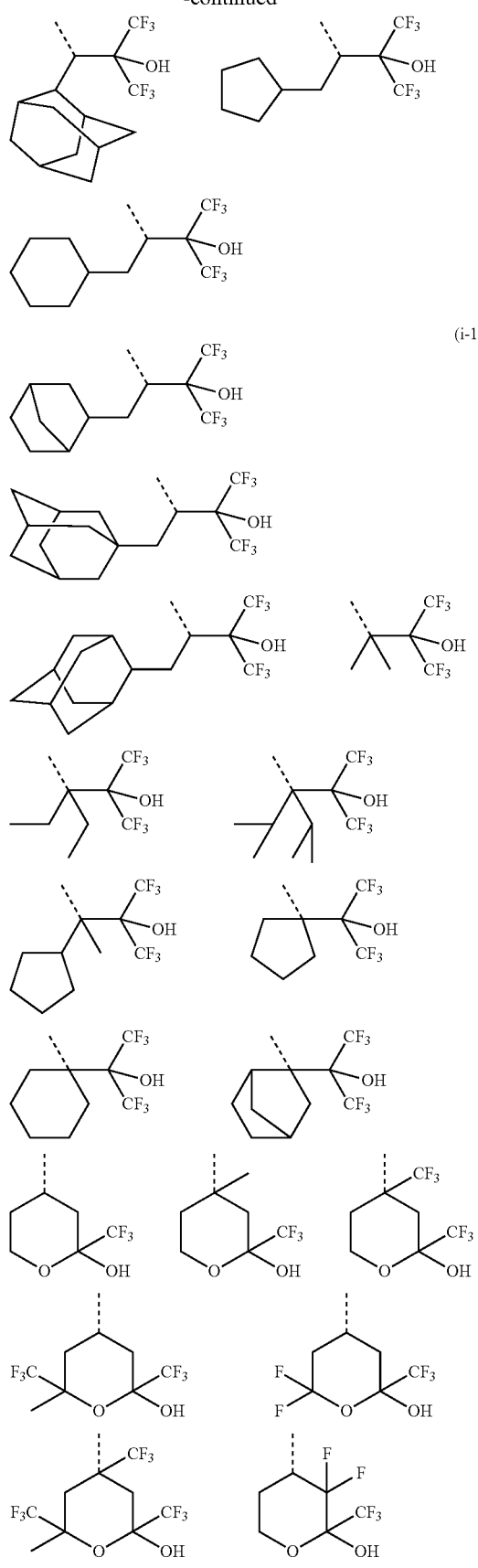
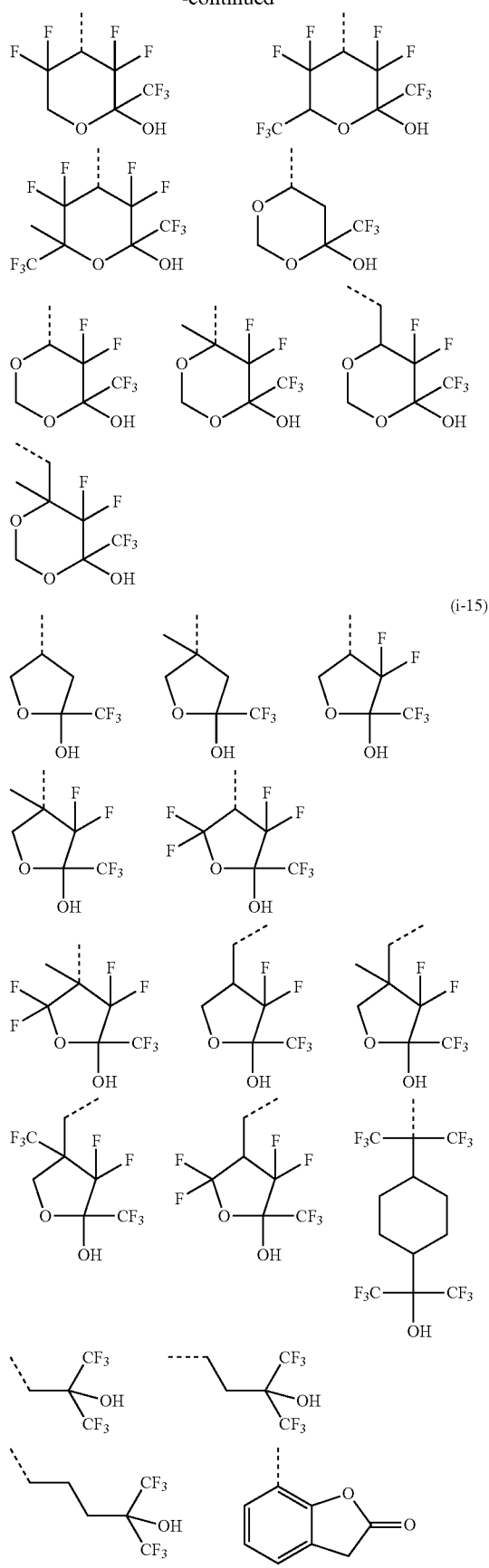
(i-14)
(i-15)

-continued

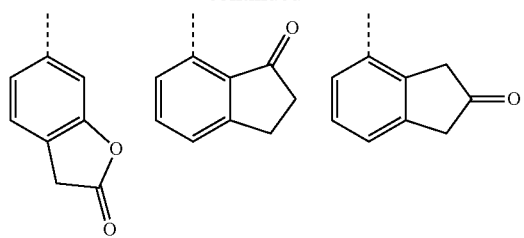
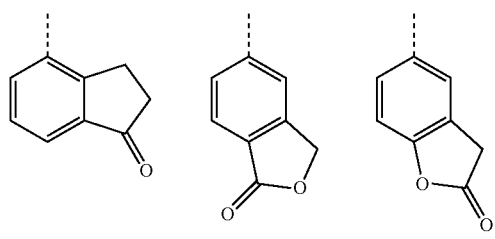
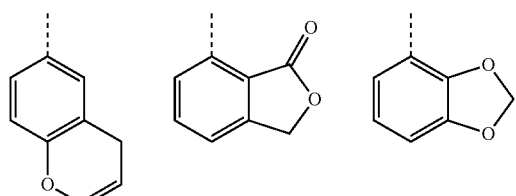
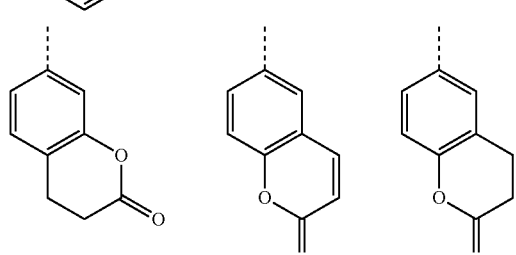
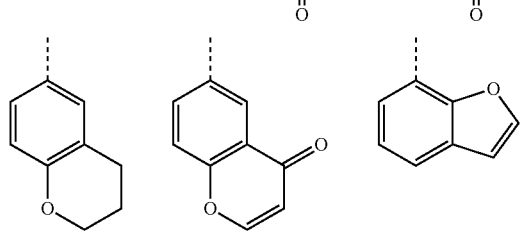
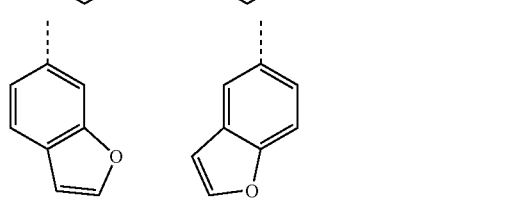
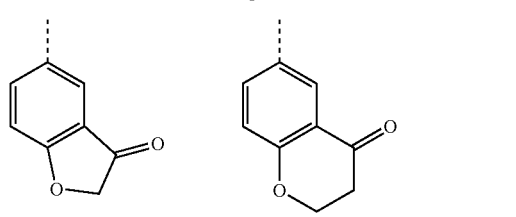

-continued

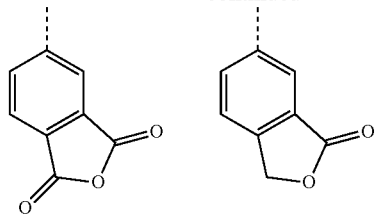
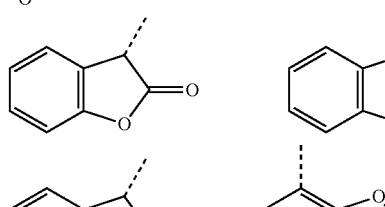
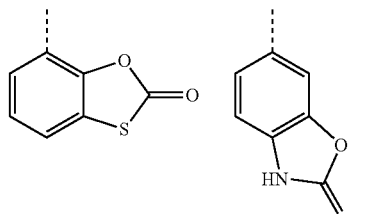
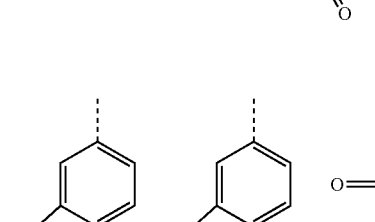

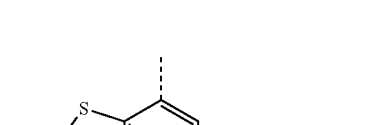      ----H      ----CH₃

----CCH₂H₃    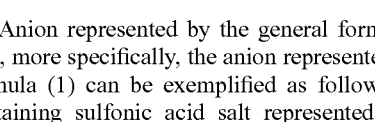    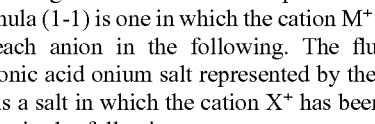

<Anion represented by the general formula (1)> Therefore, more specifically, the anion represented by the general formula (1) can be exemplified as follows. The fluorine-containing sulfonic acid salt represented by the general formula (1-1) is one in which the cation M⁺ has been bonded to each anion in the following. The fluorine-containing sulfonic acid onium salt represented by the general formula (2) is a salt in which the cation X⁺ has been bonded to each anion in the following.

(i-16)
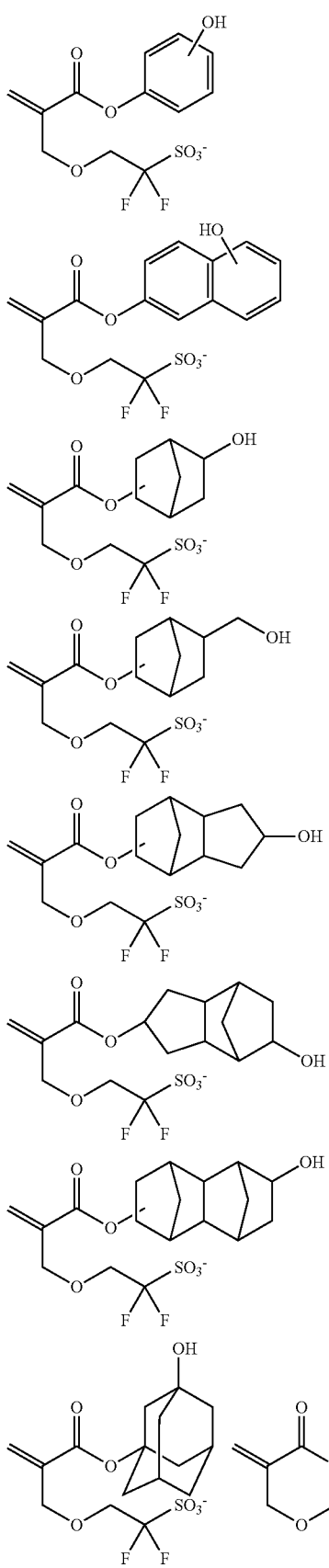
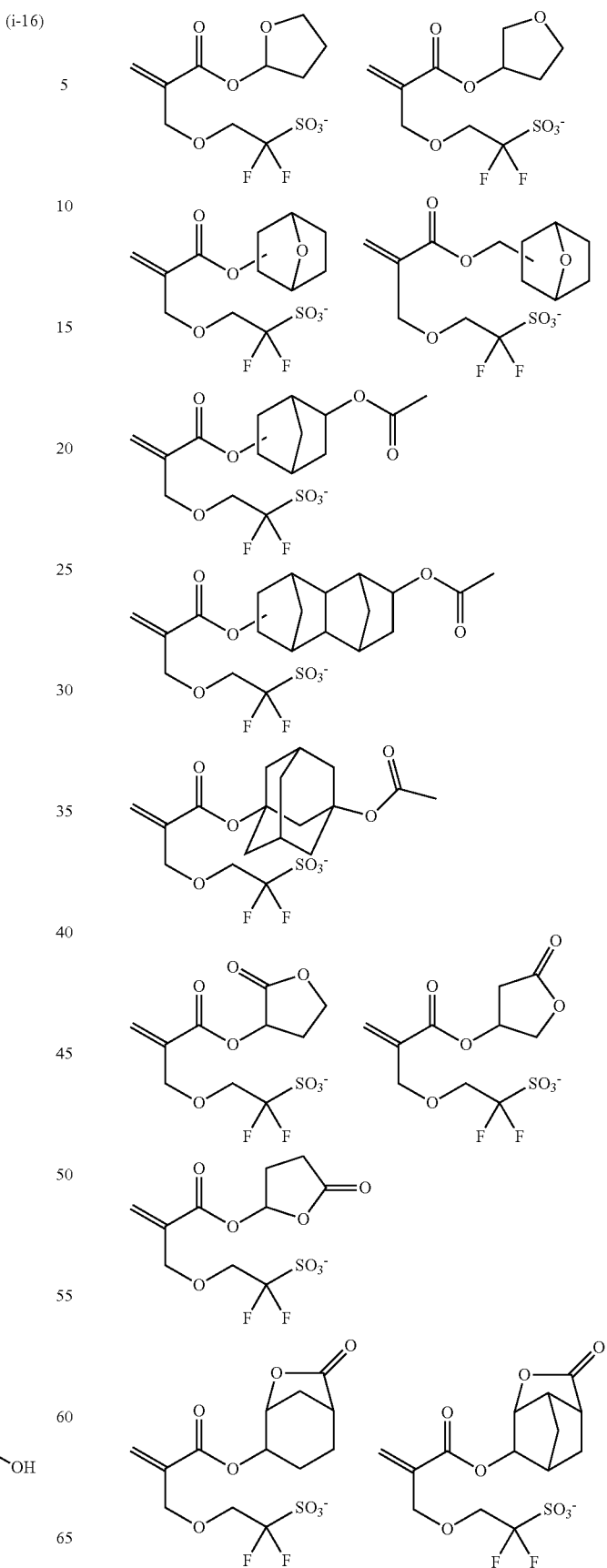

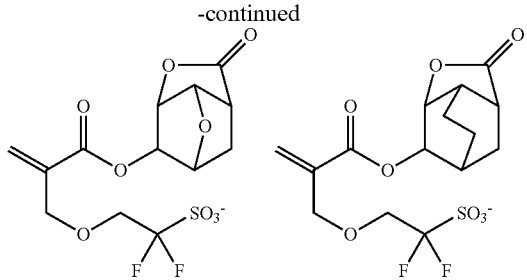
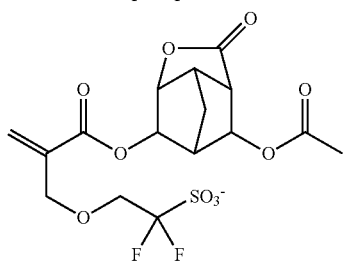
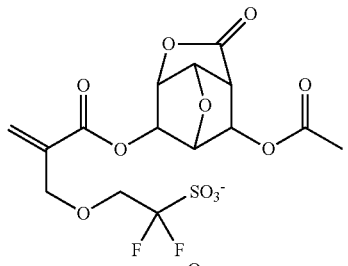
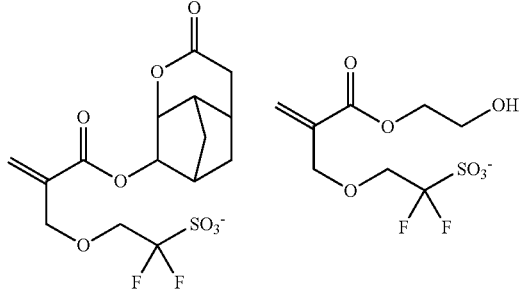
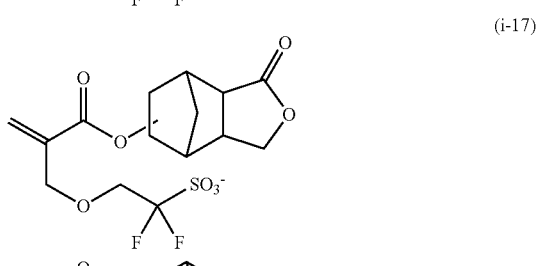
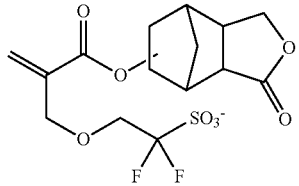
(i-17)
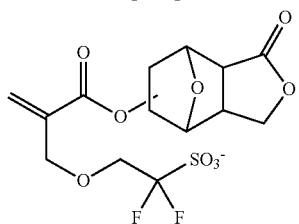
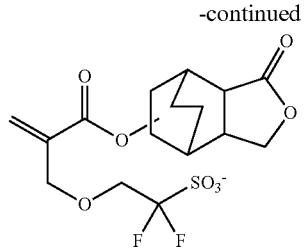
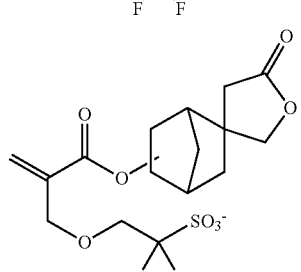
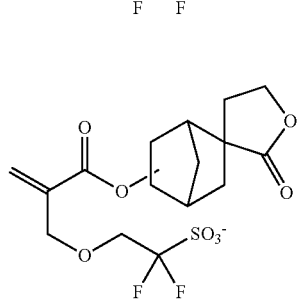
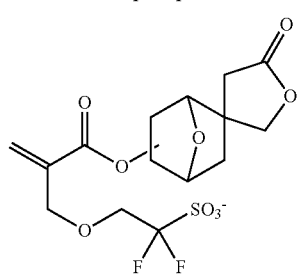
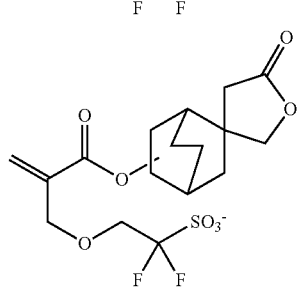
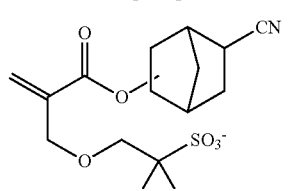
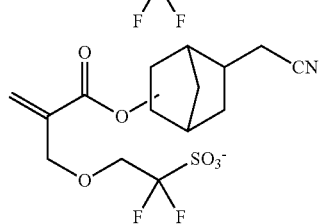

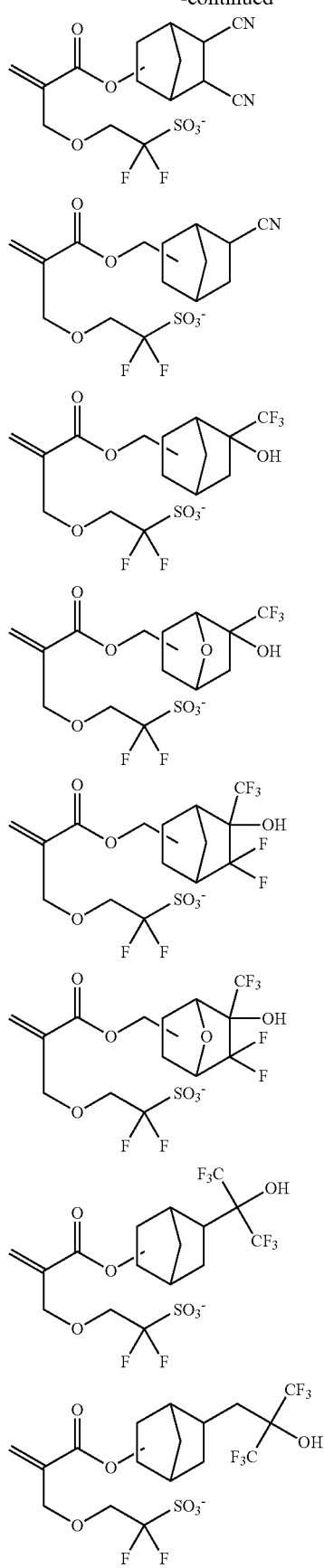
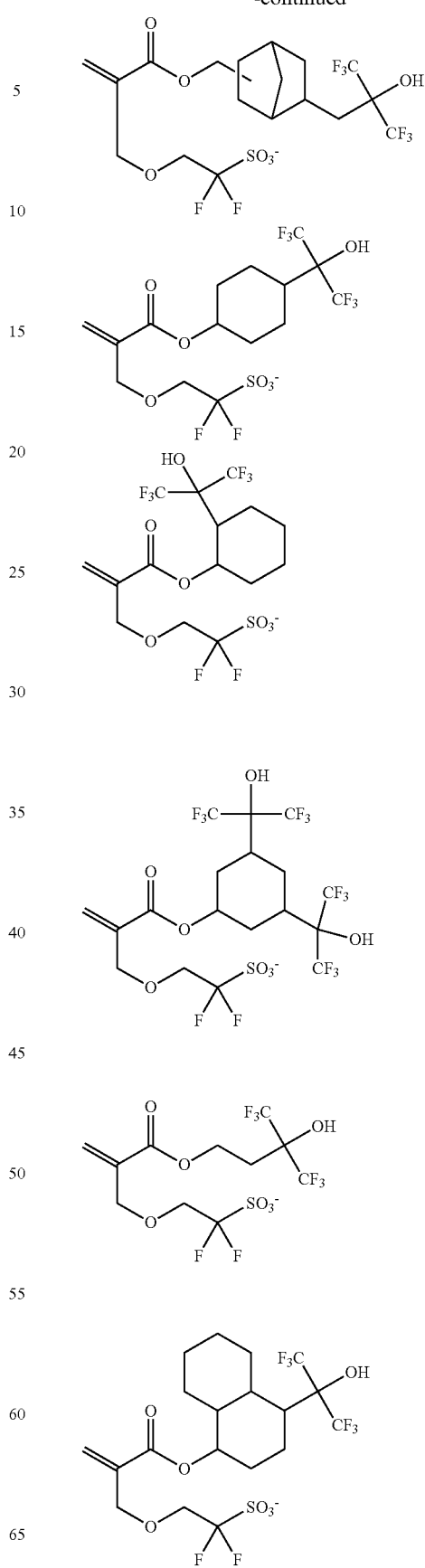

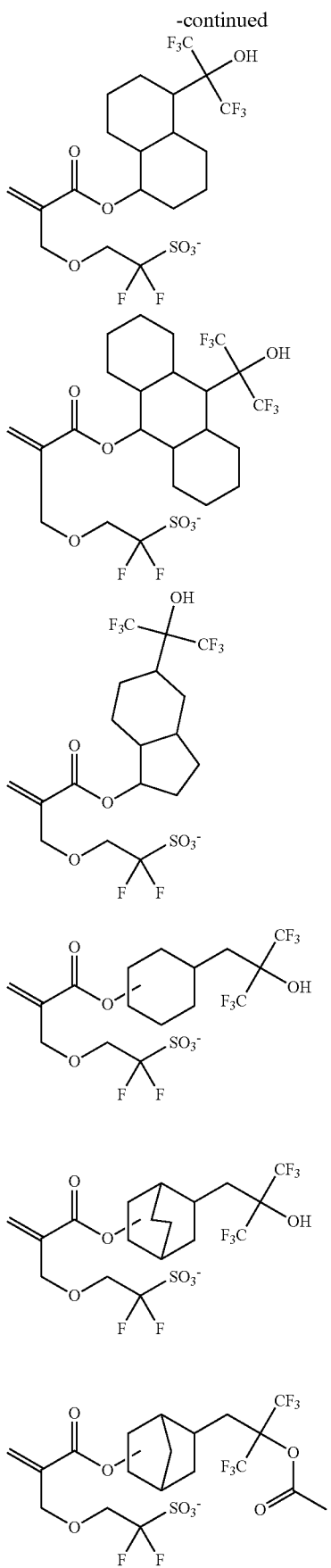
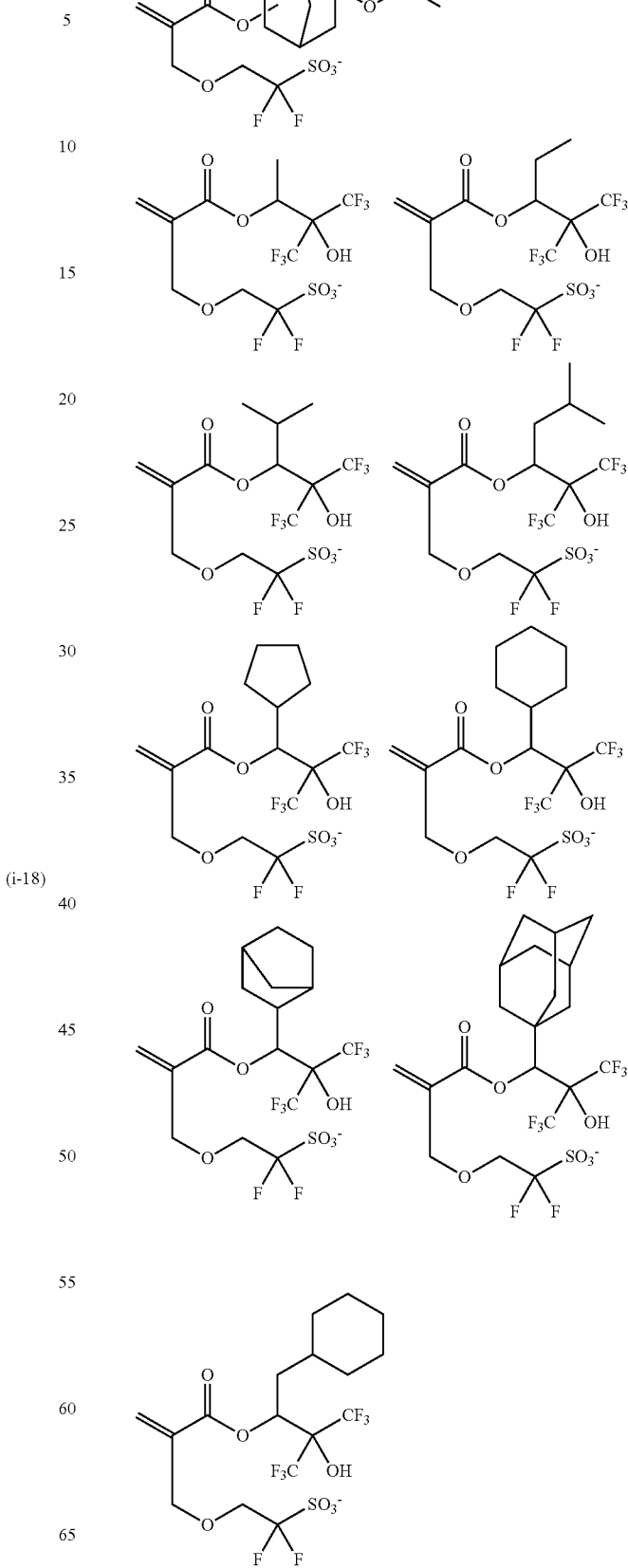
(i-18)

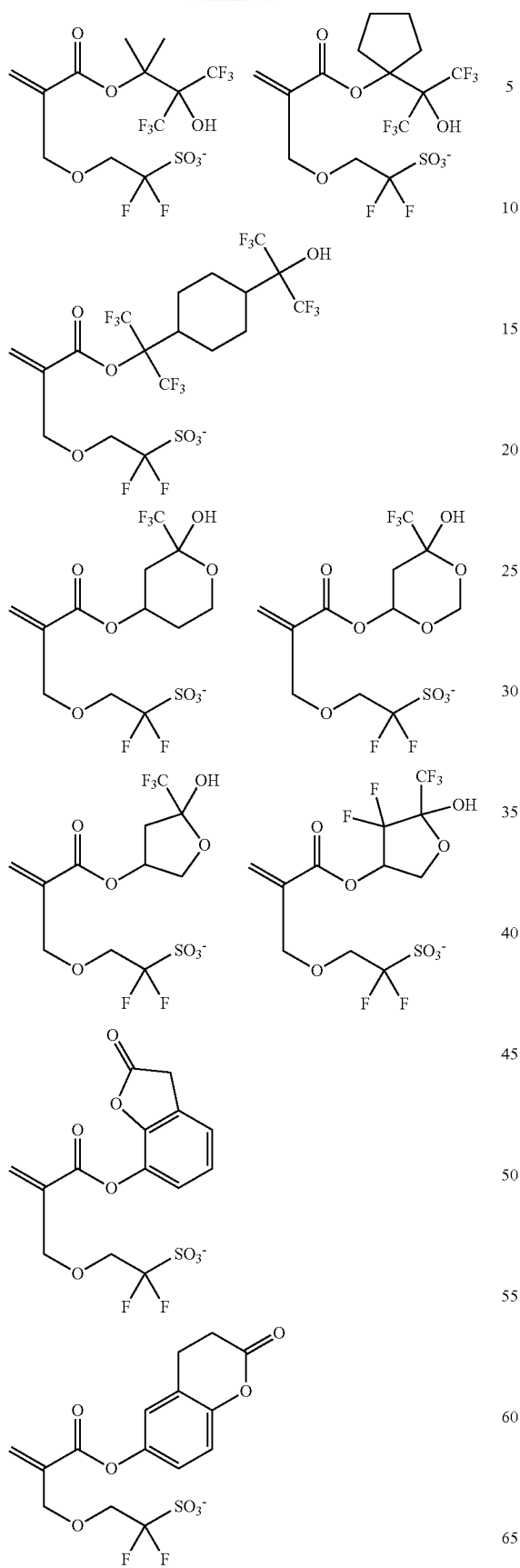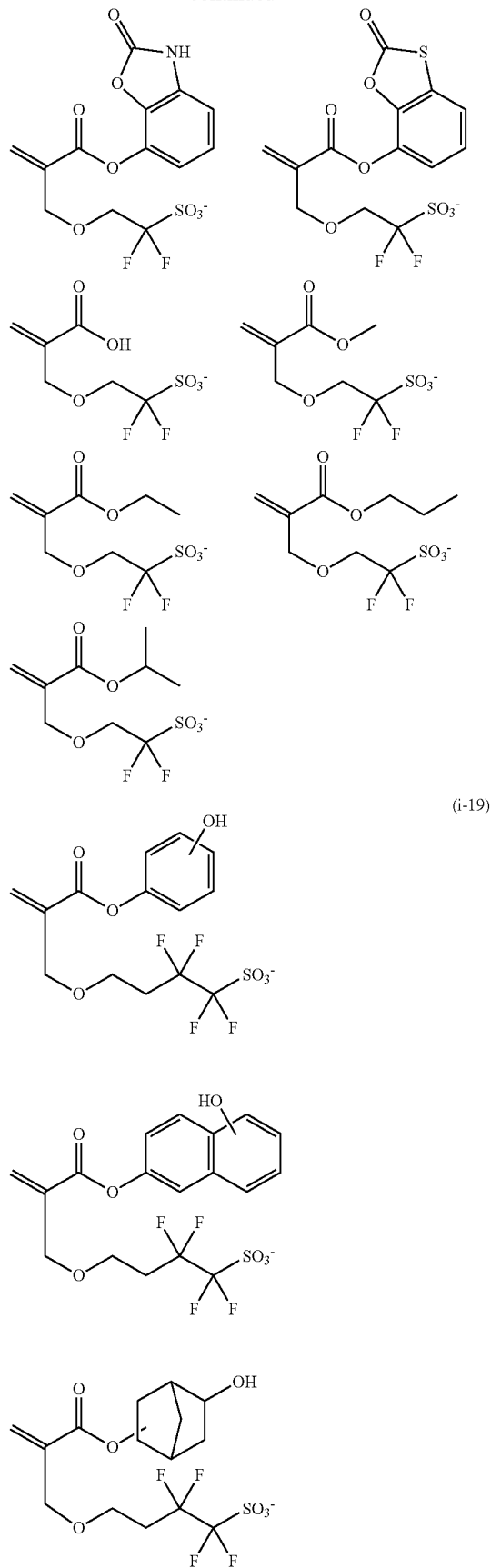
(i-19)

49
-continued
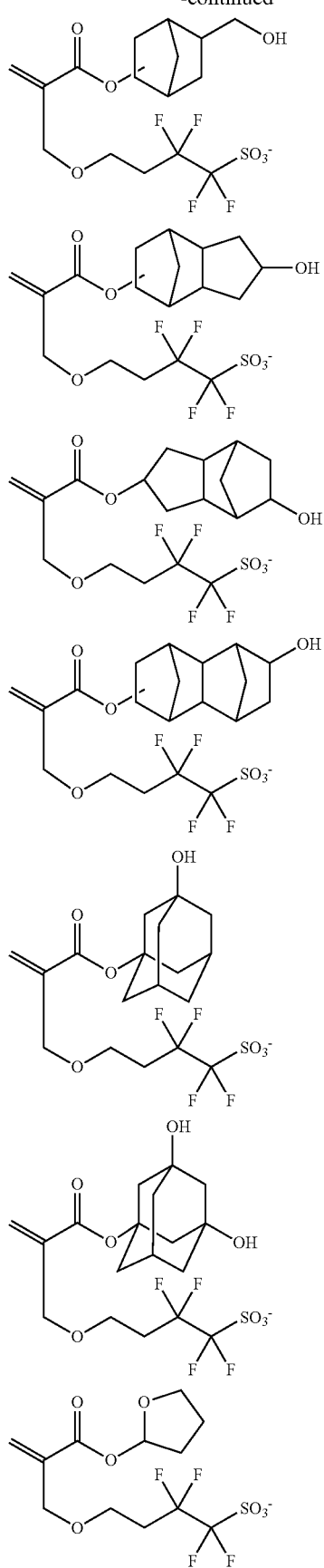
50
-continued
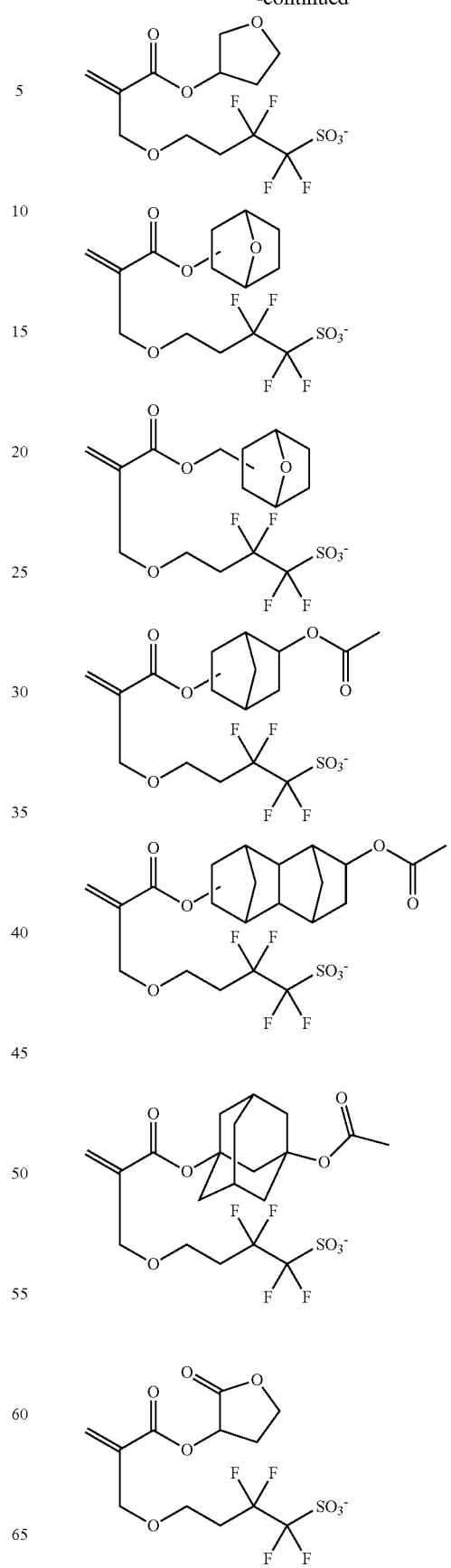

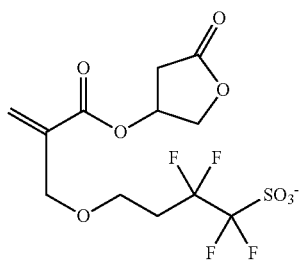
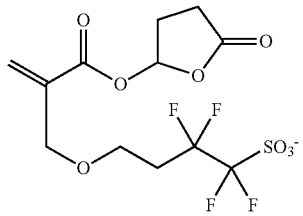
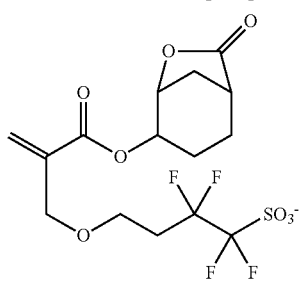
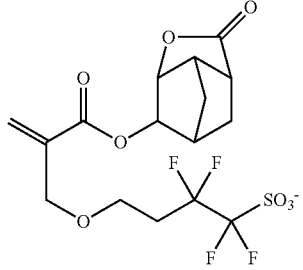
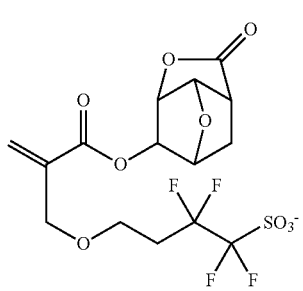
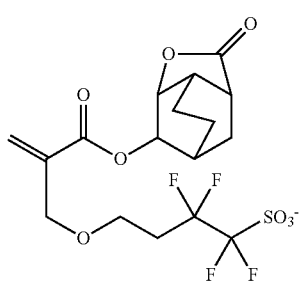
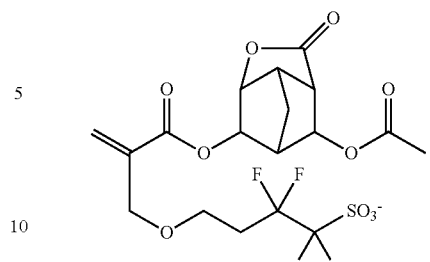
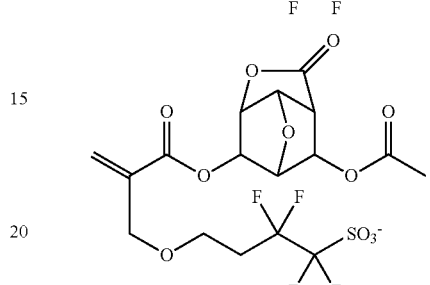
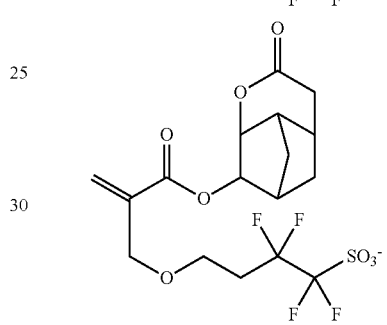
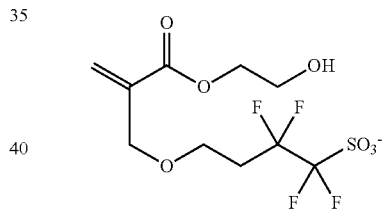
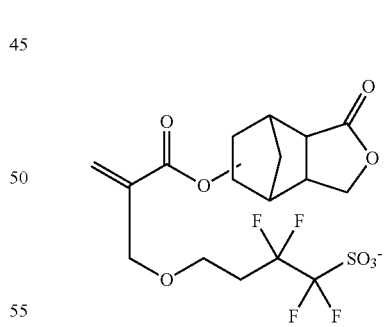
(i-20)
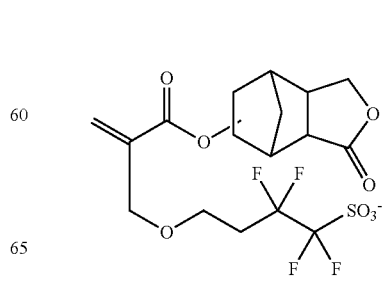

53
-continued
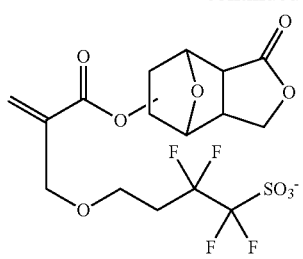
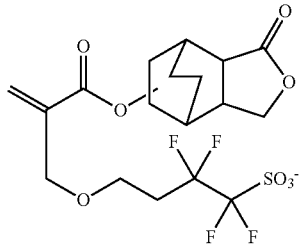
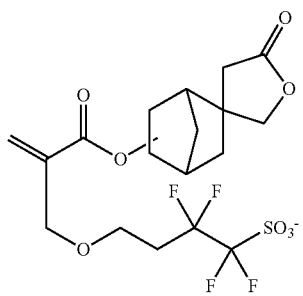
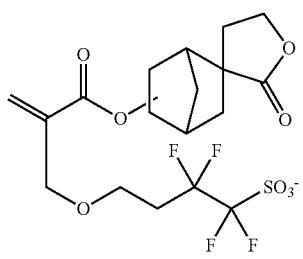
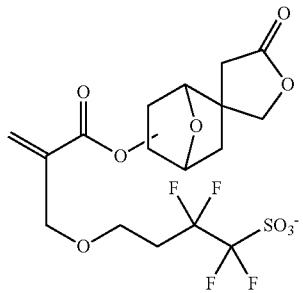
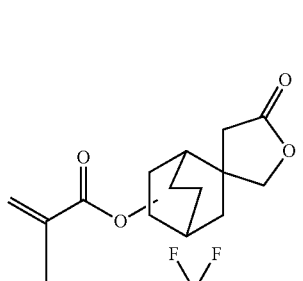
54
-continued
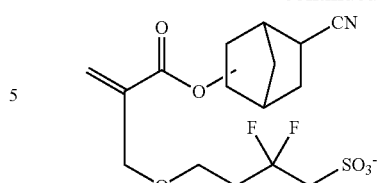
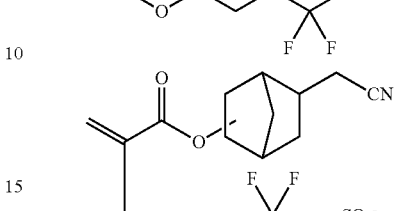
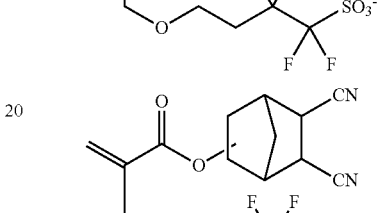
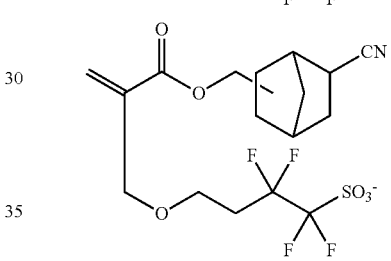
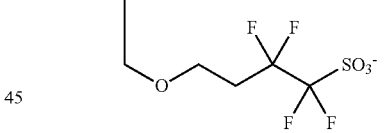
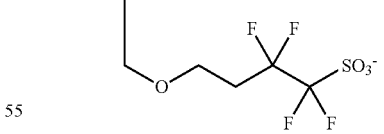
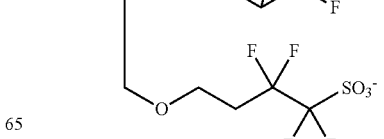

-continued
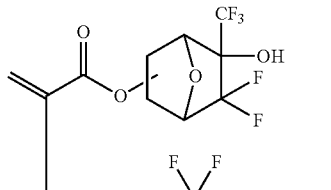
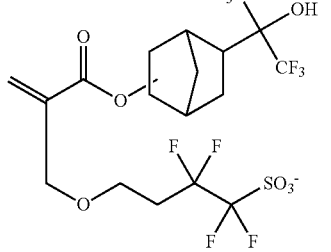
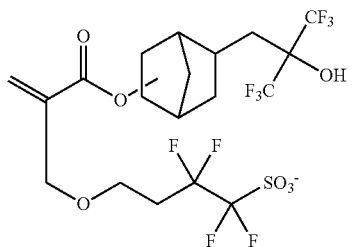
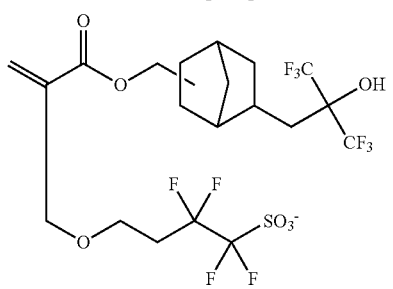
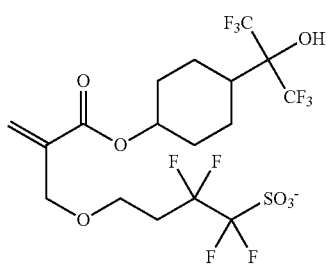
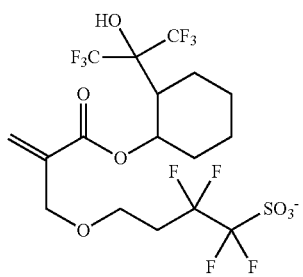
-continued
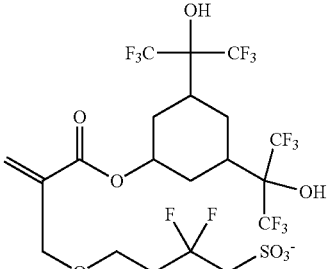
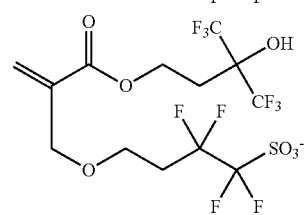
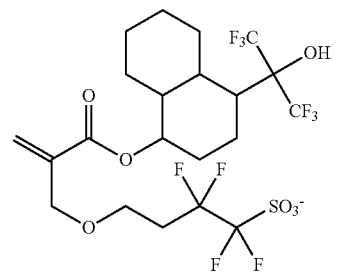
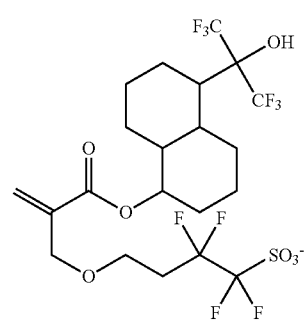
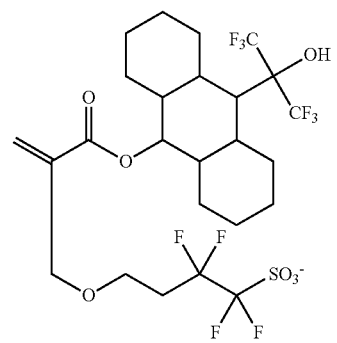

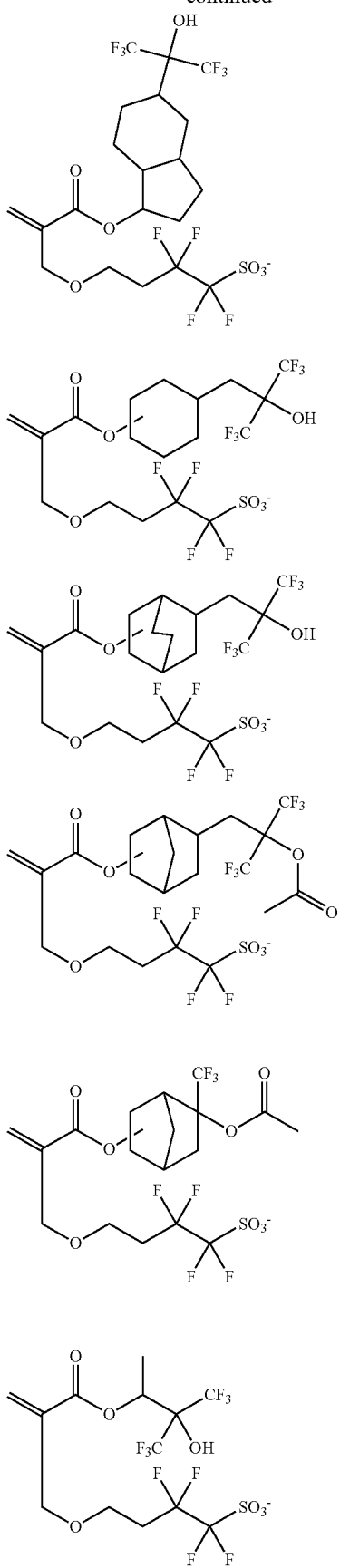
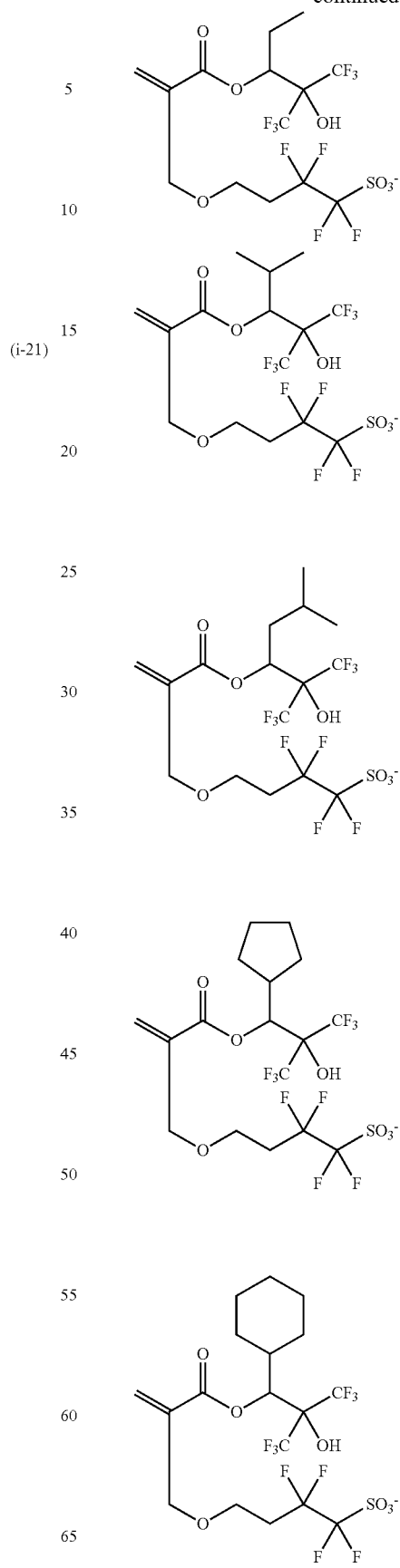
(i-21)

59
-continued
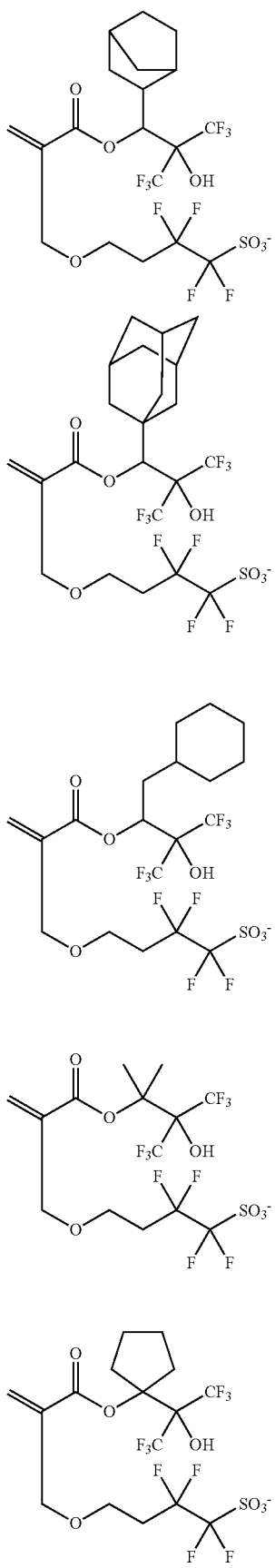
60
-continued
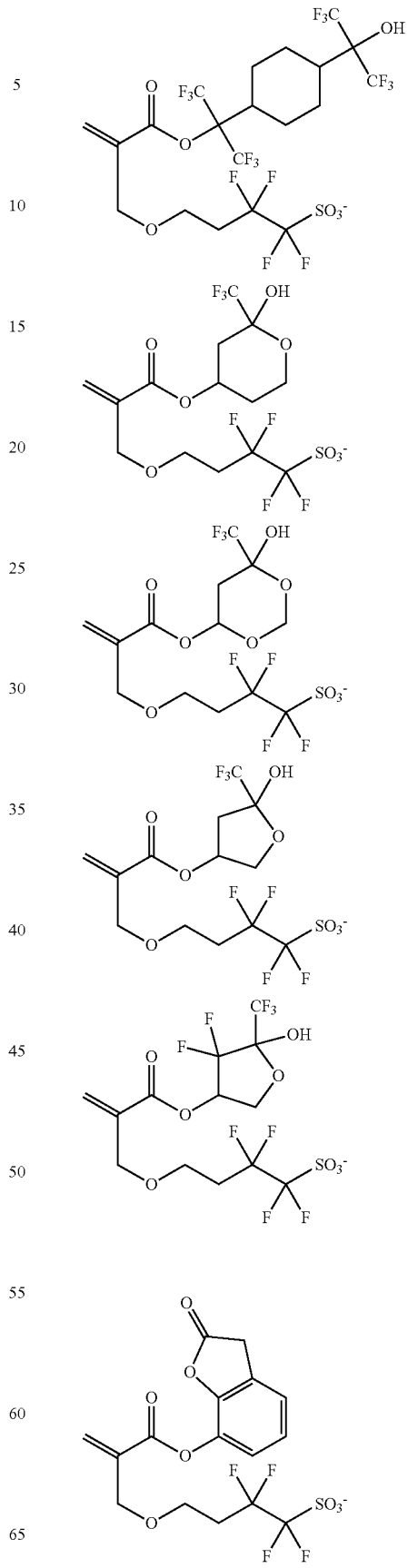

-continued
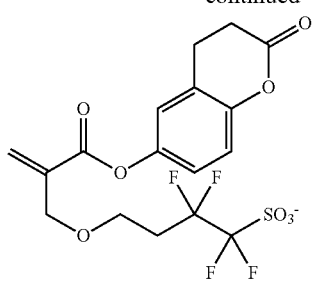
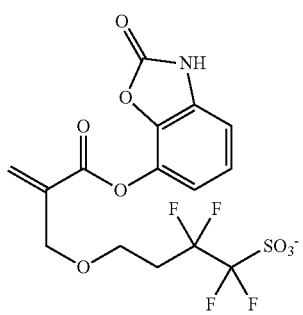
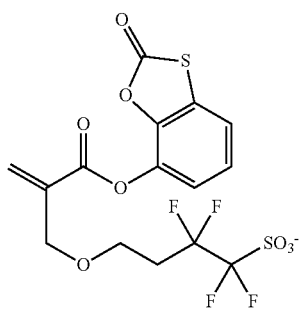
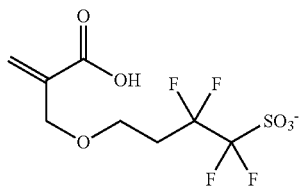
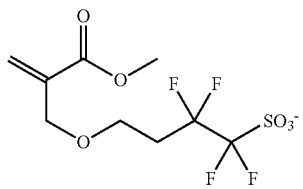
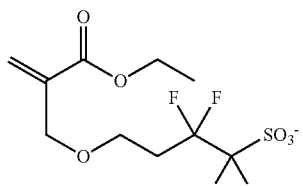
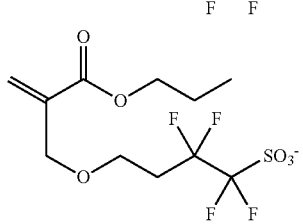
-continued
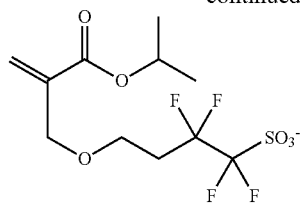
(i-22)
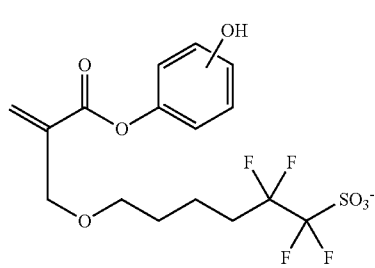
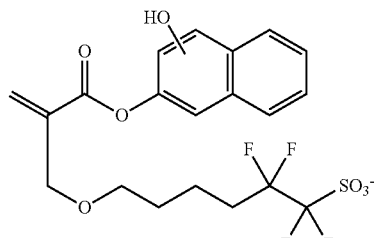
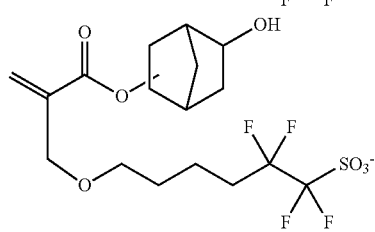
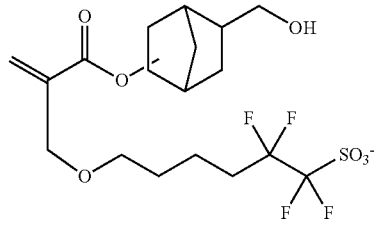
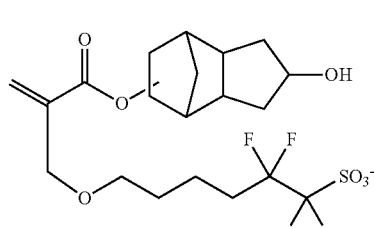
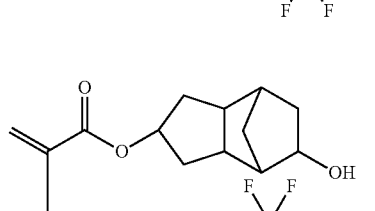

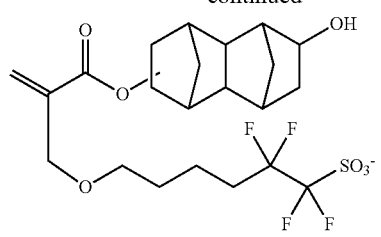
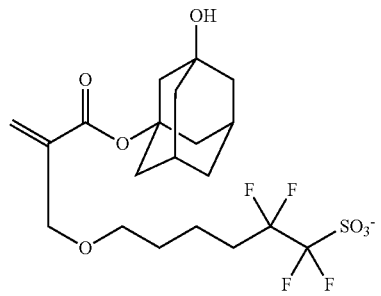
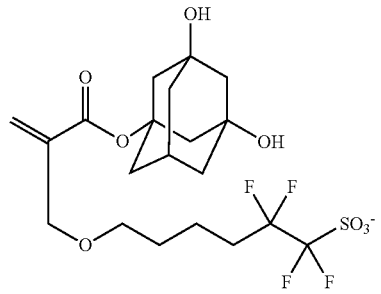
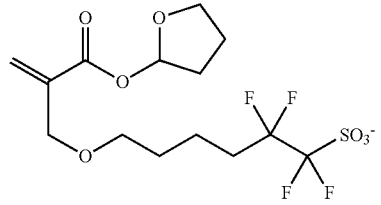
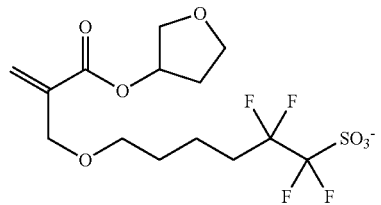
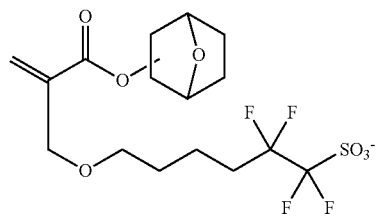
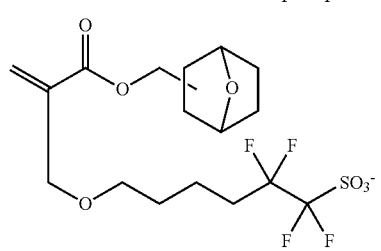
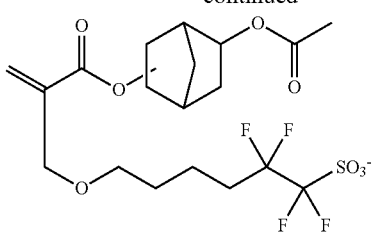
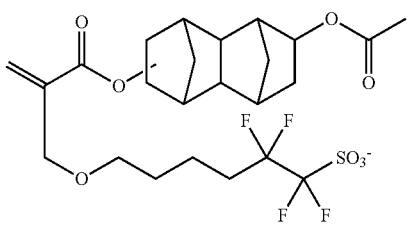
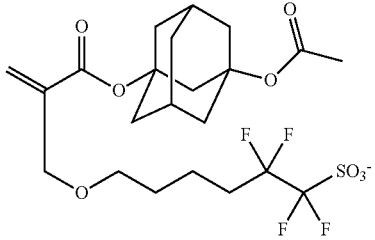
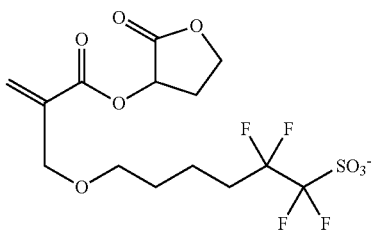
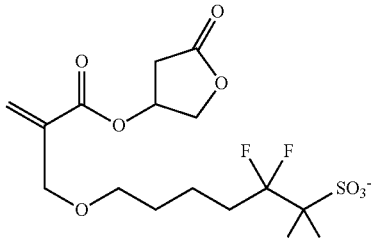
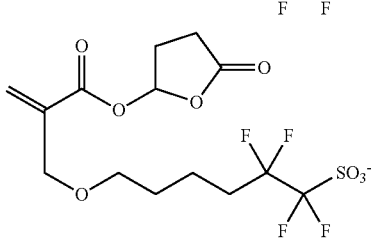
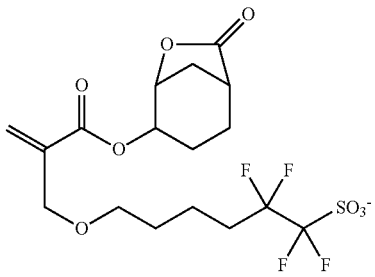

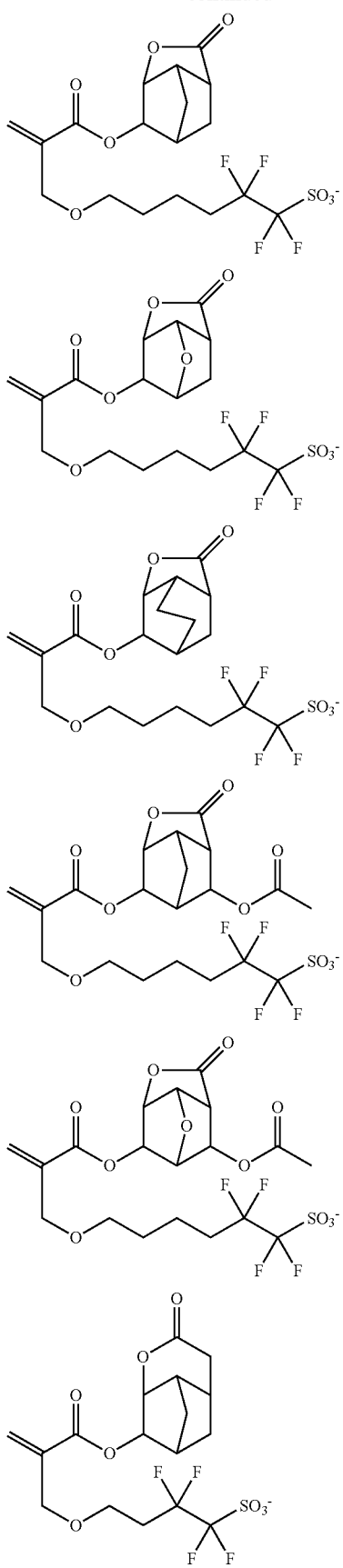
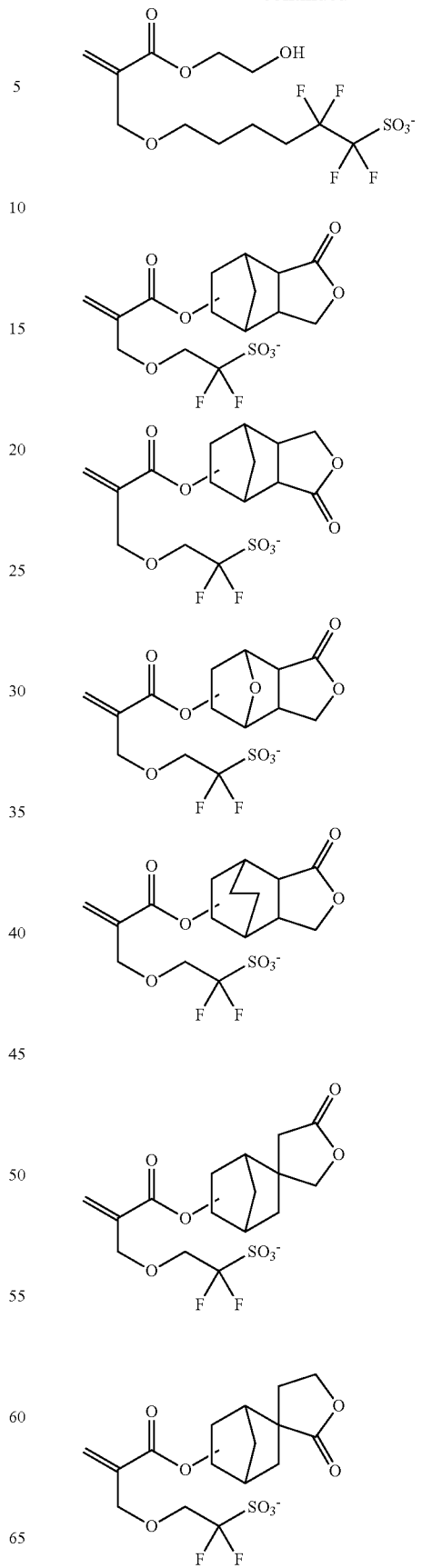
(i-23)

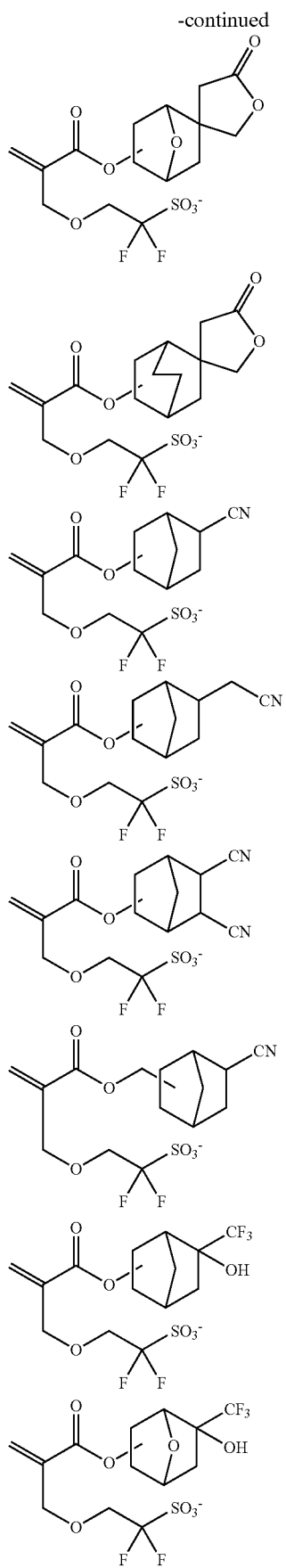
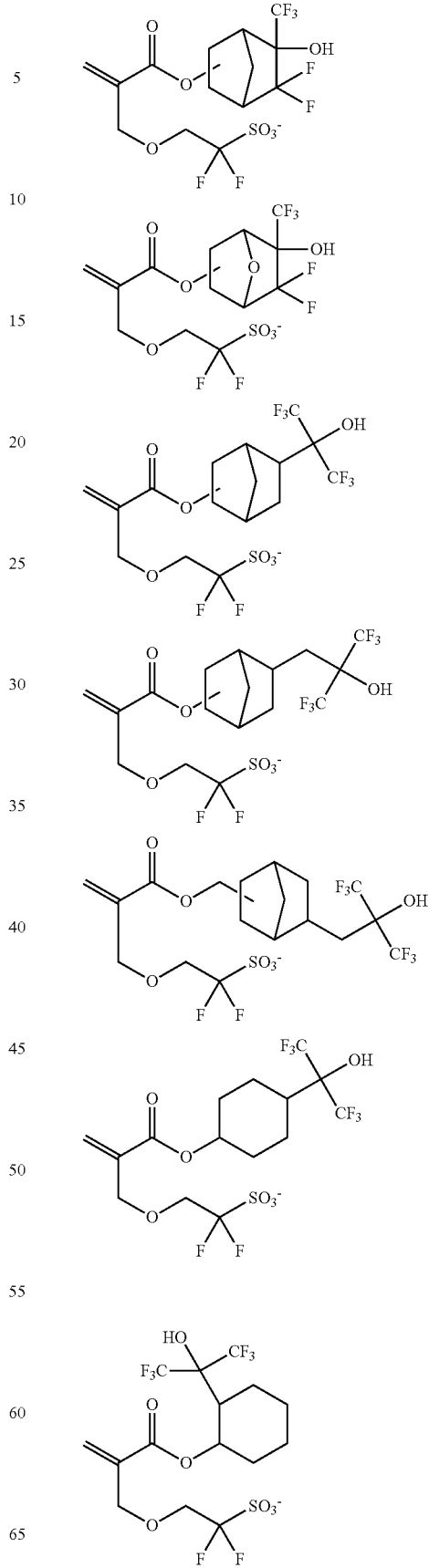

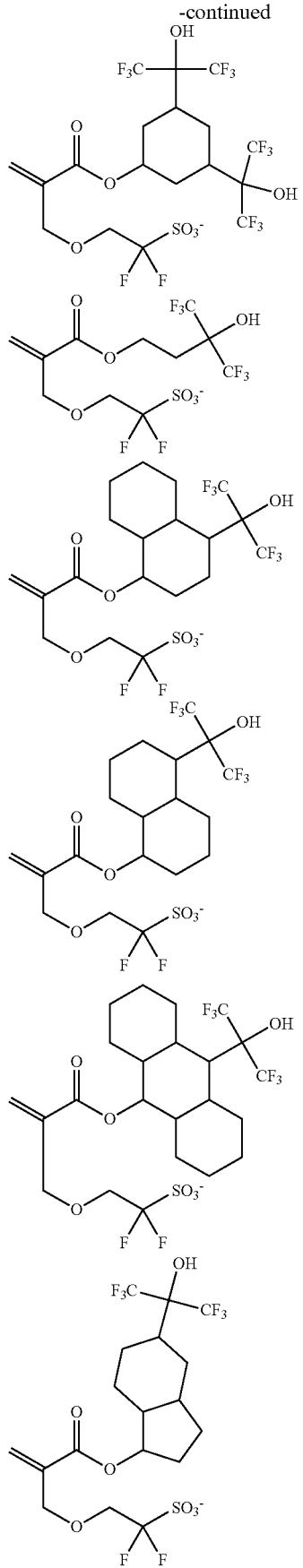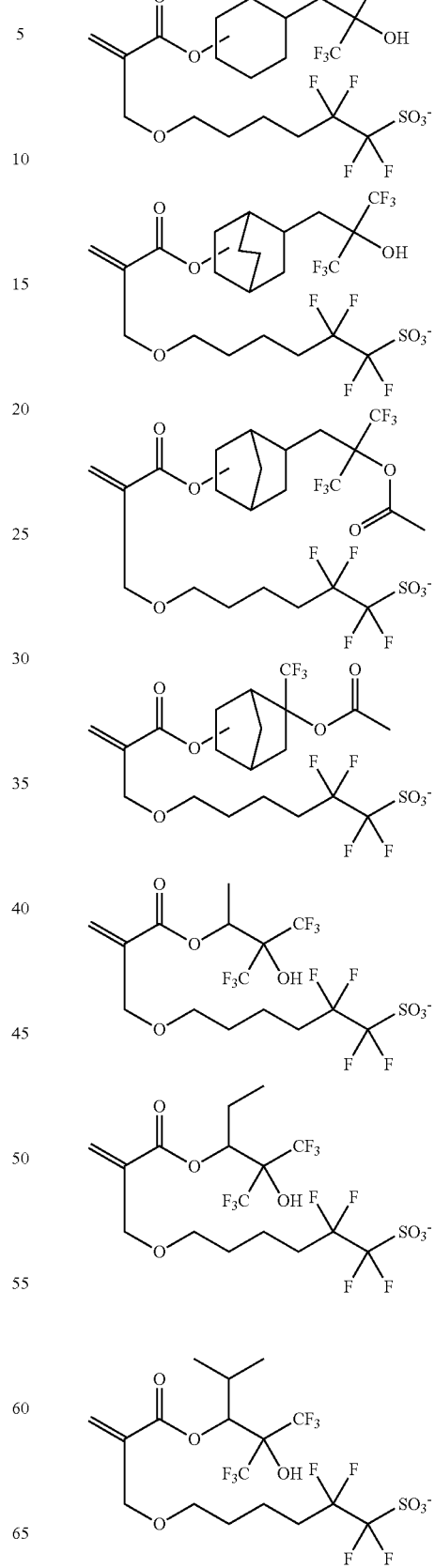
(i-24)

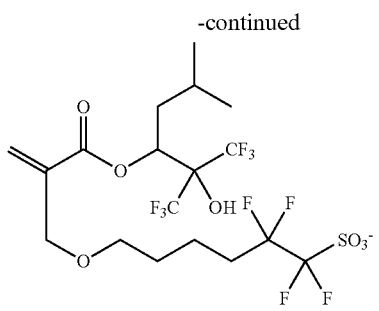
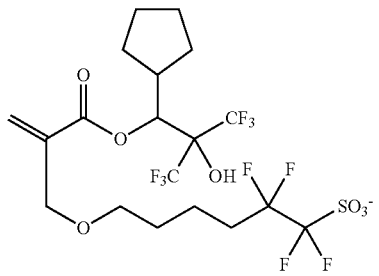
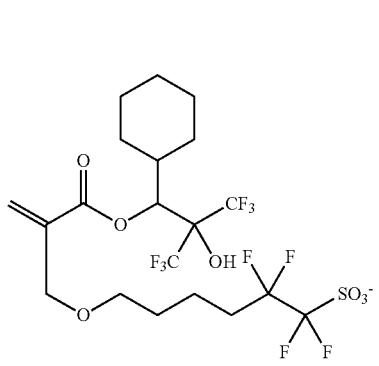
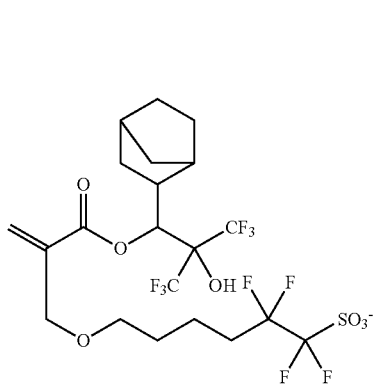
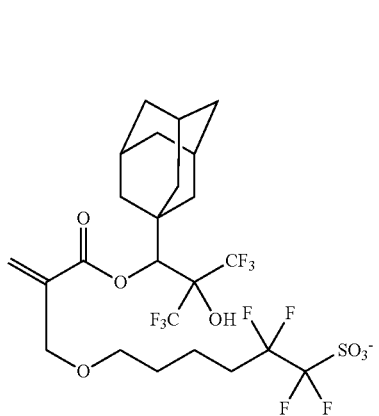
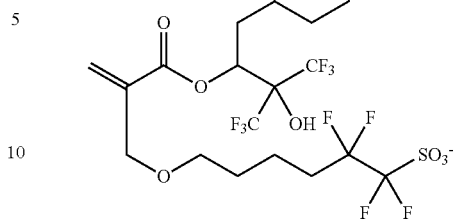
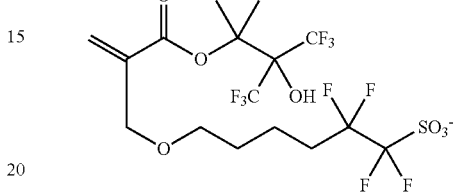
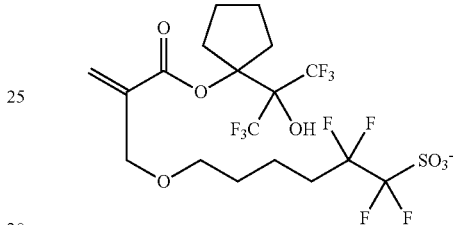
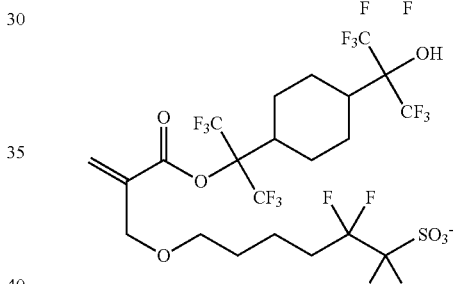
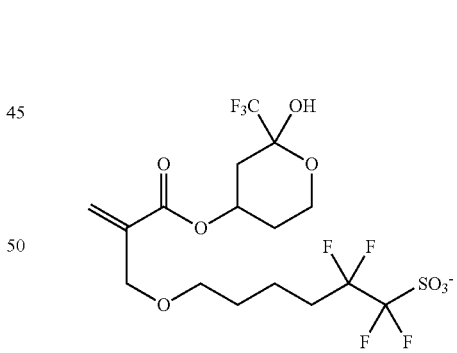
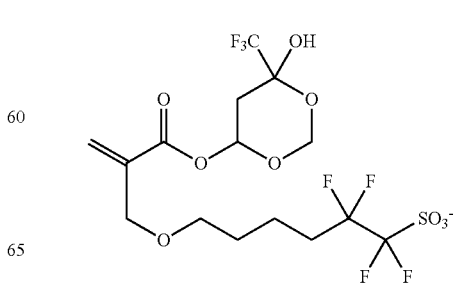

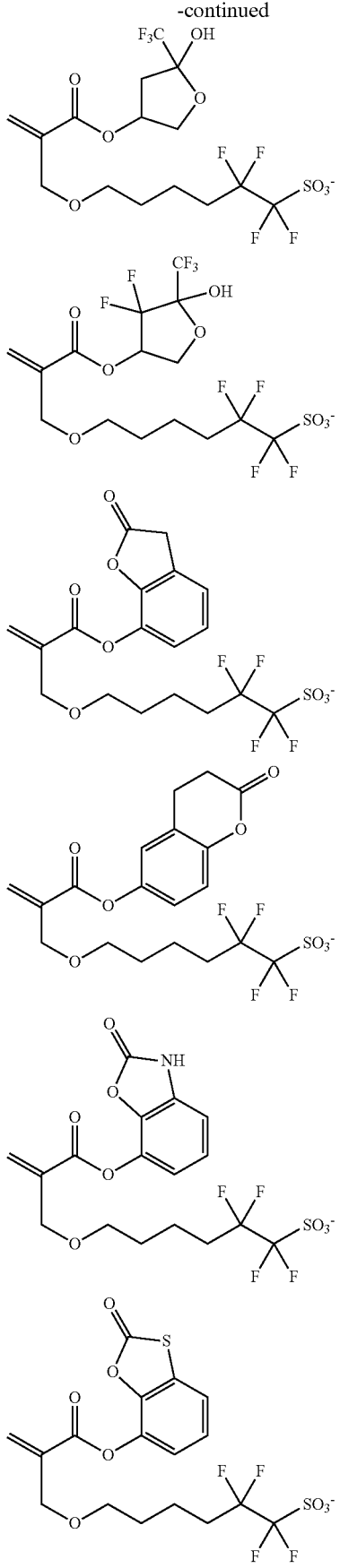

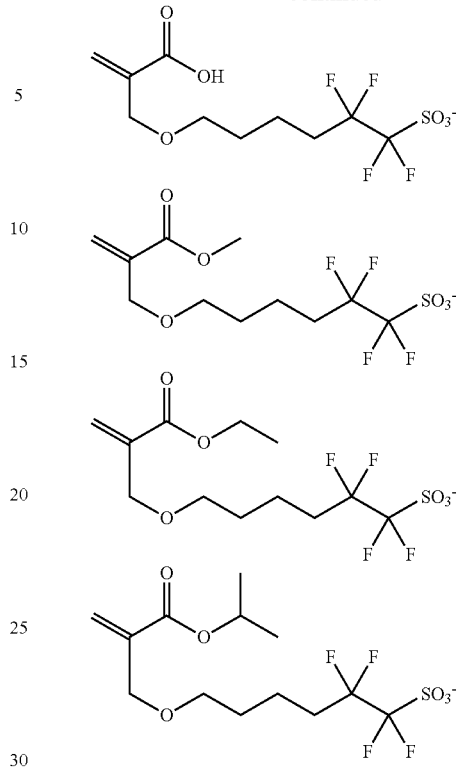

[Polymerizable, fluorine-containing, sulfonic acid onium salt] As a polymerizable fluorine-containing sulfonic acid salt having an anion represented by the general formula (1) of the present invention, it is possible to cite a polymerizable fluorine-containing sulfonic acid onium salt represented by the following general formula (2) as a preferable example.

This polymerizable fluorine-containing sulfonic acid onium salt in the form of monomer as it is or a resin obtained by its homopolymerization or copolymerization is capable of generating a fluorine-containing sulfonic acid, which is very large in acid strength, by reacting to electromagnetic waves, such as near-ultraviolet rays, far-ultraviolet rays, extreme ultraviolet rays (EUV), soft X-rays, X-rays and prays, which are generated by excimer laser and synchrotron radiation, and high energy rays such as charged particle beams such as electron beam. Therefore, the polymerizable fluorine-containing sulfonic acid onium salt or a resin obtained therefrom functions as a photoacid generator.

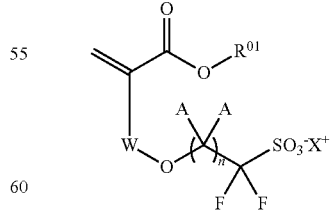

(2)

(In the formula, A, n, W and $R^{01}$ are respectively defined as those in the above-mentioned general formula (1). $X^+$ represents a sulfonium cation represented by the following general formula (CA-a) or an iodonium cation represented by the following general formula (CA-b).)

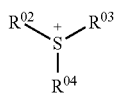
(CA-a)

(In the formula, $R^{02}$, $R^{03}$ and $R^{04}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or any two or more of $R^{02}$, $R^{03}$ and $R^{04}$ may be connected with each other to form a ring together with the sulfur atom in the formula. The alkenyl groups take a carbon number of 2 or more.)

(CA-b)

(In the formula, $R^{05}$ and $R^{06}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or $R^{05}$ and $R^{06}$ may be connected with each other to form a ring together with the iodine atom in the formula. The alkenyl groups take a carbon number of 2 or more.) Herein, the specific structure of $X^+$ is exemplified. In the following, the sulfonium cation represented by the general formula (CA-a) and the iodonium cation represented by the general formula (CA-b) are described in detail.

<Sulfonium cation represented by the general formula (CA-a)> As $R^{02}$, $R^{03}$ and $R^{04}$ in the general formula (CA-a), specifically, it is possible to cite the following ones. The substituted or unsubstituted $C_{1-20}$ alkyl group may be a straight-chain, branched or cyclic alkyl group and may have a substituent(s). It is possible to cite, for example, methyl group, ethyl group, n-propyl group, isopropyl group, cyclopropyl group, n-butyl group, sec-butyl group, isobutyl group, tert-butyl group, n-pentyl group, cyclopentyl group, n-hexyl group, n-heptyl group, 2-ethylhexyl group, cyclohexyl group, cycloheptyl group, 4-methylcyclohexyl group, cyclohexylmethyl group, n-octyl group, n-decyl group, 1-adamantyl group, 2-adamantyl group, bicyclo[2.2.1]hepten-2-yl group, 1-adamantanemethyl group, 2-adamantanemethyl group, etc.

The substituted or unsubstituted alkenyl group takes a $C_{2-20}$ straight-chain, branched or cyclic structure and may have a substituent(s). For example, it is possible to cite vinyl group, allyl group, propenyl group, butenyl group, hexenyl group, cyclohexenyl group, etc.

The substituted or unsubstituted $C_{1-20}$ oxoalkyl group may be a straight-chain, branched or cyclic oxoalkyl group and may have a substituent(s). It is possible to cite, for example, 2-oxocyclopentyl group, 2-oxocyclohexyl group, 2-oxopropyl group, 2-oxoethyl group, 2-cyclopentyl-2-oxoethyl group, 2-cyclohexyl-2-oxoethyl group, 2-(4-methylcyclohexyl)-2-oxoethyl group, etc.

As the substituted or unsubstituted $C_{6-18}$ aryl group, it is possible to cite phenyl group, naphthyl group, thienyl group, etc.; alkoxyphenyl groups such as p-methoxyphenyl group, m-methoxyphenyl group, o-methoxyphenyl group, p-ethoxyphenyl group, p-tert-butoxyphenyl group, m-tert-butoxyphenyl group, etc.; alkylphenyl groups such as 2-methylphenyl group, 3-methylphenyl group, 4-methylphenyl group, ethylphenyl group, etc.; alkylnaphthyl groups such as methylnaphthyl group, ethylnaphthyl group, etc.; dialkylnaphthyl groups such as diethylnaphthyl group, etc.; dialkoxynaphthyl groups such as dimethoxynaphthyl group, diethoxynaphthyl group, etc.

As the substituted or unsubstituted $C_{6-18}$ aralkyl group, it is possible to cite benzyl group, 1-phenylethyl group, 2-phenylethyl group, etc. As the substituted or unsubstituted $C_{6-18}$ aryloxoalkyl group, it is possible to cite 2-aryl-2-oxoethyl groups such as 2-phenyl-2-oxoethyl group, 2-(1-naphthyl)-2-oxoethyl group, 2-(2-naphthyl)-2-oxoethyl group, etc. Furthermore, in case that any two or more of $R^{02}$, $R^{03}$ and $R^{04}$ are connected with each other to form a ring through the sulfur atom, it is possible to mention as the bivalent group 1,4-butylene, 3-oxa-1,5-pentylene, etc. Furthermore, it is possible to cite an aryl group having as the substituent a polymerizable substituent, such as acryloyloxy group, methacryloyloxy group, etc. Specifically, it is possible to cite 4-(acryloyloxy)phenyl group, 4-(methacryloyloxy)phenyl group, 4-vinyloxyphenyl group, 4-vinylphenyl group, etc.

As the sulfonium cation represented by the general formula (CA-a) is shown more specifically, it is possible to cite triphenylsulfonium, (4-tert-butylphenyl)diphenylsulfonium, bis(4-tert-butylphenyl)phenylsulfonium, tris(4-tert-butylphenyl)sulfonium, (3-tert-butylphenyl)diphenylsulfonium, bis(3-tert-butylphenyl)phenylsulfonium, tris(3-tert-butylphenyl)sulfonium, (3,4-di-tert-butylphenyl)diphenylsulfonium, bis(3,4-di-tert-butylphenyl)phenylsulfonium, tris(3,4-di-tert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, 2-methoxynaphthyl-1-thiacyclopentanium, etc. More preferably, it is possible to cite triphenylsulfonium, (4-tert-butylphenyl)diphenylsulfonium, (4-tert-butoxyphenyl)diphenylsulfonium, tris(4-tert-butylphenyl)sulfonium, (4-tert-butoxycarbonylmethyloxyphenyl)diphenylsulfonium, 5-phenyldibenzothiophenium, 5-(4-methylphenyl)dibenzothiophenium, 5-(4-methoxyphenyl)dibenzothiophenium, 5-(3-methoxyphenyl)dibenzothiophenium, 5-(2-methoxyphenyl)dibenzothiophenium, 5-(4-fluorophenyl)dibenzothiophenium, 5-(4-chlorophenyl)dibenzothiophenium, 5-(4-hydroxyphenyl)dibenzothiophenium, 5-(4-hydroxy-3,5-dimethylphenyl)dibenzothiophenium, 2-methoxy-5-phenyldibenzothiophenium, etc. Furthermore, it is possible to cite 4-(methacryloyloxy)phenyldiphenylsulfonium, 4-(acryloyloxy)phenyldiphenylsulfonium, 4-(methacryloyloxy)phenyldimethylsulfonium, 4-(acryloyloxy)phenyldimethylsulfonium, etc. As these polymerizable sulfonium cations, those mentioned in Japanese Patent Application Publications Nos. Heisei 4-230645 and 2005-84365, etc. can be used.

<Iodonium cation represented by the general formula (CA-b)> As specific examples of $R^{05}$ and $R^{06}$, it is possible to cite again the same ones as those of $R^{02}$, $R^{03}$ and $R^{04}$ in the general formula (CA-a).

As specific iodonium cations, it is possible to cite bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, 4-(acryloyloxy)phenylphenyliodonium, 4-(methacryloyloxy)phenylphenyliodonium, 5-phenyldibenzothiophenium, 5-(4-methylphenyl)dibenzothiophenium, 5-(4-methoxyphenyl)dibenzothiophenium, 5-(4-fluorophenyl)dibenzothiophenium, etc. In particular, bis(4-tert-butylphenyl)iodonium is preferably used.

Herein, specific examples of the polymerizable fluorine-containing sulfonic acid onium salt represented by the general formula (2) can be exemplified by those prepared by combining the polymerizable fluorine-containing sulfonic acid salt having a structure represented by the general formula (1), which has been previously specifically exemplified, with the sulfonium cation represented by the general formula (CA-a) or the iodonium cation represented by the general formula (CA-b), which has been exemplified this time. In particular, the following structures can be exemplified as particularly preferable ones.

(i-25)

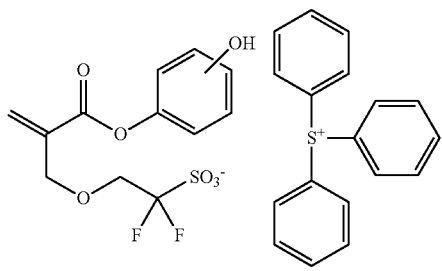

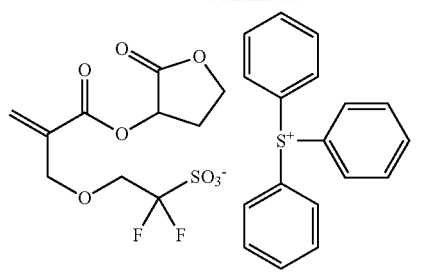

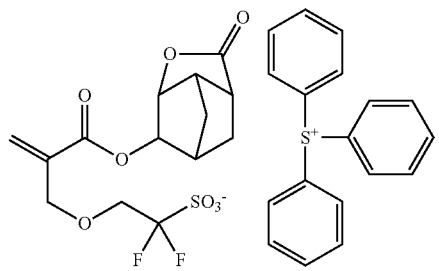

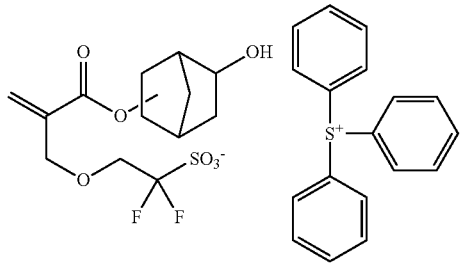

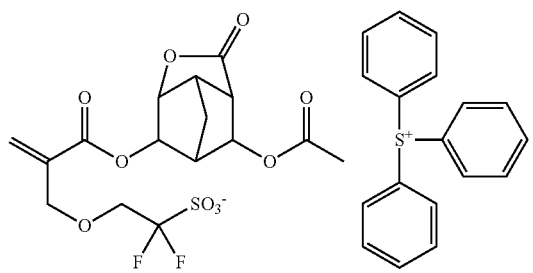

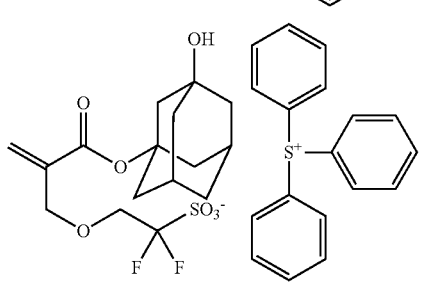

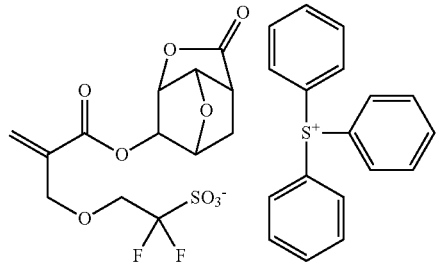

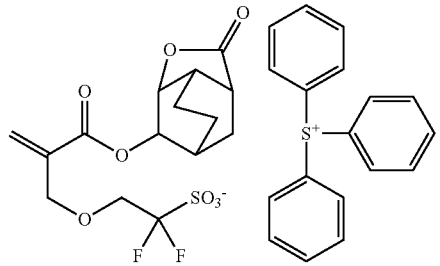

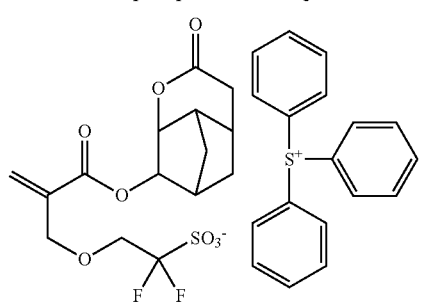

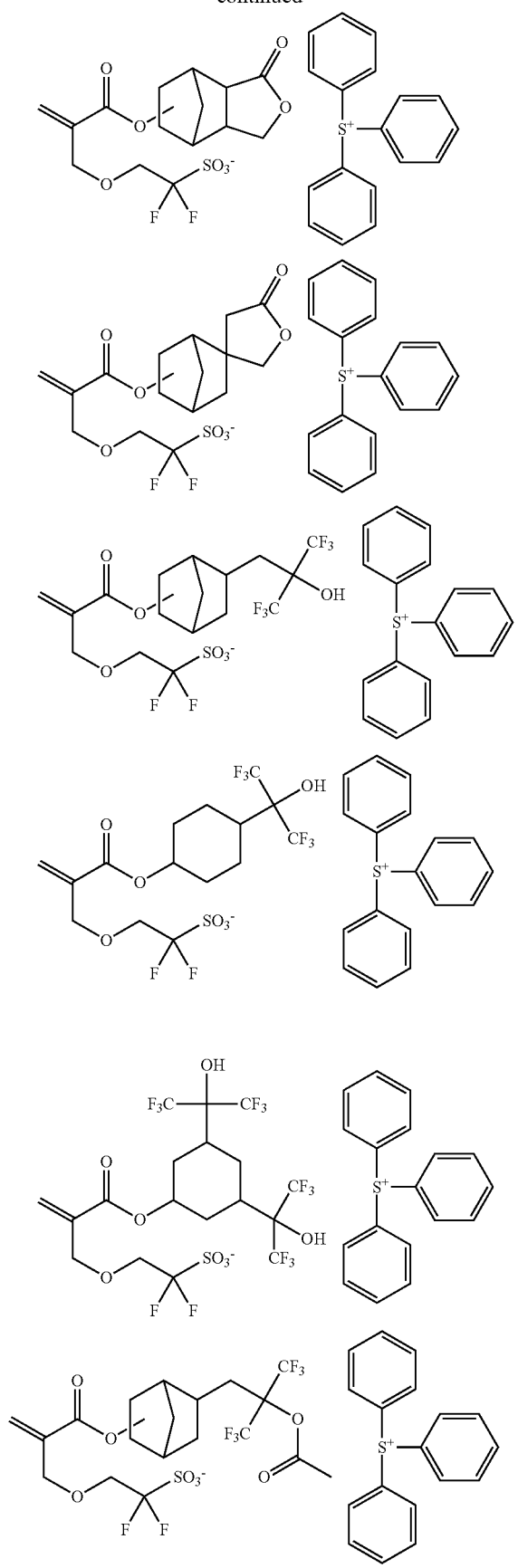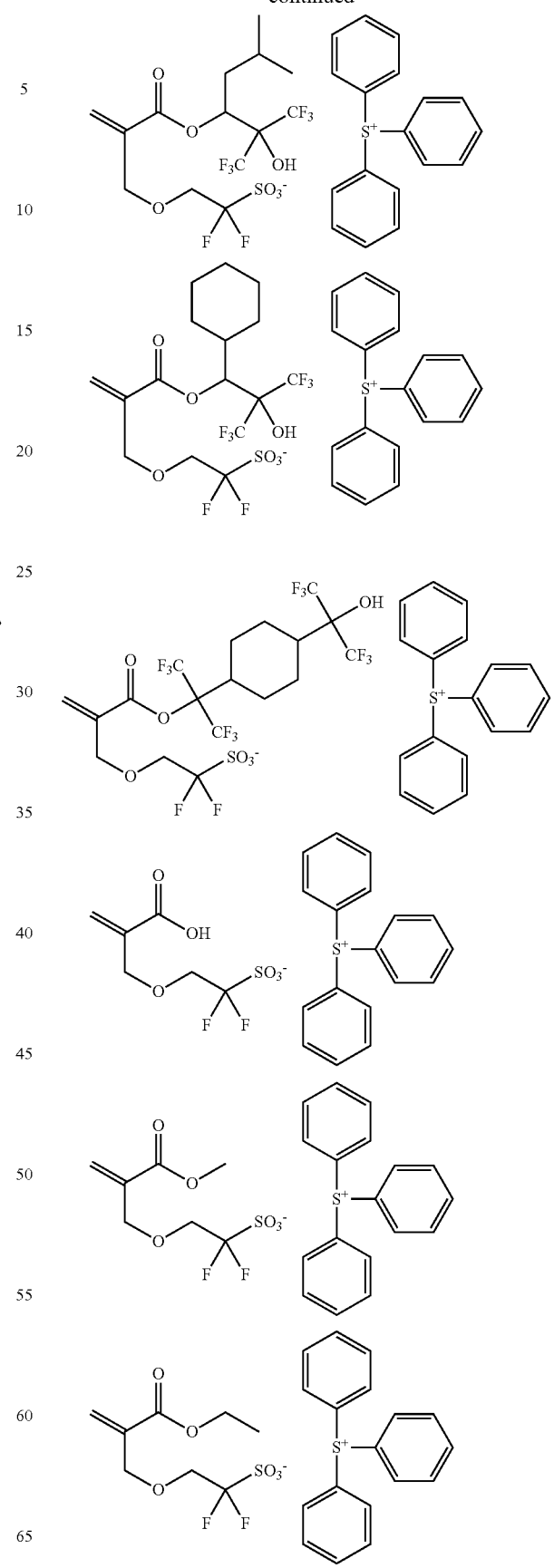

-continued
(i-26)
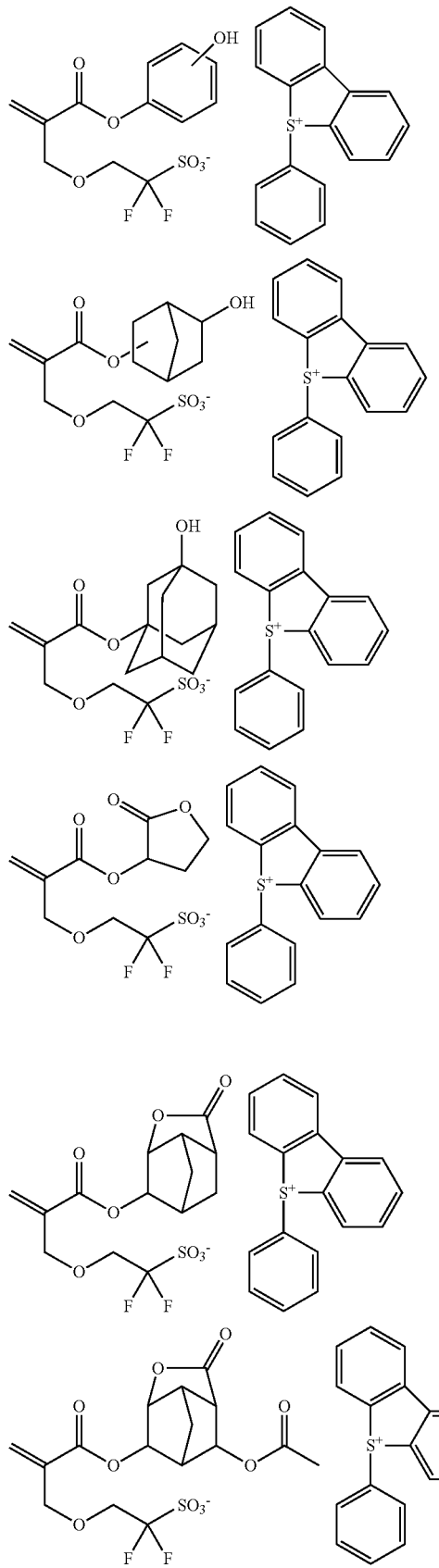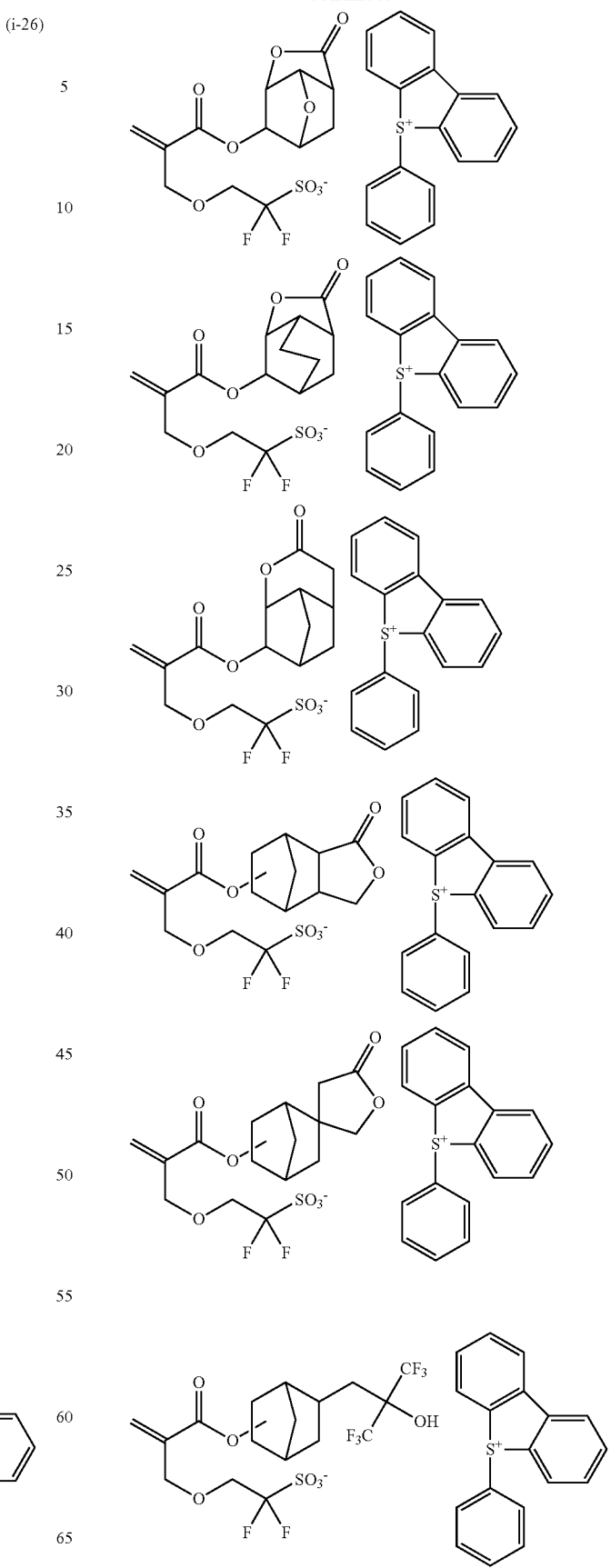

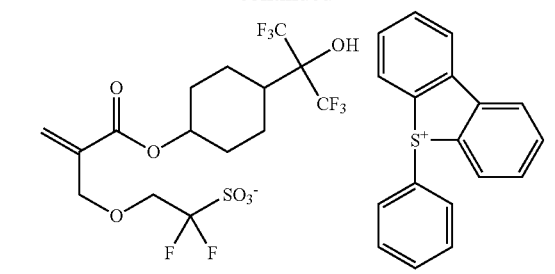
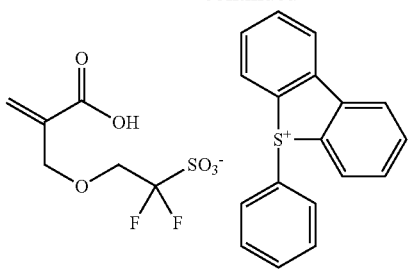
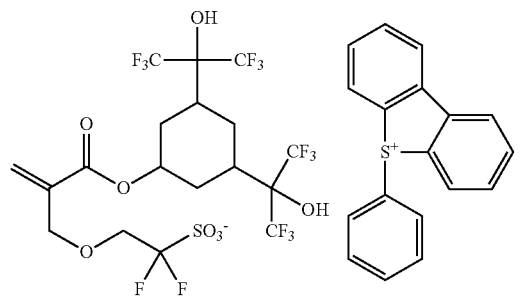
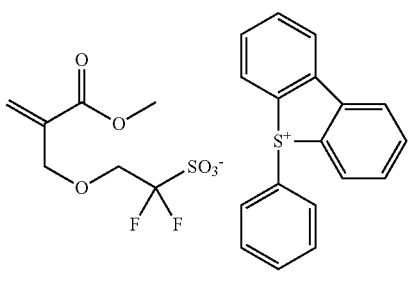
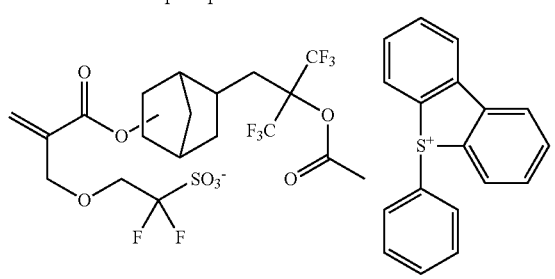
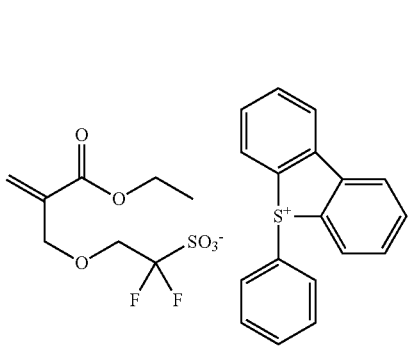
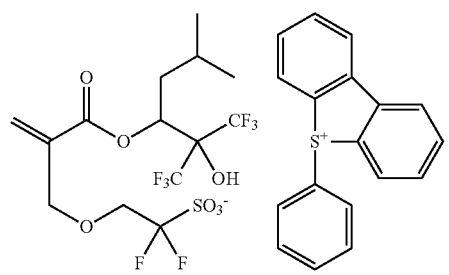
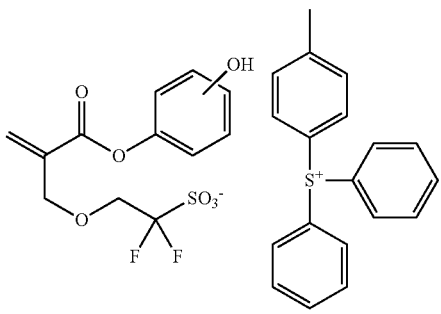
(i-27)
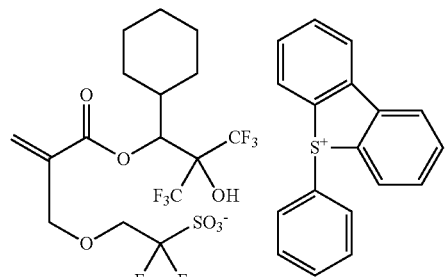
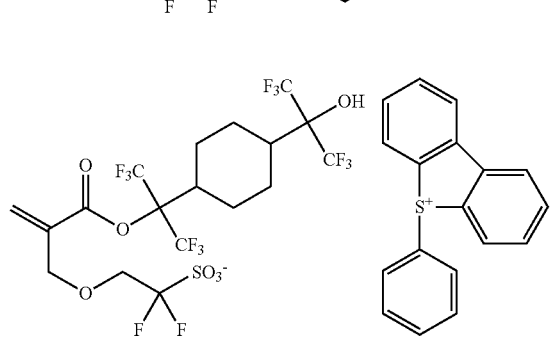
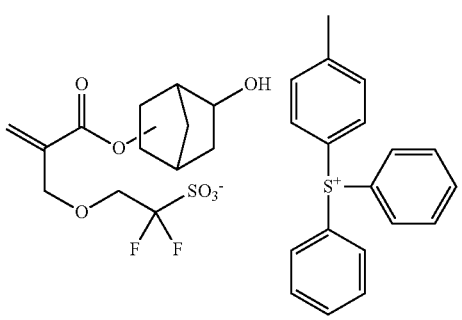

85
-continued
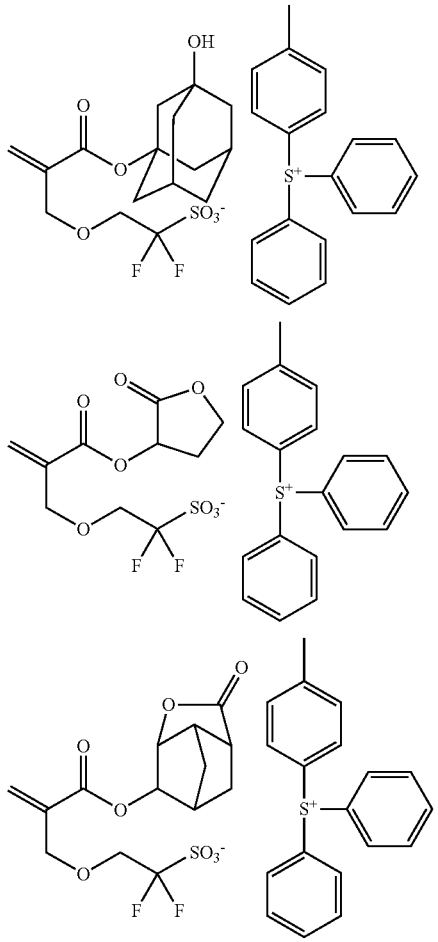
86
-continued
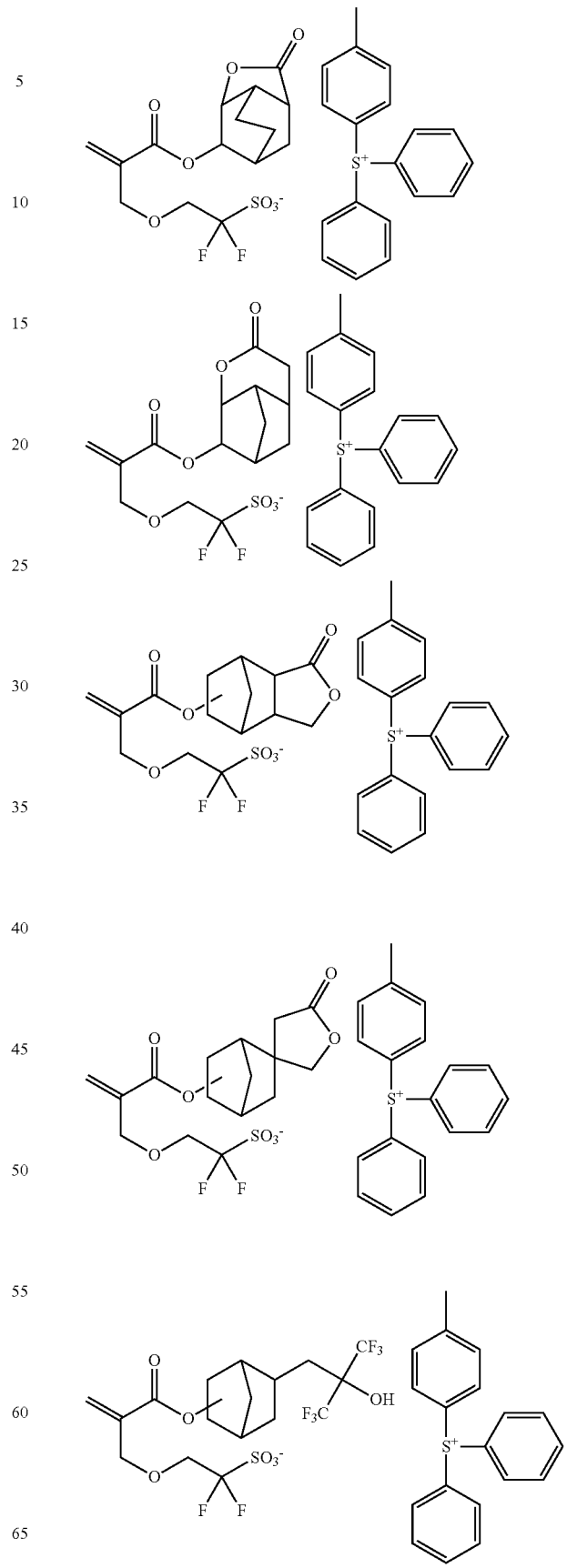

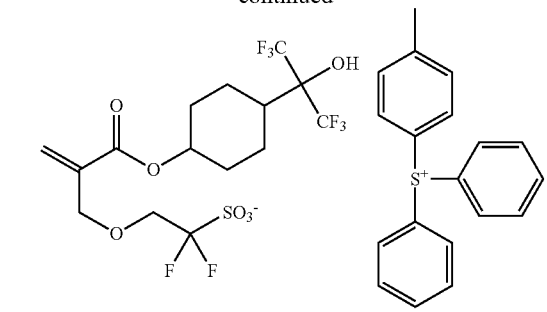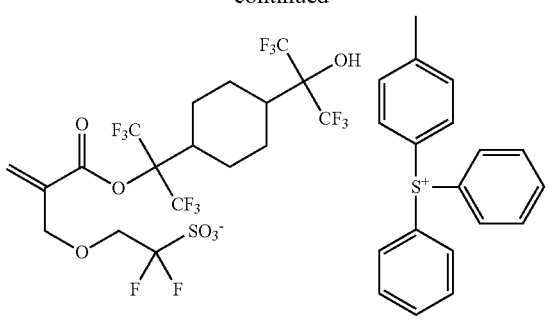
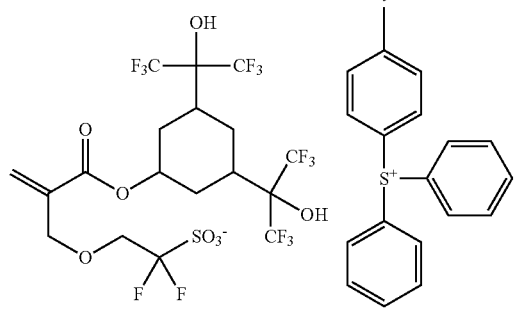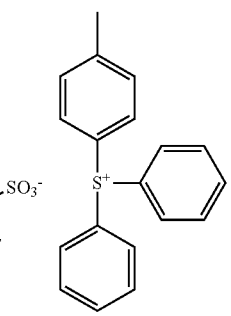
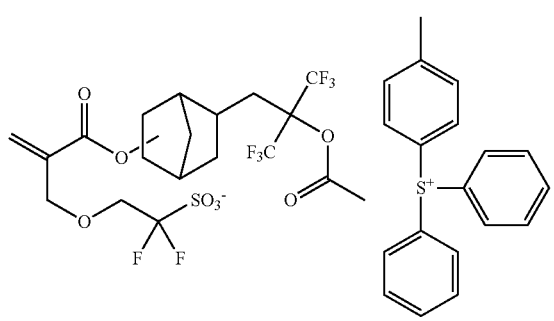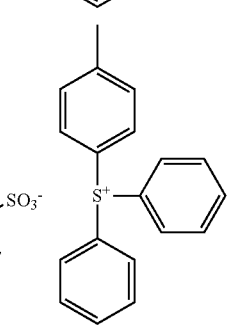
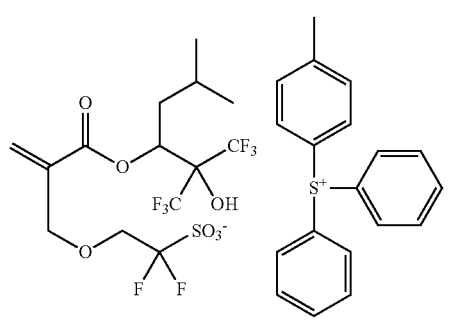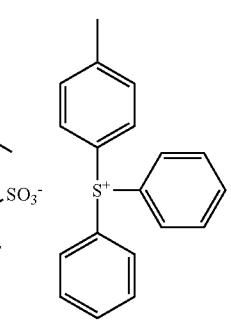
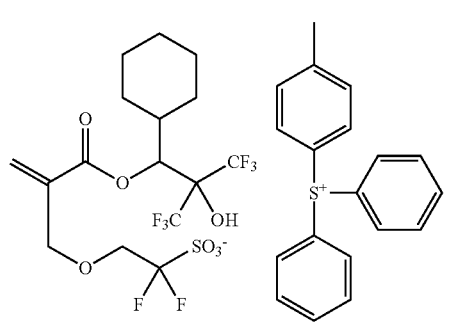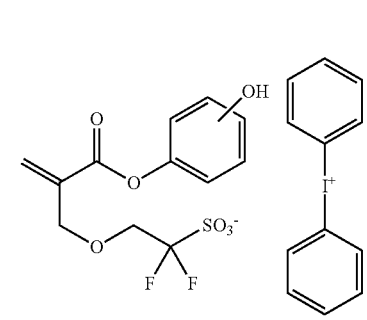
(i-28)

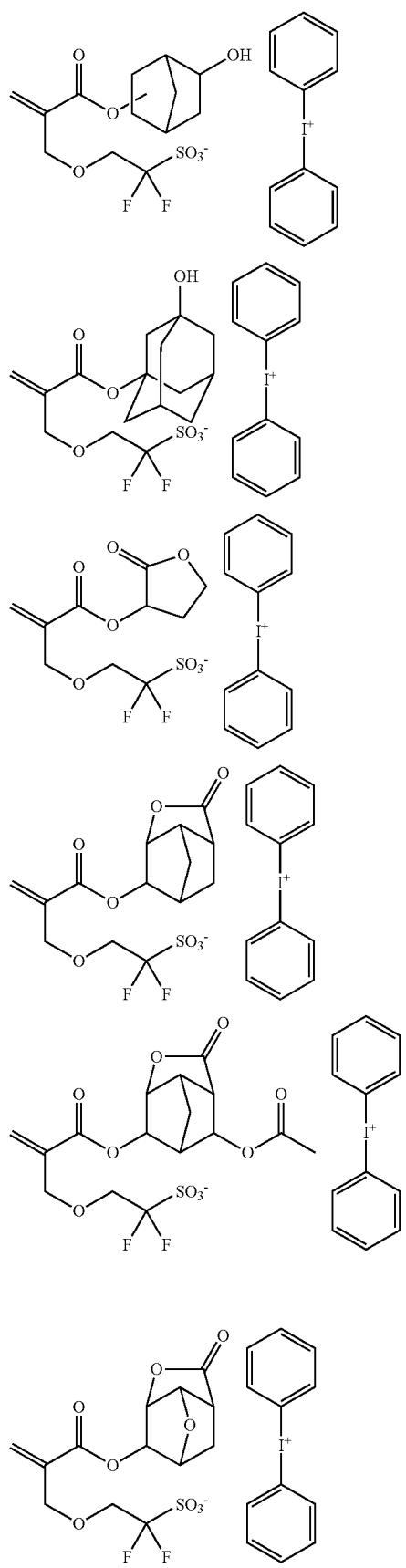
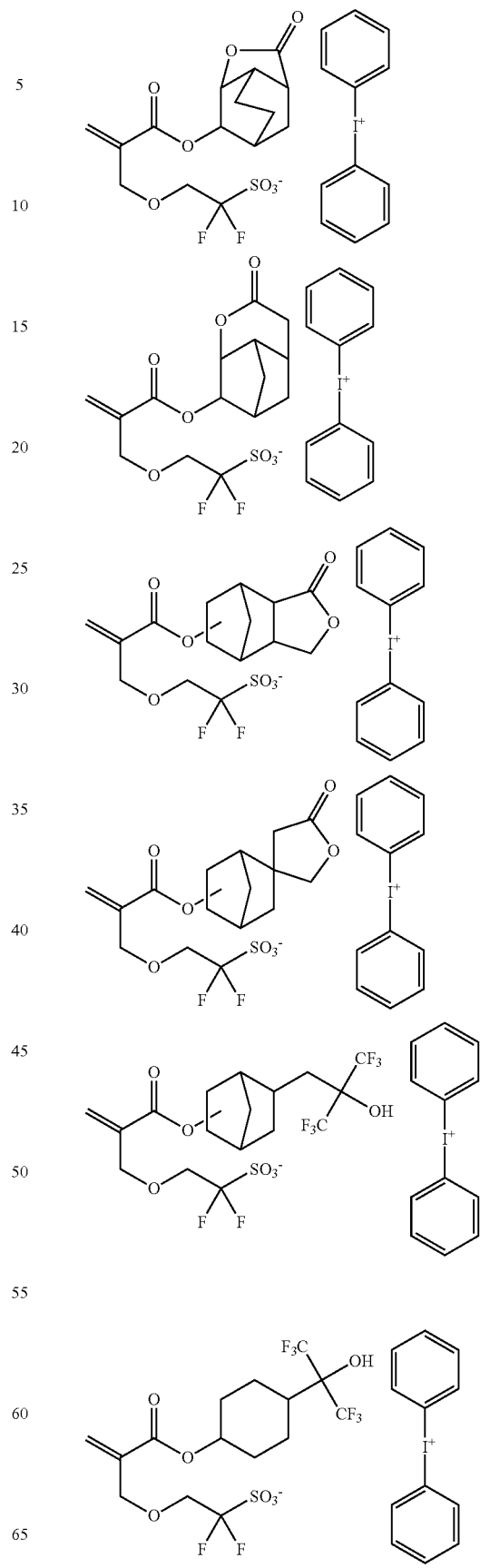

91
-continued
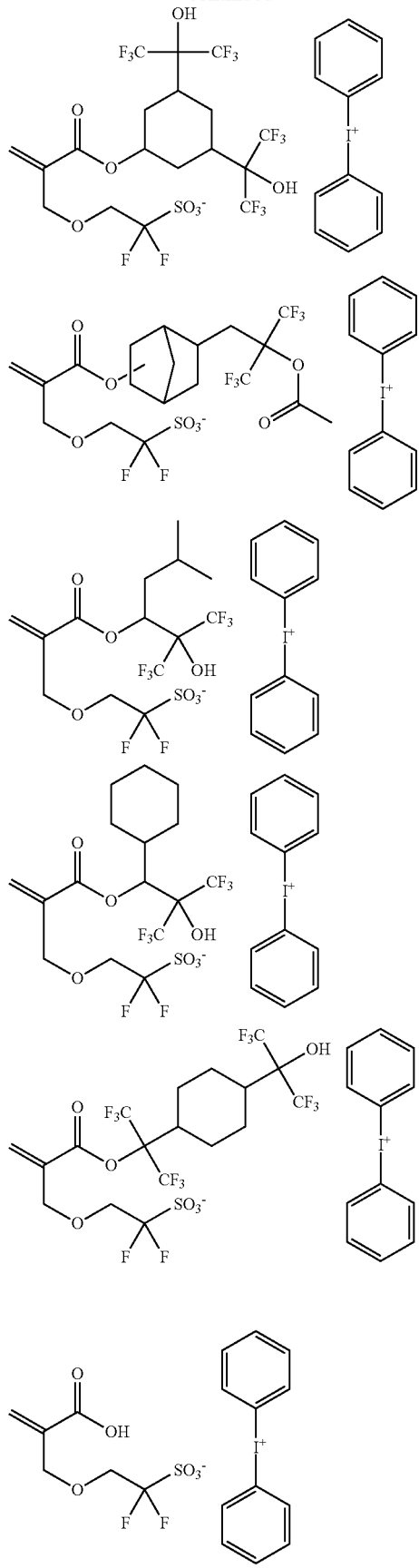
92
-continued
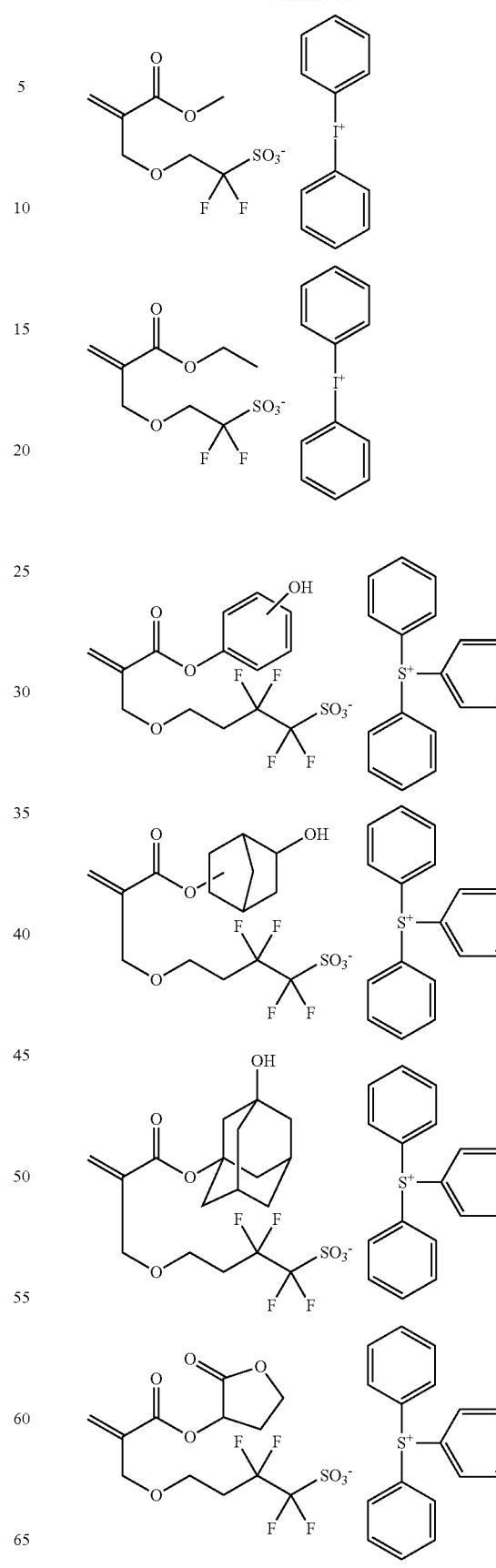
(i-29)

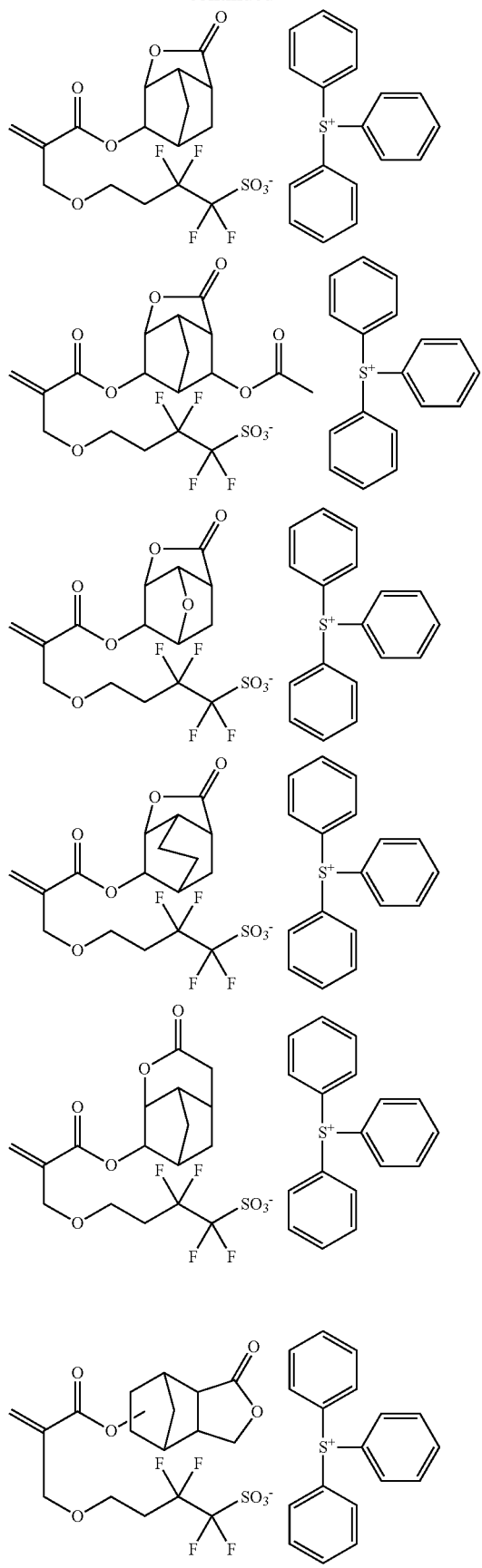
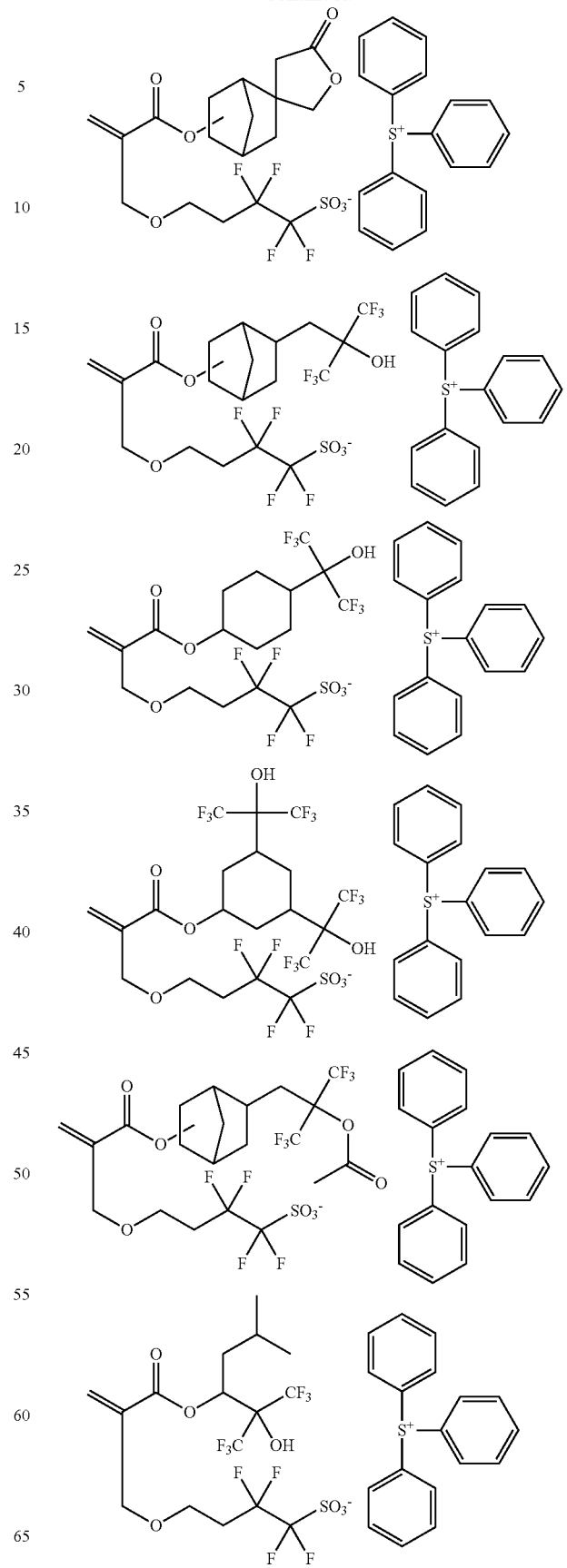

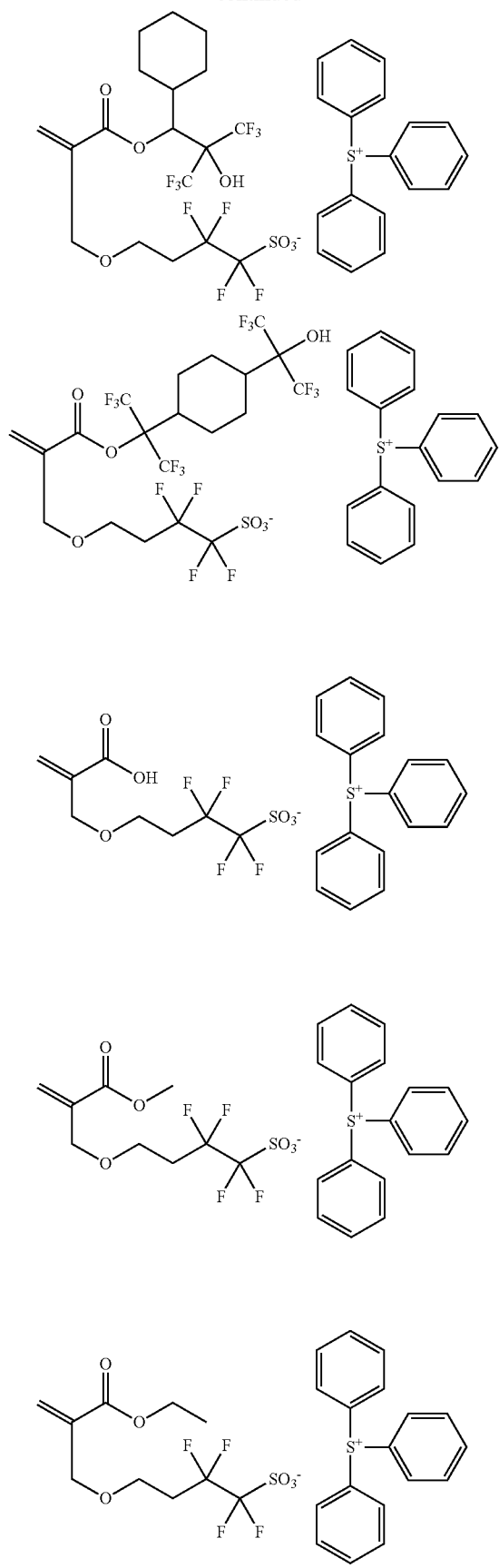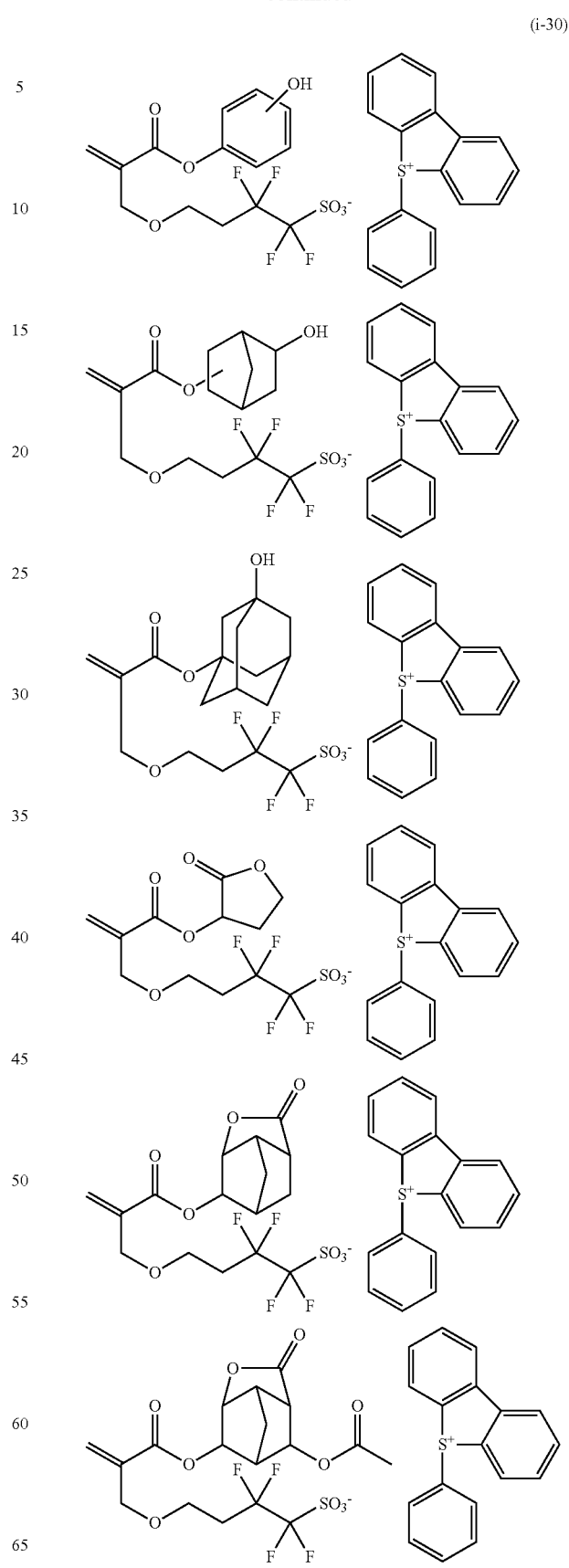

-continued
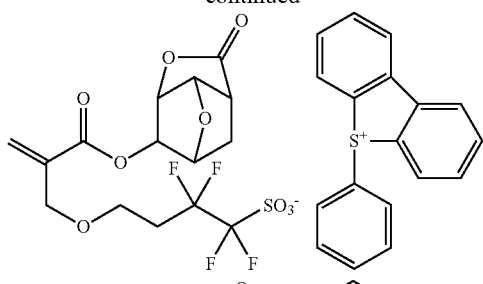
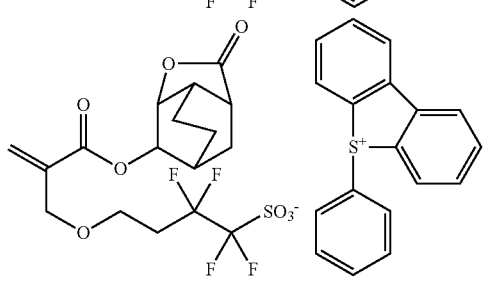
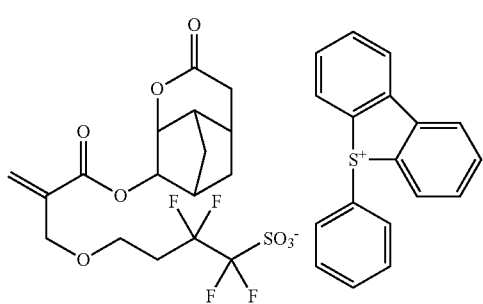
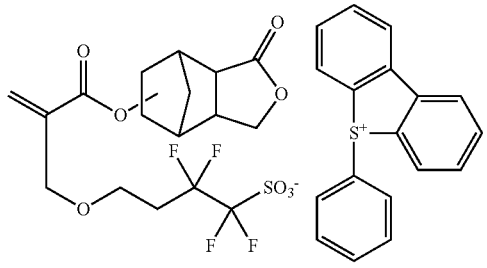
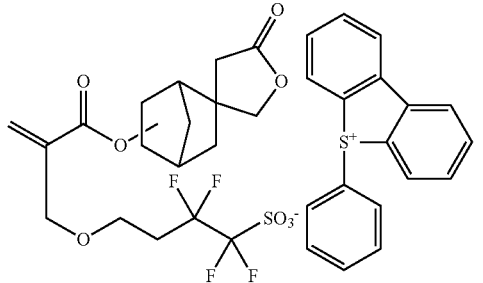
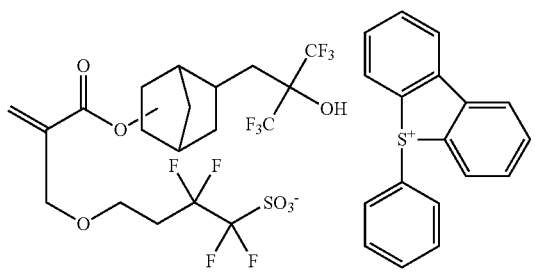
-continued
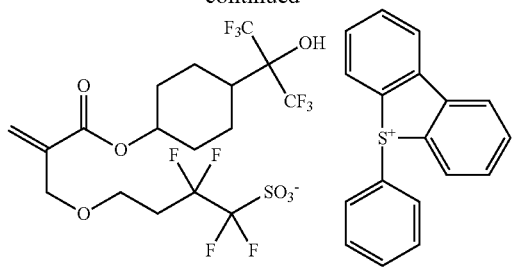
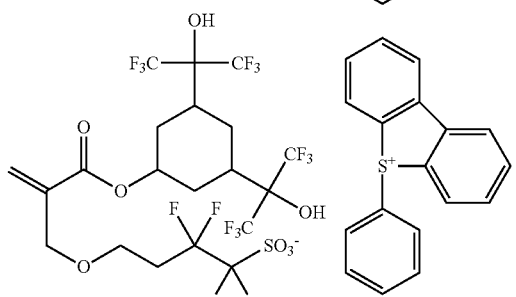
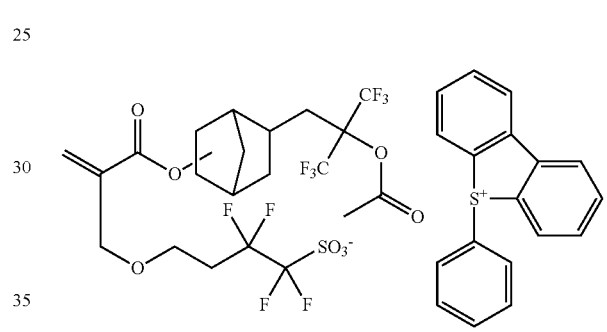
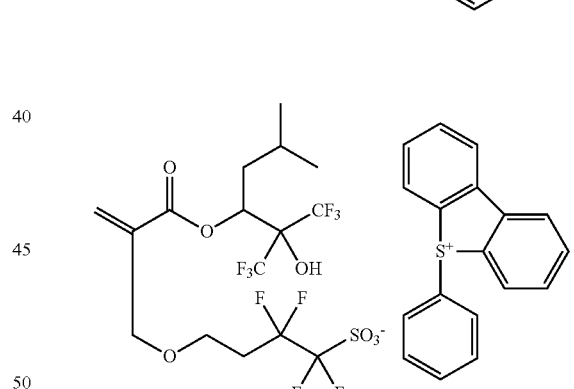
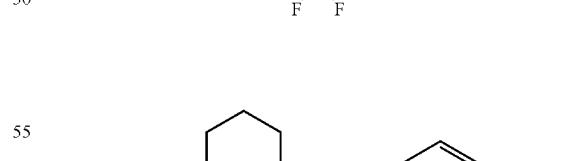
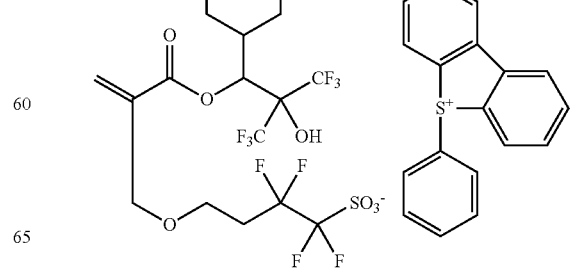

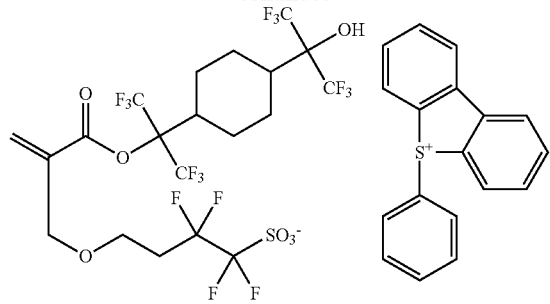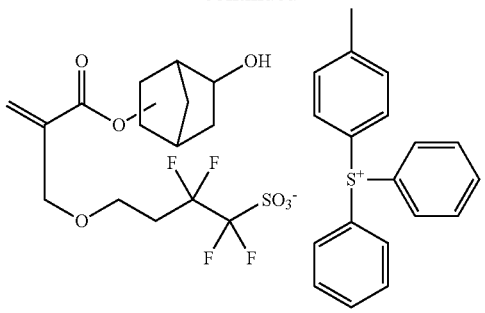
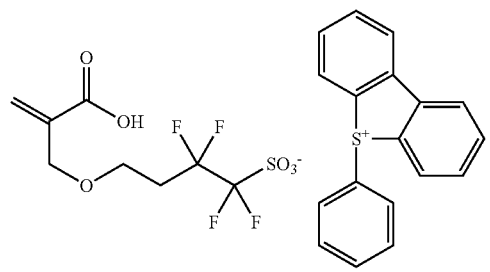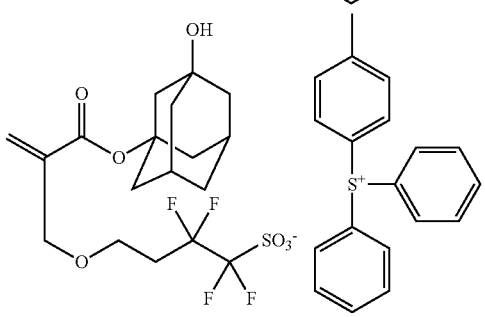
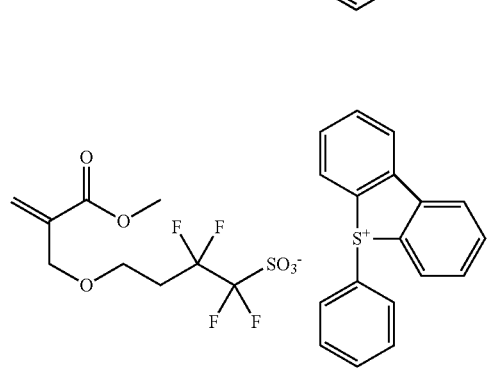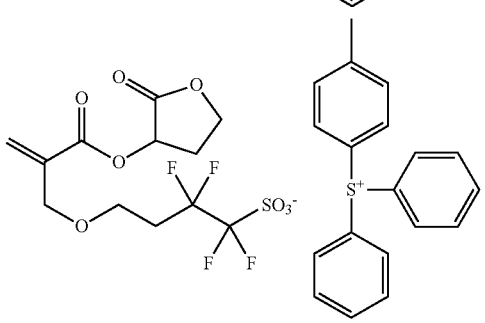
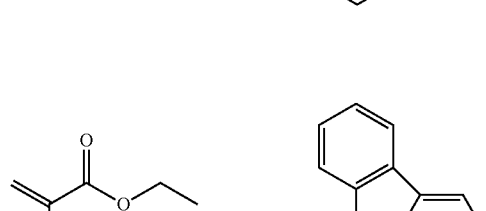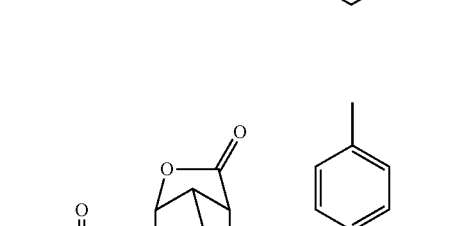
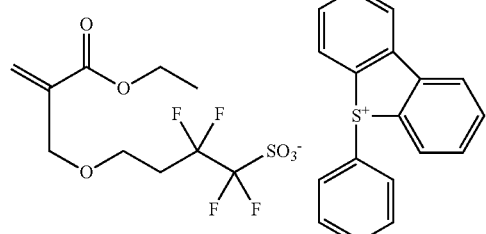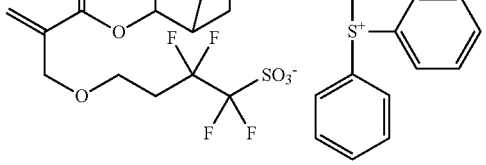
(i-31)
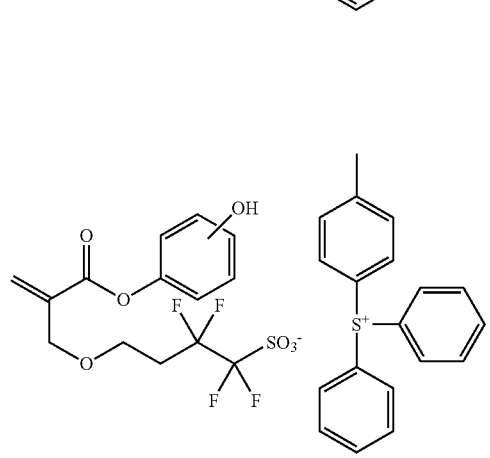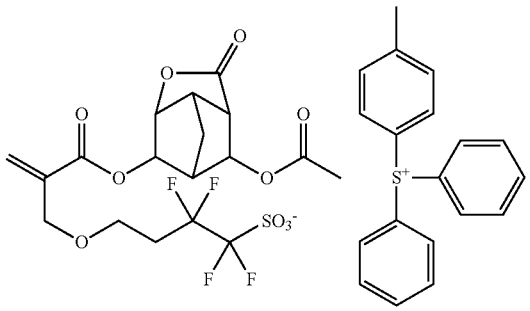

101
-continued
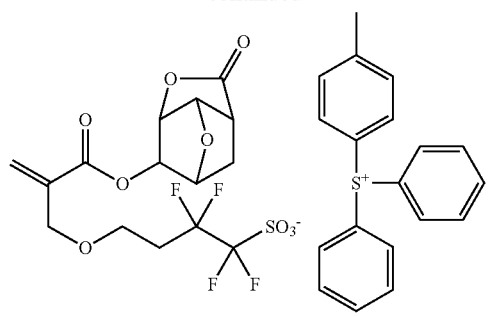
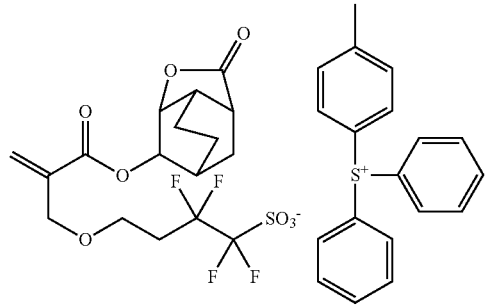
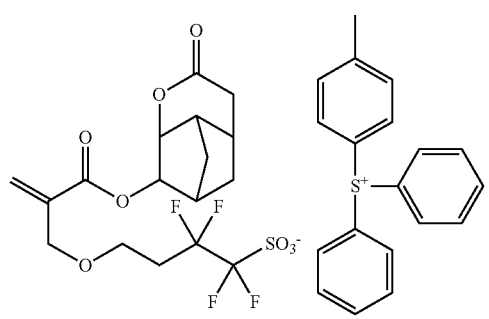
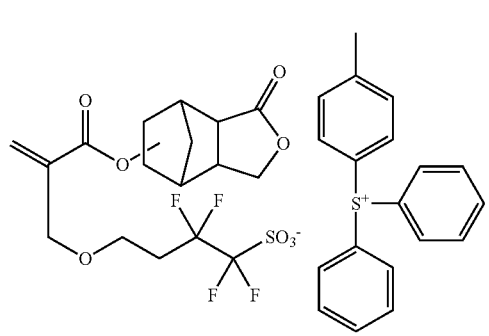
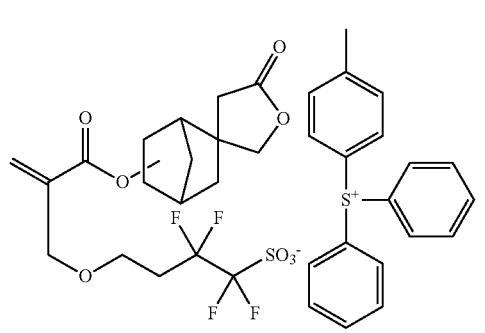
102
-continued
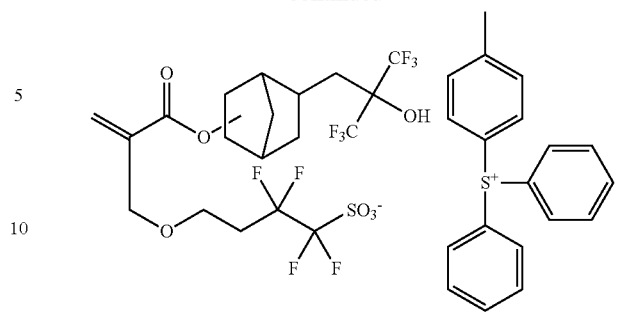
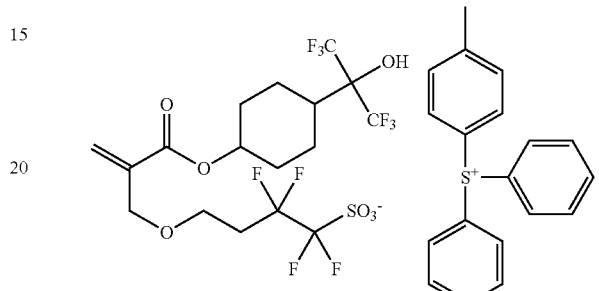
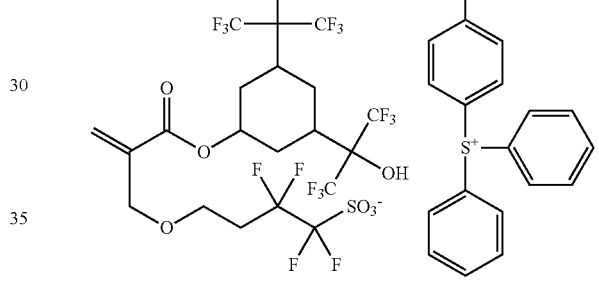
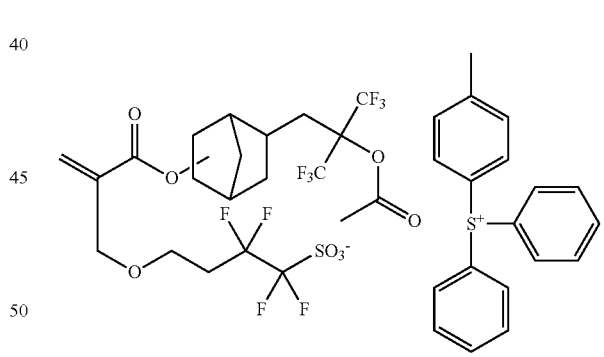
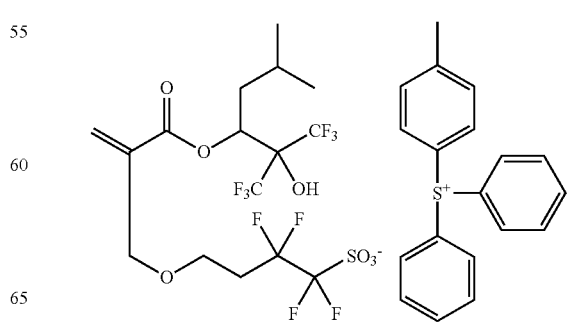

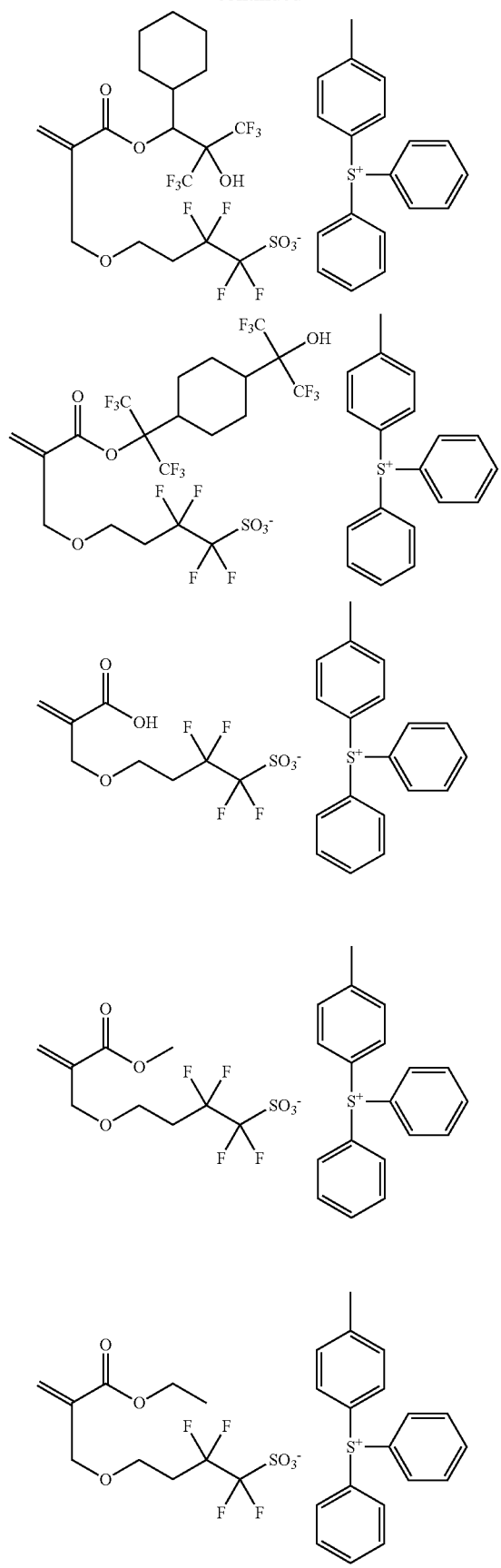

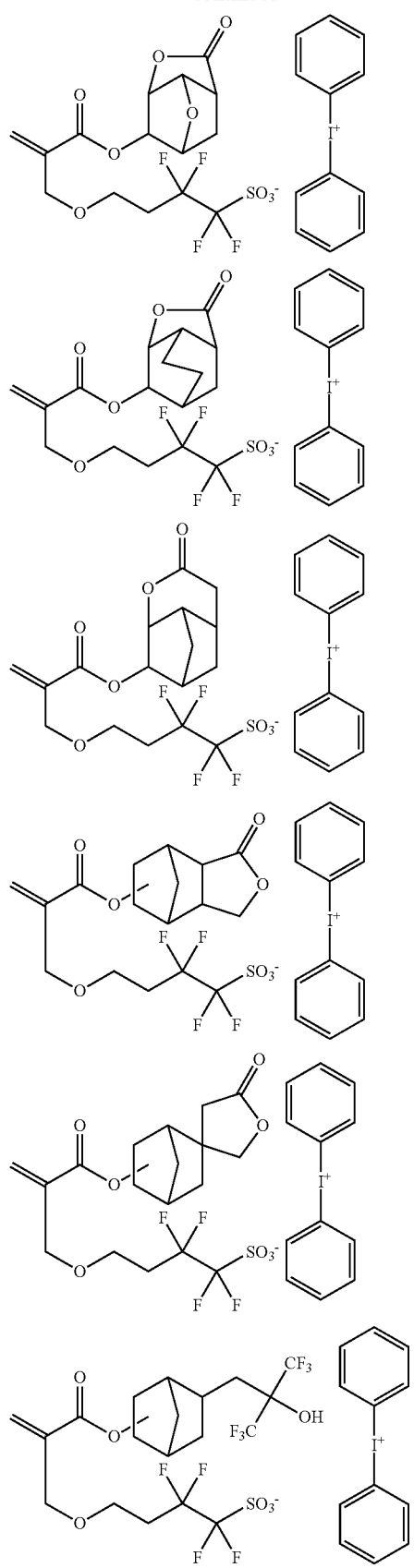
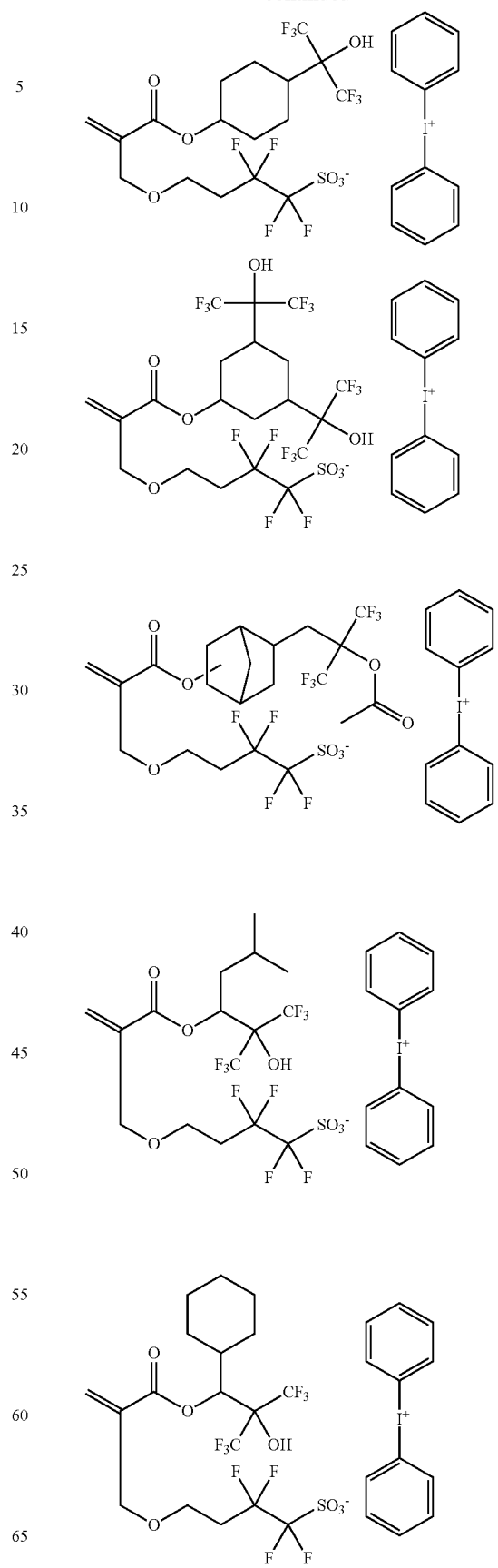

-continued

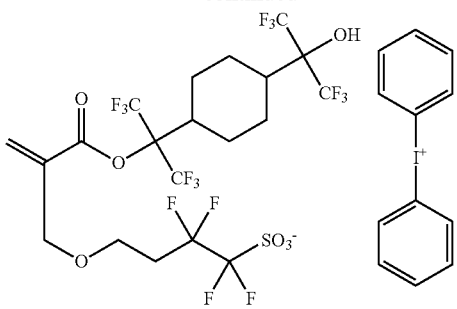

[Method for Producing the Polymerizable Fluorine-Containing Sulfonic Acid Salt]

Then, the method for producing the above-mentioned polymerizable fluorine-containing sulfonic acid salt represented by the general formula (1) is described. It is possible to produce the polymerizable fluorine-containing sulfonic acid salt represented by the general formula (1), similar to the polymerizable fluorine-containing sulfonic acid onium salt represented by the general formula (2). In the following explanation, it is possible to read $X^+$ as $M^+$.

As shown in the following Scheme (2), the polymerizable fluorine-containing sulfonic acid onium salt represented by the general formula (2) can be produced from a compound represented by the general formula (15) by a single reaction step. This step is, however, only one example, and it is not limited to only the production by this step.

Production Step

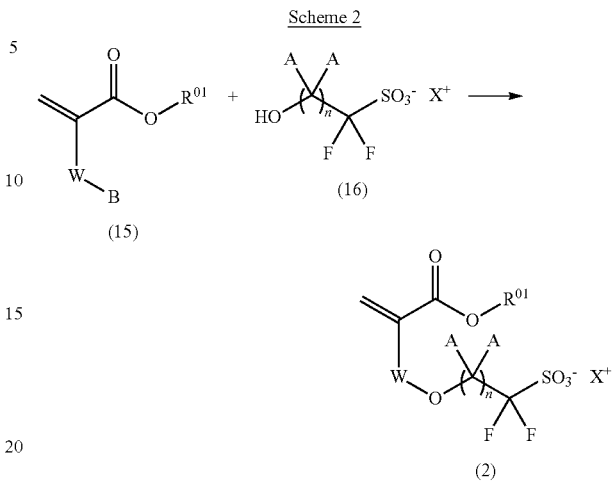

In Scheme (2), A, n, W, $R^{01}$ and $X^+$ are respectively defined as A, n, W, and $R^{01}$ in the above-mentioned general formula (1) and $X^+$ in the general formula (2). B represents a halogen atom or a leaving group. Specifically, the leaving group can be exemplified by hydroxy group, methanesulfonato group, toluenesulfonato group, nitrobenzenesulfonato group, trifluoromethanesulfonato group, etc.

As the acrylic acid derivative represented by the general formula (15), it is possible to use a commercial product as it is. Alternatively, it can be prepared by a known method or one based thereon.

The general formula (16) represents a hydroxyfluoroalkanesulfonic acid onium salt. $X^+$ represents the sulfonium cation or iodonium cation. As specific cations, it is possible to cite cations exemplified in the explanation of the general formula (2).

Specifically, it can be exemplified by triphenylsulfonium 2-hydroxy-1,1-difluoroethanesulfonate, triphenylsulfonium 4-hydroxy-1,1,2,2-tetrafluorobutanesulfonate, triphenylsulfonium 5-hydroxy-1,1,2,2-tetrafluoropentanesulfonate, triphenylsulfonium 6-hydroxy-1,1,2,2-tetrafluorohexanesulfonate, iodonium 2-hydroxy-1,1-difluoroethanesulfonate, iodonium 4-hydroxy-1,1,2,2-tetrafluorobutanesulfonate, iodonium 5-hydroxy-1,1,2,2-tetrafluoropentanesulfonate, iodonium 6-hydroxy-1,1,2,2-tetrafluorohexanesulfonate, etc. Production methods of these compounds are described in Japanese Patent Application Publication 2009-91351, International Publications 2008/56795 and 2006/121096 Pamphlets, and Japanese Patent Application Publication 2010-18573. Alternatively, they can be produced, based on those.

The production step is explained. The production step is a step for conducting a condensation between the acrylic acid derivative represented by the general formula (15) and the alcohol represented by the general formula (16). The mode of this condensation reaction is different depending on the types of W and B in the general formula (15). Any mode can be conducted by using a general condensation reaction method. Herein, three modes are shown as examples.

Mode (1) is a case in which B is a halogen atom (for example, chlorine atom, bromine atom, and iodine atom, preferably bromine atom), and in which an end of W on the side to be bonded to the halogen atom is an alkylene group (a case in which the general formula (15) represents an acrylic acid derivative having a halogenated alkyl group as "—W—B terminal".

Usage of the acrylic acid derivative represented by the general formula (15), which is made to react against the alcohol represented by the general formula (16), is not particularly limited. Normally, it is 0.1-5 moles, preferably 0.2-3 moles, more preferably 0.5-2 moles, relative to 1 mole of the alcohol represented by the general formula (16). It is particularly preferable that usage of the acrylic acid derivative is 0.8-1.5 moles.

Normally, the reaction is conducted by using an aprotic solvent, such as dichloroethane, toluene, ethylbenzene, monochlorobenzene, acetonitrile, or N,N-dimethylformamide. These solvents may be used singly, or at least two kinds may be used together.

The reaction temperature is not particularly limited. Normally, it is in a range of 0-200° C., preferably 20-180° C., more preferably 50-150° C. It is preferable to conduct the reaction with stirring.

Although the reaction time depends on the reaction temperature, too, it is normally several minutes to 100 hours, preferably 30 minutes to 50 hours, more preferably 1-20 hours. It is preferable to judge the time when the alcohol represented by the general formula (16) as the raw material has been consumed as being the end point of the reaction by using an analytical device, such as nuclear magnetic resonator (NMR).

In the present reaction, normally, a base catalyst is used. A preferable base catalyst can be exemplified by organic bases, such as trimethylamine, triethylamine, tripropylamine and tributylamine, and/or inorganic bases, such as sodium hydroxide, potassium hydroxide and lithium hydroxide. Usage of such base catalyst is not particularly limited. It is 0.0001-10 moles, preferably 0.001-5 moles, more preferably 0.01-1.5 moles, relative to 1 mole of the alcohol represented by the general formula (16).

After finishing the reaction, it is possible to obtain the polymerizable fluorine-containing sulfonic acid onium salt represented by the general formula (2) by a normal measure, such as extraction, crystallization or recrystallization. Furthermore, according to need, it is also possible to conduct a purification by recrystallization, etc.

Mode (2) is a case in which B is a halogen atom (for example, chlorine atom, bromine atom, and iodine atom, preferably chlorine atom), and in which an end of W on the side to be bonded to the halogen atom is —(C=O)— (a case in which the general formula (15) is an acid halide).

Usage of the acid halide represented by the general formula (15), which is made to react against the alcohol represented by the general formula (16), is not particularly limited. Normally, it is 0.1-5 moles, preferably 0.2-3 moles, more preferably 0.5-2 moles, relative to 1 mole of the alcohol represented by the general formula (16). It is particularly preferable that usage of the acid halide is 0.8-1.5 moles.

The reaction may be conducted with no solvent or may be conducted in a solvent that is inert against the reaction. Such solvent is not particularly limited, as long as it is a solvent that is inert to the reaction. The alcohol represented by the general formula (16) is almost not soluble in hydrocarbon-series nonpolar solvents, such as n-hexane, benzene or toluene. Therefore, it is not preferable to singly use these solvents. It is preferable to use water, a ketone-series solvent such as acetone, methyl ethyl ketone or methyl isobutyl ketone, an ester-series solvent such as ethyl acetate or butyl acetate, an ether-series solvent such as diethyl ether, diethylene glycol dimethyl ether, tetrahydrofuran or dioxane, a halogen-series solvent such as dichloromethane, chloroform, carbon tetrachloride, 1,2-dichloroethane, tetrachloroethylene, chlorobenzene or orthochlorobenzene, and a polar solvent such as acetonitrile, N,N-dimethylformamide, N,N-dimethylimidazolidinone, dimethylsulfoxide or sulfolane. These solvents may be used singly, or at least two kinds may be used together.

The reaction temperature is not particularly limited. Normally, it is a range of −78 to 150° C., preferably −20 to 120° C., more preferably 0 to 100° C.

The reaction time depends on the reaction temperature, too. Normally, it is several minutes to 100 hours, preferably 30 minutes to 50 hours, more preferably 1-20 hours. Using an analytical apparatus such as nuclear magnetic resonator (NMR), it is preferable to judge the point when the alcohol represented by the general formula (16) as the raw material has been consumed, as the end point of the reaction.

In the case of using an acid halide represented by the general formula [15], it may be conducted under no catalyst while removing a hydrogen halide produced as a by-product, out of the reaction system, or may be conducted by using a dehydrohalogenation agent (acid acceptor).

As the acid acceptor, it is exemplified by, for example, organic bases such as triethylamine, pyridine, picoline, dimethylaniline, diethylaniline, 1,4-diazabicyclo[2.2.2]octane (DABCO), and 1,8-diazabicyclo[5.4.0]undec-7-ene (DBU), or inorganic bases such as sodium hydrogencarbonate, sodium carbonate, potassium carbonate, lithium carbonate, sodium hydroxide, potassium hydroxide, calcium hydroxide, and magnesium hydroxide. Usage of such acid acceptor is not particularly limited. Relative to 1 mole of the alcohol represented by the general formula (16), it is 0.05-10 moles, preferably 0.1-5 moles, more preferably 0.5-3 moles.

After finishing the reaction, it is possible to obtain the polymerizable fluorine-containing sulfonic acid onium salt represented by the general formula (2) by a normal measure, such as extraction, crystallization or recrystallization. Furthermore, according to need, it is also possible to conduct a purification by recrystallization, etc.

Mode (3) is a case in which B is a hydroxy group (leaving group), and in which an end of W on the side to be bonded to the hydroxy group is —(C=O)— (a case in which the general formula (15) is a carboxylic acid).

Usage of the carboxylic acid represented by the general formula (15), which is made to react against the alcohol represented by the general formula (16), is not particularly limited. Normally, it is 0.1-5 moles, preferably 0.2-3 moles, more preferably 0.5-2 moles, relative to 1 mole of the alcohol represented by the general formula (16). It is particularly preferable that usage of the carboxylic acid is 0.8-1.5 moles.

In the reaction, normally, there is used an aprotic solvent, such as dichloroethane, toluene, ethylbenzene, monochlorobenzene, acetonitrile or N,N-dimethylformamide. These solvents may be used singly, or at least two kinds may be used together. The reaction temperature is not particularly limited. Normally, it is a range of 0 to 200° C., preferably 20 to 180° C., more preferably 50 to 150° C. It is preferable to conduct the reaction with stirring.

The reaction time depends on the reaction temperature, too. Normally, it is several minutes to 100 hours, preferably 30 minutes to 50 hours, more preferably 1-20 hours. Using an analytical apparatus such as nuclear magnetic resonator (NMR), it is preferable to judge the point when the alcohol represented by the general formula (16) as the raw material has been consumed, as the end point of the reaction.

In the present reaction, normally, an organic acid, such as p-toluenesulfonic acid, and/or an inorganic acid, such as sulfuric acid, is added as an acid catalyst. Alternatively, as the dehydrating agent, it is optional to add 1,1'-carbonyl diimidazole, N,N'-dicyclohexylcarbodiimide, etc. Usage of such acid catalyst is not particularly limited. It is 0.0001-10 moles, preferably 0.001-5 moles, more preferably 0.01-1.5 moles, relative to 1 mole of the alcohol represented by the general formula (16).

If the esterification reaction using an acid catalyst is conducted with dehydration by using a Dean-Stark apparatus or the like, the reaction time tends to be shortened. Therefore, that is preferable.

After finishing the reaction, it is possible to obtain the polymerizable fluorine-containing sulfonic acid onium salt represented by the general formula (2) by a normal measure, such as extraction, crystallization or recrystallization. Furthermore, according to need, it is also possible to conduct a purification by recrystallization, etc.

Then, as shown in the following Schemes (3) and (4), embodiments (in the following, referring to Mode 4 and Mode 5) for producing the polymerizable fluorine-containing sulfonic acid onium salt represented by the general formula (2) from compounds represented by the general formula (19) and the general formula (21) by a single reaction step are explained.

(Mode 4)

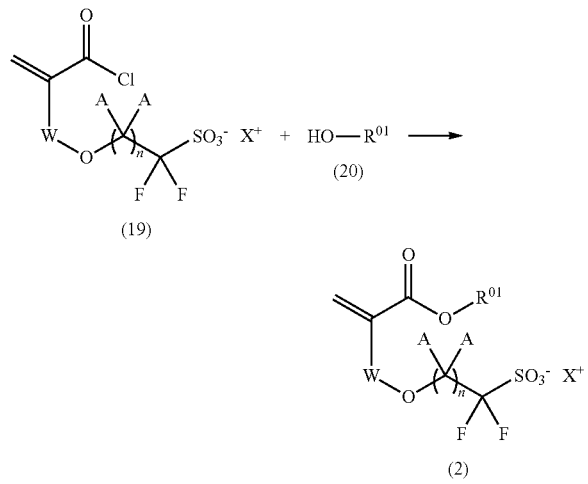

In the Scheme (3), A, n, W, $R^{01}$ and $X^+$ are as mentioned above.

The acid chloride derivative represented by the general formula (19) can be prepared by combining publicly-known methods. $X^+$ represents a sulfonium cation or an iodonium cation. As specific cations, the cations exemplified in the explanation of the general formula (2) can be shown again. Of the acid chloride derivative, the case in which W is a methylene (—$CH_2$—), n is 1 and A is a hydrogen atom, and $X^+$ is a triphenylsulfonium is particularly preferable.

$R^{01}$ in the alcohol represented by the general formula (20) represents a monovalent organic group and has the same meaning as that of $R^{01}$ in the above-mentioned general formula (1). The alcohol results from an arbitrary combination of $R^{01}$. It is possible to use a commercial product as it is. Alternatively, it can suitably be prepared by a publicly-known method by a person skilled in the art.

In the reaction, normally, there is used a solvent, such as dichloroethane, toluene, ethylbenzene, monochlorobenzene, or acetonitrile. These solvents may be used singly. Alternatively, at least two kinds may be used together.

The reaction temperature is not particularly limited. Normally, it is a range of –20 to 200° C., preferably 20 to 180° C., more preferably 0 to 50° C. It is preferable to conduct the reaction with stirring.

The reaction time depends on the reaction temperature, too. Normally, it is several minutes to 100 hours, preferably 30 minutes to 50 hours, more preferably 30 minutes to 20 hours. Using an analytical apparatus such as nuclear magnetic resonator (NMR), it is preferable to judge the point when the raw material has been consumed, as the end point of the reaction.

After finishing the reaction, it is possible to obtain the polymerizable fluorine-containing sulfonic acid onium salt represented by the general formula (2) by a normal measure, such as extraction, crystallization or recrystallization. Furthermore, according to need, it is also possible to conduct a purification by recrystallization, etc.

(Mode 5)

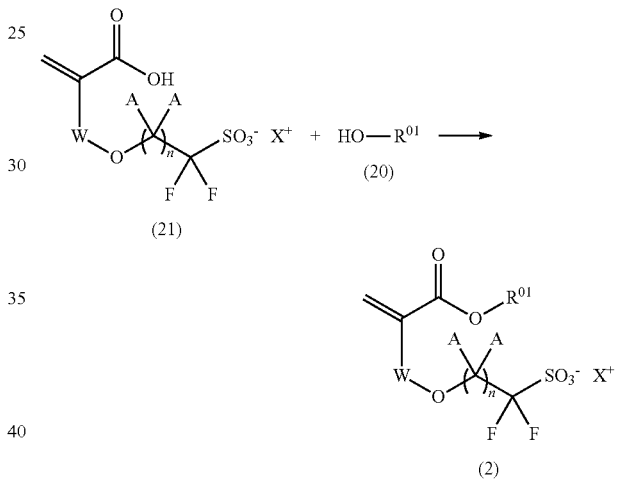

In the Scheme (4), A, n, W, $R^{01}$ and $X^+$ are as mentioned above.

The carboxylic acid derivative represented by the general formula (21) can also be prepared by combining publicly-known methods. $X^+$ represents a sulfonium cation or an iodonium cation. As specific cations, the cations exemplified in the explanation of the general formula (2) can be shown again. Of this derivative, the case in which W is a methylene (—$CH_2$—), n is 1 and A is a hydrogen atom, and $X^+$ is a triphenylsulfonium is particularly preferable.

The alcohol represented by the general formula (20) is as mentioned above.

In the reaction, normally, there is used an aprotic solvent, such as dichloroethane, toluene, ethylbenzene, monochlorobenzene, acetonitrile, or N,N-dimethylformamide. These solvents may be used singly. Alternatively, at least two kinds may be used together. The reaction temperature is not particularly limited. Normally, it is a range of 0 to 200° C., preferably 20 to 180° C., more preferably 50 to 150° C. It is preferable to conduct the reaction with stirring.

The reaction time depends on the reaction temperature, too. Normally, it is several minutes to 100 hours, preferably 30 minutes to 50 hours, more preferably 1 to 20 hours. Using an analytical apparatus such as nuclear magnetic resonator (NMR), it is preferable to judge the point when the raw material has been consumed, as the end point of the reaction.

In the present reaction, normally, an organic acid, such as 4-toluenesulfonic acid, and/or an inorganic acid, such as sulfuric acid, is added as an acid catalyst. Alternatively, as the dehydrating agent, it is optional to add 1,1'-carbonyl diimidazole, N,N'-dicyclohexylcarbodiimide, etc. Usage of such acid catalyst is not particularly limited. It is 0.0001-10 moles, preferably 0.001-5 moles, more preferably 0.01-1.5 moles, relative to 1 mole of the hydroxyfluoroalkanesulfonic acid onium salt represented by the general formula (16).

If the esterification reaction using an acid catalyst is conducted with dehydration by using a Dean-Stark apparatus or the like, the reaction time tends to be shortened. Therefore, that is preferable. After finishing the reaction, it is possible to obtain the polymerizable fluorine-containing sulfonic acid onium salt represented by the general formula (2) by a normal measure, such as extraction, crystallization or recrystallization. Furthermore, according to need, it is also possible to conduct a purification by recrystallization, etc.

[Sulfonic acid salt resin] A resin (in the present specification, it may be referred to as "sulfonic acid salt resin") containing a repeating unit represented by the following general formula (3) is formed by a cleavage of a polymerizable double bond of the polymerizable fluorine-containing sulfonic acid salt represented by the general formula (1-1). In the polymerization reaction, the structure except the polymerizable double bond does not change to maintain the original structure.

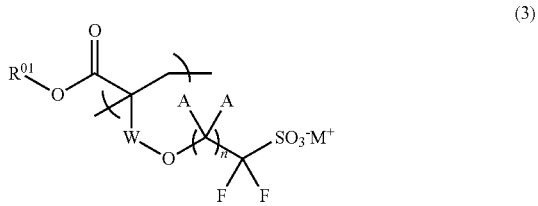

(3)

(In the formula, A, n, W and $R^{01}$ respectively have the same meanings as those of A, n, W and $R^{01}$ in the above-mentioned general formula (1). $M^+$ represents a monovalent cation.) Herein, one in which the cation ($M^+$) is an onium ion ($X^+$) is preferable. Specifically, as an example of a resin having a repeating unit formed by a cleavage of a polymerizable double bond of the polymerizable fluorine-containing sulfonic acid onium salt represented by the general formula (2), a resin having a repeating unit represented by the following general formula (4),

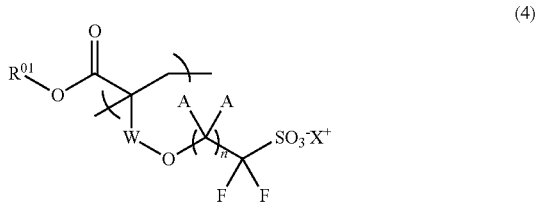

(4)

(In the formula, A, n, W and $R^{01}$ respectively have the same meanings as those of A, n, W and $R^{01}$ in the above-mentioned general formula (1). $X^+$ has the same meaning as that of $X^+$ in the above-mentioned general formula (2)) can be shown.

By an exposure to a high-energy ray, the resin having a repeating unit represented by this general formula (4) is converted to a resin having a repeating unit represented by the following general formula (5),

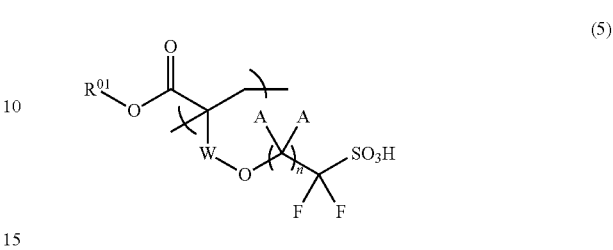

(5)

(In the formula, A, n, W and $R^{01}$ respectively have the same meanings as those of A, n, W and $R^{01}$ in the above-mentioned general formula (1).

After elimination of this $X^+$, an end of the repeating unit is difluorosulfonic acid, which shows a very strong acidity and functions as a photoacid generator used in a chemically amplified resist composition. Therefore, a resin at least having a repeating unit represented by the general formula (4) functions as a photoacid generator.

As the sulfonic acid salt resin, depending on the purpose of its use, there are provided a sulfonic acid salt resin formed of a repeating unit represented by the general formula (4) and a sulfonic acid salt resin formed of a repeating unit having an acid-labile group or a cross-linking moiety and a repeating unit represented by the general formula (4). In either case, other repeating units (in the present specification, referring to "secondary repeating units") can be contained. The secondary repeating unit refers to a repeating unit not corresponding to the repeating unit represented by the general formula (4). Furthermore, a secondary monomer refers to a monomer to form a secondary repeating unit by a cleavage of double bond.

Therefore, the sulfonic acid salt resin may be a homopolymer that is formed of only a repeating unit represented by the general formula (4) and that is obtained by a homopolymerization of a polymerizable fluorine-containing sulfonic acid onium salt represented by the general formula (2). Alternatively, it may be one containing a secondary repeating unit. In the case of not containing a repeating unit having an acid-labile group or a cross-linking moiety, these themselves cannot be used as a positive-type or negative-type resist, but can constitute a resist composition as a photoacid generator together with a base resin. In case that such use is the purpose, the sulfonic acid salt resin is that a repeating unit represented by the general formula (4) is adjusted to 0.1-100 mole %, preferably 1-100 mole %, more preferably 2-100 mole %. In either case, the remainder is a secondary repeating unit not containing a repeating unit having an acid labile group or a cross-linking moiety. If it is less than 0.1 mole %, it is necessary to separately use a large amount of a photoacid generator in order to maintain a sufficient sensitivity to high-energy rays in the resist composition. Therefore, it is not preferable.

Furthermore, in case that the sulfonic acid salt resin is a sulfonic acid salt resin formed of only a repeating unit having an acid labile group or a crosslinking moiety and a repeating unit represented by the general formula (4), the repeating unit represented by the general formula (4) is 0.1-90 mol %, preferably 0.5-50 mol %, more preferably 1-30 mol %. The remainder is a repeating unit having an acid labile group or a cross-linking moiety. In case that a repeating unit represented by the general formula (4) is less than 0.1 mol %, sensitivity does not become sufficient as a photoacid generator. Thus, another photoacid generator is used together. With this, it is not possible to sufficiently show high functionality of the sulfonic acid salt resin. Therefore, it is not preferable. Furthermore, even in the case of exceeding 90 mol %, it is possible to sufficiently show functionality as a photoacid generator. With this, it is not possible to show an advantage of containing a repeating unit having an acid labile group or a cross-liking group in the resin. Therefore, it is not preferable. On the other hand, in case that the sulfonic acid salt resin is a sulfonic acid salt resin containing a secondary repeating unit in addition to a repeating unit having an acid labile group or a crosslinking moiety and a repeating unit represented by the general formula (4), the secondary repeating unit is adjusted to 0.1-70 mol %, preferably 1-60 mol %, more preferably 10-50 mol %. It is preferable that the remainder is made to have a composition in proportion to a compositional ratio of a repeating unit having an acid labile group or a cross-linking moiety to a repeating unit represented by the general formula (4). If the secondary repeating unit is less than 0.1 mol %, it is difficult to adjust adhesion of the resist resin to substrate and etching resistance. Therefore, it is not preferable. If it exceeds 70 mol %, it is difficult to sufficiently show the function as an acid generator to be possessed by the sulfonic acid salt resin of the present invention or a positive-type or negative-type resist function. Therefore, it is not preferable.

As a sulfonic acid salt resin having both of a photoacid generator function and a positive-type or negative-type resist function, specifically, the ratio of a repeating unit represented by the general formula (4)/a repeating unit having an acid labile group or a cross-linking moiety is adjusted to 1-60 mol %/10-85 mol %, preferably 2-40 mol/10-70 mol %, more preferably 4-30 mol %/15-60 mol %. The remainder is made to be a secondary repeating unit. It is, however, not limited to this compositional range, as mentioned above.

As to molecular weight of the sulfonic acid salt resin of the present invention, in the case of making it function as a base resin too, mass average molecular weight determined by gel permeation chromatography (GPC) is 1,000 to 1,000,000, preferably 2,000 to 500,000. In the preparation of a resist composition, in the case of using a base resin other than the sulfonic acid salt resin, too, molecular weight of the sulfonic acid salt resin in terms of mass average molecular weight is 1,000 to 100,000, preferably 2,000 to 50,000. If mass average molecular weight is less than 1,000, it may diffuse and move in the resist film to diffuse until an unexposed section. This deteriorates resolution and lowers the effect as a sulfonic acid salt resin. If it exceeds 1,000,000, its solubility in solvent lowers. This makes it difficult to obtain a flat coating film of the resist. Therefore, it is not preferable. The degree of dispersion (MW/MN) is preferably 1.01-5.00, more preferably 1.01-4.00, particularly preferably 1.01-3.00, the most preferably 1.10-2.50.

As mentioned above, the sulfonic acid salt resin of the present invention may be a homopolymer or a copolymer with other monomers. By using a monomer having an acid labile group as another monomer, it is possible to obtain a sulfonic acid salt resin having a solubility change function upon exposure, usable for a positive-type resist composition. By using a monomer having a cross-linking moiety as another monomer, it is possible to obtain a sulfonic acid salt resin having solubility change function upon exposure, usable for a negative-type resist composition. As mentioned hereinafter, the monomer to be used for the copolymerization is not limited to such monomer having an acid labile group or a cross-linking moiety. For the sulfonic acid salt resin, it is possible to copolymerize various secondary monomers for the purpose of adjusting dry etching resistance, standard developing solution suitability, substrate adhesion, resist profile, and furthermore general necessary characteristics of resist, such as resolution power, heat resistance, sensitivity, etc.

<Secondary repeating unit> As a secondary repeating unit that can be combined with a repeating unit represented by the general formula (4) as a copolymerization component, there is preferably used a repeating unit formed by a cleavage of a polymerizable double bond contained in olefins, fluorine-containing olefins, acrylic esters, methacrylic esters, fluorine-containing acrylic esters, fluorine-containing methacrylic esters, norbornene compounds, fluorine-containing norbornene compounds, styrene compounds, fluorine-containing styrene compounds, vinyl ethers, and fluorine-containing vinyl ethers.

Of these copolymerization components, acrylic esters, methacrylic esters, fluorine-containing acrylic esters, fluorine-containing methacrylic esters, norbornene compounds, fluorine-containing norbornene compounds, vinyl ethers, and fluorine-containing vinyl ethers are preferable.

The olefin can be exemplified by ethylene and propylene. The fluoroolefin can be exemplified by vinyl fluoride, vinylidene fluoride, trifluoroethylene, chlorotrifluoroethylene, tetrafluoroethylene, hexafluoropropylene, and hexafluoroisobutene.

Furthermore, the acrylic esters or methacrylic esters can be used without particular limitation with respect to ester side chains. As known compounds are specified, it is possible to use alkyl esters of acrylic acid or methacrylic acid, such as methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylhexyl acrylate or methacrylate, lauryl acrylate or methacrylate, 2-hydroxyethyl acrylate or methacrylate, and 2-hydroxypropyl acrylate or methacrylate; acrylates or methacrylates containing ethylene glycol, propylene glycol and tetramethylene glycol groups; unsaturated amides such as acrylic amide, methacrylic amide, N-methylolacrylic amide, N-methylolmethacrylic amide and diacetoneacrylic amide; acrylonitrile, methacrylonitrile, alkoxysilane-containing vinyl silanes, acrylic or methacrylic esters, t-butyl acrylate or methacrylate, 3-oxocyclohexyl acrylate or methacrylate, adamantyl acrylate or methacrylate, alkyladamantyl acrylate or methacrylate, cyclohexyl acrylate or methacrylate, tricyclodecanyl acrylate or methacrylate, acrylates or methacrylates having cyclic structures such as lactone ring and norbornene ring, acrylic acid, methacrylic acid, and the like. Furthermore, as the above acrylate compounds containing an a-cyano group and as analogous compounds, it is also possible to use maleic acid, fumaric acid, maleic anhydride and the like.

The fluorine-containing acrylic ester or fluorine-containing methacrylic ester may be an acrylic ester or methacrylic ester having a fluorine atom or a fluorine atom-containing group at α-position of the acrylic group. For example, as a monomer in which a fluorine-containing alkyl group has been introduced into α-position, there is preferably used a monomer in which the above-mentioned non-fluoric acrylic ester or methacrylic ester has been provided at α-position with trifluoromethyl group, trifluoroethyl group, nonafluoro-n-butyl group or the like.

Furthermore, it may be an acrylic ester or methacrylic ester having a fluorine alkyl group that is a perfluoroalkyl group or a fluoroalkyl group as a group bonded to the ester moiety, or having a unit in which a cyclic structure and fluorine atom are coexistent in ester moiety. The cyclic structure is, for example, a fluorine-containing benzene ring, fluorine-containing cyclopentane ring, fluorine-containing cyclohexane ring, fluorine-containing cycloheptane ring or the like, in which a fluorine or trifluoromethyl group has been substituted. It is also possible to use an acrylic or methacrylic ester having an ester moiety that is a fluorine-containing t-butyl ester group. Of such units, as particularly representative ones are exemplified in the form of monomer, it is possible to cite 2,2,2-trifluoroethylacrylate, 2,2,3,3-tetrafluoropropylacrylate, 1,1,1,3,3,3-hexafluoroisopropylacrylate, heptafluoroisopropylacrylate, 1,1-dihydroheptafluoro-n-butylacrylate, 1,1,5-trihydrooctafluoro-n-pentylacrylate, 1,1,2,2-tetrahydrotridecafluoro-n-octylacrylate, 1,1,2,2-tetrahydroheptadecafluoro-n-decylacrylate, 2,2,2-trifluoroethylmethacrylate, 2,2,3,3-tetrafluoropropylmethacrylate, 1,1,1,3,3,3-hexafluoroisopropylmethacrylate, heptafluoroisopropylmethacrylate, 1,1-dihydroheptafluoro-n-butylmethacrylate, 1,1,5-trihydrooctafluoro-n-pentylmethacrylate, 1,1,2,2-tetrahydrotridecafluoro-n-octylmethacrylate, 1,1,2,2-tetrahydroheptadecafluoro-n-decylmethacrylate, perfluorocyclohexylmethylacrylate, perfluorocyclohexylmethylmethacrylate, etc.

The norbornene compounds and fluorine-containing norbornene compounds are norbornene monomers having a mononucleus or multinucleus structure. These can be used without particular limitations. Upon this, there are preferably used norbornene compounds obtained by a Diels-Alder addition reaction using an unsaturated compound such as allyl alcohol, fluorine-containing allyl alcohol, acrylic acid, α-fluoroacrylic acid, methacrylic acid, and all of the acrylic esters, methacrylic esters, fluorine-containing acrylic esters or fluorine-containing methacrylic esters, which are described in the present specification, and cyclopentadiene or cyclohexadiene.

Furthermore, it is also possible to use styrene compounds, fluorine-containing styrene compounds, vinyl ethers, fluorine-containing vinyl ethers, allyl ethers, vinyl esters, vinyl silanes, etc. Herein, as the styrene compounds and the fluorine-containing styrene compounds, it is possible to use hexafluoroacetone-added styrene compounds, styrene or hydroxystyrene prepared by replacing a hydrogen(s) with a trifluoromethyl group(s), and the above-mentioned styrene or fluorine-containing styrene compound in which a halogen, alkyl group or fluorine-containing alkyl group has been bonded to α-position, besides styrene, fluorinated styrene, hydroxystyrene, etc. The vinyl ethers and the fluorine-containing vinyl ethers may be alkyl vinyl ethers having alkyl groups such as methyl group and ethyl group or hydroxyalkyl groups such as hydroxyethyl group and hydroxybutyl group, and those prepared by partially or entirely replacing their hydrogen atoms with fluorine atoms. Furthermore, they may be cyclohexyl vinyl ether, cyclic vinyl ethers having a hydrogen atom(s) or a carbonyl bond(s) in the cyclic structures, and those in which hydrogen atoms of those cyclic vinyl ethers have partially or entirely been replaced with fluorine atoms. Furthermore, it is possible to use allyl ethers, vinyl esters and vinyl silanes without particular limitations as long as they are publicly known compounds.

The secondary repeating unit can contain in the molecule a moiety to generate an acid by a high-energy ray irradiation, a moiety to become an acid through decomposition by an acid catalyst, or a moiety to become low in solubility in alkali developing solutions by an acid catalyst. The moiety to generate an acid by a high-energy ray irradiation is a moiety that becomes an acid, such as sulfonic acid, through dissociation of an onium salt, iodonium salt, etc. of an acid, such as sulfonic acid by a high-energy ray. A repeating unit containing the same provides the copolymer with a function as an acid generator. The moiety to become an acid through decomposition by an acid catalyst is a bond, for example, an ester bond, to form an acid through decomposition using an acid as a catalyst. A repeating unit containing the same provides the copolymer with a positive-type, solubility change function upon exposure. The moiety to become low in solubility in alkali developing solutions by an acid catalyst is a moiety to form a cross-linking through a reaction with a cross-linking agent contained in the resist using an acid as a catalyst. A repeating unit containing the same provides the copolymer with a negative-type, solubility change function upon exposure.

<Secondary Repeating Unit Having a Photoacid Generator Function>

Although the polymerizable fluorine-containing sulfonic acid onium salt itself as a monomer of the present invention has a function of a photoacid generator, it is also possible to use a monomer (a polymerizable compound) having a function of a photoacid generator for the copolymerization.

As a moiety to generate an acid by light, it is possible to use one having a structure known as a moiety to generate an acid by light in photoacid generators which have been used until now for chemically amplified resists. For example, it can be exemplified by a sulfonic acid onium salt moiety, a carboxylic acid onium salt moiety, a sulfonamide acid onium salt moiety, and a carbonic acid onium salt moiety.

Of these, particularly, a repeating unit having a sulfonic acid onium salt moiety represented by the following general formula (6),

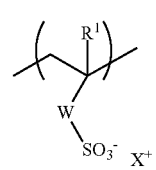

(6)

(In the formula, $R^1$ represents a hydrogen atom, a halogen atom, or a $C_{1-3}$ alkyl group or fluorine-containing alkyl group. W represents a bivalent linking group and has the same meaning as that of W in the above-mentioned general formula (1)) is preferably used.

As specific examples of W, those shown in the explanation of the general formula (1) can be shown again. As specific examples of $X^+$, those shown in the explanation of the general formula (2) can be shown again.

The anion moiety can be exemplified more specifically by the following structures.

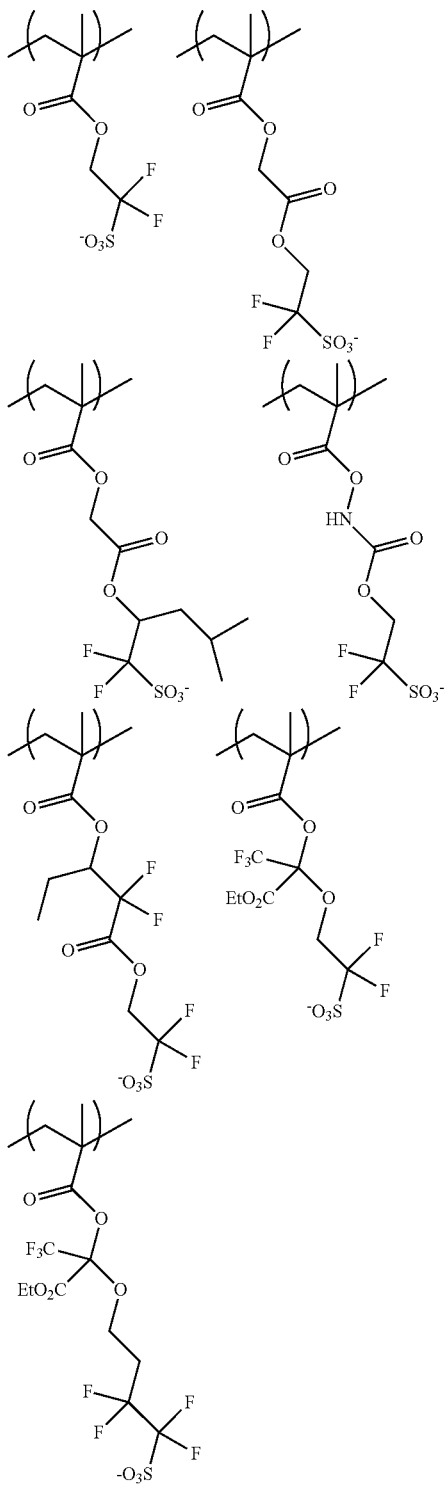

(i-33)

In the sulfonic acid salt resin containing a repeating unit formed by cleavage of a polymerizable double bond of a monomer having a photoacid generator function, the proportion of this repeating unit in the second repeating units is 0-90 mol %, preferably 2-80 mol %, more preferably 5-70%.

It is not always necessary to contain this repeating unit in the sulfonic acid salt resin. In case that this repeating unit exceeds 90 mol %, the range of adjustment of functions, such as adhesion to substrate and resist resistance, which should be carried by the second repeating units, becomes narrow. With this, the design of resist resin becomes difficult. Therefore, it is not preferable.

<A Repeating Unit Having a Positive-Type or Negative-Type Solubility Change Function Upon Exposure>

It is possible to obtain a sulfonic acid salt resin having a repeating unit having a positive-type or negative-type solubility change function upon exposure by copolymerizing a monomer having a positive-type or negative-type solubility change function upon exposure with the polymerizable fluorine-containing sulfonic acid onium salt represented by the general formula (2).

A sulfonic acid salt resin having a solubility change function upon exposure as a positive-type resist is a resin having a repeating unit having at a side chain a leaving moiety, such as carboxyl group or hydroxy group, protected with an acid-labile group. The main chain is composed of a repeating unit that is represented by —(CH$_2$—C(R$^1$))— (R$^1$ represents a C$_{1-3}$ alkyl group or fluorine-containing alkyl group or a cyano group) and that is formed by cleavage of a polymerizable double bond of a vinyl group, a substituted vinyl group, such as 1-methylvinyl group, 1-fluorovinyl group, 1-trifluoromethylvinyl group, or 1-cyanovinyl group, norbornenyl group, or the like. The main chain and the leaving moiety are bonded together via a linking group W. Using a linking group W$^1$, the linking group W is represented by (the main chain)-W$^1$—O-(the acid-labile group) or (the main chain)-W$^1$—C(=O)—O-(the acid-labile group). Herein, the main chain portion is represented by "(the main chain)", and the acid-labile group of the leaving moiety is represented by "(the acid-labile group)". The acid-labile group is a group that becomes an acid through elimination by action of an acid generated from a photoacid generator, etc. to generate a function of increasing the rate of dissolution of a resin containing the acid-labile group in alkali developing solutions. A partial structure containing an acid-labile group having such function, for example, an ester structure (—(C=O)OR$^{12}$, an alkoxycarbonyl group) or an ether structure (—O—R$^{12}$, an alkoxy group, R$^{12}$ represents an acid-labile group), may be referred to as an acid-decomposable group or a leaving moiety.

As a preferable one as a repeating unit having a positive-type solubility change function upon exposure, it is possible to cite a repeating unit represented by the following general formula (7) or (7-1).

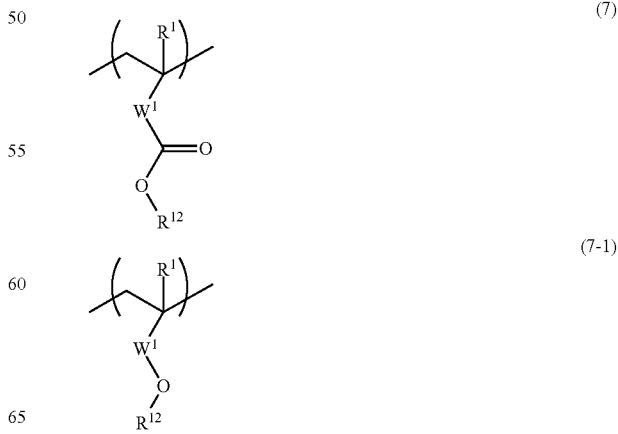

In the above formula, $R^1$ represents a hydrogen atom, a halogen atom or a $C_{1-3}$ alkyl group or fluorine-containing alkyl group. $W^1$ represents the above-mentioned bivalent linking group. $R^{12}$ represents an acid-labile group.

Furthermore, a sulfonic acid salt resin having a solubility change function upon exposure as a negative-type resist is a resin having a repeating unit having at a side chain a cross-linking moiety, such as hydroxy group or carboxyl group. The main chain is composed of a repeating unit that is represented by —($CH_2$—C($R^1$))— ($R^1$ represents a $C_{1-3}$ alkyl group or fluorine-containing alkyl group or a cyano group) and that is formed by cleavage of a polymerizable double bond of a vinyl group, a substituted vinyl group, such as 1-methylvinyl group, 1-fluorovinyl group, 1-trifluoromethylvinyl group, or 1-cyanovinyl group, norbornenyl group, or the like. The main chain and the cross-linking moiety are bonded together via a linking group W. Using a linking group $W^2$, the linking group W is represented by (the main chain)-$W^2$—(OH) or (the main chain)-$W^2$—C(=O)—(OH). Herein, the main chain portion is represented by "(the main chain)", and OH group of the cross-linking moiety is represented by "(OH)". This hydroxy group is an alcoholic hydroxy group. The alcohol hydroxy group is an almost neutral hydroxy group. Normally, it is not involved in resin dissolution in alkali solutions. It refers to a hydroxy group having a function of making an alkali-soluble resin component insoluble in alkali solutions through cross-linking by a hydroxy group-involved reaction of an ester bond, ether bond, ureido bond or the like with the after-mentioned cross-linking agent.

The linking groups W, $W^1$ and $W^2$ are explained.

In the repeating unit, the linking group $W^1$ for connecting the leaving moiety and the main chain in the positive-type one is a bivalent linking group that is a single one selected from the group consisting of a single bond, —($CR^{21}R^{22}$)n— (n represents an integer of 1-10), —O—, —C(=O)—, —C(=O)O— or —O—C(=O)—, a bivalent alicyclic hydrocarbon group, a bivalent aromatic hydrocarbon group, a bivalent heterocyclic group, a thioether group, an ester bond, an amide bond, a sulfonamide bond, a urethane bond, or a urea bond, or a combination of these.

Furthermore, the linking group $W^2$ for connecting the cross-linking moiety and the main chain in the negative-type one is a group of the linking group $W^1$, not containing any of a bivalent aromatic hydrocarbon group and an aromatic heterocyclic group.

Of these, as the linking group $W^1$ obtained by a combination, it is possible to cite —($CR^{21}R^{22}$)$_m$—C(=O)—O—($CR^{21}R^{22}$)$_n$—, —($CR^{21}R^{22}$)$_m$—C(=O)—O—($CR^{21}R^{22}$)$_n$-G-($CR^{21}R^{22}$)$_l$—, —($CR^{21}R^{22}$)$_m$—O—($CR^{21}R^{22}$)$_n$—, —($CR^{21}R^{22}$)$_m$—O—($CR^{21}R^{22}$)$_n$-G-(CRR$^{21}R^{22}$)$_l$—, —($CR^{21}R^{22}$)$_n$-G-($CR^{21}R^{22}$)$_l$—C(=O)—O—($CR^{21}R^{22}$)$_m$—, —($CR^{21}R^{22}$)$_n$-G-($CR^{21}R^{22}$)$_l$—O—($CR^{21}R^{22}$)$_m$—, etc. Herein, G is a cyclic group that is a bivalent alicyclic hydrocarbon group, a bivalent aromatic hydrocarbon group, or a bivalent hetero ring group. Each of l, m and n is an integer of 0-10. m is preferably 0. Each of l and n is preferably 0 or 1.

As the linking group $W^2$, it is possible to cite —($CR^{21}R^{22}$)$_m$—C(=O)—O—($CR^{21}R^{22}$)$_n$—, —($CR^{21}R^{22}$)$_m$—C(=O)—O—($CR^{21}R^{22}$)$_n$-G'-($CR^{21}R^{22}$)$_l$—, —($CR^{21}R^{22}$)$_m$—O—($CR^{21}R^{22}$)$_n$—, —($CR^{21}R^{22}$)$_m$—O—($CR^{21}R^{22}$)$_n$-G'-($CR^{21}R^{22}$)$_l$—, —($CR^{21}R^{22}$)$_n$-G'-($CR^{21}R^{22}$)$_l$—C(=O)—O—($CR^{21}R^{22}$)$_m$—, —($CR^{21}R^{22}$)$_n$-G'-($CR^{21}R^{22}$)$_l$—O—($CR^{21}R^{22}$)$_m$—, etc. Herein, G' is a cyclic group that is a bivalent alicyclic hydrocarbon group or a bivalent hetero ring group. Each of l, m and n is an integer of 0-10. m is preferably 0. Each of l and n is preferably 0 or 1.

Of this, the explanation of the substituted or substituted methylene group represented by —($CR^{21}R^{22}$)— is not repeated, since the same explanation of the substituted or substituted methylene group represented by the general formula (14) with respect to the linking group W can be applied.

The cyclic group represented by G is similar to the bivalent alicyclic hydrocarbon group, the bivalent aromatic hydrocarbon group, and the bivalent hetero ring group for constituting a main skeleton of the linking group $W^1$. Therefore, the explanation is not repeated.

Furthermore, the cyclic group represented by G' is similar to the bivalent alicyclic hydrocarbon group or the bivalent hetero ring group for constituting a main skeleton of the linking group $W^2$. Therefore, the explanation is not repeated.

More specifically, as the linking group W', it is possible to cite—(a single bond), —$CH_2$—, —$CH_2$—$CH_2$—, —$CH_2$-G-, -G-$CH_2$—, —$C_6H_4$—, —O—$C_6H_4$—, —C(=O)—O—$CH_2$—, —C(=O)—O—$CH_2$—$CH_2$—, —C(=O)—O-G-, —$CH_2$—C(=O)—O—$CH_2$—, —O—$CH_2$—, —O—$CH_2$—$CH_2$—, —$CH_2$—O—$CH_2$—, —O-G- and —C(=O)—O—($CR^{21}R^{22}$)$_2$—, or —$C_6H_4$—O—($CR^{21}R^{22}$)$_2$—, etc.

Herein, it is preferable that each of $R^{21}$ and $R^{22}$ is independently a hydrogen atom, a fluorine atom, an alkyl group, a substituted alkyl group, or an alicyclic hydrocarbon group. These may be ones in which at least one hydrogen atom has been replaced with a fluorine atom(s). Of these, as more preferable ones, it is possible to cite —C(=O)—O—$CH_2$—, —$C_6H_4$—, and —C(=O)—O—($CR^{21}R^{22}$)$_2$— wherein each of $R^{21}$ and $R^{22}$ is independently a hydrogen atom, a fluorine atom, a lower alkyl group, or a lower fluorine-containing alkyl group.

More specifically, as the linking group $W^2$, it is possible to cite—(a single bond), —$CH_2$—, —$CH_2$—$CH_2$—, —$CH_2$-G'-, -G'-, -G'-$CH_2$—, —C(=O)—O—$CH_2$—, —C(=O)—O—$CH_2$—$CH_2$—, —C(=O)—O-G'-, —$CH_2$—C(=O)—O—$CH_2$—, —O—$CH_2$—, —O—$CH_2$—$CH_2$—, and —$CH_2$—O—$CH_2$—, —O-G'- and/or —C(=O)—O—($CR^{21}R^{22}$)$_2$—, etc.

Herein, it is preferable that each of $R^{21}$ and $R^{22}$ is independently a hydrogen atom, a fluorine atom, an alkyl group, a substituted alkyl group, or an alicyclic hydrocarbon group. These may be ones in which at least one hydrogen atom has been replaced with a fluorine atom(s). Of these, as more preferable ones, it is possible to cite —C(=O)—O—, —C(=O)—O—$CH_2$—, —C(=O)—O-G'-, and —C(=O)—O—($CR^{21}R^{22}$)$_2$— wherein each of $R^{21}$ and $R^{22}$ is independently a hydrogen atom, a fluorine atom, a lower alkyl group, or a lower fluorine-containing alkyl group.

Furthermore, a repeating unit represented by the following general formula (13-1) can specifically be shown as an example, as an acid labile group is $R^{12}$ and as a main chain is —($CH_2$—C($R^1$))—.

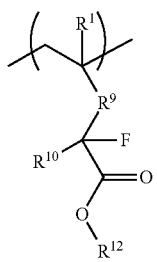

(13-1)

In the formula, $R^1$ represents a hydrogen atom, a halogen atom, or a $C_{1-3}$ alkyl group or fluorine-containing alkyl group. $R^{10}$ represents a hydrogen atom, a fluorine atom, or a fluorine-containing alkyl group. $R^{12}$ is preferably an acid labile group represented by any of the after-mentioned general formulas (AL-1) to (AL-5). $R^9$ is a bivalent linking group. —$R^9$—($CR^{10}F$)— corresponds to the above-mentioned $W^1$. Thus, the same explanation of the above-mentioned linking group $W^1$ is applied.

<Acid labile group> The acid labile group in the sulfonic acid salt resin having a solubility change function upon exposure of the present invention is an acid labile group represented by any of the following general formulas (AL-1) to (AL-5).

$$R^{X1}\text{—O—C}(\text{=O})\tag{AL-1}$$

In the general formula (AL-1), $R^{X1}$ represents a $C_{1-4}$ alkyl group with an optional substituent, a $C_{3-30}$ alicyclic hydrocarbon group with an optional substituent, or a $C_{6-14}$ aryl group with an optional substituent.

$$R^{X1}\text{—O—CHR}^{X2}\text{—}\tag{AL-2}$$

In the general formula (AL-2), $R^{X1}$ has the same meaning as that of $R^{X1}$ in the above-mentioned general formula (AL-1). $R^{X2}$ represents a hydrogen atom, a $C_{1-4}$ alkyl group with an optional substituent, a $C_{3-30}$ alicyclic hydrocarbon group with an optional substituent, a $C_{1-6}$ alkoxy group with an optional substituent, a $C_{2-4}$ alkenyl group with an optional substituent, a $C_{6-14}$ aryl group with an optional substituent, or a $C_{7-20}$ aralkyl group with an optional substituent.

$$CR^{X3}R^{X4}R^{X5}\tag{AL-3}$$

In the general formula (AL-3), $R^{X3}$, $R^{X4}$ and $R^{X5}$ may be the same or different. They represent $C_{1-4}$ alkyl groups with an optional substituent(s), $C_{3-30}$ alicyclic hydrocarbon groups with an optional substituent(s), $C_{2-4}$ alkenyl groups with an optional substituent(s), $C_{6-14}$ aryl groups with an optional substituent(s), or $C_{7-20}$ aralkyl groups with an optional substituent(s). Furthermore, two groups of $R^{X3}$ to $R^{X5}$ may be bonded to form a ring.

$$\text{SiR}^{X3}R^{X4}R^{X5}\text{—}\tag{AL-4}$$

In the general formula (AL-4), $R^{X3}$, $R^{X4}$ and $R^{X5}$ have the same meanings as those of $R^{X3}$, $R^{X4}$ and $R^{X5}$ in the general formula (AL-3).

$$R^{X1}\text{—C}(\text{=O})\text{—}\tag{AL-5}$$

In the general formula (AL-5), $R^{X1}$ has the same meaning as that of $R^{X1}$ in the above-mentioned general formula (AL-1).

In the general formula (AL-5), $R^{X1}$ has the same meaning as that of $R^{X1}$ in the above-mentioned general formula (AL-1).

In the above-mentioned general formulas (AL-1) to (AL-5), $R^{X1}$, $R^{X2}$, $R^{X3}$, $R^{X4}$ and $R^{X5}$ represent monovalent organic groups explained in the following. Of these, (AL-1), (AL-2) and (AL-3) function as a chemically amplified type. Therefore, they are particularly preferable to be used as a resist composition applied to a pattern forming method in which exposure is conducted with a high energy ray.

$R^{X1}$ represents an alkyl group, an alicyclic hydrocarbon group, or an aryl group. $R^{X2}$ represents a hydrogen atom, an alkyl group, an alicyclic hydrocarbon group, an alkenyl group, an aralkyl group, an alkoxy group or an aryl group. $R^{X3}$, $R^{X4}$ and $R^{X5}$ may be the same or different and represent alkyl groups, alicyclic hydrocarbon groups, alkenyl groups, aralkyl groups, or aryl groups. Furthermore, two groups of $R^{X3}$ to $R^{X5}$ may be bonded to form a ring.

In the case of using an ArF excimer laser as a light source for exposure, as the acid labile group, it is possible to cite as preferable ones tertiary alkyl groups such as tert-butyl group and tert-amyl group, alkoxyethyl groups such as 1-ethoxyethyl group, 1-butoxyethyl group, 1-isobutoxyethyl group and 1-cyclohexyloxyethyl group, and alkoxymethyl groups such as methoxymethyl group and ethoxymethyl group, and the above-mentioned acid labile groups containing alicyclic hydrocarbon groups such as adamantyl group and isobornyl group, and acid labile groups containing lactones, etc.

As a repeating unit represented by the general formula (13-1), specifically, it is possible to cite the following ones as particularly preferable ones. Furthermore, it is also preferable to combine these repeating units with other secondary repeating units.

(i-34)

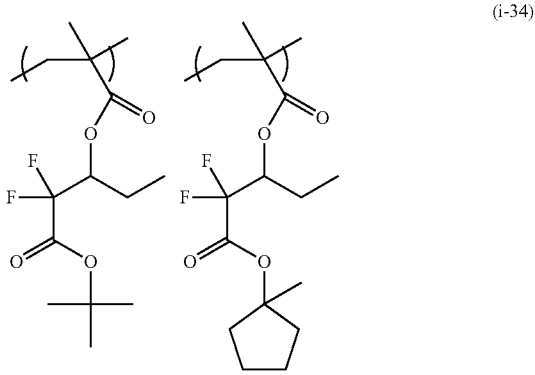

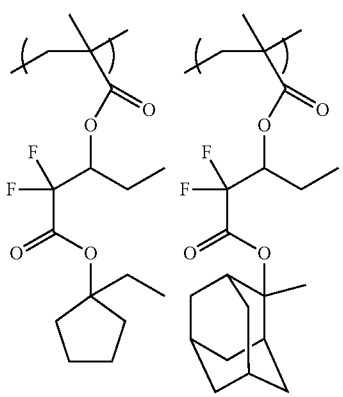

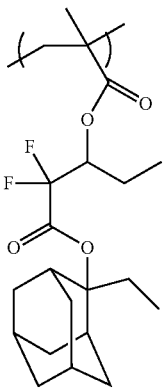

In the sulfonic acid salt resin, as a secondary repeating unit, a repeating unit represented by the following general formula (8) is preferably used.

(8)

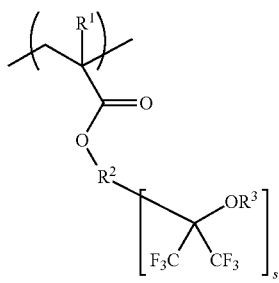

In the general formula (8), $R^1$ represents a hydrogen atom, a halogen atom or a $C_{1-3}$ alkyl group or fluorine-containing alkyl group. $R^2$ is a substituted or unsubstituted aliphatic hydrocarbon group, a substituted or unsubstituted aromatic group, or a bivalent organic group obtained by linking a plurality of them. In $R^2$, any number of hydrogen atoms may be replaced with a fluorine atom(s). $R^2$ may contain an ether bond(s) or a carbonyl group(s). $R^3$ is a hydrogen atom, a substituted or unsubstituted $C_{1-25}$ aliphatic hydrocarbon group, or a substituted or unsubstituted $C_{1-25}$ aromatic hydrocarbon group. In $R^3$, any number of hydrogen atoms may be replaced with a fluorine atom(s). $R^3$ may contain an ether bond(s) or a carbonyl group(s). Furthermore, s represents an integer of 2-8.

As $R^1$ of the general formula (8), the halogen atom can be exemplified by fluorine, chlorine, bromine, etc., the $C_{1-3}$ alkyl group can be exemplified by methyl group, ethyl group, propyl group, isopropyl group, etc., and the $C_{1-3}$ fluorine-containing alkyl group can be exemplified by those in which hydrogen atoms of the alkyl groups have partially or entirely been replaced with a fluorine atom(s). In particular, the fluorine-containing alkyl group can be exemplified by trifluoromethyl group —$CF_3$, trifluoroethyl group —$CH_2CF_3$, 1,1,1,3,3,3-hexafluoroisopropyl group, heptafluoroisopropyl group, etc. Of these, it is possible to cite a hydrogen atom, a fluorine atom, a methyl group, and a trifluoromethyl group as particularly preferable ones.

Furthermore, $R^2$ of the general formula (8) is a substituted or unsubstituted aliphatic hydrocarbon group, a substituted or unsubstituted aromatic group, or a bivalent organic group obtained by linking a plurality of them. In $R^2$, any number of hydrogen atoms may be replaced with a fluorine atom(s). The aliphatic hydrocarbon group may be any of straight chain, branched or cyclic one. As $R^2$, it is possible to cite, for example, straight chain or branched, aliphatic hydrocarbon groups, such as methylene, ethylene, isopropylene, and t-butylene, cyclic aliphatic hydrocarbon groups, such as cyclobutylene, cyclohexylene, bivalent norbornene, and bivalent adamantane group, aromatic groups, such as phenylene group, bivalent groups in which a hydrogen atom(s) contained in these has been replaced with any substituent(s), and bivalent groups in which a carbon atom(s) contained in those has been replaced with an ether bond(s) or a carbonyl group(s). It can be used with no limitation in its structure.

Of the structure represented by the general formula (8), as particularly preferable structures, repeating units represented by the following general formulas (8-1), (9) and (10) can be shown as examples.

(8-1)

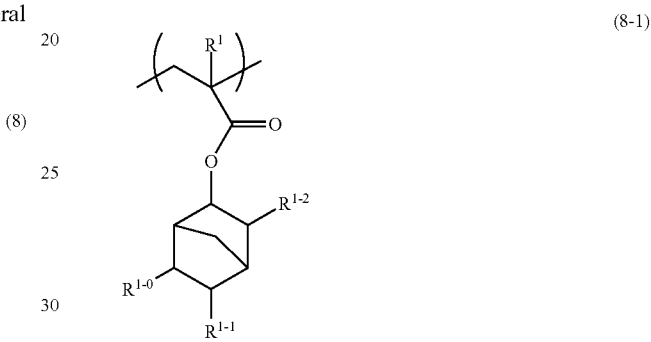

(9)

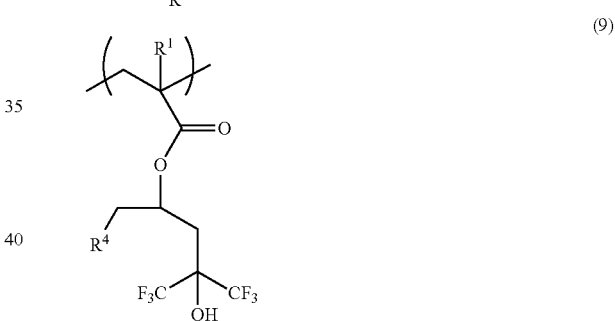

(10)

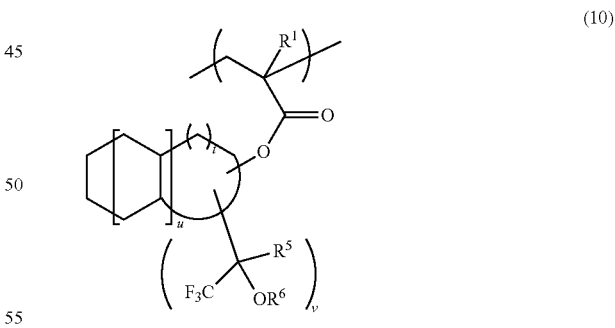

In the general formula (8-1), $R^1$ has the same meaning as $R^1$ in the general formula (8). Any one of $R^{1-0}$, $R^{1-1}$ and $R^{1-2}$ is a group of $CF_3C(CF_3)(OH)CH_2$—, and the other two are hydrogen atoms.

In the general formula (9), $R^1$ has the same meaning as $R^1$ in the general formula (8). $R^4$ is a hydrogen atom or a $C_{1-6}$ alkyl group or fluorine-containing alkyl group. Specifically, it can be exemplified by methyl group, ethyl group, n-propyl group, isopropyl group, n-butyl group, sec-butyl group, tert-butyl group, cyclopentyl group, cyclohexyl group, fluoromethyl group, difluoromethyl group, trifluoromethyl group, or perfluoroethyl group, etc. In the general formula (10), $R^1$ has the same meaning as $R^1$ in the general formula (8). $R^5$ represents a methyl group or a trifluoromethyl group. $R^6$ is a hydrogen atom, a substituted or unsubstituted $C_{1-25}$ aliphatic hydrocarbon group, or a substituted or unsubstituted $C_{1-25}$ aromatic hydrocarbon group and may partially contain a fluorine atom(s), an oxygen atom(s) (an ether bond(s)), or a carbonyl group(s). u represents an integer of 0-2. t and v represent any integers to satisfy "$v \leq t+2$". In case that $R^5$ and $R^6$ are in plural number (in case that v is 2 or greater), $R^5$ and $R^6$ may respectively be the same or different. As $R^6$, a hydrogen atom is particularly preferable.

A substituted or unsubstituted $C_{1-25}$ aliphatic hydrocarbon group, or a substituted or unsubstituted $C_{1-25}$ aromatic hydrocarbon group, which is usable as $R^6$ in the general formula (10), can be exemplified by methyl group, ethyl group, propyl group, isopropyl group, cyclopropyl group, n-propyl group, sec-butyl group, tert-butyl group, n-pentyl group, cyclopentyl group, sec-pentyl group, neopentyl group, hexyl group, cyclohexyl group, ethylhexyl group, norbornel group, adamantyl group, vinyl group, allyl group, butenyl group, pentenyl group, ethynyl group, phenyl group, benzyl group, 4-methoxybenzyl group, etc., and those in which hydrogen atoms of these groups have partially or entirely been replaced with a fluorine atom(s) are also fine. Furthermore, as those having oxygen atom, it is possible to mention alkoxycarbonyl group, acetal group, acyl group, etc. The alkoxycarbonyl group can be exemplified by tert-butoxycarbonyl group, tert-amyloxycarbonyl group, methoxycarbonyl group, ethoxycarbonyl group, i-propoxycarbonyl group, etc. As the acetal group, it is possible to mention chain-like ethers of methoxymethyl group, methoxyethoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group and ethoxyisobutyl group, and cyclic ethers such as tetrahydrofuranyl group and tetrahydropyranyl group. As the acyl group, it is possible to cite acetyl group, propionyl group, butyryl group, heptanoyl group, hexanoyl group, valeryl group, pivaloyl group, isovaleryl group, lauryloyl group, myristoyl group, palmytoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, isonicotinoyl group, etc. Furthermore, it is also possible to cite those in which hydrogen atoms of the above-mentioned groups have partially or entirely been replaced with a fluorine atom(s).

As the repeating unit represented by the general formula (9) or the general formula (10), specifically, the following ones can be cited as particularly preferable ones. Furthermore, it is also preferable to combine these repeating units and other secondary repeating units.

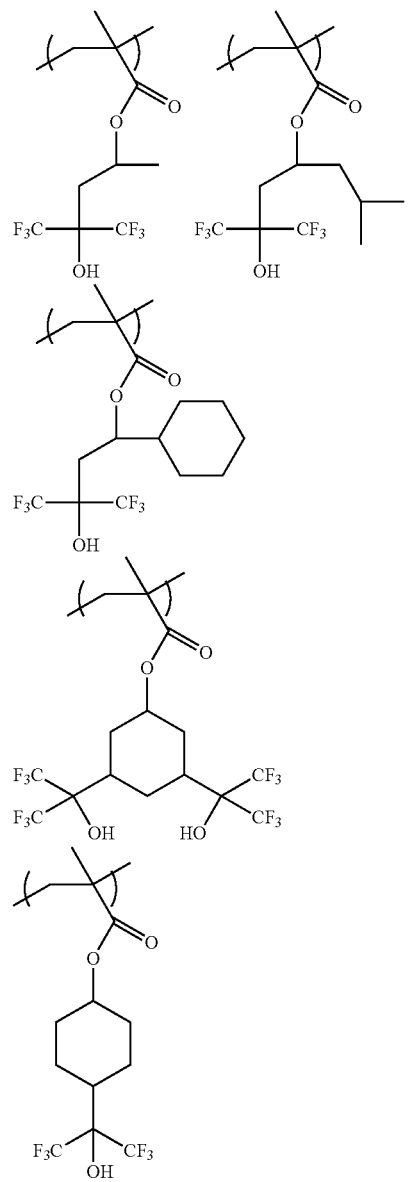

(i-35)

Furthermore, in the sulfonic acid salt resin, as a secondary repeating unit, a repeating unit represented by the following general formula (11) is preferably used.

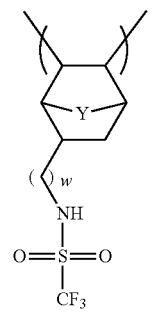

(11)

In the general formula (11), Y represents any of —CH$_2$—, —O—, and —S—. r represents an integer of 2-6.

As a repeating unit represented by the general formula (11), specifically, the following ones can be cited as particularly preferable ones. Furthermore, it is also preferable to combine these repeating units and other secondary repeating units.

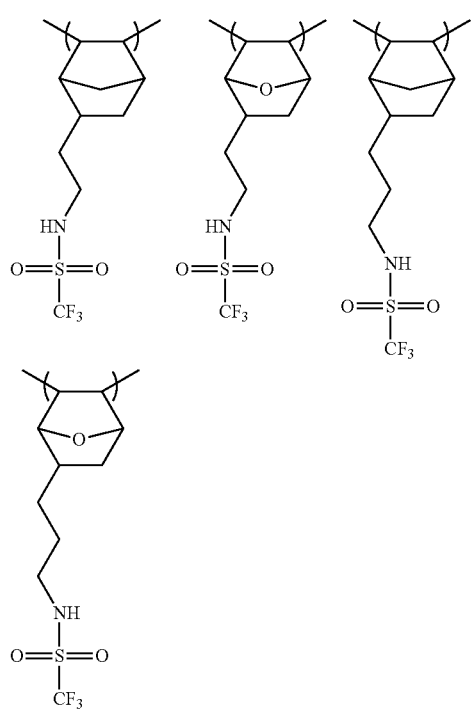

(i-36)

Furthermore, in the sulfonic acid salt resin, as a secondary repeating unit, a repeating unit represented by the following general formula (12) is preferably used.

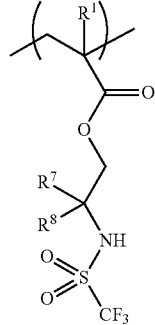

(12)

In the general formula (12), R$^1$ has the same meaning as that of R$^1$ in the general formula (8). Each of R$^7$ and R$^8$ is independently a hydrogen atom, a substituted or unsubstituted C$_{1-25}$ straight-chain, branched or cyclic aliphatic hydrocarbon group, or a substituted or unsubstituted C$_{1-25}$ aromatic hydrocarbon group, is that any number of hydrogen atoms may be replaced with a fluorine atom(s), and may contain an ether bond(s), or a carbonyl group(s). Specifically, substituents shown as examples of R$^6$ in the above-mentioned general formula (10) can be shown again as its examples.

As a repeating unit represented by the general formula (12), specifically, the following ones can be cited as particularly preferable ones. Furthermore, it is also preferable to combine these repeating units and other secondary repeating units.

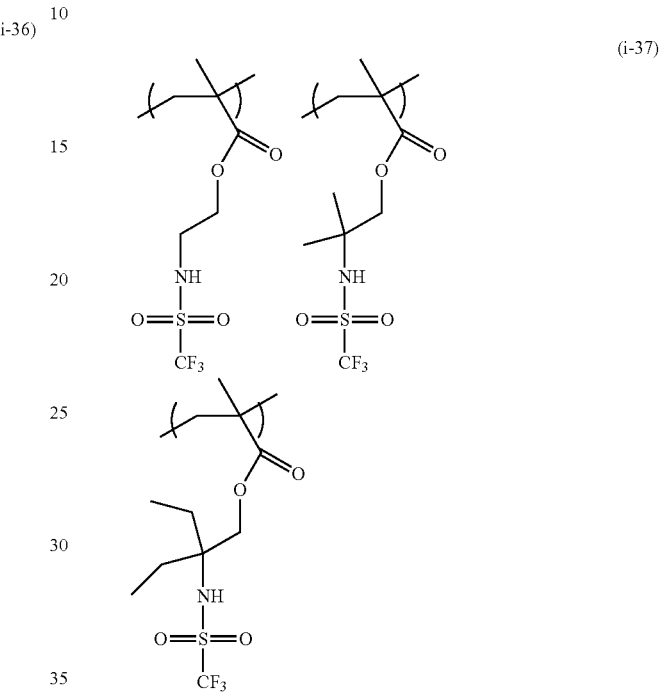

(i-37)

Furthermore, in the sulfonic acid salt resin, as a secondary repeating unit, a repeating unit represented by the following general formula (13) is preferably used.

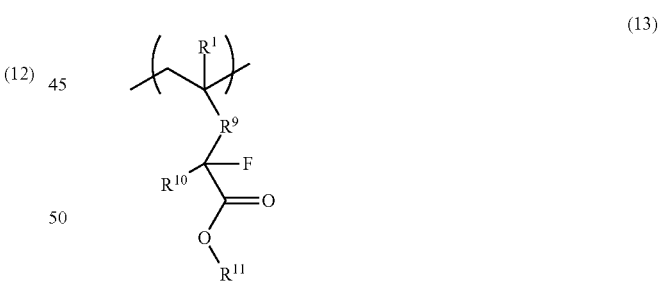

(13)

In the general formula (13), R$^1$ has the same meaning as that of R$^1$ in the general formula (8). The explanation of R$^6$ in the above-mentioned general formula (10) is applied to that of R$^1$. R$^9$ is a bivalent linking group, and the explanations of the above-mentioned linking groups W and W$^1$ are applied to that of R$^9$. Furthermore, R$^{10}$ is a hydrogen atom, a fluorine atom, or a fluorine-containing alkyl group. Such fluorine-containing alkyl group is not particularly limited, but is one having a carbon number of 1-12, preferably one having a carbon number of 1-3. It is possible to cite trifluoromethyl group, pentafluoroethyl group, 2,2,2-trifluoroethyl group, n-heptafluoropropyl group, 2,2,3,3,3-pentafluoropropyl group, 3,3,3-trifluoropropyl group, 1,1,1,3,3,3- hexafluoroisopropyl group, etc. $R^{10}$ is more preferably a fluorine atom or a trifluoromethyl group.

(i-38)

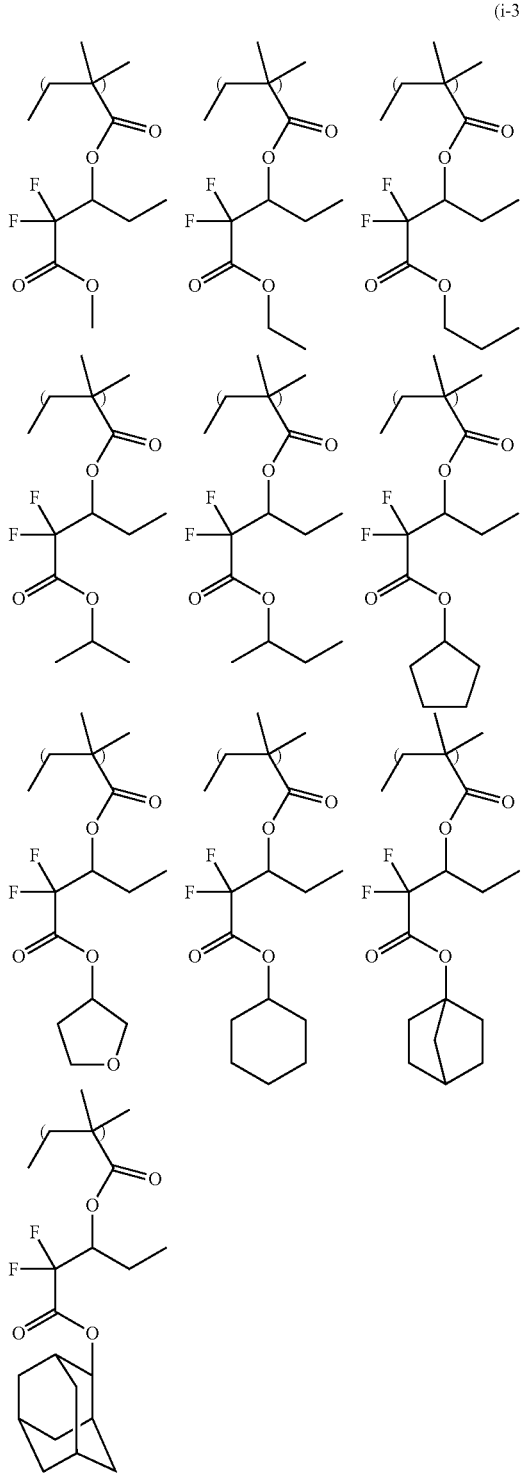

[Polymerization of the sulfonic acid salt resin] The method for polymerizing a resin having a repeating unit represented by the general formula (4) of the present invention is not particularly limited, as long as it is a method used in general. Radical polymerization, ion polymerization, etc. are preferable. In some cases, it is also possible to use coordination anion polymerization, living anion polymerization, cation polymerization, ring-opening metathesis polymerization, vinylene polymerization, vinyl addition, etc. As each polymerization method, it is possible to apply a publicly-known method. In the following, a method by radical polymerization is explained, but it is possible to easily conduct a polymerization by other methods with reference to publicly-known publications, etc.

The radical polymerization may be conducted by a publicly-known polymerization method, such as bulk polymerization, solution polymerization, suspension polymerization or emulsion polymerization, in the presence of a radical polymerization initiator or radical initiating source, with a batch-wise, half-continuous or continuous operation.

The radical polymerization initiator is not particularly limited. As the examples, azo compounds, peroxide compounds and redox compounds are cited. In particular, azobisisobutyronitrile, dimethyl 2,2-azobis(2-methylpropionate), tert-butylperoxypivalate, di-tert-butylperoxide, i-butyrylperoxide, lauroylperoxide, succinic acid peroxide, dicinnamylperoxide, di-n-propylperoxydicarbonate, tert-butylperoxyallyl monocarbonate, benzoyl peroxide, hydrogen peroxide, ammonium persulfate, etc. are preferable.

The reaction vessel used in the polymerization reaction is not particularly limited. Furthermore, a polymerization solvent may be used in the polymerization reaction. As the polymerization solvent, one that does not interfere with the radical polymerization is preferable. Representative ones are ester solvents such as ethyl acetate and n-butyl acetate, ketone solvents such as acetone and methyl isobutyl ketone, hydrocarbon solvents such as toluene and cyclohexane, alcohol solvents such as methanol, isopropyl alcohol and ethylene glycol monomethyl ether, etc. Furthermore, it is also possible to use solvents such as water, ethers, cyclic ethers, fluorohydrocarbons, and aromatics. These solvents can be used singly or in a mixture of at least two types. Furthermore, it may be accompanied in use with a molecular weight adjusting agent such as mercaptan. The reaction temperature of the copolymerization reaction is suitably changed, depending on the radical polymerization initiator or radical polymerization initiating source. Normally, 20-200° C. is preferable. In particular, 30-140° C. is preferable.

As a method of removing an organic solvent or water from the obtained solution or dispersion of the fluorine-containing polymer compound, a method, such as reprecipitation, filtration, or heating distillation under reduced pressure, is possible.

[Resist composition] The resin having a repeating unit represented by the general formula (4) of the present invention is used as a resist composition formed of a solution prepared by adding other components. This sulfonic acid salt resin functions as a photoacid generator. Of this, a sulfonic acid salt resin additionally having a repeating unit having an acid labile group or a cross-linking moiety can be used even singly as a chemically amplified resist without separately adding a resin (base resin) having a repeating unit having an acid labile group or a cross-linking moiety. Furthermore, in the case of a resin having a repeating unit represented by the general formula (4) and not having any of a repeating unit having an acid labile group or a cross-linking moiety, a resist composition is prepared by containing a base resin as an essential component. Besides solvent, it is possible to contain various additives normally used for resist compositions, such as additional resins, quencher, dissolution suppressing agent, plasticizer, stabilizer, coloring agent, surfactant, tackifier, leveling agent, defoaming agent, compatibility enhancing agent, adhesion enhancing agent, antioxidant, etc. In the case of a negative-type resist composition, it is possible to further contain various additives, such as crosslinking agent, basic compounds, etc. As these additives, it is possible to suitably use publicly-known ones, besides those explained in the following.

<Base resin> The base resin is a resin that has an acid labile group or a cross-linking moiety and has a positive-type or negative-type resist function. The above-mentioned sulfonic acid salt resin having a solubility change function upon exposure may take a mode of the base resin.

The base resin used for a positive-type resist composition is a resin having at its side chain a leaving moiety, such as a carboxyl group or hydroxy group, protected with an acid labile group. The main chain is composed of a repeating unit formed by cleavage of a polymerizable double bond of acrylic acid, methacrylic acid, α-trifluoromethylacrylic acid, vinyl group, aryl group, norbornene group, etc.

The base resin used for a negative-type resist composition is a resin having at its side chain a cross-linking moiety, such as a hydroxy group or a carboxyl group. The main chain is composed of a repeating unit formed by cleavage of a polymerizable double bond of acrylic acid, methacrylic acid, α-trifluoromethylacrylic acid, vinyl group, aryl group, norbornene group, etc.

In many cases, the base resin is in the form of a copolymer in order to adjust characteristics of the resist. Various resins are known. As to their copolymerization components, acid labile group, cross-linking moiety, linking group for connecting a polymer main chain and an acid labile group, etc., each explanation mentioned above of the present specification can be applied. A particularly preferable copolymerization component in the base resin is a monomer having a lactone ring. It is useful for improving adhesion of the resist to substrate.

These base resins can contain a repeating unit represented by the general formula (4).

As to molecular weight of the base resin, mass average molecular weight determined by gel permeation chromatography (GPC) is 1,000 to 1,000,000, preferably 2,000 to 500,000. If mass average molecular weight is less than 1,000, strength of the coating film is insufficient. If it exceeds 1,000,000, its solubility in solvent lowers. This makes it difficult to obtain a flat coating film. Therefore, it is not preferable.

The degree of dispersion (MW/MN) is preferably 1.01-5.00, more preferably 1.01-4.00, particularly preferably 1.01-3.00, the most preferably 1.10-2.50.

<Additives, etc.> In the case of a negative-type resist composition, it is possible to freely select a cross-linking agent used for chemically amplified negative-type resist compositions from publicly-known ones and use that.

As the cross-linking agent, it is possible to cite compounds obtained by reacting an amino group-containing compound, such as melamine, acetoguanamine, benzoguanamine, urea, ethylene urea, propylene urea or glycoluril, with formaldehyde or with formaldehyde and lower alcohol to replace a hydrogen atom of the amino group with a hydroxymethyl or lower alkoxymethyl group. Herein, those obtained by using melamine are referred to melamine series crosslinking agent. Those obtained by using urea are referred to as urea series crosslinking agent. Those obtained by using alkylene urea, such as ethylene urea or propylene urea, are referred to as alkylene urea series crosslinking agent. Those obtained by using glycoluril are referred to as glycoluril series crosslinking agent. The crosslinking agent is preferably at least one selected from these crosslinking agents. In particular, glycoluril series crosslinking agent is preferable.

As melamine series crosslinking agent, it is possible to cite hexamethoxymethylmelamine, hexaethoxymethylmelamine, hexapropoxymethylmelamine, hexabutoxybutylmelamine, etc. In particular, hexamethoxymethylmelamine is preferable.

As urea series crosslinking agent, it is possible to cite bismethoxymethyl urea, bisethoxymethyl urea, bispropoxymethyl urea, bisbutoxymethyl urea, etc. In particular, bismethoxymethyl urea is preferable.

As alkylene urea series crosslinking agent, it is possible to cite, for example, ethylene urea series crosslinking agents, such as mono and/or dihydroxymethylated ethylene urea, mono and/or dimethoxymethylated ethylene urea, mono and/or diethoxymethylated ethylene urea, mono and/or dipropoxymethylated ethylene urea, and mono and/or dibutoxymethylated ethylene urea; propylene urea series crosslinking agents, such as mono and/or dihydroxymethylated propylene urea, mono and/or dimethoxymethylated propylene urea, mono and/or diethoxymethylated propylene urea, mono and/or dipropoxymethylated propylene urea, and mono and/or dibutoxymethylated propylene urea; 1,3-di (methoxymethyl)-4,5-dihydroxy-2-imidazolidinone, 1,3-di (methoxymethyl)-4,5-dimethoxy-2-imidazolidinone, etc.

As glycoluril series crosslinking agent, it is possible to cite mono, di, tri and/or tetrahydroxymethylated glycoluril, mono, di, tri and/or tetramethoxymethylated glycoluril, mono, di, tri and/or tetraethoxymethylated glycoluril, mono, di, tri and/or tetrapropoxymethylated glycoluril, mono, di, tri and/or tetrabutoxymethylated glycoluril, etc.

The content of the crosslinking agent component as a whole in the negative-type resist composition of the present invention is preferably 3-30 parts by mass, more preferably 3-25 parts by mass, still more preferably 5-20 parts by mass, relative to 100 parts by mass of the base resin. If the crosslinking agent component is less than 3 parts by weight, the crosslink formation does not proceed sufficiently. Thus, a good resist pattern is not obtained. If it exceeds 30 parts by mass, the resist composition may become inferior in storage stability. Thus, sensitivity may deteriorate over time.

Into a resist composition of the present invention, it is preferable to mix a basic compound as a quencher, or in order to improve resist pattern shape, post exposure stability, etc., or as an optional component.

As this basic compound component, it is possible to use publicly-known ones, for example, primary, secondary and tertiary aliphatic amines, aromatic amines, hetero ring amines, nitrogen-containing compounds having a hydroxyphenyl group, alcoholic nitrogen-containing compounds, amide derivatives, etc. Of these, secondary aliphatic amines, tertiary aliphatic amines, aromatic amines, and hetero ring amines are preferable.

As the aliphatic amine, it is possible to cite an alkyl amine or alkylalcohol amine, in which at least one hydrogen atom of ammonia ($NH_3$) has been replaced with an alkyl group or hydroxyalkyl group having a carbon number of 12 or less. As its specific examples, it is possible to cite monoalkyl amines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; alkylalcohol amines such as diethanolamine, triethanolamine, diisopropanolamine, triisopropanolamine, di-n-octanolamine, and tri-n-octanolamine. Of these, alkylalcohol amines and trialkylamines are preferable, and alkylalcohol amines are more preferable. Of alkylalcohol amines, triethanolamine and triisopropanolamine are more preferable.

Furthermore, as other basic compounds, for example, the following compounds can be cited. As the aromatic amines and the hetero ring amines, it is possible to cite, for example, aniline derivatives, such as aniline, N-methylaniline, N-ethylaniline, N-propylaniline, N,N-dimethylaniline, 2-methylaniline, 3-methylaniline, 4-methylanilinie, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine; hetero ring amines, such as 1,5-diazabicyclo[4.3.0]non-5-ene, 1,8-diazabicyclo[5.4.0]undec-7-ene, 1,4-diazabicyclo[2.2.2]octane, 4-dimethylaminopyridine, hexamethylenetetramine, and 4,4-dimethylimidazoline; hindered amines such as bis(1,2,2,6,6-pentamethyl-4-piperidyNebacate; alcoholic nitrogen-containing compounds, such as 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperadine, and 1-[2-(2-hydroxyethoxyl)ethyl]piperadine.

These may be used singly. Alternatively, at least two kinds may be combined for use.

The basic compound component is used normally in a range of 0.01-5 parts by mass, relative to 100 parts by mass of the base resin.

In a negative-type resist composition of the present invention, it is possible to contain an organic carboxylic acid, or phosphorus oxoacid or its derivative, for the purpose of preventing the sensitivity deterioration caused by mixing of the basic compound component, or improving the resist pattern shape, post exposure stability, etc., or as an optional component. These can be used with the basic compound component. Alternatively, any one kind can also be used.

As the organic carboxylic acid, for example, malonic acid, citric acid, malic acid, succinic acid, benzoic acid, salicylic acid, etc. are preferable.

As the phosphorus oxoacid or its derivative, it is possible to cite phosphoric acid or its derivatives like esters, such as phosphoric acid, di-n-butyl phosphate and diphenyl phosphate, phosphonic acid and its derivatives like esters, such as phosphonic acid, dimethyl phosphonate, di-n-butyl phosphonate, phenyl phosphonate, diphenyl phosphonate and dibenzyl phosphonate, and phosphinic acid and its derivatives like esters, such as phosphinic acid and phenyl phosphinate. Of these, phosphonic acid is particularly preferable.

<Solvent> As a method for forming a resist composition of the present invention into a thin film, for example, it is possible to use a film-forming method by dissolving in an organic solvent, applying and drying. The organic solvent to be used is not particularly limited, as long as the sulfonic acid salt resin is soluble. It is possible to use ketones such as acetone, 2-butanone, cyclohexanone, methyl isoamyl ketone, and 2-heptanone; polyhydric alcohols and their derivatives such as ethylene glycol, ethylene glycol monoacetate, diethylene glycol, diethylene glycol monoacetate, propylene glycol, propylene glycol monoacetate, propylene glycol monomethyl ether, propylene glycol monomethyl ether acetate (PGMEA), dipropylene glycol, or monomethyl ether, monoethyl ether, monopropyl ether, monobutyl ether or monophenyl ether of dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate, and ethyl ethoxypropionate; aromatic solvents such as xylene and toluene; fluorine-containing solvents such as chlorofluorocarbons, alternatives for chlorofluorocarbons, perfluoro compounds, and hexafluoroisopropyl alcohol; terpene-series petroleum naphtha solvents, which are high-boiling-point weak solvents, for improving coatability; and paraffin-series solvents. These may be used singly. Alternatively, at least two kinds may be mixed together for use.

<Surfactant> It is preferable that the resist composition of the present invention contains a surfactant, preferably either or at least two kinds of fluorine-series and/or silicon-series surfactant (a fluorine-series surfactant and a silicon-series surfactant, a surfactant containing both of fluorine atom and silicon atom).

By containing the surfactant in the resist composition of the present invention, when an exposure light source of 250 nm or shorter, particularly that of 220 nm or shorter is used, or when the line width of pattern is further narrow, it is particularly effective and becomes possible to provide a resist pattern with good sensitivity and resolution, adhesion and few development defects.

<Acid generator> In the resist composition of the present invention, it is possible to use a normal type photoacid generator, which is not in the form of resin, together with the sulfonic acid salt resin. As the photoacid generator, it is possible to select and use any of those used as acid generators of chemically amplified resists. As examples of such acid generator, it is possible to cite bissulfonyldiazomethanes, nitrobenzyl derivatives, onium salts, halogen-containing triazine compounds, cyano group-containing oximesulfonate compounds, other oximesulfonate compounds, etc. These photoacid generators may be used singly. Alternatively, at least two kinds may be combined for use. Its content is selected normally in a range of 0.5-20 parts by mass relative to 100 parts by mass of the resist composition. If this amount is less than 0.5 parts by mass, the image forming property is insufficient. If exceeding 20 parts by mass, it is difficult to form a homogeneous solution, causing a tendency of lowering of storage stability. Therefore, they are not preferable. Of 100 parts by mass of the photoacid generator in total, the sulfonic acid salt resin of the present invention is 1-100 parts by mass, preferably 10-100 parts by mass, more preferably 30-100 parts by mass.

<Additional resins> Additional resins to be added to the resist composition for various purposes are not particularly limited, as long as they are resins that are soluble in the solvent used and miscible with other components constituting the resist composition. They function as plasticizer, stabilizer, tackifier, leveling agent, antifoaming agent, compatibility enhancing agent, adhesion enhancing agent, etc.

[Pattern forming method] A resist composition of the present invention can be used in a resist pattern forming method of a conventional photoresist technique. That is, firstly, a solution of the resist composition is applied onto a substrate like silicon wafer by using a spinner or the like, followed by drying to form a photosensitive layer. This is irradiated with a high-energy ray or electron beam with an exposure apparatus or the like through a desired mask pattern, followed by heating. Then, this is subjected to a development treatment using a developing solution, for example, an alkali aqueous solution such as 0.1-10 mass % tetramethylammonium hydroxide aqueous solution. This forming method makes it possible to obtain a pattern conforming to the mask pattern.

The high-energy ray used in the resist pattern forming method of the present invention is not particularly limited. It is effective to use an exposure apparatus equipped with a source for generating ultraviolet rays having short wavelengths of 300 nm or shorter or high-energy rays such as electron beams. It is effective to use an immersion exposure device that makes it possible to conduct a more efficient fine processing in numerical aperture and effective wavelength by using a medium, such as water or fluorine-containing solvent, in which the high-energy ray to be used has a less absorption, at a part of the optical path. The resist composition of the present invention is also preferable in the case of use in such device.

EXAMPLES

In the following, the present invention is shown in detail by examples, but embodiments of the present invention are not limited to these.

Synthesis Example 1

Triphenylsulfonium 2-[2-(2-oxotetrahydrofuran-3-yloxycarbonyl)-2-methyleneethoxy]-1,1-difluoroethanesulfonate (PAG-1)

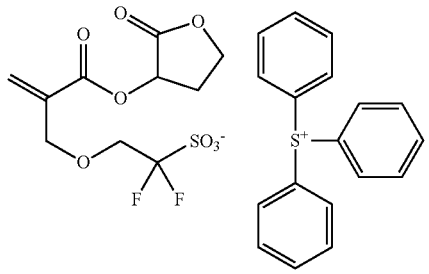

47 g of 5 mass % sodium hydroxide aqueous solution was put into a 100 ml flask, followed by cooling in an iced water bath with stirring. There, 22.5 g (purity: 95 mass %) of triphenylsulfonium 2-hydroxy-1,1-difluoroethanesulfonate was gradually added. Then, it was returned to room temperature (about 25° C., it is the same in the following), followed by stirring for 30 minutes. Then, it was cooled again in an iced water bath, followed by adding 15 mg of tetrabutylammonium iodide and stirring for 10 minutes. There, a solution prepared by diluting 11.0 g of 2-oxotetrahydrofuran-3-yl 2-bromomethyl acrylate with 15 g of acetonitrile was added in a dropwise manner. After the dropping, stirring was conducted at room temperature for 2 hours.

To a lower layer obtained by separation of the reaction liquid having two layers after standing still, 33 g of chloroform was added, followed by washing with 33 g of water three times. The obtained solution was solidified by concentration under reduced pressure. Then, 22 g of methyl ethyl ketone was added, followed by dissolution at 40° C. and then slowly adding 44 g of diisopropyl ether in a dropwise manner. After stirring at room temperature for one hour, it was confirmed that crystals appeared. After filtration, the obtained crystals were dried under reduced pressure, thereby obtaining 15 g (purity: 96 mass %) of the target substance as a white solid.

<Property of Triphenylsulfonium 2-[2-(2-oxotetrahydrofuran-3-yloxycarbonyl)-2-methyleneethoxy]-1,1-difluoroethanesulfonate> $^1$H-NMR (measurement solvent: deuterated chloroform, standard material: tetramethylsilane); δ=7.73-7.61 (m, 15H), 6.13 (s, 1H), 5.76 (s, 1H), 5.45 (t, J=8.4 Hz, 1H), 4.46 (td, J=9.2 Hz, 2.4 Hz, 1H), 4.29 (td, J=9.2 Hz, 6.4 Hz, 1H), 4.26 (s, 2H), 4.15 (t, J=16.0 Hz, 2 H), 2.7 (m, 1H), 2.31 (m, 1H).

Synthesis Example 2

Phenyldibenzothiophenium 4-[2-(3,3,3-trifluoro-2-acetyloxy-2-(trifluoromethyl)propyl)bicyclo[2.2.1]hepta-2-yloxycarbonyl-2-methyleneethoxy]-1,1,2,2-tetrafluorobutanesulfonate (PAG-2)

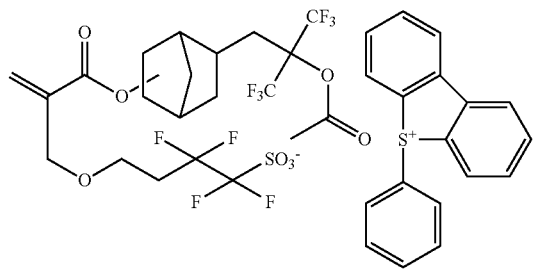

31 g of 5 mass % sodium hydroxide aqueous solution was put into a 100 ml flask, followed by cooling in an iced water bath with stirring. There, 17.2 g (purity: 93 mass %) of phenyldibenzothiophenium 4-hydroxy-1,1,2,2-tetrafluorobutanesulfonate was gradually added. Then, it was returned to room temperature, followed by stirring for 45 minutes. Then, it was cooled again in an iced water bath, followed by adding 10 mg of tetrabutylammonium iodide and stirring for 15 minutes. There, a solution prepared by diluting 14.1 g of (3,3,3-trifluoro-2-acetyloxy-2-(trifluoromethyl)propyl)bicyclo[2.2.1]hepta-2-yl 2-bromomethylacrylate with 21 g of acetonitrile was added in a dropwise manner. After the dropping, stirring was conducted at room temperature for 4 hours.

To a lower layer obtained by separation of the reaction liquid having two layers after standing still, 42 g of chloroform was added, followed by washing with 42 g of water three times. The obtained solution was solidified by concentration under reduced pressure. Then, 28 g of methyl ethyl ketone was added, followed by dissolution at 40° C. and then slowly adding 56 g of diisopropyl ether in a dropwise manner. After stirring at room temperature for three hours, it was confirmed that crystals appeared. After filtration, the obtained crystals were dried under reduced pressure, thereby obtaining 23 g (purity: 92 mass %) of the target substance as a white solid.

<Property of Phenyldibenzothiophenium 4-[2-(3,3,3-trifluoro-2-acetyloxy-2-(trifluoromethyl)propyl)bicyclo[2.2.1]hepta-2-yloxycarbonyl-2-methyleneethoxy]-1,1,2,2-tetrafluorobutanesulfonate> $^1$H-NMR (measurement solvent: deuterated chloroform, standard material: tetramethylsilane); δ=7.74-7.55 (m, 13H), 6.12 (s, 1H), 5.77 (s, 1H), 4.65 (m, 1H), 4.26 (s, 2H), 4.18 (m, 2H), 3.23 (m, 1H), 2.75 (m, 2H), 2.05 (s, 3H), 1.93 (m, 10H).

Synthesis Example 3

Diphenyl-p-tolylsulfonium 2-[2-(3,5-bis(hexafluoro-2-hydroxypropan-2-yl)cyclohexyloxycarbonyl)-2-methyleneethoxy]-1,1-difluoroethanesulfonate (PAG-3)

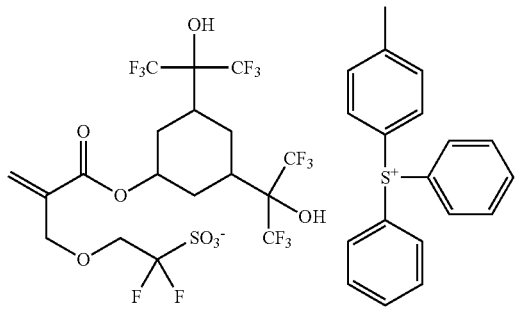

22 g of 5 mass % sodium hydroxide aqueous solution was put into a 100 ml flask, followed by cooling in an iced water bath with stirring. There, 15.8 g (purity: 95 mass %) of diphenyl-p-tolylsulfonium 2-hydroxy-1,1-difluoroethanesulfonate was gradually added. Then, it was returned to room temperature, followed by stirring for 40 minutes. Then, it was cooled again in an iced water bath, followed by adding 8 mg of tetrabutylammonium iodide and stirring for 15 minutes. There, a solution prepared by diluting 11.9 g of 3,5-bis(hexafluoro-2-hydroxypropan-2-yl)cyclohexyl 2-bromomethylacrylate with 18 g of acetonitrile was added in a dropwise manner. After the dropping, stirring was conducted at room temperature for 3 hours.

To a lower layer obtained by separation of the reaction liquid having two layers after standing still, 36 g of chloroform was added, followed by washing with 36 g of water three times. The obtained solution was solidified by concentration under reduced pressure. Then, 24 g of methyl ethyl ketone was added, followed by dissolution at 40° C. and then slowly adding 48 g of diisopropyl ether in a dropwise manner. After stirring at room temperature for five hours, it was confirmed that crystals appeared. After filtration, the obtained crystals were dried under reduced pressure, thereby obtaining 17 g (purity: 90 mass %) of the target substance as a white solid.

<Property of Diphenyl-p-tolylsulfonium 2-[2-(3,5-bis(hexafluoro-2-hydroxypropan-2-yl)cyclohexyloxycarbonyl)-2-methyleneethoxy]-1,1-difluoroethanesulfonate>
$^1$H-NMR (measurement solvent: deuterated chloroform, standard material: tetramethylsilane); δ=7.75-7.58 (m, 14H), 6.11 (s, 1H), 5.75 (s, 1H), 5.05 (m, 1H), 4.26 (s, 2H), 4.14 (t, J=16.0 Hz, 2H), 3.14 (m, 2H), 2.36 (s, 3H), 2.34 (m, 5H), 1.53 (m, 3H).

Synthesis Example 4

Diphenyliodonium 4-[2-(1,1,1-trifluoro-2-hydroxy-6-methyl-2-(trifluoromethyl)hepta-4-yloxycarbonyl)-2-methyleneethoxy-1,1,2,2-tetrafluorobutanesulfonate (PAG-4)

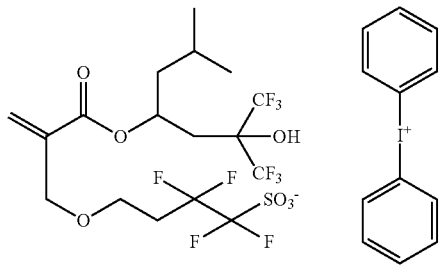

31 g of 5 mass % sodium hydroxide aqueous solution was put into a 100 ml flask, followed by cooling in an iced water bath with stirring. There, 17.9 g (purity: 94 mass %) of diphenyliodonium 4-hydroxy-1,1,2,2-tetrafluorobutanesulfonate was gradually added. Then, it was returned to room temperature, followed by stirring for one hour. Then, it was cooled again in an iced water bath, followed by adding 10 mg of tetrabutylammonium iodide and stirring for 30 minutes. There, a solution prepared by diluting 12.2 g of 1,1,1-trifluoro-2-hydroxy-6-methyl-2-(trifluoromethyl) hepta-4-yl 2-bromomethylacrylate with 18 g of acetonitrile was added in a dropwise manner. After the dropping, stirring was conducted at room temperature for 3 hours.

To a lower layer obtained by separation of the reaction liquid having two layers after standing still, 36 g of chloroform was added, followed by washing with 36 g of water three times. The obtained solution was solidified by concentration under reduced pressure. Then, 24 g of methyl ethyl ketone was added, followed by dissolution at 40° C. and then slowly adding 48 g of diisopropyl ether in a dropwise manner. After stirring at room temperature for four hours, it was confirmed that crystals appeared. After filtration, the obtained crystals were dried under reduced pressure, thereby obtaining 22 g (purity: 90 mass %) of the target substance as a white solid.

<Property of Diphenyliodonium 4-[2-(1,1,1-trifluoro-2-hydroxy-6-methyl-2-(trifluoromethyl)hepta-4-yloxycarbonyl)-2-methyleneethoxy-1,1,2,2-tetrafluorobutanesulfonate> $^1$H-NMR (measurement solvent: deuterated chloroform, standard material: tetramethylsilane); δ=7.73-7.61 (m, 10H), 6.52 (s, 1H; OH), 6.11 (s, 1H), 5.74 (s, 1H), 5.03 (m, 1H), 4.27 (s, 2H), 4.19 (m, 2H), 2.74 (m, 2H), 2.26 (m, 2H), 1.89 (m, 1H), 1.72 (m, 1H), 1.39 (m, 1H), 0.96 (d, J=6.8 Hz, 3H), 0.89 (d, J=6.8 Hz, 3H).

Synthesis Examples 5-9

Similar to Synthesis Examples 1-4, syntheses were conducted (Synthesis examples 5-9), thereby respectively making PAG-5 to PAG-9. Purities are shown in Table 1. Structural formulas are mentioned hereinafter.

TABLE 1

| Synthesis example | PAG | Purity |
|---|---|---|
| Synthesis example 5 | PAG-5 | 91% |
| Synthesis example 6 | PAG-6 | 88% |
| Synthesis example 7 | PAG-7 | 84% |
| Synthesis example 8 | PAG-8 | 81% |
| Synthesis example 9 | PAG-9 | 93% |

Synthesis Example 10

Diphenyl[4-(phenylsulfonyl)phenyl]sulfonium 2-[2-(1,1,1-trifluoro-2-hydroxy-2-(trifluoromethyl)penta-4-yloxycarbonyl)-2-methylene-ethoxy]-1,1-difluoroethanesulfonate (PAG-10)

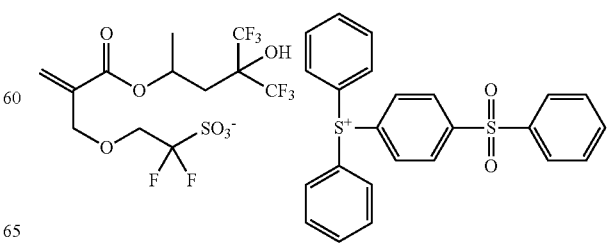

In a 200 ml flask, 15 g of diisopropyl ether and 15 g (0.022 mol) of diphenyl[4-(phenylsulfonyl)phenyl]sulfonium 2-[2-chlorocarbonyl-2-methyleneethoxy]-1,1-difluoroethanesulfonate were weighed. While cooling in an iced bath, there, 6.6 g (0.029 mol) of 1,1,1-trifluoro-2,4-dihydroxy-2-(trifluoromethyl)pentane was added in a dropwise manner. Furthermore, 3.2 g of triethylamine was added in a dropwise manner, followed by stirring at room temperature for 3 hours. After termination of the reaction, while cooling again, 45 g of 4 mass % hydrochloric acid was added, followed by stirring for 30 minutes. After standing still, the organic layer was separated and then washed with 30 g of water one time, 30 g of 3 mass % sodium bicarbonate water one time, and 30 g of water two times. The organic layer after the washing was concentrated under reduced pressure. A crude product of the obtained target substance was purified by column chromatography, thereby obtaining 4.1 g of the target substance as a colorless, transparent oil. (yield: 21%)

<Property of Diphenyl[4-(phenylsulfonyl)phenyl]sulfonium 2-[2-(1,1,1-trifluoro-2-hydroxy-2-(trifluoromethyl)penta-4-yloxycarbonyl)-2-methylene-ethoxy]-1,1-difluoroethanesulfonate> $^{1}$H-NMR (measurement solvent: DMSO-$d_6$, standard material: tetramethylsilane); δ=8.41-7.52 (m, 19H), 6.20 (s, 1H), 5.89 (s, 1H), 4.13 (m, 1H), 4.04 (s, 2H), 3.70 (t, 2H), 1.64 (d, 2H), 1.40 (d, 2H).

Synthesis Example 11

Tri-p-tolylsulfonium 2-[4-(2,2,2-trifluoro-1-hydroxy-1-(trifluoromethyl)ethylphenoxycarbonyl)-2-methylene-ethoxy]-1,1-difluorohexanesulfonate (PAG-11)

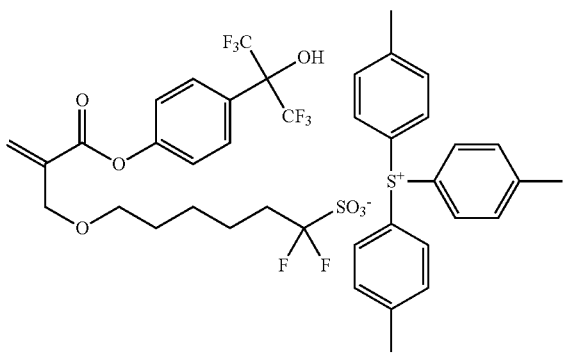

In a 200 ml flask, 15 g of acetonitrile, 15 g (0.029 mol) of tri-p-tolylsulfonium 2-(2-carboxy-2-methyleneethoxy)-1,1-difluorohexanesulfonate, and 30 g (0.115 mol) of 4-[2,2,2-trifluoro-1-hydroxy-1-(trifluoromethyl)ethyl]phenol were respectively weighed. There, 0.6 g of concentrated sulfuric acid was added, followed by heating for 3 hours under reflux. After returning to room temperature, 60 g of chloroform was added to the reaction liquid, followed by washing two times using 30 g of water. Furthermore, washing was conducted two times using 30 g of saturated sodium bicarbonate water and two times using 30 g of water. The organic layer after the washing was concentrated under reduced pressure. A crude product of the obtained target substance was purified by column chromatography, thereby obtaining 5.7 g of the target substance as a colorless, transparent oil. (yield: 25%)

<Property of Tri-p-tolylsulfonium 2-[4-(2,2,2-trifluoro-1-hydroxy-1-(trifluoromethyl)ethylphenoxycarbonyl)-2-methyleneethoxy]-1,1-difluorohexanesulfonate> $^{1}$H-NMR (measurement solvent: DMSO-$d_6$, standard material: tetramethylsilane); δ=7.53 (d, 2H), 7.26-7.01 (m, 14H), 6.24 (s, 1H), 5.70 (s, 1H), 4.04 (s, 2H), 3.73 (t, 2H), 2.35 (s, 9H).

Synthesis Example 12

1-(4-t-butylphenyl)tetrahydrothiophenium 2-[2-(6-(cyanomethyl)bicyclo[2.2.1]hept-2-yloxycarbonyl)-2-methylene-ethoxy]-1,1-difluoroethanesulfonate (PAG-12)

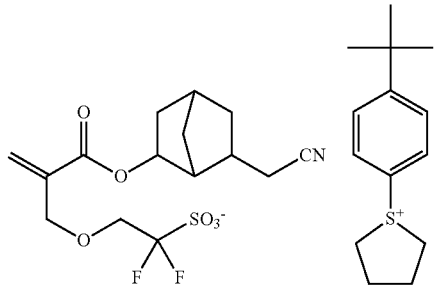

In a 200 ml flask, 12 g of diisopropyl ether and 11.6 g (0.024 mol) of 1-(4-t-butylphenyl)tetrahydrothiophenium 2-(2-chlorocarbonyl-2-methylene-ethoxy)-1,1-difluoroethanesulfonate were weighed. While cooling in an iced bath, there, 4.7 g (0.031 mol) of 2-(6-hydroxybicyclo[2.2.1]hept-2-yl)acetonitrile was added in a dropwise manner. Furthermore, 3.4 g of triethylamine was added in a dropwise manner, followed by stirring at room temperature for 3 hours. After termination of the reaction, while cooling again, 48 g of 4 wt % hydrochloric acid was added, followed by stirring for 30 minutes. After standing still, the organic layer was separated and then washed with 23 g of water one time, 23 g of 3 wt % sodium bicarbonate water one time, and 23 g of water two times. The organic layer after the washing was concentrated under reduced pressure. A crude product of the obtained target substance was purified by column chromatography, thereby obtaining 3.2 g of the target substance as a colorless, transparent oil. (yield: 22%)

<Property of 1-(4-t-butylphenyl)tetrahydrothiophenium 2-[2-(6-(cyanomethyl)bicyclo[2.2.1]hepta-2-yloxycarbonyl)-2-methylene-ethoxy]-1,1-difluoroethanesulfonate> $^{1}$H-NMR (measurement solvent: DMSO-$d_6$, standard material: tetramethylsilane); δ=8.06 (d, 2H), 7.59 (d, 2H), 6.38 (s, 1H), 5.69 (s, 1H), 4.25 (t, 2H), 4.01 (s, 2H), 3.90 (m, 1H), 3.75 (m, 2H), 2.40 (dd, 1H), 2.21 (dd, 1H), 2.08-2.01 (m, 5H), 1.76 (ddd, 1H), 1.55-1.24 (m, 16H).

Synthesis Example 13

Triphenylsulfonium 2-[2-(1,1,1-trifluoro-2-hydroxy-2-(trifluoromethyl)penta-5-yloxycarbonyl)-2-methyleneethoxy]-1,1-difluoroethanesulfonate (PAG-13)

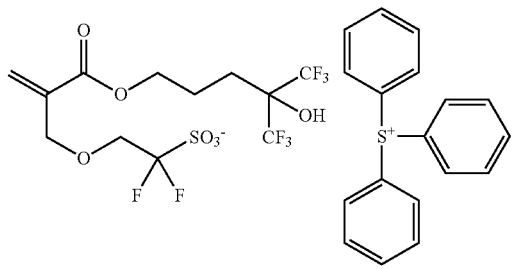

In a 200 ml flask, 15 g of acetonitrile, 15 g (0.029 mol) of triphenylsulfonium 2-(2-carboxy-2-methyleneethoxy)-1,1-difluoroethanesulfonate, and 30 g (0.133 mol) of 1,1,1-trifluoro-2,5-dihydroxy-2-(trifluoromethyl)pentane were respectively weighed. There, 0.6 g of concentrated sulfuric acid was added, followed by heating for 3 hours under reflux. After returning to room temperature, 60 g of chloroform was added to the reaction liquid, followed by washing two times using 30 g of water. Furthermore, washing was conducted two times using 30 g of saturated sodium bicarbonate water and two times using 30 g of water. The organic layer after the washing was concentrated under reduced pressure. A crude product of the obtained target substance was purified by column chromatography, thereby obtaining 6.9 g of the target substance as a colorless, transparent oil. (yield: 33%)

<Property of Triphenylsulfonium 2-[2-(1,1,1-trifluoro-2-hydroxy-2-(trifluoromethyl)pent-5-yloxycarbonyl)-2-methyleneethoxy]-1,1-difluoroethanesulfonate> $^1$H-NMR (measurement solvent: DMSO-$d_6$, standard material: tetramethylsilane); δ=7.88-7.76 (m, 10H), 6.21 (s, 1H), 5.90 (s, 1H), 4.26 (s, 2H), 4.14 (t, J=6.4 Hz, 2H), 3.93 (t, J=16.4 Hz, 2H), 1.99-1.67 (m, 4H).

Synthesis Example 14

Bis(4-t-butylphenyl)iodonium 2-[2-(3,5-bis(hexafluoro-2-hydroxy-propan-2-yl)cyclohexyloxycarbonyl)-2-methyleneethoxy]-1,1-difluoroethanesulfonate (PAG-14)

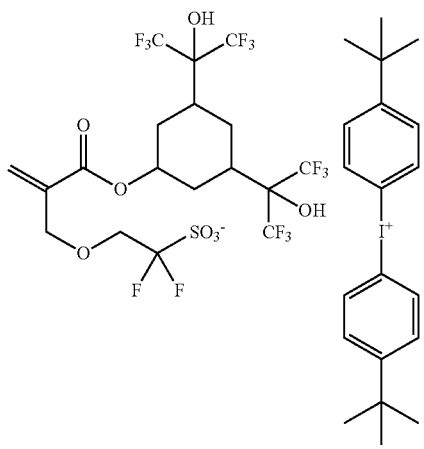

37 g of 5 mass % sodium hydroxide aqueous solution was put into a 100 ml flask, followed by cooling in an iced water bath with stirring. There, 22.9 g (purity: 95 mass %) of bis(4-t-butylphenyl)iodonium 2-hydroxy-1,1-difluoroethanesulfonate was gradually added. Then, it was returned to room temperature, followed by stirring for 40 minutes. Then, it was cooled again in an iced water bath, followed by adding 12 mg of tetrabutylammonium iodide and stirring for 15 minutes. There, a solution prepared by diluting 19.8 g of 3,5-bis(hexafluoro-2-hydroxy-2-propan-2-yl)cyclohexyl 2-bromomethyl acrylate with 30 g of acetonitrile was added in a dropwise manner. After the dropping, stirring was conducted at room temperature for 3 hours.

To a lower layer obtained by separation of the reaction liquid having two layers after standing still, 59 g of chloroform was added, followed by washing with 59 g of water three times. The obtained solution was concentrated under reduced pressure. Then, a crude product obtained by silica gel chromatography was purified, thereby obtaining 32.3 g of the target substance (purity: 96 mass %) as a yellow liquid.

<Property of Bis(4-t-butylphenyl)iodonium 2-[2-(3,5-bis(hexafluoro-2-hydroxy-propyl)cyclohexyloxycarbonyl)-2-methyleneethoxy]-1,1-difluoroethanesulfonate> $^1$H-NMR (measurement solvent: deuterated chloroform, standard material: tetramethylsilane); δ=7.81 (d, 4H), 7.10 (d, 4H), 6.11 (s, 1H), 5.75 (s, 1H), 5.05 (m, 1H), 4.26 (s, 2H), 4.14 (t, J=16.0 Hz, 2H), 3.14 (m, 2H), 2.36 (s, 3H), 2.34 (m, 5H), 1.53 (m, 3H), 1.33 (s, 18H).

Synthesis example 15

[(4-trifluoromethyl)phenyl]diphenylsulfonium 4-(4-oxa-tricyclo[5.2.1.0(2,6)]decan-3-on-8-yloxycarbonyl-2-methylene-ethoxy)-1,1-difluorobutanesulfonate (PAG-15)

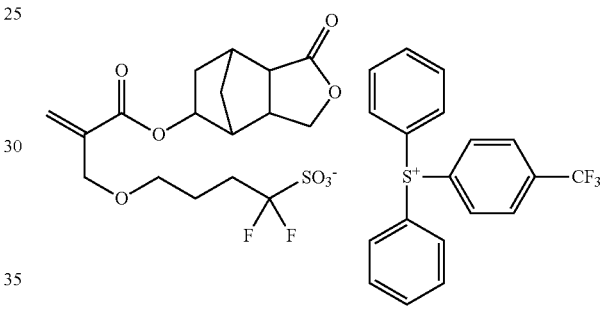

33 g of 5 mass % sodium hydroxide aqueous solution was put into a 100 ml flask, followed by cooling in an iced water bath with stirring. There, 19.4 g (purity: 94 mass %) of [(4-trifluoromethyl)phenyl]diphenylsulfonium 4-hydroxy-1,1-difluorobutanesulfonate was gradually added. Then, it was returned to room temperature, followed by stirring for 45 minutes. Then, it was cooled again in an iced water bath, followed by adding 11 mg of tetrabutylammonium iodide and stirring for 15 minutes. There, a solution prepared by diluting 9.8 g of 4-(4-oxa-tricyclo[5.2.1.0(2,6)]decan-3-on-8-yl 2-bromomethyl acrylate with 15 g of acetonitrile was added in a dropwise manner. After the dropping, stirring was conducted at room temperature for 4 hours.

To a lower layer obtained by separation of the reaction liquid having two layers after standing still, 29 g of chloroform was added, followed by washing with 29 g of water three times. The obtained solution was concentrated under reduced pressure. Then, a crude product obtained by silica gel chromatography was purified, thereby obtaining 20.9 g of the target substance (purity: 94 mass %) as a yellow liquid.

<Property of [(4-trifluoromethyl)phenyl]diphenylsulfonium 4-(4-oxa-tricyclo[5.2.1.0(2,6)]decan-3-on-8-yloxycarbonyl-2-methylene-ethoxy)-1,1-difluorobutanesulfonate> $^1$H-NMR (measurement solvent: deuterated chloroform, standard material: tetramethylsilane); δ=7.84-7.53 (m, 14H), 6.41 (s, 1H), 5.79 (s, 1H), 4.39 (dd, 2H), 4.14 (dd, 2H), 4.04 (s, 1H), 3.90 (m, 1H), 3.37 (t, 2H), 2.65 (m, 1H), 2.25-2.02 (m, 5H), 1.76 (ddd, 1H), 1.55-1.30 (m, 5H).

Synthesis Example 16

(4-t-butoxyphenyl)diphenylsulfonium 2-(2-ethoxy-carbonyl-2-methyleneethoxy)-1,1-difluoroethanesulfonate (PAG-16)

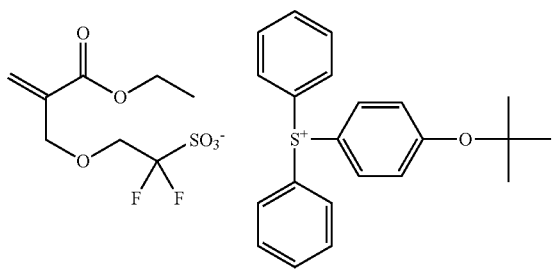

In a 200 ml flask, 16 g of diisopropyl ether and 16.1 g (0.027 mol) of (4-t-butoxyphenyl)diphenylsulfonium 2-(2-chlorocarbonyl-2-methylene-ethoxy)-1,1-difluoroethane-sulfonate were weighed. While cooling in an iced bath, there, 1.6 g (0.035 mol) of ethanol was added in a dropwise manner. Furthermore, 3.8 g of triethylamine was added in a dropwise manner, followed by stirring at room temperature for 3 hours. After termination of the reaction, while cooling again, 54 g of 4 wt % hydrochloric acid was added, followed by stirring for 30 minutes. After standing still, the organic layer was separated and then washed with 32 g of water one time, 32 g of 3 wt % sodium bicarbonate water one time, and 32 g of water two times. The organic layer after the washing was concentrated under reduced pressure. A crude product of the obtained target substance was purified by column chromatography, thereby obtaining 4.3 g of the target substance as a colorless, transparent oil. (yield: 25%)

<Property of (4-t-butoxyphenyl)diphenylsulfonium 2-(2-ethoxycarbonyl-2-methylene-ethoxy)-1,1-difluoroethane-sulfonate> $^1$H-NMR (measurement solvent: DMSO-$d_6$, standard material: tetramethylsilane): δ=7.89-7.77 (m, 12H), 7.35 (d, 2H), 6.41 (s, 1H), 5.80 (s, 1H), 4.25 (t, 2H), 4.18 (q, 2H), 4.04 (s, 2H), 1.46 (s, 9H), 1.30 (t, 3H).

Synthesis Example 17

(4-t-butylphenyl)diphenylsulfonium 2-[6-(3,3,3-trifluoro-2-hydroxy-2-(trifluoromethyl)propyl)bicyclo[2.2.1]heptan-2-yloxycarbonyl-2-methyleneethoxy]-1,1-difluoroethanesulfonate (PAG-17)

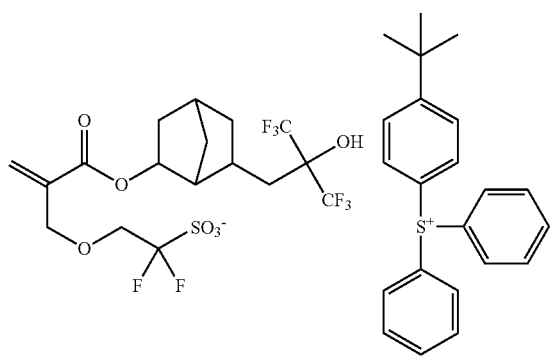

37 g of 5 mass % sodium hydroxide aqueous solution was put into a 100 ml flask, followed by cooling in an iced water bath with stirring. There, 19.9 g (purity: 95 mass %) of (4-t-butylphenyl)diphenylsulfonium 2-hydroxy-1,1-difluoroethanesulfonate was gradually added. Then, it was returned to room temperature, followed by stirring for 45 minutes. Then, it was cooled again in an iced water bath, followed by adding 12 mg of tetrabutylammonium iodide and stirring for 15 minutes. There, a solution prepared by diluting 5.4 g of 6-(3,3,3-trifluoro-2-hydroxy-2-(trifluoromethyl)propyl)bicyclo[2.2.1]heptan-2-yl 2-bromomethylacrylate with 23 g of acetonitrile was added in a dropwise manner. After the dropping, stirring was conducted at room temperature for 4 hours.

To a lower layer obtained by separation of the reaction liquid having two layers after standing still, 46 g of chloroform was added, followed by washing with 46 g of water three times. The obtained solution was concentrated under reduced pressure. Then, a crude product obtained by silica gel chromatography was purified, thereby obtaining 26.6 g of the target substance (purity: 94 mass %) as a yellow liquid.

<Property of (4-t-butylphenyl)diphenylsulfonium 2-[6-(3,3,3-trifluoro-2-hydroxy-2-(trifluoromethyl)propyl)bicyclo[2.2.1]heptan-2-yloxycarbonyl-2-methyleneethoxy]-1,1-difluoroethanesulfonate> $^1$H-NMR (measurement solvent: deuterated chloroform, standard material: tetramethylsilane); δ=7.71-7.53 (m, 14H), 6.41 (s, 1H), 5.79 (s, 1H), 4.25 (t, 2H), 4.04 (s, 2H), 3.90 (m, 1H), 2.03 (m, 1H), 1.73 (ddd, 1H), 1.57-1.22 (m, 18H).

Reference Example 1

A comparison between solubilities of the polymerizable fluorine-containing sulfonic acid onium salts in propylene glycol monomethyl ether acetate (PGMEA) is shown in Table 2.

TABLE 2

| Polymerizable monomer | Solvent | Solubility (g/100 g) |
|---|---|---|
| PAG-1 | PGMEA | 38 |
| PAG-2 | | 50 |
| PAG-3 | | 55 |
| PAG-4 | | 51 |
| PAG-5 | | 35 |
| PAG-6 | | 47 |
| PAG-7 | | 53 |
| PAG-8 | | 42 |
| PAG-9 | | 40 |
| PAG-10 | | 48 |
| PAG-11 | | 45 |
| PAG-12 | | 35 |
| PAG-13 | | 47 |
| PAG-14 | | 53 |
| PAG-15 | | 42 |
| PAG-16 | | 40 |
| PAG-17 | | 45 |
| PAG-C1 | | 10 |
| PAG-C2 | | 11 |

Solubility: Amount (g) of each polymerizable monomer dissolved in 100 g of PGMEA
Polymerizable monomer: fluorine-containing sulfonium salt onium salt Structures and symbols of polymerizable fluorine-containing sulfonic acid onium salts (polymerizable monomers) used in examples, etc. are shown in the following. Of these, PAG-1 to PAG-17 are polymerizable fluorine-containing sulfonic acid onium salts according to the present invention.

(PAG-1) 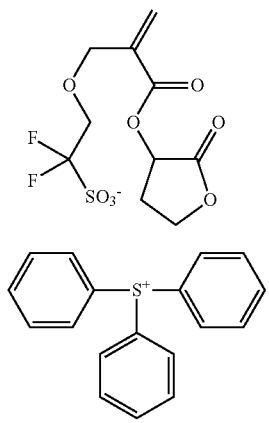
(PAG-2) 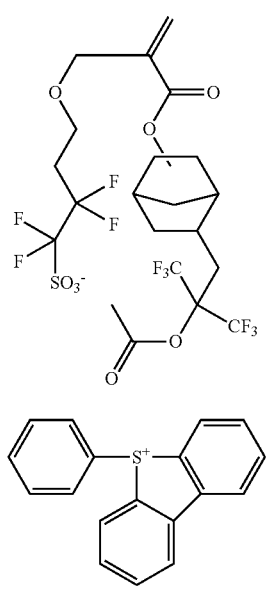
(PAG-3) 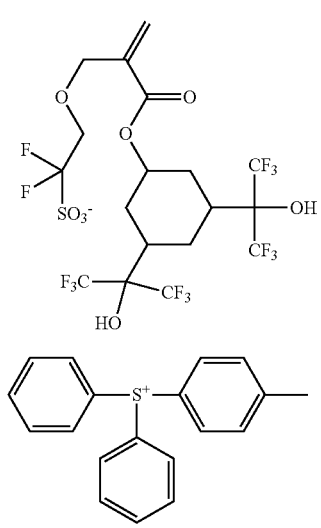
(PAG-4) 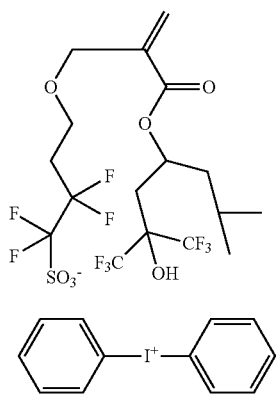
(PAG-5) 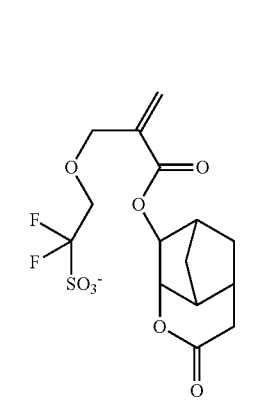
(PAG-6) 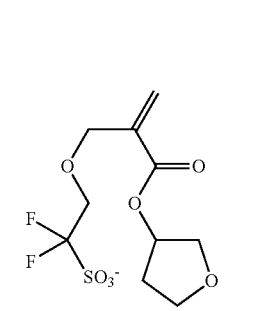

-continued
(PAG-7)
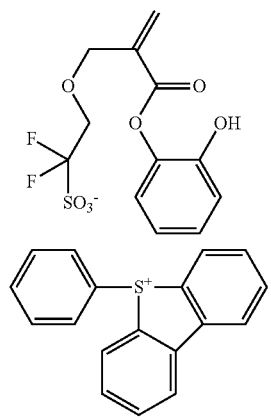
(PAG-8)
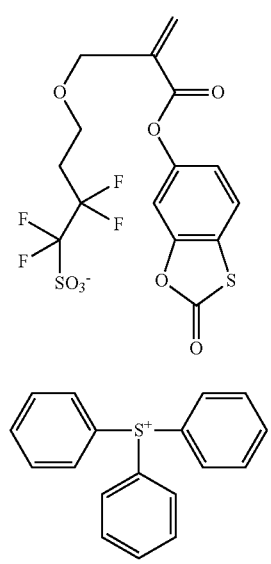
(PAG-9)
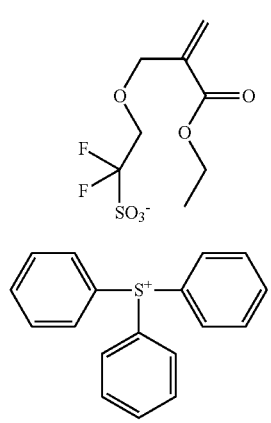
-continued
(PAG-10)
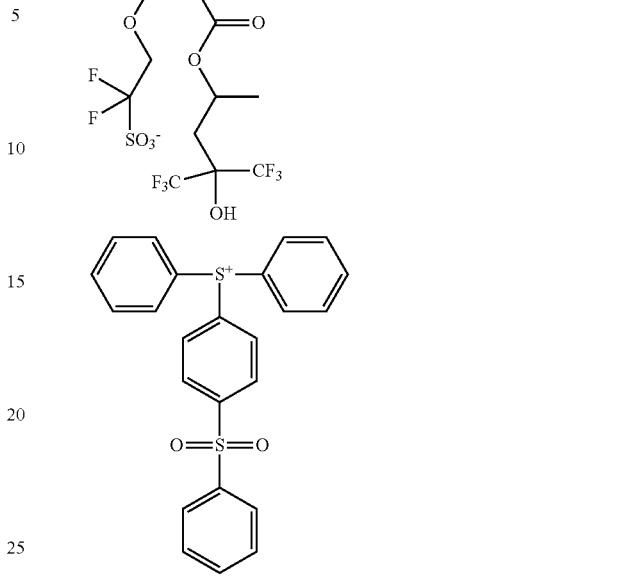
(PAG-11)
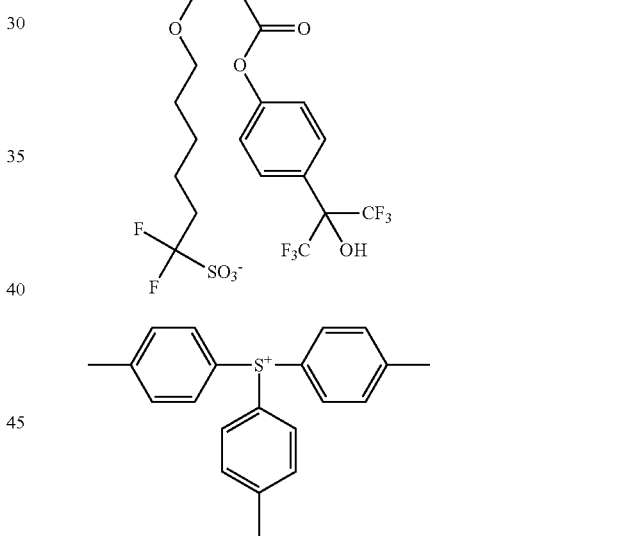
(PAG-12)
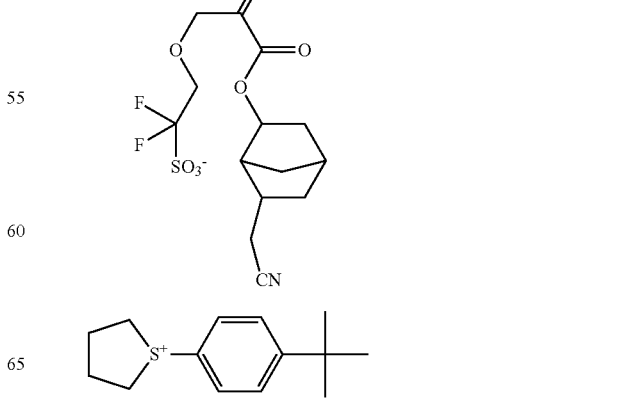

(PAG-13)
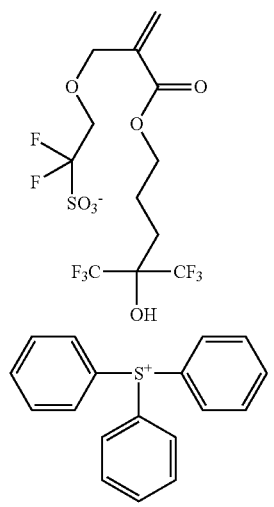
(PAG-14)
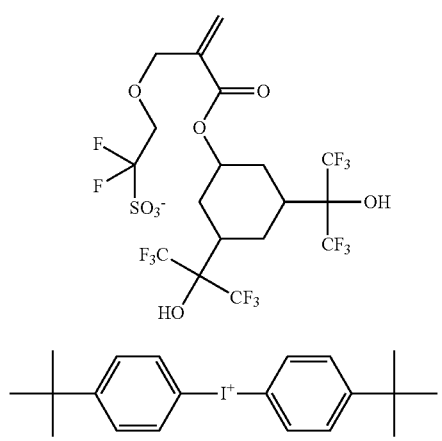
(PAG-15)
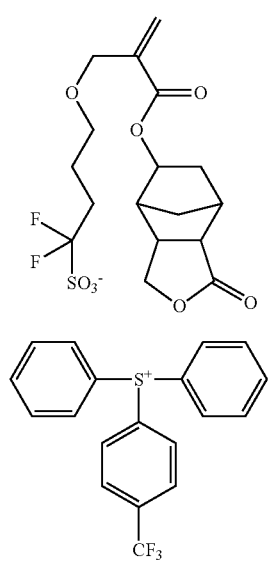
(PAG-16)
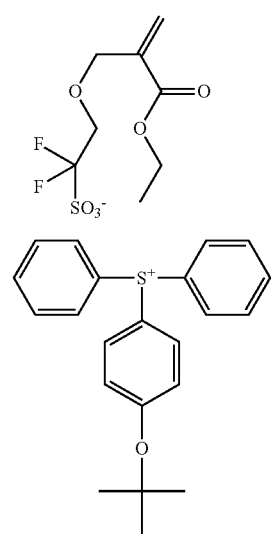
(PAG-17)
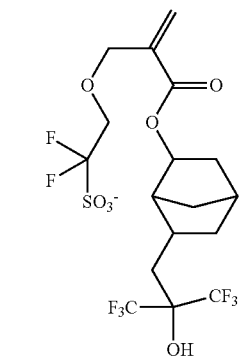
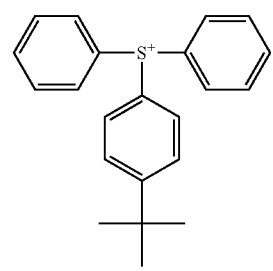
(PAG-C1)
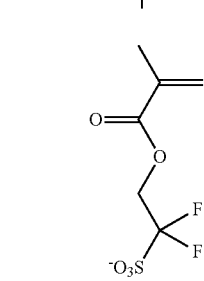
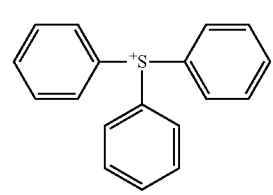

(PAG-C2)

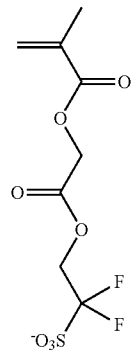

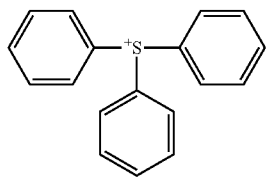

From the results of the above Table, the polymerizable monomers of the present invention have extremely higher solubilities than those of conventional polymerizable monomers.

[Resin production] Structures and symbols of the polymerizable monomers used in Polymerization Examples, Examples and Comparative Examples are shown in the following. The polymerizable fluorine-containing sulfonic acid onium salts are mentioned as above.

(A-1)

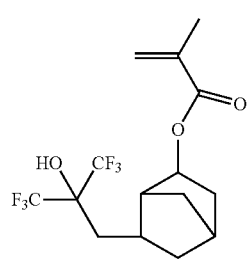

(A-2)

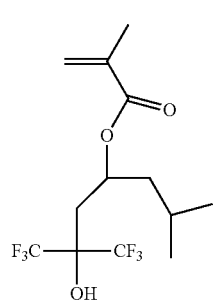

(A-3)

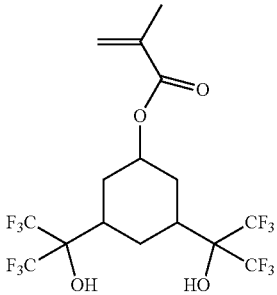

(A-4)

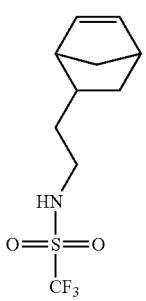

(A-5)

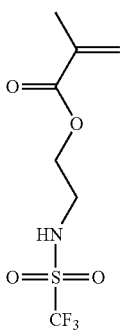

(A-6)

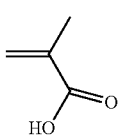

(A-7)

-continued (B-1)
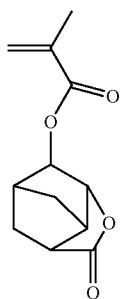

(B-2)
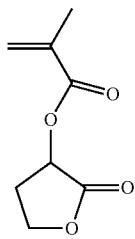

(C-1)
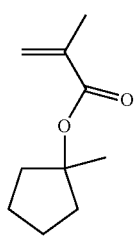

(C-2)

(D-1)
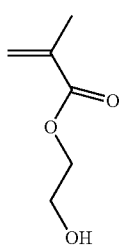

Polymerization Example P-1

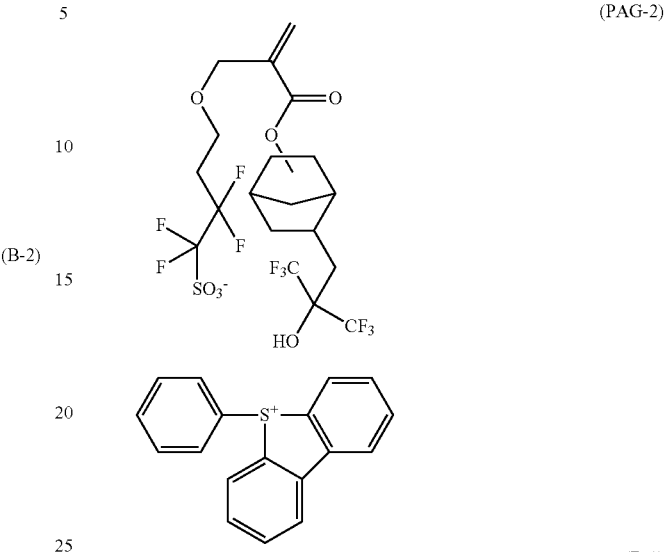

(PAG-2)

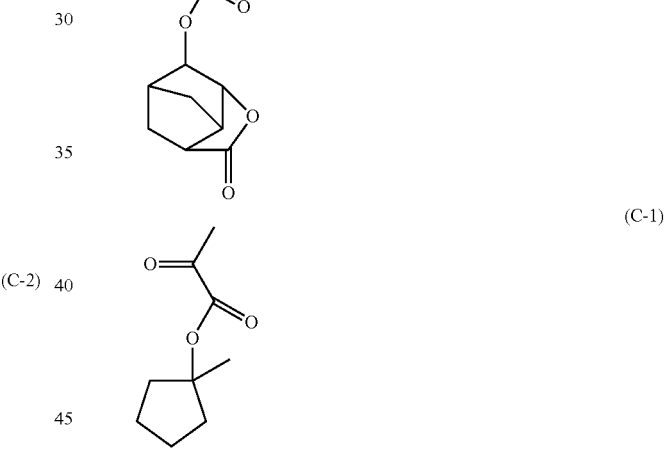

(B-1)

(C-1)

A monomer solution was prepared by dissolving 3.0 g (15 mol %) of Compound (PAG-2), 2.3 g (45 mol %) of Compound (B-1) and 1.5 g (40 mol %) of Compound (C-1) in 20 g of 2-butanone and then adding 3.40 g of 2,2'-azobis (2-methylpropionate). Furthermore, 10 g of 2-butanone was put into a 100 ml three-necked flask. This flask was purged with nitrogen for 30 minutes, and then heated to 80° C. with stirring. There, the monomer solution previously prepared was added in a dropwise manner from a dropping funnel by spending 3 hours. The start of dropping was set as the start of polymerization. The polymerization reaction was conducted for 6 hours. After termination of the polymerization, the polymerization solution was cooled to about 25° C. by water cooling and then put into 200 g of methanol. A white powder then precipitated was separated by filtration.

The white powder separated by filtration was washed two times in the form of slurry with 40 g of methanol, followed by separation by filtration and then drying at 50° C. for 17 hours, thereby obtaining a polymer as a white-color powder (7.4 g). This polymer was 7,600 in mass average molecular weight (MW). As a result of $^{13}$C-NMR analysis, it was a copolymer in which the content ratio of a repeating unit derived from Compound (PAG-2), a repeating unit derived from Compound (B-1) and a repeating unit derived from Compound (C-1) was 13.4:45.8:40.8 (mol %). This copolymer was named Resin (P-1).

Polymerization Example P-2

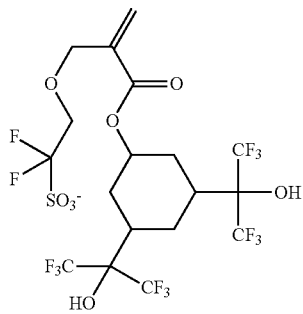
(PAG-3)

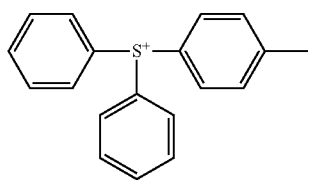
(B-1)

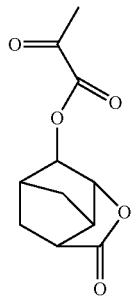

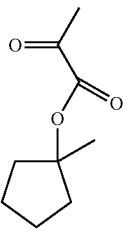
(C-1)

A monomer solution was prepared by dissolving 3.2 g (15 mol %) of Compound (PAG-3), 2.1 g (45 mol %) of Compound (B-1) and 1.4 g (40 mol %) of Compound (C-1) in 20 g of 2-butanone and then adding 0.3 g of 2,2'-azobis (2-methylpropionate). Furthermore, 100 g of 2-butanone was put into a 100 ml three-necked flask. This flask was purged with nitrogen for 30 minutes, and then heated to 80° C. with stirring. There, the monomer solution previously prepared was added in a dropwise manner from a dropping funnel by spending 3 hours. The start of dropping was set as the start of polymerization. The polymerization reaction was conducted for 6 hours. After termination of the polymerization, the polymerization solution was cooled to about 25° C. by water cooling and then put into 200 g of methanol. A white powder then precipitated was separated by filtration.

The white powder separated by filtration was washed two times in the form of slurry with 40 g of methanol, followed by separation by filtration and then drying at 50° C. for 17 hours, thereby obtaining a polymer as a white-color powder (6.7 g). This polymer was 8,100 in MW. As a result of $^{13}$C-NMR analysis, it was a copolymer in which the content ratio of a repeating unit derived from Compound (PAG-3), a repeating unit derived from Compound (B-1) and a repeating unit derived from Compound (C-1) was 14.2: 43.7:42.1 (mol %). This copolymer was named Resin (P-2).

Polymerization Examples P-3 to P-66 & N-1 to N-11

Similar to Polymerization Example P-1 or P-2, Resins (P-3 to P-66 & N-1 to N-11) were produced. Regarding the types of monomers used in the copolymerizations, their ratio and polymer, the molar ratio of the repeating units obtained from monomers and mass average molecular weight (MW) are shown in Table 3 to Table 6.

TABLE 3

| Polymer-ization Example Resin Name | Raw Material Composition | | | | | | | Molar Ratio of Repeating units in Resin | | | | Molecular Weight MW |
|---|---|---|---|---|---|---|---|---|---|---|---|---|
| | Monomer 1 | | Monomer 2 | | Monomer 3 | | Monomer 4 | | | | | |
| | Type | Mol % | Type | Mol % | Type | Mol % | Type | Mol % | Monomer 1 | Monomer 2 | Monomer 3 | Monomer 4 | |
| P-1 | PAG-2 | 15 | — | — | B-1 | 45 | C-1 | 40 | 13 | — | 46 | 41 | 7,600 |
| P-2 | PAG-3 | 15 | — | — | B-1 | 45 | C-1 | 40 | 14 | — | 44 | 42 | 8,100 |
| P-3 | PAG-1 | 15 | — | — | B-1 | 45 | C-1 | 40 | 13 | — | 45 | 42 | 7,900 |
| P-4 | PAG-4 | 15 | — | — | B-1 | 45 | C-1 | 40 | 12 | — | 46 | 42 | 8,300 |
| P-5 | PAG-5 | 15 | — | — | B-1 | 45 | C-1 | 40 | 13 | — | 44 | 43 | 8,400 |
| P-6 | PAG-6 | 15 | — | — | B-1 | 45 | C-1 | 40 | 13 | — | 45 | 42 | 7,700 |
| P-7 | PAG-7 | 15 | — | — | B-1 | 45 | C-1 | 40 | 14 | — | 46 | 40 | 9,100 |
| P-8 | PAG-8 | 15 | — | — | B-1 | 45 | C-1 | 40 | 12 | — | 45 | 43 | 8,800 |
| P-9 | PAG-9 | 15 | — | — | B-1 | 45 | C-1 | 40 | 14 | — | 46 | 40 | 9,300 |
| P-10 | PAG-1 | 15 | A-1 | 15 | B-1 | 35 | C-1 | 35 | 13 | 14 | 35 | 38 | 7,400 |
| P-11 | PAG-1 | 15 | A-2 | 20 | B-1 | 35 | C-1 | 30 | 14 | 19 | 37 | 30 | 8,900 |
| P-12 | PAG-1 | 15 | A-3 | 15 | B-1 | 35 | C-1 | 35 | 13 | 15 | 35 | 37 | 8,300 |
| P-13 | PAG-1 | 15 | A-4 | 5 | B-1 | 35 | C-1 | 45 | 15 | 5 | 36 | 44 | 8,100 |
| P-14 | PAG-1 | 15 | A-5 | 20 | B-1 | 35 | C-1 | 30 | 13 | 20 | 37 | 30 | 8,100 |

TABLE 3-continued

| Polymer-ization Example Resin Name | Raw Material Composition | | | | | | | | Molar Ratio of Repeating units in Resin | | | | Molecular Weight MW |
|---|---|---|---|---|---|---|---|---|---|---|---|---|---|
| | Monomer 1 | | Monomer 2 | | Monomer 3 | | Monomer 4 | | Monomer 1 | Monomer 2 | Monomer 3 | Monomer 4 | |
| | Type | Mol % | Type | Mol % | Type | Mol % | Type | Mol % | | | | | |
| P-15 | PAG-1 | 15 | A-1 | 15 | B-1 | 35 | C-1 | 35 | 14 | 15 | 36 | 35 | 7,500 |
| P-16 | PAG-2 | 15 | A-1 | 15 | B-1 | 35 | C-1 | 35 | 13 | 14 | 36 | 37 | 7,200 |
| P-17 | PAG-2 | 15 | A-2 | 20 | B-1 | 35 | C-1 | 30 | 14 | 19 | 35 | 32 | 8,500 |
| P-18 | PAG-2 | 15 | A-3 | 15 | B-1 | 35 | C-1 | 35 | 13 | 14 | 35 | 38 | 8,100 |
| P-19 | PAG-2 | 15 | A-4 | 5 | B-1 | 35 | C-1 | 45 | 14 | 5 | 37 | 44 | 7,600 |
| P-20 | PAG-2 | 15 | A-5 | 20 | B-1 | 35 | C-1 | 30 | 13 | 20 | 36 | 31 | 7,400 |
| P-21 | PAG-2 | 15 | A-1 | 15 | B-1 | 35 | C-1 | 35 | 14 | 14 | 36 | 36 | 7,700 |
| P-22 | PAG-3 | 15 | A-1 | 15 | B-1 | 35 | C-1 | 35 | 13 | 15 | 35 | 37 | 9,100 |
| P-23 | PAG-3 | 15 | A-2 | 20 | B-1 | 35 | C-1 | 30 | 12 | 19 | 36 | 33 | 9,200 |
| P-24 | PAG-3 | 15 | A-3 | 15 | B-1 | 35 | C-1 | 35 | 14 | 14 | 37 | 35 | 8,800 |
| P-25 | PAG-3 | 15 | A-4 | 5 | B-1 | 35 | C-1 | 45 | 12 | 4 | 35 | 49 | 8,600 |

TABLE 4

| Polymer-ization Example Resin Name | Raw Material Composition | | | | | | | | Molar Ratio of Repeating units in Resin | | | | Molecular Weight MW |
|---|---|---|---|---|---|---|---|---|---|---|---|---|---|
| | Monomer 1 | | Monomer 2 | | Monomer 3 | | Monomer 4 | | Monomer 1 | Monomer 2 | Monomer 3 | Monomer 4 | |
| | Type | Mol % | Type | Mol % | Type | Mol % | Type | Mol % | | | | | |
| P-26 | PAG-3 | 15 | A-5 | 20 | B-1 | 35 | C-1 | 30 | 13 | 19 | 36 | 32 | 7,900 |
| P-27 | PAG-3 | 15 | A-1 | 15 | B-1 | 35 | C-2 | 35 | 12 | 15 | 34 | 39 | 7,700 |
| P-28 | PAG-4 | 15 | A-1 | 15 | B-1 | 35 | C-1 | 35 | 14 | 14 | 36 | 36 | 8,700 |
| P-29 | PAG-4 | 15 | A-2 | 20 | B-1 | 35 | C-1 | 30 | 15 | 18 | 37 | 30 | 8,100 |
| P-30 | PAG-4 | 15 | A-3 | 15 | B-1 | 35 | C-1 | 35 | 13 | 14 | 34 | 39 | 7,900 |
| P-31 | PAG-4 | 15 | A-4 | 5 | B-1 | 35 | C-1 | 45 | 14 | 4 | 35 | 47 | 9,100 |
| P-32 | PAG-4 | 15 | A-5 | 20 | B-1 | 35 | C-1 | 30 | 12 | 19 | 38 | 31 | 9,300 |
| P-33 | PAG-4 | 15 | A-1 | 15 | B-1 | 35 | C-2 | 35 | 13 | 14 | 33 | 40 | 8,600 |
| P-34 | PAG-5 | 15 | A-1 | 15 | B-1 | 35 | C-1 | 35 | 12 | 16 | 37 | 35 | 8,400 |
| P-35 | PAG-5 | 15 | A-3 | 20 | B-1 | 35 | C-1 | 30 | 14 | 21 | 35 | 30 | 8,500 |
| P-36 | PAG-6 | 15 | A-1 | 15 | B-1 | 35 | C-1 | 35 | 14 | 14 | 34 | 38 | 7,800 |
| P-37 | PAG-6 | 15 | A-3 | 20 | B-1 | 35 | C-1 | 30 | 13 | 21 | 37 | 29 | 8,100 |
| P-38 | PAG-7 | 15 | A-1 | 15 | B-1 | 35 | C-1 | 35 | 15 | 19 | 32 | 34 | 8,800 |
| P-39 | PAG-7 | 15 | A-3 | 20 | B-1 | 35 | C-1 | 30 | 14 | 22 | 33 | 31 | 9,100 |
| P-40 | PAG-8 | 15 | A-1 | 15 | B-1 | 35 | C-1 | 35 | 12 | 18 | 36 | 36 | 7,900 |
| P-41 | PAG-8 | 15 | A-3 | 20 | B-1 | 35 | C-1 | 30 | 14 | 20 | 34 | 32 | 8,800 |
| P-42 | PAG-9 | 15 | A-1 | 15 | B-1 | 35 | C-1 | 35 | 13 | 16 | 35 | 36 | 8,200 |
| P-43 | PAG-9 | 15 | A-3 | 20 | B-1 | 35 | C-1 | 30 | 14 | 21 | 35 | 30 | 8,600 |
| P-44 | PAG-2 | 20 | A-6 | 30 | — | — | C-1 | 50 | 17 | 31 | — | 52 | 9,600 |
| P-45 | PAG-3 | 20 | A-6 | 25 | B-1 | 25 | C-1 | 30 | 18 | 27 | 26 | 29 | 7,400 |
| P-46 | PAG-3 | 15 | A-6 | 25 | B-1 | 25 | C-1 | 35 | 14 | 26 | 26 | 34 | 9,100 |
| P-47 | PAG-2 | 15 | A-6 | 25 | B-2 | 30 | C-1 | 30 | 13 | 26 | 32 | 29 | 9,400 |
| P-48 | PAG-2 | 20 | A-6 | 20 | B-2 | 30 | C-2 | 30 | 19 | 21 | 32 | 28 | 8,100 |
| P-49 | PAG-2 | 5 | — | — | B-1 | 50 | C-1 | 45 | 4 | — | 51 | 45 | 7,100 |
| P-50 | PAG-3 | 5 | — | — | B-1 | 50 | C-1 | 45 | 5 | — | 52 | 43 | 7,200 |

TABLE 5

| Polymer-ization Example Resin Name | Raw Material Composition | | | | | | | | Molar Ratio of Repeating units in Resin | | | | Molecular Weight MW |
|---|---|---|---|---|---|---|---|---|---|---|---|---|---|
| | Monomer 1 | | Monomer 2 | | Monomer 3 | | Monomer 4 | | Monomer 1 | Monomer 2 | Monomer 3 | Monomer 4 | |
| | Type | Mol % | Type | Mol % | Type | Weight MW | Type | Mol % | | | | | |
| P-51 | PAG-10 | 15 | — | — | B-1 | 45 | C-1 | 40 | 14 | 16 | 37 | 33 | 9000 |
| P-52 | PAG-11 | 15 | — | — | B-1 | 45 | C-1 | 40 | 13 | 18 | 36 | 33 | 9100 |
| P-53 | PAG-12 | 15 | — | — | B-1 | 45 | C-1 | 40 | 15 | 23 | 38 | 24 | 8900 |
| P-54 | PAG-13 | 15 | — | — | B-1 | 45 | C-1 | 40 | 12 | 15 | 35 | 38 | 8800 |
| P-55 | PAG-14 | 15 | — | — | B-1 | 45 | C-1 | 40 | 15 | 19 | 34 | 32 | 8800 |
| P-56 | PAG-15 | 15 | — | — | B-1 | 45 | C-1 | 40 | 16 | 14 | 34 | 36 | 9000 |
| P-57 | PAG-16 | 15 | — | — | B-1 | 45 | C-1 | 40 | 13 | 18 | 33 | 36 | 9000 |
| P-58 | PAG-17 | 15 | — | — | B-1 | 45 | C-1 | 40 | 14 | 14 | 32 | 40 | 7800 |
| P-59 | PAG-10 | 15 | A-1 | 15 | B-1 | 30 | C-1 | 40 | 14 | 20 | 28 | 38 | 8100 |

TABLE 5-continued

| Polymer-ization Example | Raw Material Composition | | | | | | | | Molar Ratio of Repeating units in Resin | | | | Molecular |
|---|---|---|---|---|---|---|---|---|---|---|---|---|---|
| | Monomer 1 | | Monomer 2 | | Monomer 3 | | Monomer 4 | | | | | | |
| Resin Name | Type | Mol % | Type | Mol % | Type | Weight MW | Type | Mol % | Monomer 1 | Monomer 2 | Monomer 3 | Monomer 4 | Weight MW |
| P-60 | PAG-11 | 15 | A-1 | 15 | B-1 | 35 | C-1 | 35 | 13 | 16 | 35 | 36 | 8200 |
| P-61 | PAG-12 | 15 | A-3 | 20 | B-1 | 35 | C-1 | 30 | 14 | 21 | 35 | 30 | 8600 |
| P-62 | PAG-13 | 15 | A-1 | 15 | B-1 | 35 | C-1 | 35 | 14 | 22 | 34 | 30 | 8500 |
| P-63 | PAG-14 | 15 | A-3 | 20 | B-1 | 35 | C-1 | 30 | 13 | 23 | 33 | 31 | 8600 |
| P-64 | PAG-15 | 15 | A-1 | 15 | B-1 | 35 | C-1 | 35 | 13 | 19 | 35 | 33 | 8700 |
| P-65 | PAG-16 | 15 | A-3 | 20 | B-1 | 35 | C-1 | 30 | 14 | 20 | 38 | 28 | 7900 |
| P-66 | PAG-17 | 15 | A-1 | 15 | B-1 | 35 | C-1 | 35 | 15 | 16 | 40 | 29 | 9100 |

TABLE 6

| Polymer-ization Example | Raw Material Composition | | | | | | | | Molar Ratio of Repeating units in Resin | | | | Molecular |
|---|---|---|---|---|---|---|---|---|---|---|---|---|---|
| | Monomer 1 | | Monomer 2 | | Monomer 3 | | Monomer 4 | | | | | | |
| Resin Name | Type | Mol % | Type | Mol % | Type | Mol % | Type | Mol % | Monomer 1 | Monomer 2 | Monomer 3 | Monomer 4 | Weight MW |
| N-1 | PAG-2 | 15 | — | — | B-1 | 10 | A-7 | 40 | 13 | — | 11 | 39 | 9,500 |
| | | | | | | | D-1 | 35 | | | | 37 | |
| N-2 | PAG-3 | 15 | A-2 | 60 | B-2 | 5 | A-6 | 20 | 12 | 63 | 6 | 19 | 9,000 |
| N-3 | PAG-2 | 15 | A-2 | 20 | A-3 | 25 | D-1 | 40 | 13 | 21 | 24 | 42 | 7,800 |
| N-4 | PAG-3 | 15 | — | — | A-3 | 50 | A-6 | 35 | 14 | — | 49 | 37 | 10,100 |
| N-5 | PAG-1 | 15 | A-2 | 20 | A-3 | 25 | D-1 | 40 | 13 | 21 | 24 | 42 | 7,800 |
| N-6 | PAG-4 | 15 | A-2 | 20 | A-3 | 25 | D-1 | 40 | 13 | 21 | 23 | 43 | 7,800 |
| N-7 | PAG-5 | 15 | A-2 | 30 | A-3 | 30 | D-1 | 25 | 13 | 33 | 31 | 23 | 8,400 |
| N-8 | PAG-6 | 15 | A-2 | 15 | A-3 | 40 | A-6 | 30 | 14 | 16 | 39 | 31 | 9,500 |
| N-9 | PAG-7 | 15 | — | — | A-3 | 40 | D-1 | 45 | 14 | — | 42 | 44 | 8,800 |
| N-10 | PAG-8 | 15 | A-2 | 20 | A-3 | 35 | D-1 | 30 | 13 | 21 | 37 | 29 | 9,300 |
| N-11 | PAG-9 | 15 | A-2 | 20 | A-3 | 35 | D-1 | 30 | 14 | 19 | 36 | 31 | 9,500 |

Examples 1-78

[Resist solution preparation] A resist composition was prepared by mixing together each resin produced, a solvent, other additives, and triphenylsulfonium nonafluorobutane-sulfonate (PAG-C3) as an existing photoacid generator (PAG).

The proportion of each component in the resist composition prepared is shown in Table 6 to Table 8. Furthermore, each resist solution was prepared by filtrating each resist composition with a membrane filter of 0.2 μm.

The used solvents, basic compounds, and cross-linking agent are as follows.

S-1: propylene glycol monomethyl ether acetate (PGMEA)

S-2: γ-butyrolactone

S-3: ethyl lactate

S-4: cyclohexanone

O-1: N,N-dibutylaniline

O-2: 2,6-diisopropylaniline

O-3: diazabicyclo[4.3.0]nonene

O-4: 2,4,5-triphenylimidazole

O-5: trioctylamine

Cross-linking agent: NIKALAC MX-270 (a glycoluril series crosslinking agent, a product of SANWA CHEMICAL CO., LTD.)

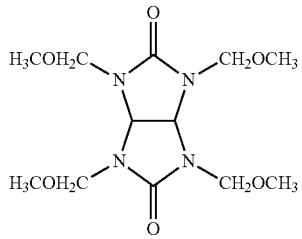

PAG: triphenylsulfonium nonafluorobutanesulfonate (PAG-C3)

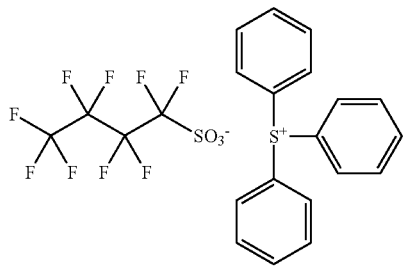

(PAG-C3)

[Pattern formation] Then, each resist solution was applied onto a silicon wafer by spin coating to obtain a resist film having a film thickness of about 250 nm. After conducting a preliminary baking at 110° C., an exposure to a 248 nm ultraviolet ray was conducted through a photomask. Then, a post exposure baking was conducted at 120° C. Then, a development was conducted at 23° C. for 1 minute using 2.38 mass % tetramethylammonium hydroxide aqueous solution. A high-resolution pattern shape was obtained from each resist composition. There were not found inferiority defect in adhesion to substrate, film-forming inferiority defect, development defect, and etching resistance inferiority defect. Composition and evaluation result of each resist are shown in Table 7 to Table 10.

TABLE 7

| Ex. | Resin 1 Type | Resin 1 Parts by mass | Resin 2 Type | Resin 2 Parts by mass | Additive | Solvent Type | Solvent Parts by mass | Pattern shape |
|---|---|---|---|---|---|---|---|---|
| 1 | P-1 | 40 | None | — | O-1 | S-1 | 400 | Fine rectangle |
| 2 | P-2 | 40 | None | — | O-1 | S-2 | 400 | Fine rectangle |
| 3 | P-3 | 40 | None | — | O-2 | S-1 | 400 | Fine rectangle |
| 4 | P-4 | 25 | P'-3 | 15 | O-3 | S-1 | 400 | Fine rectangle |
| 5 | P-5 | 40 | None | — | O-3 | S-1 | 400 | Fine rectangle |
| 6 | P-6 | 40 | None | — | O-3 | S-1 | 400 | Fine rectangle |
| 7 | P-7 | 40 | None | — | O-1 | S-1 | 400 | Fine rectangle |
| 8 | P-8 | 40 | None | — | O-1 | S-1 | 400 | Fine rectangle |
| 9 | P-9 | 40 | None | — | O-1 | S-3 | 400 | Fine rectangle |
| 10 | P-10 | 25 | P'-3 | 15 | O-4 | S-4 | 400 | Fine rectangle |
| 11 | P-11 | 40 | None | — | O-5 | S-1 | 400 | Fine rectangle |
| 12 | P-12 | 40 | None | — | O-5 | S-1 | 400 | Fine rectangle |
| 13 | P-13 | 40 | None | — | O-5 | S-1 | 400 | Fine rectangle |
| 14 | P-14 | 40 | None | — | O-5 | S-1 | 400 | Fine rectangle |
| 15 | P-15 | 40 | None | — | O-1 | S-1 | 400 | Fine rectangle |
| 16 | P-16 | 40 | None | — | O-1 | S-2 | 400 | Fine rectangle |
| 17 | P-17 | 40 | None | — | O-2 | S-1 | 400 | Fine rectangle |
| 18 | P-18 | 25 | P'-3 | 15 | O-3 | S-1 | 400 | Fine rectangle |
| 19 | P-19 | 40 | None | — | O-3 | S-1 | 400 | Fine rectangle |
| 20 | P-20 | 40 | None | — | O-3 | S-1 | 400 | Fine rectangle |
| 21 | P-21 | 40 | None | — | O-1 | S-1 | 400 | Fine rectangle |
| 22 | P-22 | 40 | None | — | O-1 | S-1 | 400 | Fine rectangle |
| 23 | P-23 | 40 | None | — | O-1 | S-3 | 400 | Fine rectangle |
| 24 | P-24 | 25 | P'-3 | 15 | O-4 | S-4 | 400 | Fine rectangle |
| 25 | P-25 | 40 | None | — | O-5 | S-1 | 400 | Fine rectangle |

Basic compound (addition: 0.15 parts by mass):
O-1: N,N-dibutylaniline
O-2: 2,6-diisopropylaniline
O-3: diazabicyclo[4.3.0]nonene
O-4: 2,4,5-triphenylimidazole
O-5: trioctylamine
Solvent:
S-1: propylene glycol monomethyl ether acetate (PGMEA)
S-2: γ-butyrolactone
S-3: ethyl lactate
S-4: cyclohexanone

TABLE 8

| Ex. | Resin 1 Type | Resin 1 Parts by mass | Resin 2 Type | Resin 2 Parts by mass | Additive | Solvent Type | Solvent Parts by mass | Pattern shape |
|---|---|---|---|---|---|---|---|---|
| 26 | P-26 | 40 | None | — | O-1 | S-1 | 400 | Fine rectangle |
| 27 | P-27 | 40 | None | — | O-1 | S-2 | 400 | Fine rectangle |
| 28 | P-28 | 40 | None | — | O-2 | S-1 | 400 | Fine rectangle |
| 29 | P-29 | 25 | P'-3 | 15 | O-2 | S-1 | 400 | Fine rectangle |
| 30 | P-30 | 40 | None | — | O-3 | S-1 | 400 | Fine rectangle |
| 31 | P-31 | 40 | None | — | O-3 | S-1 | 400 | Fine rectangle |
| 32 | P-32 | 40 | None | — | O-1 | S-1 | 400 | Fine rectangle |
| 33 | P-33 | 25 | P'-3 | 15 | O-1 | S-1 | 400 | Fine rectangle |
| 34 | P-34 | 40 | None | — | O-4 | S-3 | 400 | Fine rectangle |
| 35 | P-35 | 40 | None | — | O-4 | S-4 | 400 | Fine rectangle |
| 36 | P-36 | 40 | None | — | O-5 | S-1 | 400 | Fine rectangle |
| 37 | P-37 | 25 | P'-3 | 15 | O-5 | S-1 | 400 | Fine rectangle |
| 38 | P-38 | 40 | None | — | O-5 | S-1 | 400 | Fine rectangle |
| 39 | P-39 | 40 | None | — | O-5 | S-1 | 400 | Fine rectangle |
| 40 | P-40 | 40 | None | — | O-1 | S-1 | 400 | Fine rectangle |
| 41 | P-41 | 40 | None | — | O-1 | S-2 | 400 | Fine rectangle |
| 42 | P-42 | 25 | P'-3 | 15 | O-2 | S-1 | 400 | Fine rectangle |
| 43 | P-43 | 40 | None | — | O-2 | S-1 | 400 | Fine rectangle |
| 44 | P-44 | 40 | None | — | O-2 | S-1 | 400 | Fine rectangle |
| 45 | P-45 | 40 | None | — | O-3 | S-1 | 400 | Fine rectangle |
| 46 | P-46 | 40 | None | — | O-1 | S-1 | 400 | Fine rectangle |
| 47 | P-47 | 40 | None | — | O-1 | S-1 | 400 | Fine rectangle |
| 48 | P-48 | 40 | None | — | O-1 | S-3 | 400 | Fine rectangle |
| 49 | P-49 | 40 | None | — | O-4 | S-4 | 400 | Fine rectangle |
| 50 | P-50 | 40 | None | — | O-5 | S-1 | 400 | Fine rectangle |

Basic compound (addition: 0.15 parts by mass):
O-1: N,N-dibutylaniline
O-2: 2,6-diisopropylaniline
O-3: diazabicyclo[4.3.0]nonene
O-4: 2,4,5-triphenylimidazole
O-5: trioctylamine
Solvent:
S-1: propylene glycol monomethyl ether acetate (PGMEA)
S-2: γ-butyrolactone
S-3: ethyl lactate
S-4: cyclohexanone

TABLE 9

| Ex. | Resin 1 Type | Resin 1 Parts by mass | Resin 2 Type | Resin 2 Parts by mass | Additive | Solvent Type | Solvent Parts by mass | Pattern shape |
|---|---|---|---|---|---|---|---|---|
| 51 | P-51 | 40 | None | — | O-1 | S-1 | 400 | Fine rectangle |
| 52 | P-52 | 25 | P'-3 | 15 | O-2 | S-2 | 400 | Fine rectangle |
| 53 | P-53 | 40 | None | — | O-3 | S-1 | 400 | Fine rectangle |
| 54 | P-54 | 40 | None | — | O-1 | S-1 | 400 | Fine rectangle |
| 55 | P-55 | 25 | P'-3 | 15 | O-1 | S-2 | 400 | Fine rectangle |
| 56 | P-56 | 40 | None | — | O-4 | S-1 | 400 | Fine rectangle |
| 57 | P-57 | 40 | None | — | O-1 | S-1 | 400 | Fine rectangle |
| 58 | P-58 | 40 | None | — | O-5 | S-2 | 400 | Fine rectangle |
| 59 | P-59 | 40 | None | — | O-2 | S-1 | 400 | Fine rectangle |
| 60 | P-60 | 40 | None | — | O-3 | S-1 | 400 | Fine rectangle |
| 61 | P-61 | 40 | None | — | O-1 | S-1 | 400 | Fine rectangle |
| 62 | P-62 | 25 | P'-3 | 15 | O-1 | S-2 | 400 | Fine rectangle |
| 63 | P-63 | 40 | None | — | O-4 | S-1 | 400 | Fine rectangle |

TABLE 9-continued

| Ex. | Resin 1 Type | Parts by mass | Resin 2 Type | Parts by mass | Additive | Solvent Type | Parts by mass | Pattern shape |
|---|---|---|---|---|---|---|---|---|
| 64 | P-64 | 40 | None | — | O-1 | S-1 | 400 | Fine rectangle |
| 65 | P-65 | 40 | None | — | O-5 | S-2 | 400 | Fine rectangle |
| 66 | P-66 | 40 | None | — | O-2 | S-1 | 400 | Fine rectangle |

Basic compound (addition: 0.15 parts by mass):
O-1: N,N-dibutylaniline
O-2: 2,6-diisopropylaniline
O-3: diazabicyclo[4.3.0]nonene
O-4: 2,4,5-triphenylimidazole
O-5: trioctylamine
Solvent:
S-1: propylene glycol monomethylether acetate (PGMEA)
S-2: γ-butyrolactone
S-3: ethyl lactate
S-4: cyclohexanone

TABLE 10

| Ex. | Resin 1 Type | Parts by mass | Resin 2 Type | Parts by mass | Additive | Solvent Type | Parts by mass | Pattern shape |
|---|---|---|---|---|---|---|---|---|
| 67 | N-1 | 40 | None | — | O-5 | S-1 | 400 | Fine rectangle |
| 68 | N-1 | 20 | N-4 | 20 | O-5 | S-1 | 400 | Fine rectangle |
| 69 | N-2 | 40 | None | — | O-1 | S-1 | 400 | Fine rectangle |

TABLE 10-continued

| Ex. | Resin 1 Type | Parts by mass | Resin 2 Type | Parts by mass | Additive | Solvent Type | Parts by mass | Pattern shape |
|---|---|---|---|---|---|---|---|---|
| 70 | N-3 | 40 | None | — | O-4 | S-2 | 400 | Fine rectangle |
| 71 | N-4 | 40 | None | — | O-5 | S-1 | 400 | Fine rectangle |
| 72 | N-5 | 40 | None | — | O-5 | S-1 | 400 | Fine rectangle |
| 73 | N-6 | 40 | None | — | O-5 | S-1 | 400 | Fine rectangle |
| 74 | N-7 | 40 | None | — | O-4 | S-2 | 400 | Fine rectangle |
| 75 | N-8 | 40 | None | — | O-5 | S-1 | 400 | Fine rectangle |
| 76 | N-9 | 40 | None | — | O-4 | S-1 | 400 | Fine rectangle |
| 77 | N-10 | 40 | None | — | O-1 | S-1 | 400 | Fine rectangle |
| 78 | N-11 | 40 | None | — | O-1 | S-1 | 400 | Fine rectangle |

Cross-linking agent: NIKALAC MX-270 (a glycoluril series crosslinking agent, a product of SANWA CHEMICAL CO., LTD.) added by 3 parts by mass
Basic compound (addition: 0.15 parts by mass):
O-1: N,N-dibutylaniline
O-4: 2,4,5-triphenylimidazole
O-5: trioctylamine
Solvent:
S-1: propylene glycol monomethyl ether acetate (PGMEA)
S-2: γ-butyrolactone Reference Polymerization Example 1

As shown in Table 11, using each monomer, resins (P'-1 to P'-5) with no use of polymerizable sulfonic acid salt were synthesized by a method similar to Polymerization Example 1 or 2. The molar ratio of repeating units of the obtained resin and the mass average molecular weight (MW) are shown in Table 11.

TABLE 11

| Polymerization Example Resin Name | Raw Material Composition | | | | | | Molar Ratio of Repeating Units in Resin | | | Molecular Weight MW |
|---|---|---|---|---|---|---|---|---|---|---|
| | Monomer 1 Type | Mol % | Monomer 2 Type | Mol % | Monomer 3 Type | Mol % | Monomer 1 | Monomer 2 | Monomer 3 | |
| P'-1 | A-1 | 20 | B-1 | 45 | C-1 | 35 | 22 | 45 | 33 | 8,200 |
| P'-2 | A-2 | 25 | B-1 | 45 | C-1 | 30 | 25 | 44 | 31 | 8,900 |
| P'-3 | A-3 | 20 | B-1 | 45 | C-1 | 35 | 19 | 46 | 35 | 9,000 |
| P'-4 | A-4 | 10 | B-1 | 45 | C-1 | 45 | 11 | 46 | 43 | 8,500 |
| P'-5 | A-1 | 20 | B-1 | 45 | C-2 | 35 | 21 | 45 | 34 | 9,200 |

Reference Polymerization Example 2

As shown in Table 12, using each monomer, resins (P-C1 to P-C4) were synthesized using conventional polymerizable fluorine-containing sulfonic acid onium salts (PAG-C1 and PAG-C2), not polymerizable fluorine-containing sulfonic acid onium salts according to the present invention, by a method similar to Polymerization Example 1 or 2. The molar ratio of repeating units of the obtained resin and the mass average molecular weight (MW) are shown in Table 12.

TABLE 12

| Polymerization Example Resin Name | Raw Material Composition | | | | | | | | Molar Ratio of Repeating Units in Resin | | | | Molecular Weight MW |
|---|---|---|---|---|---|---|---|---|---|---|---|---|---|
| | Monomer 1 Type | Mol % | Monomer 2 Type | Mol % | Monomer 3 Type | Mol % | Monomer 4 Type | Mol % | Monomer 1 | Monomer 2 | Monomer 3 | Monomer 4 | |
| P-C1 | PAG-C1 | 15 | — | — | B-1 | 45 | C-1 | 40 | 12 | — | 46 | 42 | 7,700 |
| P-C2 | PAG-C2 | 15 | — | — | B-1 | 45 | C-1 | 40 | 13 | — | 44 | 43 | 8,100 |

TABLE 12-continued

| Polymerization Example | Raw Material Composition | | | | | | | Molar Ratio of Repeating Units in Resin | | | | Molecular |
|---|---|---|---|---|---|---|---|---|---|---|---|---|
| Resin Name | Monomer 1 | | Monomer 2 | | Monomer 3 | | Monomer 4 | | Mono- | Mono- | Mono- | Mono- | Weight |
| | Type | Mol % | Type | Mol % | Type | Mol % | Type | Mol % | mer 1 | mer 2 | mer 3 | mer 4 | MW |
| P-C3 | PAG-C1 | 20 | A-6 | 30 | — | — | C-1 | 50 | 17 | 31 | — | 52 | 9,600 |
| P-C4 | PAG-C2 | 20 | A-6 | 25 | B-1 | 25 | C-1 | 30 | 18 | 27 | 26 | 29 | 7,400 |

Comparative Examples

Similar to Examples, it was tried to synthesize resist compositions by mixing together resins produced by Reference Polymerization Example 2 using conventional polymerizable fluorine-containing sulfonic acid onium salts, solvents, and other additives.

Many resins were slightly soluble in propylene glycol monomethyl ether acetate (PGMEA) and were not completely soluble therein even if the amount of PGMEA was doubled. In the case of using cyclohexanone as the solvent, some resins were soluble therein. From these, similar to Examples, resist solutions were prepared to conduct a pattern forming. The results are shown in Table 13.

TABLE 13

| | Resin 1 | | Basic Comp. | Solvent | | Resist Comp. Prep. & Pattern Shape |
|---|---|---|---|---|---|---|
| C. E. | Type | Parts by mass | | Type | Parts by mass | |
| 1 | P-C1 | 40 | O-1 | S-1 | 400 | Slightly soluble in solvent & incapable of preparing resist comp. |
| 2 | P-C1 | 40 | O-1 | S-1 | 800 | Slightly soluble in solvent & incapable of preparing resist comp. |
| 3 | P-C1 | 40 | O-1 | S-4 | 400 | Slightly distorted rectangle |
| 4 | P-C2 | 40 | O-1 | S-1 | 400 | Slightly soluble in solvent & incapable of preparing resist comp. |
| 5 | P-C2 | 40 | O-1 | S-1 | 800 | Slightly soluble in solvent & incapable of preparing resist comp. |
| 6 | P-C2 | 40 | O-1 | S-4 | 400 | Slightly distorted rectangle |
| 7 | P-C3 | 40 | O-1 | S-1 | 400 | Slightly soluble in solvent & incapable of preparing resist comp. |
| 8 | P-C3 | 40 | O-1 | S-1 | 800 | Slightly soluble in solvent & incapable of preparing resist comp. |
| 9 | P-C3 | 40 | O-1 | S-4 | 400 | Slightly soluble in solvent & incapable of preparing resist comp. |
| 10 | P-C4 | 40 | O-1 | S-1 | 400 | Slightly soluble in solvent & incapable of preparing resist comp. |
| 11 | P-C4 | 40 | O-1 | S-1 | 800 | Slightly soluble in solvent & incapable of preparing resist comp. |
| 12 | P-C4 | 40 | O-1 | S-4 | 400 | Slightly soluble in solvent & incapable of preparing resist comp. |

Basic compound (Addition: 0.15 parts by mass):
O-1: N,N-dibutylaniline
Solvent:
S-1: propylene glycol monomethyl ether acetate (PGMEA)
S-4: cyclohexanone Examples 79 & 80

Similar to P-1, a resist composition was prepared by using Resin P'-1 obtained by Reference Polymerization Example 1 as a base resin and using a polymerizable fluorine-containing sulfonic acid onium salt according to the present invention as an acid generator. Then, similar to other resists, a pattern was formed to observe the pattern shape. A high-resolution pattern shape was obtained from each resist composition. There were not found inferiority defect in adhesion to substrate, film-forming inferiority defect, development defect, and etching resistance inferiority defect. Composition and evaluation result of each resist are shown in Table 14.

TABLE 14

| | Resin 1 | | PAG | | | Solvent | | |
|---|---|---|---|---|---|---|---|---|
| Ex. | Type | Parts by mass | Type | Parts by mass | Additive | Type | Parts by mass | Pattern shape |
| 79 | P'-1 | 40 | PAG-2 | 2 | O-1 | S-1 | 400 | Fine rectangle |
| 80 | P'-2 | 40 | PAG-3 | 2 | O-1 | S-1 | 400 | Fine rectangle |

Basic compound (addition: 0.15 parts by mass):
O-1: N,N-dibutylaniline
Solvent:
S-1: propylene glycol monomethyl ether acetate (PGMEA)

INDUSTRIAL APPLICABILITY

A resin according to the present invention can be used as a photoacid generator for photoresist use and by itself as a positive-type or negative-type resist resin. Furthermore, the polymerizable fluorine-containing onium salt for synthesizing these resins is also useful as a raw material for producing other polymers.

The invention claimed is:

1. A fluorine-containing sulfonic acid salt resin having a repeating unit represented by the following general formula (3),

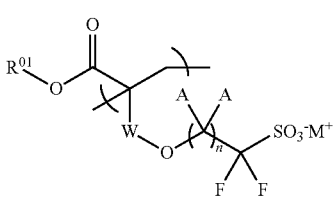

(3)

wherein each A independently represents a hydrogen atom, a fluorine atom or a trifluoromethyl group, n represents an integer of 1-10, W represents a bivalent linking group, $R^{01}$ represents a hydrogen atom or a monovalent organic group, and $M^+$ represents a monovalent cation.

2. The fluorine-containing sulfonic acid salt resin of claim 1, wherein the monovalent organic group $R^{01}$ is a $C_{1-50}$ organic group and a group containing any group of the following (a) to (g),
- (a) an alicyclic group having a carbon ring containing an ether bond (—O—) or carbonyl group (—C(=O)—) wherein any hydrogen atom bonded to a carbon of the ring may be replaced with a hydroxy group or an acetoxy group,
- (b) a group having an aromatic ring in which at least one hydrogen atom has been replaced with a hydroxy group,
- (c) a fluoroalcohol group,
- (d) a group having a ring prepared by a condensation of a ring containing an ether bond (—O—), a thioether bond (—S—), an imino group (—NH—), a carbonyl group (—C(=O)—) or a thiocarbonyl group (—C(=S)—), with an aromatic ring,
- (e) a $C_{1-3}$ alkyl group,
- (f) an alicyclic group in which a hydroxy group and a fluorine atom or trifluoromethyl group have been bonded to the same carbon of the ring, and
- (g) an alicyclic group in which any hydrogen atom has been replaced with a cyano group-containing group, a hydroxy group, or an acetoxy group.

3. The fluorine-containing sulfonic acid salt resin of claim 1, wherein the monovalent organic group $R^{01}$ comprises a group selected from a lactone ring group, a cyclic ether group, 2-hydroxy-hexafluoroisopropyl group (HFIP group), 2-acetoxy-hexafluoroisopropyl group, and a group represented by the following formula,

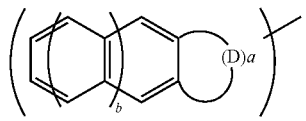

(23)

wherein each D independently represents a methylene group (—CH$_2$—), a methine group (=C—), an oxygen atom, a sulfur atom, a carbonyl group, a thiocarbonyl group or an imino group, a ring portion containing D has at least one hetero atom, a represents an integer of 2-5, and b represents an integer of 0-2.

4. The fluorine-containing sulfonic acid salt resin of claim 1, wherein the repeating unit represented by the general formula (3) is a repeating unit represented by the following repeating unit (4),

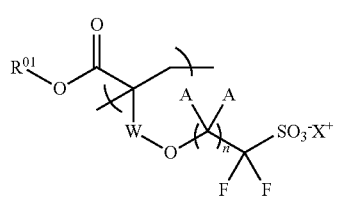

(4)

wherein A, n, W and $R^{01}$ are respectively defined as those in the above-mentioned general formula (3), $X^+$ represents a sulfonium cation represented by the following general formula (CA-a) or an iodonium cation represented by the following general formula (CA-b),

(CA-a)

wherein $R^{02}$, $R^{03}$ and $R^{04}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or any two or more of $R^{02}$, $R^{03}$ and $R^{04}$ may be connected with each other to form a ring together with the sulfur atom in the formula, and the alkenyl groups take a carbon number of 2 or more,

(CA-b)

wherein $R^{05}$ and $R^{06}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or $R^{05}$ and $R^{06}$ may be connected with each other to form a ring together with the iodine atom in the formula, and the alkenyl groups take a carbon number of 2 or more.

5. The fluorine-containing sulfonic acid salt resin of claim 1, comprising a repeating unit represented by the following general formula (5),

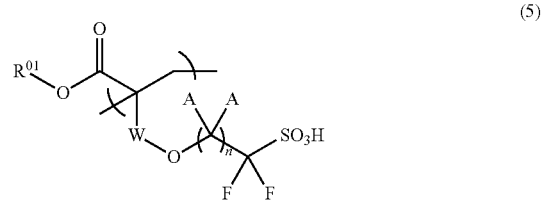

(5)

wherein A, n, W and $R^{01}$ are respectively defined as those in the above-mentioned general formula (3).

6. The fluorine-containing sulfonic acid salt resin of claim 1, further comprising at least one repeating unit selected from the group consisting of repeating units formed by a cleavage of a polymerizable double bond contained in an olefin, a fluorine-containing olefin, an acrylic acid ester, a methacrylic acid ester, a fluorine-containing acrylic acid ester, a fluorine-containing methacrylic acid ester, a norbornene compound, a fluorine-containing norbornene compound, a styrene compound, a fluorine-containing styrene compound, a vinyl ether, or a fluorine-containing vinyl ether.

7. The fluorine-containing sulfonic acid salt resin of claim 6, wherein the olefin, the fluorine-containing olefin, the acrylic acid ester, the methacrylic acid ester, the fluorine-containing acrylic acid ester, the fluorine-containing methacrylic acid ester, the norbornene compound, the fluorine-containing norbornene compound, the styrene compound, the fluorine-containing styrene compound, the vinyl ether, or the fluorine-containing vinyl ether is a polymerizable compound containing in the molecule a moiety that generates an acid by a high-energy ray irradiation.

8. The fluorine-containing sulfonic acid salt resin of claim 6, wherein the olefin, the fluorine-containing olefin, the acrylic acid ester, the methacrylic acid ester, the fluorine-containing acrylic acid ester, the fluorine-containing methacrylic acid ester, the norbornene compound, the fluorine-containing norbornene compound, the styrene compound, the fluorine-containing styrene compound, the vinyl ether, or the fluorine-containing vinyl ether is a polymerizable compound containing in the molecule a moiety that is decomposed by an acid catalyst to become an acid.

9. The fluorine-containing sulfonic acid salt resin of claim 6, wherein the olefin, the fluorine-containing olefin, the acrylic acid ester, the methacrylic acid ester, the fluorine-containing acrylic acid ester, the fluorine-containing methacrylic acid ester, the norbornene compound, the fluorine-containing norbornene compound, the styrene compound, the fluorine-containing styrene compound, the vinyl ether, or the fluorine-containing vinyl ether is a polymerizable compound containing in the molecule a moiety that is lowered in solubility in alkali developing solutions through a reaction with a cross-linking agent by an acid catalyst.

10. The fluorine-containing sulfonic acid salt resin of claim 1, further comprising a repeating unit represented by the following general formula (6),

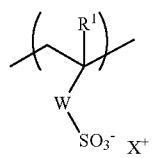

(6)

wherein $R^1$ represents a hydrogen atom, a halogen atom, or a $C_{1-3}$ alkyl group or fluorine-containing alkyl group, W represents a bivalent linking group and is defined as in the general formula (3), and $X^+$ is defined as in the general formula (4).

11. The fluorine-containing sulfonic acid salt resin of claim 1, further comprising a repeating unit represented by the following general formula (7),

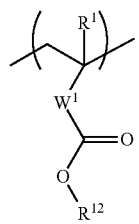

(7)

wherein $R^1$ represents a hydrogen atom, a halogen atom, or a $C_{1-3}$ alkyl group or fluorine-containing alkyl group, $W^1$ represents a bivalent linking group, and $R^{12}$ represents an acid-labile group.

12. The fluorine-containing sulfonic acid salt resin of claim 1, further comprising a repeating unit represented by the following general formula (13-1) or (13),

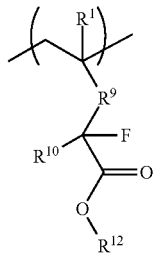

(13-1)

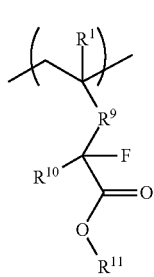

(13)

wherein $R^1$ represents a hydrogen atom, a halogen atom, or a $C_{1-3}$ alkyl group or fluorine-containing alkyl group, $R^{10}$ represents a hydrogen atom, a fluorine atom, or a fluorine-containing alkyl group, $R^9$ represents a bivalent linking group, $R^{12}$ represents an acid-labile group, and $R^{11}$ is a hydrogen atom, a substituted or unsubstituted, $C_{1-25}$ aliphatic hydrocarbon group or a substituted or unsubstituted, $C_{1-25}$ aromatic hydrocarbon group, and a part of $R^{11}$ may contain a fluorine atom, an ether bond, or a carbonyl group.

13. The fluorine-containing sulfonic acid salt resin of claim 1, further comprising a repeating unit represented by the following general formula (8),

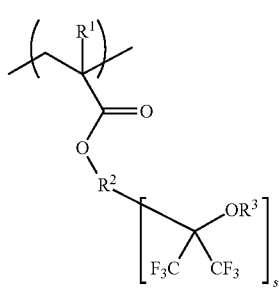

(8)

wherein $R^1$ represents a hydrogen atom, a halogen atom, or a $C_{1-3}$ alkyl group or fluorine-containing alkyl group, $R^2$ is a substituted or unsubstituted aliphatic hydrocarbon group, a substituted or unsubstituted aromatic group, or an organic group prepared by linking a plurality of those, and may have a fluorine atom substituted for an arbitrary number of hydrogen atom, $R^3$ is a hydrogen atom, a substituted or unsubstituted, $C_{1-25}$ aliphatic hydrocarbon group or a substituted or unsubstituted $C_{1-25}$ aromatic hydrocarbon group, may have a fluorine atom substituted for an arbitrary number of hydrogen atom, and may contain an ether bond or a carbonyl group, and, s represents an integer of 1-2.

14. The fluorine-containing sulfonic acid salt resin of claim 1, further comprising a repeating unit represented by the following general formula (8-1), (9) or (10),

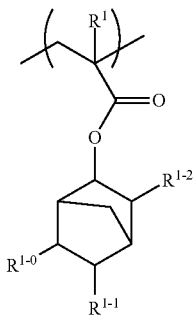
(8-1)

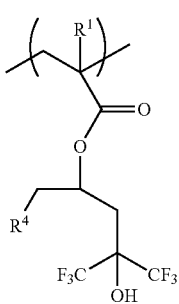
(9)

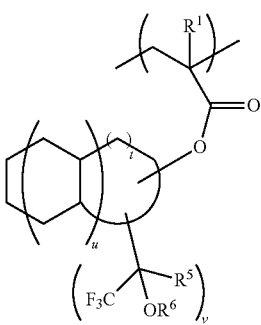
(10)

wherein $R^1$ represents a hydrogen atom, a halogen atom, or a $C_{1-3}$ alkyl group or fluorine-containing alkyl group, any one of $R^{1-0}$, $R^{1-1}$ and $R^{1-2}$ is a $CF_3C(CF_3)(OH)CH_2$—group, and remaining two are hydrogen atoms, $R^4$ represents a hydrogen atom, or a $C_{1-4}$ alkyl group or fluorine-containing alkyl group, $R^5$ represents a methyl group or a trifluoromethyl group, $R^6$ represents a hydrogen atom or a group containing a substituted or unsubstituted $C_{1-25}$ aliphatic hydrocarbon group or a substituted or unsubstituted $C_{1-25}$ aromatic hydrocarbon group, $R^6$ may contain a fluorine atom, an ether bond, or a carbonyl group, u represents an integer of 0-2, t and v are integers of 1-8, and v≤t+2 is satisfied, and in case that v is 2-8, $R^5$ and $R^6$ may respectively be the same or different.

15. The fluorine-containing sulfonic acid salt resin of claim 1, further comprising a repeating unit represented by the following general formula (11),

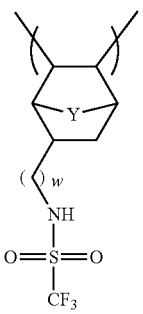
(11)

wherein Y represents any of —$CH_2$—, —O—, and —S—, and w represents an integer of 2-6.

16. The fluorine-containing sulfonic acid salt resin of claim 1, further comprising a repeating unit represented by the following general formula (12),

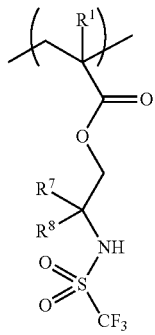
(12)

wherein $R^1$ represents a hydrogen atom, a halogen atom, or a $C_{1-3}$ alkyl group or fluorine-containing alkyl group, each of $R^7$ and $R^8$ independently represents a hydrogen atom, a substituted or unsubstituted $C_{1-25}$ aliphatic hydrocarbon group or a substituted or unsubstituted $C_{1-25}$ aromatic hydrocarbon group, and a part of $R^7$ and $R^8$ may contain a fluorine atom, an ether bond, or a carbonyl group.

17. A resist composition comprising at least the fluorine-containing sulfonic acid salt resin of claim 1 and a solvent.

18. The resist composition of claim 17, further comprising an acid-labile group-containing resin.

19. The resist composition of claim 17, further comprising a cross-linking agent.

20. The resist composition of claim 19, further comprising a cross-linking group-containing resin.

21. The resist composition of claim 17, further comprising a compound that generates an acid by radiation exposure.

22. A pattern forming method, comprising:
(a) applying the resist composition of claim 17 onto a substrate,
(b) conducting an exposure with a high-energy ray having a wavelength of 300 nm or less through a photomask after a heating treatment; and
(c) conducting a development using a developing solution, after conducting a heating treatment if necessary.

23. The pattern forming method of claim 22, wherein step (b) is an immersion lithography method in which an ArF excimer laser having a wavelength of 193 nm is used, and in which water or a liquid having a refractive index higher than that of air and being other than water is inserted between a substrate, on which the resist composition has been applied, and a projection lens.

24. The pattern forming method of claim 22, that in the step of conducting the exposure wherein in step (b) a soft X-ray (EUV light) having a wavelength of 10-14 nm is used.

25. A polymerizable fluorine-containing sulfonic acid or a polymerizable fluorine-containing sulfonic acid salt, having an anion represented by the following general formula (1),

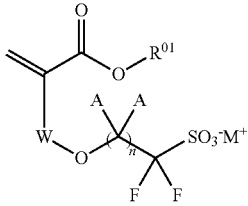
(1)

wherein each A independently represents a hydrogen atom, a fluorine atom or a trifluoromethyl group, n represents an integer of 1-10, W represents a bivalent linking group, $R^{01}$ represents a hydrogen atom or a monovalent organic group, and $M^+$ represents a monovalent cation.

26. The polymerizable fluorine-containing sulfonic acid salt of claim 25, which is a polymerizable fluorine-containing sulfonic acid onium salt represented by the following general formula (2),

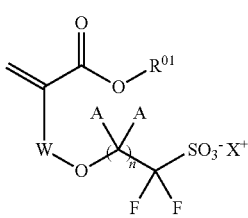
(2)

wherein A, n, W and $R^{01}$ are respectively defined as those in the above-mentioned general formula (1), $X^+$ represents a sulfonium cation represented by the following general formula (CA-a) or an iodonium cation represented by the following general formula (CA-b),

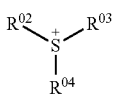
(CA-a)

wherein $R^{02}$, $R^{03}$ and $R^{04}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or any two or more of $R^{02}$, $R^{03}$ and $R^{04}$ may be connected with each other to form a ring together with the sulfur atom in the formula, and the alkenyl groups take a carbon number of 2 or more,

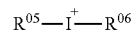
(CA-b)

wherein $R^{05}$ and $R^{06}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or $R^{05}$ and $R^{06}$ may be connected with each other to form a ring together with the iodine atom in the formula, and the alkenyl groups take a carbon number of 2 or more.

27. A method for producing a polymerizable fluorine-containing sulfonic acid onium salt represented by the general formula (2)

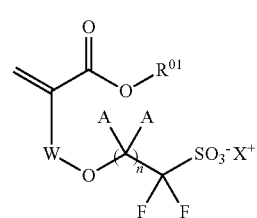
(2)

wherein A, n, W, $R^{01}$ and $X^+$ are respectively defined as those in the general formulas (15) and (16)), wherein in the presence of a base catalyst a condensation reaction is conducted between an acrylic acid derivative represented by the following general formula (15)

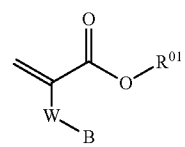
(15)

wherein W represents a bivalent linking group, $R^{01}$ represents a hydrogen atom or a monovalent organic group, and B represents a halogen atom or a leaving group, and a hydroxyalkanesulfonic acid onium salt represented by the following general formula (16)

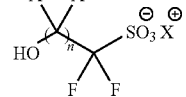
(16)

wherein each A independently represents a hydrogen atom, a fluorine atom or a trifluoromethyl group, and n represents an integer of 1-10, and $X^+$ represents a sulfonium cation represented by the following general formula (CA-a) or an iodonium cation represented by the following general formula (CA-b),

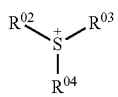
(CA-a)

wherein $R^{02}$, $R^{03}$ and $R^{04}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or any two or more of $R^{02}$, $R^{03}$ and $R^{04}$ may be connected with each other to form a ring together with the sulfur atom in the formula, and the alkenyl groups take a carbon number of 2 or more,

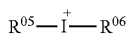
(CA-b)

wherein $R^{05}$ and $R^{06}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or $R^{05}$ and $R^{06}$ may be connected with each other to form a ring together with the iodine atom in the formula, and the alkenyl groups take a carbon number of 2 or more.

28. The production method of claim 27, wherein W of the acrylic acid derivative represented by the general formula (15) is methylene.

29. The production method of claim 27, wherein the acrylic acid derivative represented by the general formula (15) is the following general formula (17) or general formula (18),

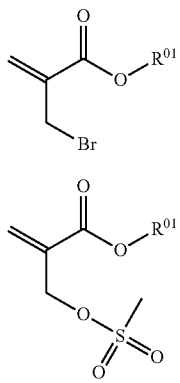
(17)

(18)

wherein $R^{01}$ is defined as that in the above-mentioned general formula (2).

30. The production method of claim 27, wherein, in the hydroxyalkanesulfonic acid onium salt represented by the general formula (16), n is 1, and A is a hydrogen.

31. The production method of claim 27, wherein $X^+$ of the hydroxyalkanesulfonic acid onium salt represented by the general formula (16) is a triphenylsulfonium.

32. A method for producing a polymerizable fluorine-containing sulfonic acid onium salt represented by the general formula (2)

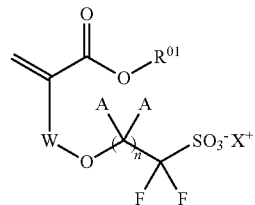
(2)

wherein A, n, W, $R^{01}$ and $X^+$ are respectively defined as those in the general formulas (19) and (20), wherein an acid chloride derivative represented by the following general formula (19)

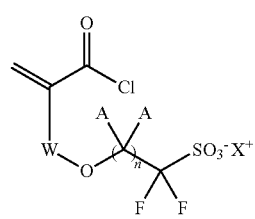
(19)

wherein W is a bivalent linking group, and each A independently represents a hydrogen atom, a fluorine atom or a trifluoromethyl group, n represents an integer of 1-10, $X^+$ represents a sulfonium cation represented by the following general formula (CA-a) or an iodonium cation represented by the following general formula (CA-b),

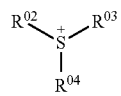
(CA-a)

wherein $R^{02}$, $R^{03}$ and $R^{04}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or any two or more of $R^{02}$, $R^{03}$ and $R^{04}$ may be connected with each other to form a ring together with the sulfur atom in the formula, and the alkenyl groups take a carbon number of 2 or more,

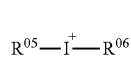
(CA-b)

wherein $R^{05}$ and $R^{06}$ mutually independently represent substituted or unsubstituted $C_{1-20}$ alkyl groups, alkenyl groups or oxoalkyl groups; or substituted or unsubstituted $C_{6-18}$ aryl groups, aralkyl groups or aryloxoalkyl groups; or $R^{05}$ and $R^{06}$ may be connected with each other to form a ring together with the iodine atom in the formula, and the alkenyl groups take a carbon number of 2 or more, or a carboxylic acid derivative represented by the following general formula (21)

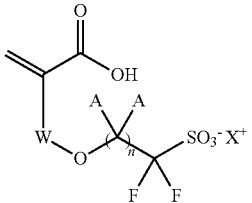 (21)

wherein W, A, n, and $X^+$ are defined as in the general formula (19), is reacted with an alcohol body represented by the following general formula (20)

$$HO-R^{01} \qquad (20)$$

wherein $R^{01}$ represents a monovalent organic group.

33. The production method of claim 32, wherein W of the acid chloride derivative represented by the general formula (19) or the carboxylic acid derivative represented by the general formula (21) is methylene.

34. The production method of claim 32, wherein in the acid chloride derivative represented by the general formula (19) or the carboxylic acid derivative represented by the general formula (21), n is 1, and A is a hydrogen.

35. The production method of claim 32, wherein $X^+$ of the acid chloride derivative represented by the general formula (19) or the carboxylic acid derivative represented by the general formula (21) is a triphenylsulfonium.

* * * * *